US011999959B2

(12) United States Patent
Pasin et al.

(10) Patent No.: US 11,999,959 B2
(45) Date of Patent: *Jun. 4, 2024

(54) BINARY VECTORS AND USES OF SAME

(71) Applicant: Juan Antonio García Álvarez, Madrid (ES)

(72) Inventors: Fabio Pasin, Madrid (ES); Juan Antonio García Álvarez, Madrid (ES); Leonor Cecilia Bedoya Rojas, Madrid (ES); Maria del Carmen Simón Mateo, Madrid (ES); Diego Vicente Orzáez Calatayud, Madrid (ES); Juan Miguel Bernabé Orts, Madrid (ES)

(73) Assignee: Juan Antonio García Álvarez, Madrid (ES)

( * ) Notice: Subject to any disclaimer, the term of this patent is extended or adjusted under 35 U.S.C. 154(b) by 0 days.

This patent is subject to a terminal disclaimer.

(21) Appl. No.: 18/114,264

(22) Filed: Feb. 26, 2023

(65) Prior Publication Data

US 2023/0365983 A1 Nov. 16, 2023

Related U.S. Application Data

(63) Continuation of application No. 16/622,037, filed as application No. PCT/ES2018/070421 on Jun. 12, 2018, now Pat. No. 11,597,939.

(30) Foreign Application Priority Data

Jun. 12, 2017 (ES) .................................. 201730792

(51) Int. Cl.
*C12N 15/82* (2006.01)

(52) U.S. Cl.
CPC ..... *C12N 15/8205* (2013.01); *C12N 15/8241* (2013.01)

(58) Field of Classification Search
None
See application file for complete search history.

(56) References Cited

U.S. PATENT DOCUMENTS

| | | | | |
|---|---|---|---|---|
| 11,597,939 | B2 * | 3/2023 | Pasin | C12N 15/8241 |
| 2007/0059768 | A1 | 3/2007 | Gill et al. | |
| 2008/0184393 | A1 | 7/2008 | Zhang et al. | |

FOREIGN PATENT DOCUMENTS

WO 2017040343 A1 3/2017

OTHER PUBLICATIONS

Thole et al., "The pCLEAN Dual Binary Vector System for Agrobacterium-Mediated Plant Transformation," Plant Physiology, (20071200), vol. 145, pp. 1211-1219.
Komari et al., "Binary Vectors and Super-binary Vectors," Methods in Molecular Biology, (20060000), vol. 343, pp. 15-41.
Daley et al., "Co-transformation with one Agrobacterium tumefaciens strain containing two binary plasmids as a method for producing marker-free transgenic plants," Plant Cell Reports, (19980000), vol. 17, pp. 489-496, Abstract submitted herewith.
International Search Report and Written Opinion in corresponding International Patent Application No. PCT/ES2018/070421, mailed on Dec. 20, 2018, 20 Pages with English Translation.
Hajdukiewicz, Peter, Zora Svab, and Pal Maliga. "The small, versatile pPZP family of Agrobacterium binary vectors for plant transformation," Plant Molecular Biology 25.6 (1994): 989-994. (Year: 1994).

* cited by examiner

*Primary Examiner* — Weihua Fan
(74) *Attorney, Agent, or Firm* — FisherBroyles, LLP; Andrew K. Gonsalves

(57) ABSTRACT

The invention relates to binary vectors based on compatible and autonomous origins, specifically based on the pBBR1 and RK2 replication origins. These binary vectors are useful for having a wide range of hosts, for their maintenance in *Agrobacterium* sp. and *Escherichia coli*, and as a new tool for plant synthetic biology as well as a flexible framework for assembly, transfer and characterization of multiple DNA elements. The binary vectors disclosed are small, preferably less than 3.8 kb in size, stable, include an origin compatible with the most commonly used binary T-DNA vectors, comply with current standards for plant synthetic biology, and allow the administration of multiple T-DNA cassettes by means of the multiplexing of the vectors. The present invention also relates to methods for transferring and expressing nucleic acid sequences using said binary vectors, and to the uses of the same.

20 Claims, 16 Drawing Sheets

Specification includes a Sequence Listing.

BINARY VECTORS AND USES OF SAME

CROSS-REFERENCE TO RELATED APPLICATIONS

This application is a continuation of U.S. patent application Ser. No. 16/622,037, filed Apr. 28, 2020, issuing as U.S. Pat. No. 11,597,939 on Mar. 7, 2023, which is a U.S. National Phase filing under 35 U.S.C. § 371 of International Application No. PCT/ES2018/070421, filed Jun. 12, 2018, which claims foreign priority benefit of Spanish Patent Appl. No. P 201730792, filed Jun. 12, 2017, the disclosures of which are hereby incorporated by reference herein in their entirety.

REFERENCE TO AN ELECTRONIC SEQUENCE LISTING

The contents of the electronic sequence listing (20230808_SequenceListing_ST26_13431001US2.xml; Size: 335,331 bytes; and Date of Creation: Aug. 8, 2023) is herein incorporated by reference in its entirety.

DESCRIPTION

The invention relates in general to the field of molecular biology and to agents useful for the manipulation of eukaryotic organisms. In particular, the present invention provides methods to assemble, transfer, and express DNA sequences using binary vectors, the binary vectors themselves, and uses of the same.

BACKGROUND ART

Plants are plastic organisms that sense and respond to environmental stimuli. These responses or specific plant features might not fit human needs, and can be manipulated by targeted use of plant-interacting microorganisms or by plant genetic transformation. Plant biotechnology uses advanced tools to generate plants with new functions, enhanced agronomic traits, or to produce new products. Synthetic biology applies engineering principles to facilitate the production of organisms with customized functions and for precise control of specific biological functions. Genetic components of complex biological systems are reduced to DNA parts with modular and defined assignments. Once characterized with the aid of computational tools, libraries of parts are assembled to yield pathways and networks with predictable outputs. Methods to analyze dynamic molecular devices have been used to genetically engineer plants with tunable functions.

Assembled DNA constructs are transferred directly to plants, or are introduced into disarmed-pTi *Agrobacterium tumefaciens* strains which serve as shuttle chassis for delivery to plants of constructs maintained in T-DNA binary vectors. From 1986 to 2000, T-DNA binary vectors were generated using diverse replication origins and parts (Murai N., Am. J. Plant Sci. 2013, 4, 932-939). Disadvantages of existing binary vectors, for example the 12-kb pBIN19 (Bevan M., Nucleic Acids Res. 1984, 12, 8711-8721), are their difficult-to-handle size, and their low-copy number, which leads to low yields of DNA plasmids and makes cloning procedures difficult. To improve the low DNA yields and ease cloning procedures, plasmid backbones can be amplified by PCR and used in one-step DNA assembly reactions. Due to the large sizes of many binary vectors, amplification of the plasmid backbones by PCR is not practical. The pPZP and pGreen series of binary vectors include origins with a high copy number that give high plasmid yields (Hajdukiewicz P., et al., Plant Mol. Biol. 1994, 25, 989-994; Helles R., et al., Plant Molecular Biology. 2000, 42, 819-832). Unstable replication origins can lead to variable plasmid losses during replication. The pGreen vector, which is very small (4.6 kb in size), is not autonomous and lacks elements required for stable multiplication in agrobacteria; thus, it can only be used with specific *Agrobacterium* strains (Helles R., et al., Plant Molecular Biology. 2000, 42, 819-832). For certain applications, use of origins with a high copy number is not desirable, since it could promote deletions/alterations of large DNA inserts, of sequences with bacterial toxicity, or of repeated sequence elements. Instability is particularly evident for DNA components used multiple times within constructs. For example, it is not uncommon that a given plant-expressible promoter is used to drive expression of different protein coding regions in a transgenic plant. Other genetic components such as 3' untranslated regions (i.e., sequences that determine transcription termination and polyadenylation addition) and even very similar protein-coding regions can be duplicated or present in several copies within a single T-DNA region. As mentioned above, these repeated sequence elements, which can occur in either inverted or directly repeated orientations, are targets for intramolecular recombination that can lead to DNA deletions and other rearrangements.

The described binary vectors lack features that reduce undesired expression of T-DNA sequences in bacterial hosts. Undesired expression of exogenous sequences can lead to production of toxic products during vector propagation in bacteria, and could increase insert and vector instability. Natural or synthetic transcription terminators are known to insulate against promoters active in bacteria (Chen Y. J., et al., Nat Methods. 2013, 10, 7, 659-664).

In the early series of binary vectors, there is also frequently a lack of a sufficient restriction enzyme sites for cloning desired sequences into the T-DNA cassettes, or the vectors only permit the use of a few selectable markers.

More recent versions of previously described vectors were reported (Murai N., Am. J. Plant Sci. 2013, 4, 932-939). These versions generally adopt the described backbones, modified to include sequences to improve delivery of T-DNA cassettes to eukaryotic cells, and to facilitate insertion of exogenous sequences into the T-DNA cassettes. For decades, the most common approaches for assembling DNA constructs in binary vectors relied on the specificity of restriction endonucleases to create compatible ends that can be joined using DNA ligases. The presence or absence of restriction sites in the vector and insert sequences can limit possible assemblies, particularly those involving multiple inserts. Cloning methods have been developed to overcome these constraints, thus allowing high-throughput assembly of DNA constructs. Recombinase-based technologies such as Gateway, Creator, Echo, and Univector cloning are very efficient and are based on enzymes that specifically recombine insert and vector sequences. Recombinase-based technologies are limited to vectors with appropriate recombination sequences, they allow simultaneous cloning of small number of inserts, and are not always scar-benign, as they leave >20-bp scars between building blocks. New cloning strategies developed in the past decade use Type IIS restriction endonuclease- and overlap-based assembly methods (e.g., Golden Gate and Gibson assembly) to overcome sequence requirements, and allow assembly of multiple inserts in a given reaction. Only a small number of described binary vectors allow generation of T-DNA constructs by high-throughput DNA assembly methods as those based on Type IIS restriction endonucleases and overlaps. Golden Gate is a robust system used by many plant scientists (Patron N.J., et al., New Phytol. 2015, 208, 13-19). Gibson assembly is very versatile, since it requires no domestication of parts, is able to join 2-10 fragments in a predetermined order, and has no sequence restrictions or scars (Gibson D. G., et al., Nat. Methods 2009, 6, 343-345); nonetheless, it has not been widely adopted for building plant constructs. To substantially reduce background of unwanted vector-only colonies in Gibson assembly reactions, the vector should be a PCR product rather than a restriction fragment, and should be DpnI-treated to remove template carryover. The large size of many binary vectors makes backbone linearization by PCR impractical, and small-sized binary vectors are therefore desirable for efficient construct cloning by Gibson assembly and other overlap-based assembly methods.

Multigene transfer is imperative in multiplexed gene editing, and to design and genetically engineer complex traits, circuits and metabolic pathways. In plants, conventional stacking methods require substantial breeding effort, which can be overcome by placing several genes within a single T-DNA, or by simultaneous infection of plant cells with multiple *A. tumefaciens* strains, each harboring a different T-DNA binary vector. A single *A. tumefaciens* strain can deliver two unlinked T-DNA cassettes and transform them in the same eukaryotic cell; simultaneous use of compatible T-DNA binary vectors is nonetheless a seldom-applied strategy in plant biotechnology. Moreover, in most current binary vector systems, selectable markers cannot be removed from transgenic lines at a later time. Delivery of unlinked T-DNA cassettes allows use of a selectable marker during plant regeneration, and subsequent recovery of marker-free progeny.

Binary vector systems are known wherein two T-DNA cassettes were delivered to plants by a single *A. tumefaciens* strain. Specifically, a single binary vector hosting two T-DNA cassettes (Komari T., et al., Plant J. 1996, 10, 165-174), or two T-DNA cassettes hosted in two compatible binary vectors (Daley M., et al., Plant Cell Rep. 1998, 17, 489-496) were delivered to plants by a single *A. tumefaciens* strain. Technical constraints of known systems include limited cloning flexibility due to the large plasmid size (>15 kb), incompatibility with high-throughput methods for construct assembly, or lack of replication independence of the binary vectors used.

Another operational disadvantage of binary vectors is the use of common components in their backbone sequences, which hampers their simultaneous maintenance in a single bacterial cell. As is well known to those skilled in the field of molecular biology, use of origins belonging to identical incompatibility groups impedes vector replication and maintenance in the same cell. Moreover, large sequence repeats can lead to DNA deletions and other rearrangements, particularly when the repeats are part of the plasmid structure. Such rearrangements can lead to partial or complete loss of the T-DNA region, resulting in little or no transfer of the intact, desired foreign sequences into eukaryotic cells.

Another disadvantage of binary vectors are the plasmid mobilization sequences needed to mobilize the vectors into *Agrobacterium* by triparental mating. The presence of mobilization sequences in binary vectors contributes to their size increase and to reducing their biological safety. Moreover, the origin of transfer of certain plasmids can interfere with the desired T-DNA processing and its delivery to eukaryotic cells (Buchanan-Wollaston V., et al., Nature 1987, 328, 172-175). In this sense it is known that plasmids can be transformed into *Agrobacterium* by physical approaches such as electroporation or freeze-thaw methods (Höfgen R. & Willmitzer L., Nucleic Acids Res. 1988, 16, 9877).

In consideration of the hereinabove disadvantages, it would be desirable to design improved binary vectors and binary vector systems without the above-mentioned limitations. There is thus a need for a binary vector of reduced size and with features that render it stable and limit its horizontal transfer. Further, there is a need for a binary vector compatible with advanced, high-throughput DNA cloning methods and that facilitates assembly of multiple components. It is also desirable to provide a binary vector system that incorporates minimal, single, compatible broad-host range replication origins that allow simultaneous maintenance of multiple binary vectors in a single bacterial cell. Consequently, the necessary binary vectors, binary vector systems, compositions, uses and methods comprising the same can be applied to improve the transformation process to integrate full-length T-DNA constructs into the eukaryotic cell or organism, and which are free of any residual sequence of the binary vector backbone. There is thus further a need for a binary vector system that facilitates delivery of multiple T-DNA cassettes to eukaryotic cells. The development of a novel, improved plant transformation system provides significant benefits for cell biologists, for agronomic uses, and for production of pharmaceutical compounds and recombinant proteins.

SUMMARY OF THE INVENTION

The invention resolves the problems described above by generation of the pLX series, a set of T-DNA binary vectors that facilitate the assembly and delivery of multicomponent constructs. The T-DNA binary vectors of the present invention are a new tool for plant synthetic biology as well as a flexible framework for multigene transfer and the characterization of DNA parts. The advantages of the T-DNA binary vectors of the present invention are: (a) a reduced size, preferably less than 3.8 kb; (b) a single, autonomous, broad-host range replication origin for maintenance in bacteria, preferably in *Escherichia coli* and *Agrobacterium tumefaciens*; (c) the use of a replication origin compatible with the most commonly used T-DNA binary vectors; (d) the presence of transcription terminators to reduce undesired expression of T-DNA sequences in bacterial hosts and to promote plasmid stability; (e) the incorporation of T-DNA cassettes with unique rare-cutting recognition sites; (f) consistency with current standards for plant synthetic biology, to allow high-throughput assembly of T-DNA constructs using pre-made DNA elements and Type IIS restriction endonuclease-based cloning methods; (g) the possibility of adopting overlap-dependent methods for high-throughput assembly of T-DNA constructs; (h) the possibility of being amplified and linearized by PCR to improve efficiency of overlap-based cloning; (i) incorporation of a pair of binary vectors with compatible origins, specifically engineered to have no backbone regions with >28 nucleotide identity; and (j) the possibility of delivering multiple T-DNA cassettes by a binary vector system that allows the multiplexing of vectors in a single bacterial cell.

The T-DNA binary vectors of the present invention comprise a minimal replication origin derived from the pBBR1 (pBBR1-based pLX) or RK2 (RK2-based pLX) plasmids, preferably from the pBBR1 plasmid (Antoine R. & Locht C., Mol. Microbiol. 1992, 6, 1785-1799). The size of the pBBR1-based backbone and the RK2-based backbone of the pLX vectors of the invention is substantially smaller than the widely used pBIN19- and pCAMBIA-based vectors, and is equal to pGreen-based vectors, the smallest available binary plasmids (FIG. 2A and FIG. 9). Replication of the pGreen vectors in *A. tumefaciens* requires a co-resident plasmid that supplies the pSa-RepA gene (e.g., pSoup). In contrast, the pLX binary vectors of the present invention facilitate flexible experimental designs, since their replication is autonomous in both *E. coli* and *A. tumefaciens*, and consequently does not require additional factors for their maintenance in bacterial hosts. The pLX binary vectors of the present invention are therefore useful for their autonomous replication in diverse bacteria, and for the presence of T-DNA cassettes.

The pLX binary vectors of the invention also include diverse selectable markers (the nptI, aadA, or aacC1 genes) for their selection in bacterial host cells, a T-DNA cassette with borders from an octopine- or succinamopine-type pTi from *A. tumefaciens*, and a second left border sequence that reduces backbone transfer (FIG. 2A). Bacterial synthetic terminators based on different scaffolds (T1, T2, λT1 and/or λT2) were included to reduce undesired expression of T-DNA sequences in the bacterial hosts and to increase plasmid stability. An AscI rare-cutting recognition site outside the T-DNA cassette was included to modify the pLX vector backbone of the present invention for a given purpose, for example, without limitation, by inserting toxin-antitoxin, counter segregation systems, or virulence gene sequences to improve plasmid stability and/or enhance transformation efficiency, such as, and without limitation, the hok/sok, parD/parE, and virG genes. Additionally, the pLX binary vectors of the present invention facilitate molecular cloning procedures, since the T-DNA cassettes comprise the PmlI and SbfI rare-cutting recognition sites that are useful for standard restriction endonuclease/DNA ligase cloning, and BsaI and BsmBI recognition sites compatible with high-throughput Type IIS restriction endonuclease-based methods, such as Golden Gate and GoldenBraid cloning. The BsaI- and BsmBI-produced overhangs comply with proposed standards for plant synthetic biology and ease assembly of pre-made DNA elements available in public libraries. The T-DNA cassettes also include divergent primer annealing regions with no secondary structures and sequence similarity among them. The mini T-DNA binary vectors of the present invention can thus be easily linearized by PCR, DpnI treated, and used in overlap-dependent cloning methods with high efficiency and no background of unwanted vector-only colonies. The binary pLX vectors of the present invention are therefore a set of mini T-DNA binary plasmids suitable for standard restriction endonuclease/DNA ligase cloning, and for advanced, Type IIS restriction endonuclease- and overlap-based assembly methods, such as and without limitation, Golden Gate/Golden Braid and Gibson assembly.

Given their small size, the pLX vectors might be delivered directly to eukaryotic cells, for example, by cell/protoplast transfection. Alternatively, the pLX vectors can use suitable bacterial strains, preferably *Agrobacterium* sp. strains, as shuttle chassis for transfer of their T-DNA cassette to eukaryotic cells. The pLX vectors can be introduced into bacteria by physical methods (e.g., electroporation, heat shock), and unwanted horizontal transfer of the pLX vector is less likely, since they do not include an origin of conjugative transfer or other plasmid mobilization regions. Transfer of the pLX vector backbone sequences flanking the T-DNA cassettes is predicted to be reduced by the incorporation of double left borders. *Escherichia coli, Agrobacterium tumefaciens* and plants have been used in the examples of the present invention, although the binary vectors of the invention are suitable for use in alternative systems such as in prokaryotic chassis other than *E. coli* and *A. tumefaciens*, and to transform eukaryotic organisms other than higher plants, such as algal, fungal, and animal cells.

The binary pLX vectors of the present invention include the pBBR1 origin, which shows no incompatibility with known plasmids. A vector system that uses, without limitation, the pBBR1-based and RK2-based pLX binary vectors of the invention facilitates multiple T-DNA delivery to eukaryotic cells, since it includes vectors with compatible replication origins, diverse selectable markers, and low sequence similarity to reduce homologous recombination events. Simultaneous use of the pBBR1-based and RK2-based pLX vectors as a transformation system, e.g. a two-vector/one-*Agrobacterium* strain system, allows multiple T-DNA and multigene delivery to eukaryotic organisms, such as plants, fungi, and animals.

The use of alternative compatible replication origins might further expand the multigene delivery design to an "N-vector/one-strain" system. This system can be combined by co-infection with multiple *A. tumefaciens* strains to further increase the number of T-DNA cassettes delivered.

The binary vectors disclosed in the present invention have been tested (see examples below) for transient and stable transformation of plants, genome editing, agro-inoculation of a new viral infectious clone, and for delivery of exogenous sequences to plants by viral vectors. The inventors have used a two-vector/one-strain system to deliver multiple T-DNA cassettes to plant germ line cells, and to express in plants the components of a simple buffer gate activated by a chemical inducer.

Applications of the binary pLX vectors of the present invention include, without limitation, their use for assembly of large T-DNA constructs and transcription units; for transient and stable transgene expression; for generation of transgenic plants free of drug-resistance markers; for launching viral infections by agro-inoculation; for exogenous sequence delivery and recombinant protein production using viral vectors; for genome editing; for delivery of clustered regularly interspaced short palindromic repeats (CRISPR)/CRISPR-associated protein (Cas) system components; for delivery of chemically-regulated expression systems; and for delivery of components of genetic circuits.

In this sense, a first aspect of the present invention relates to a binary vector, hereinafter first binary vector of the invention (the pBBR1-based pLX vector), comprising at least three modules: (a) a T-DNA cassette module comprising at least a T-DNA right border and a T-DNA left border; (b) a replication origin module comprising a pBBR1 minimal origin, or a variant functionally equivalent thereof; and (c) at least a selectable marker module.

In a preferred embodiment, the pBBR1-based pLX vector of the invention comprises a T-DNA cassette comprising one T-DNA right border and two T-DNA left borders.

In a further preferred embodiment of the pBBR1-based pLX vector of the invention, the pBBR1 origin comprises the pBBR1-oriV and -rep regions, or a variant functionally equivalent thereof. In a more preferred embodiment, the pBBR1 origin comprises the SEQ ID NO: 105.

In another preferred embodiment, the pBBR1-based pLX vector of the invention comprises a T-DNA cassette which is flanked by at least two transcription terminators, preferably selected from T1 (SEQ ID NO: 108), T2 (SEQ ID NO: 109), λT1 (SEQ ID NO: 110), λT2 (SEQ ID NO: 111), or any combinations thereof.

In a second aspect, the present invention further relates to another binary vector, named as RK2-based pLX vector, comprising at least three modules: (a) a T-DNA cassette module comprising at least a T-DNA right border and a T-DNA left border; (b) a replication origin module comprising an RK2 minimal origin, or a variant functionally equivalent thereof; and (c) at least a selectable marker module.

In an embodiment of the second aspect, the present invention relates to another binary vector that can preferably be used in combination with the pBBR1-based pLX vector of the invention, comprising at least three modules: (a) a T-DNA cassette module comprising at least a T-DNA right border and a T-DNA left border; (b) a replication origin module comprising an origin compatible with the pBBR1 origin, preferably selected form the list consisting of origins of the IncQ, IncW, IncU, pRi, pVS1, IncP-α plasmid incompatibility groups; and (c) at least a selectable marker module.

In a preferred embodiment, the RK2-based pLX vector of the invention comprises a T-DNA cassette comprising one T-DNA right border and two T-DNA left borders.

In a more preferred embodiment, the replication origin module is an origin of the IncP-α plasmid incompatibility group, and more preferably is the RK2 origin. In a further preferred embodiment of the RK2 origin comprises the RK2-oriV and -trfA regions, or a variant functionally equivalent thereof. In a more preferred embodiment the RK2 origin comprises the SEQ ID NO: 106 or SEQ ID NO: 107.

In another preferred embodiment, the RK2-based pLX vector of the invention comprises a T-DNA cassette that is flanked by at least two transcription terminators, preferably, bacterial transcription terminators.

In another preferred embodiment, the selectable marker gene of the RK2-based pLX vector differs from the selectable marker gene of the pBBR1-based pLX vector.

In another preferred embodiment, the backbone of the RK2-based pLX vector has no backbone regions with >28 nucleotide identity to the pBBR1-based pLX vector of the present invention.

In a third aspect, the present invention relates to a binary vector system comprising: (a) a first binary vector being the pBBR1-based pLX binary vector disclosed in the present invention; and (b) a second binary vector selected from the RK2-based pLX vector or a vector that can be used preferably in combination with the first binary vector of the invention, wherein the pBBR1 origin module is replaced by any of the replication origin selected from origins of the plasmid incompatibility groups: IncQ, IncW, IncU, pRi, pVS1, IncP-α; and wherein each of the binary vectors of (a) and (b) has replication and bacterial selection mechanisms enabling a mutual and autonomous coexistence with each other in the same host cell.

In a preferred embodiment of the binary vector system of the invention, the origin module of the second binary vector is an origin of the IncP-α plasmid incompatibility group, and more preferably is the RK2 origin according to the present invention. In a more preferred embodiment, the second binary vector is the RK2-based pLX vector of the present invention.

Another aspect of the present invention relates to a host cell comprising the pBBR1-based pLX vector, the RK2-based pLX vector, or the binary vector system disclosed in the present invention.

Another aspect of the present invention relates to a culture cell comprising the host cell of the present invention.

Another aspect of the present invention relates to a method for delivering at least one nucleotide sequence of interest into at least one plant cell comprising: (a) inserting at least one nucleotide sequence of interest into the first or the second binary vector, or into the binary vector system of the invention; (b) introducing the binary vector or binary vector system of step (a) into at least one bacterial host cell; and (c) contacting the host cell of step (b) with at least one eukaryotic cell.

Another aspect of the present invention relates to a method for in vitro delivering at least one nucleotide sequence of interest into at least one eukaryotic organism, comprising: (a) inserting at least one nucleotide sequence of interest into the binary vector or the binary vector system of the invention; and (b) introducing the binary vector or binary vector system of step (a) into at least one eukaryotic organism.

Another aspect of the present invention relates to a method for obtaining a genetically-engineered plant cell or plant comprising the step of introducing into a plant cell the binary vector, the binary vector system, or the bacterial host cell of the invention. Another aspect of the present invention relates to a genetically-engineered plant cell or plant obtainable by the method for obtaining a genetically-engineered plant cell or plant of the present invention.

Another aspect of the present invention relates to a method for in vitro obtaining a genetically-engineered eukaryotic cell or organism comprising the step of introducing into a eukaryotic cell the binary vector or the binary vector system of the present invention. Another aspect of the present invention relates to a genetically engineered eukaryotic cell or organism obtainable by the method for in vitro obtaining a genetically engineered eukaryotic cell or organism according to the present invention.

As used herein, the term "genetically engineered" refers to a plant cell, plant, eukaryotic cell or organism which has been generated through the aforementioned methods.

The present invention furthermore relates to a genetically modified, preferably transformed, mutant or modified plant system, to a regenerated cell or a regenerated plant therefrom, to their progeny or seeds therefrom generated in accordance with the methods of the invention described hereinabove. In a particular embodiment of the present invention, this transformed plant system is characterized by single or multiple modifications of the plant cell genome, epigenome, transcriptome, or metabolome, and in that it may or may not comprise any sequence segments of the abovementioned vectors, vector system and their T-DNA cassettes.

Another aspect of the present invention relates to a method for transforming eukaryotic cells or eukaryotic organisms comprising the step of introducing into the eukaryotic cell or organism the binary vector, the binary vector system, the host cell, the genetically-engineered plant cell or plant, or the genetically-engineered eukaryotic cell or organism, disclosed in the present invention.

Another aspect of the present invention relates to methods to assemble synthetic, genomic, metagenomic, and/or cDNA sequences of interest into the binary vector or the binary vector system disclosed in the present invention. According to the present invention, a variety of methods can be used for nucleic acid assembly. In a preferred embodiment, the sequences of interest are assembled by use of high-throughput restriction endonuclease-, preferably and without limitations Type IIS restriction endonucleases, or overlap-dependent assembly methods, such as and without limitation, Golden Gate, Golden Braid or Gibson assembly.

Another aspect of the present invention relates to the in vitro or ex vivo use of the binary vector, the binary vector system, the host cell, or the culture cell of the invention: (a)

for site-specific gene knockout; (b) for site-specific genome editing; (c) for DNA sequence-specific interference; (d) for site-specific epigenome editing; (e) for site-specific transcription modulation; or (1 for multiplex genome engineering; and provided the in vitro or ex vivo use does not comprise a process for modifying the germ line genetic identity of human beings.

Another aspect of the present invention relates to a kit comprising the binary vector, the binary vector system, the host cell, or the culture cell of the invention.

Module 1, 2, and 3 refer to the T-DNA cassette, the pBBR1 origin, and the selectable marker, respectively. Each module includes one or several DNA parts, which are flanked by two diverse assembly linkers (diamonds): Linker_1 (SEQ ID NO: 112), Linker_2 (SEQ ID NO: 113), Linker_3 (SEQ ID NO: 114). Parts from the three modules were obtained by PCR or chemical synthesis, and were joined by one-step isothermal DNA assembly to generate the pLX-B2 (SEQ ID NO: 3), pLX-B3 (SEQ ID NO: 4), pLX-B4 (SEQ ID NO: 5) binary vectors.

Figure 2:
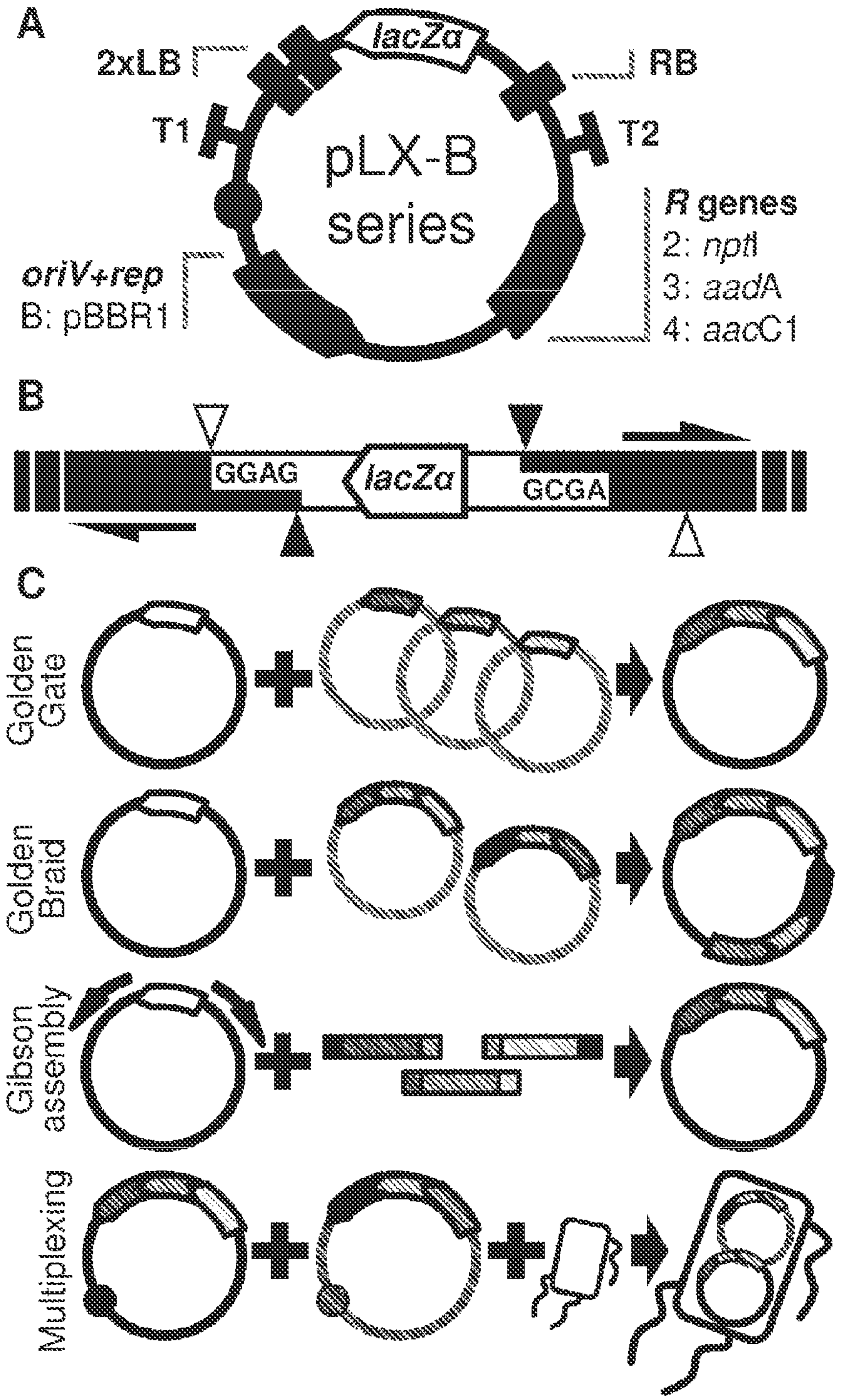

FIG. 2. Novel T-DNA binary vectors of the pLX series and their features (A) Organization of the pBBR1-based pLX plasmids. The binary vectors are composed of three modules, (i) a T-DNA cassette that includes a right border, an *Escherichia coli* reporter gene, two left borders, and is flanked by bacterial transcription terminators (T1 and T2); (ii) the broad host-range pBBR1 origin suitable for plasmid replication in *E. coli* and *Agrobacterium tumefaciens* (oriV+rep); and (iii) a selectable marker such as antibiotic resistance (R) genes. The plasmid vectors are indicated by a letter that reflects their origin module (B, pBBR1-derived origin) and a digit according the R gene: 2, nptI, gene that confers resistance to kanamycin; 3, aadA, gene that confers resistance to spectinomycin/streptomycin; 4, aacC1, gene that confers resistance to gentamicin. (B) Cloning features of a T-DNA cassette of the pLX vectors. The lacZα reporter is flanked by two divergent BsaI recognition sites (solid triangles); the nonpalindromic overhangs generated by BsaI digestion allow assembly of transcription units by one-step digestion-ligation cloning (Golden Gate). Convergent BsmBI sites (open triangles) are included to build multiple transcription unit constructs by GoldenBraid assembly. Alternatively, pLX vectors can be linearized by inverse PCR using divergent primers (arrows), DpnI treated, and used to join one or several overlapping inserts by one-step isothermal DNA assembly (Gibson assembly). (C) Diagrams of pLX vector cloning features. Parts or transcription units can be assembled into pLX vectors using the BsaI-based Golden Gate and GoldenBraid standards. Overlapping DNA fragments can be joined into the linearized pLX vectors by Gibson assembly. The pLX vectors can be used for multiple T-DNA delivery by vector multiplexing into *Agrobacterium* cells.

Figure 3:
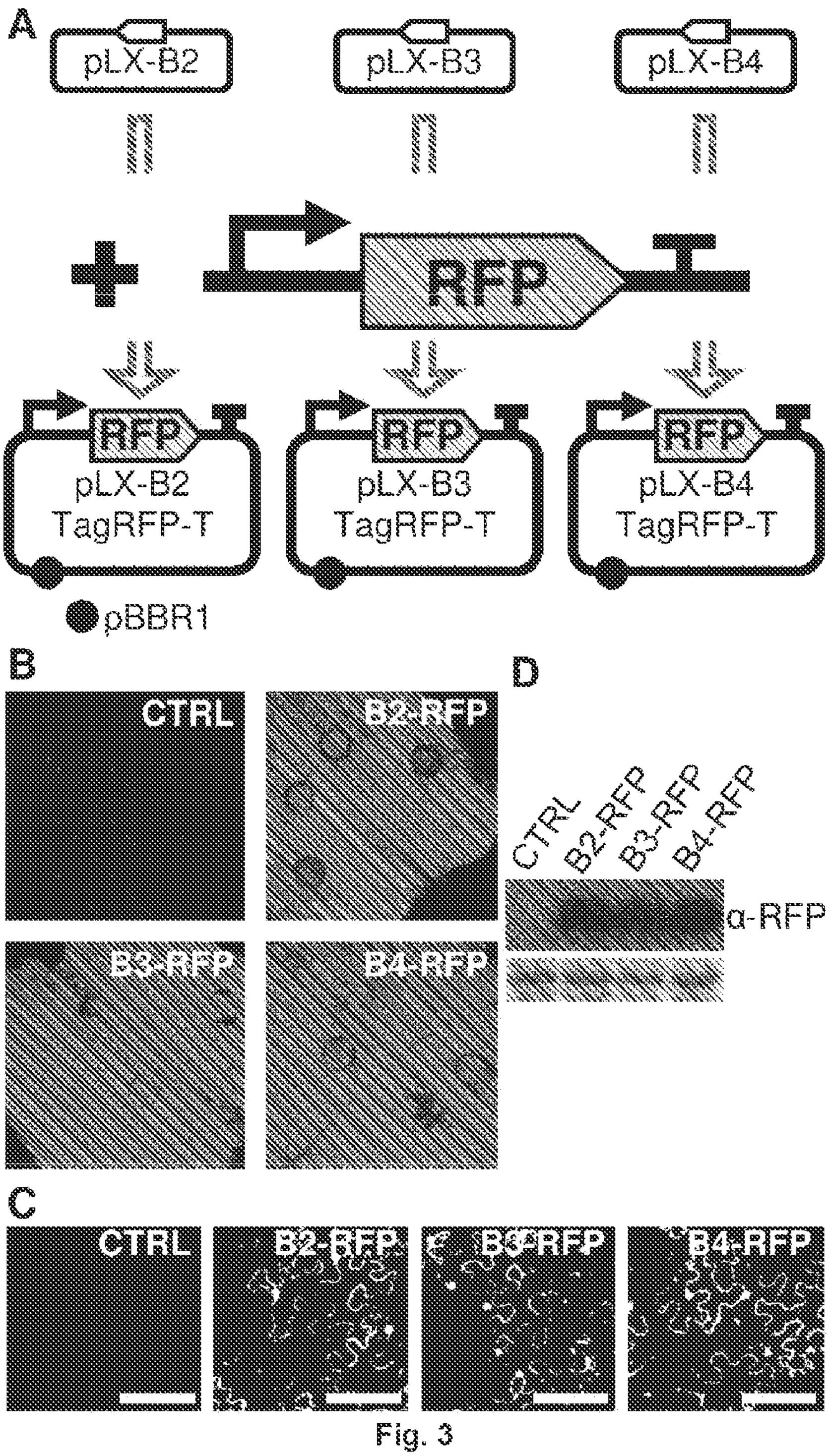

FIG. 3. Transient transgene expression in plants using the pLX vector series (A) Construct scheme of the transgene for transient transformation of *Nicotiana benthamiana* plants. The TagRFP-T gene (RFP) driven by the cauliflower mosaic virus (CaMV) 35S promoter was inserted into different pLX-derived backbones, which were delivered to plants by agro-infiltration. Data were collected at 6 days post-agro-infiltration (dpa); CTRL, an empty control; B2-RFP indicates pLX-B2-TagRFP-T (SEQ ID NO: 13); B3-RFP, pLX-B3-TagRFP-T (SEQ ID NO: 14); B4-RFP, pLX-B4-TagRFP-T (SEQ ID NO: 15). (B) RFP fluorescence of infiltrated leaves was imaged under a fluorescence stereoscope. (C) Cell RFP fluorescence was imaged by confocal microscopy; bars, 100 μm. (D) RFP accumulation was assessed by immunoblot analysis. Ponceau red-stained blot is shown as a loading control.

Figure 4:
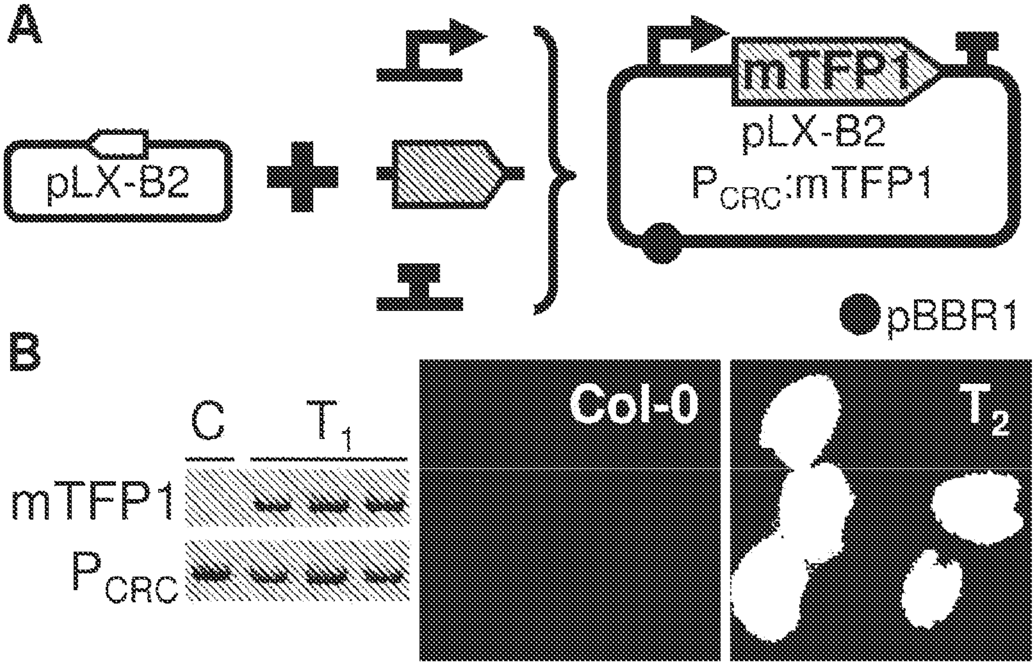

FIG. 4. Stable transgene expression in plants using the pLX vector series (A) A transgene construct for stable transformation of *Arabidopsis thaliana* plants was assembled in pLX-B2-$P_{CRC}$:mTFP1 (SEQ ID NO: 23), and included a cyan fluorescent protein gene (mTFP1) driven by the *A. thaliana* cruciferin C promoter, which is active in seeds ($P_{CRC}$). (B) To confirm stable integration of the transgene, PCR assays of genomic DNA were performed using transgene-specific (mTFP1; 765 bp) or control primers ($P_{CRC}$; 1081 bp). Each lane represents a single plant sample; C, untransformed plant sample; $T_1$, independent lines selected by cyan fluorescence of seed collected from the *Agrobacterium*-treated plants. Fluorescence images of untransformed seeds (Col-0) and those collected from a single $T_1$ plant ($T_2$).

Figure 5:
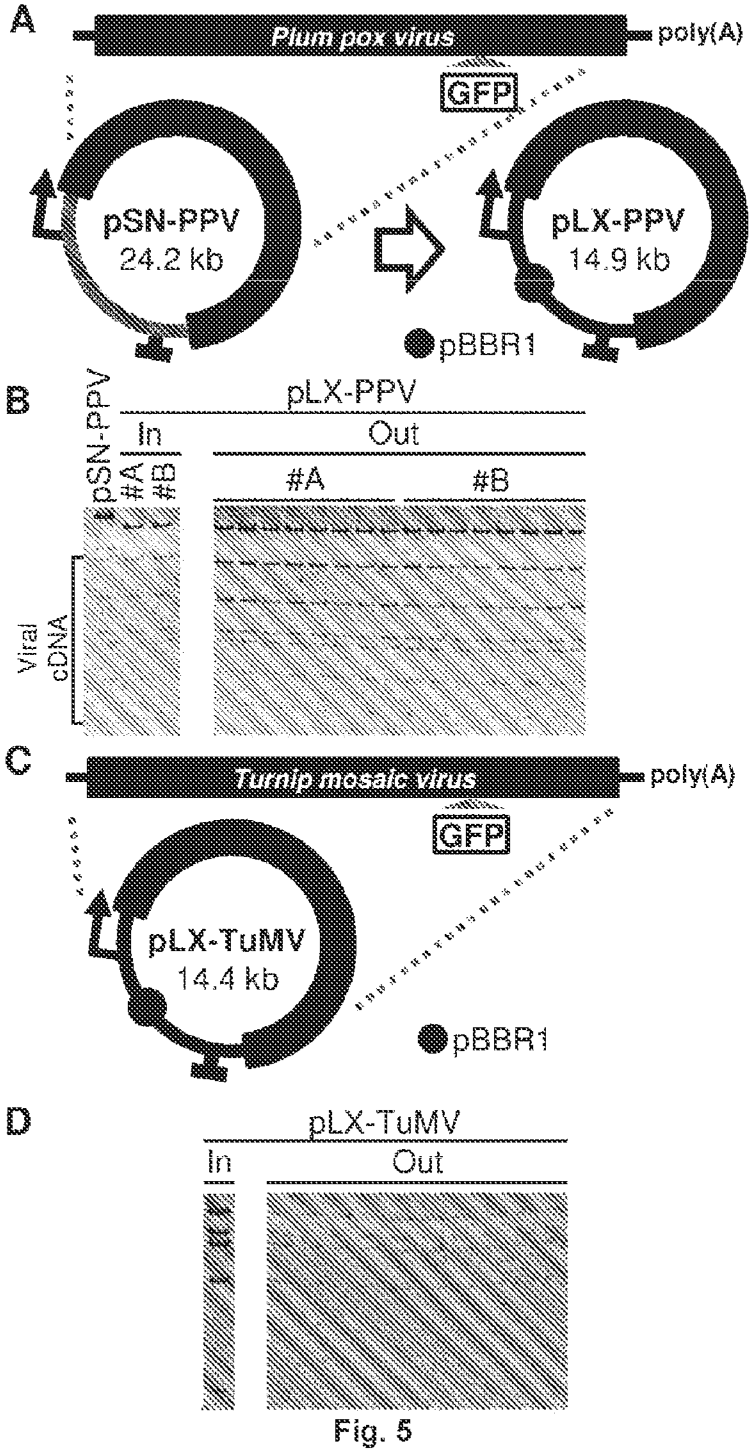

FIG. 5. Stability of the pLX vector series in *Escherichia coli* cells (A) The expression cassette of a GFP-tagged plum pox virus (PPV) cDNA clone was subcloned from a pBIN19-derived vector (pSN-PPV) to a pLX plasmid, to generate the pLX-PPV vector (SEQ ID NO: 21). Schemes are not to scale. (B) Clones #A and #B of the new pLX-PPV vector were transformed in *E. coli* cells to evaluate the plasmid stability, inputs (In). For each transformation, eight individual colonies were picked and subjected to six growth cycles (24 h, 37° C.). The purified plasmids (Out, outputs) were EcoRI-digested and resolved by agarose gel electrophoresis. Fragments derived from the cDNA copy cassette of the PPV genome are indicated (left); upper bands are backbone-specific fragments. (C) To generate the pLX-TuMV vector (SEQ ID NO: 28), the expression cassette of a GFP-tagged turnip mosaic virus (TuMV) cDNA clone was subcloned from a pUC-based vector (p35Tunos-vec01-NAT1) to a pLX-B2-derived plasmid. (D) pLX-TuMV (SEQ ID NO: 28) was transformed into *E. coli* cells to evaluate plasmid stability, input (In). Ten individual colonies were picked and subjected to six growth cycles (24 h, 37° C.). The purified plasmids (Out, outputs) were EcoRI-digested and resolved by agarose gel electrophoresis.

Figure 6:
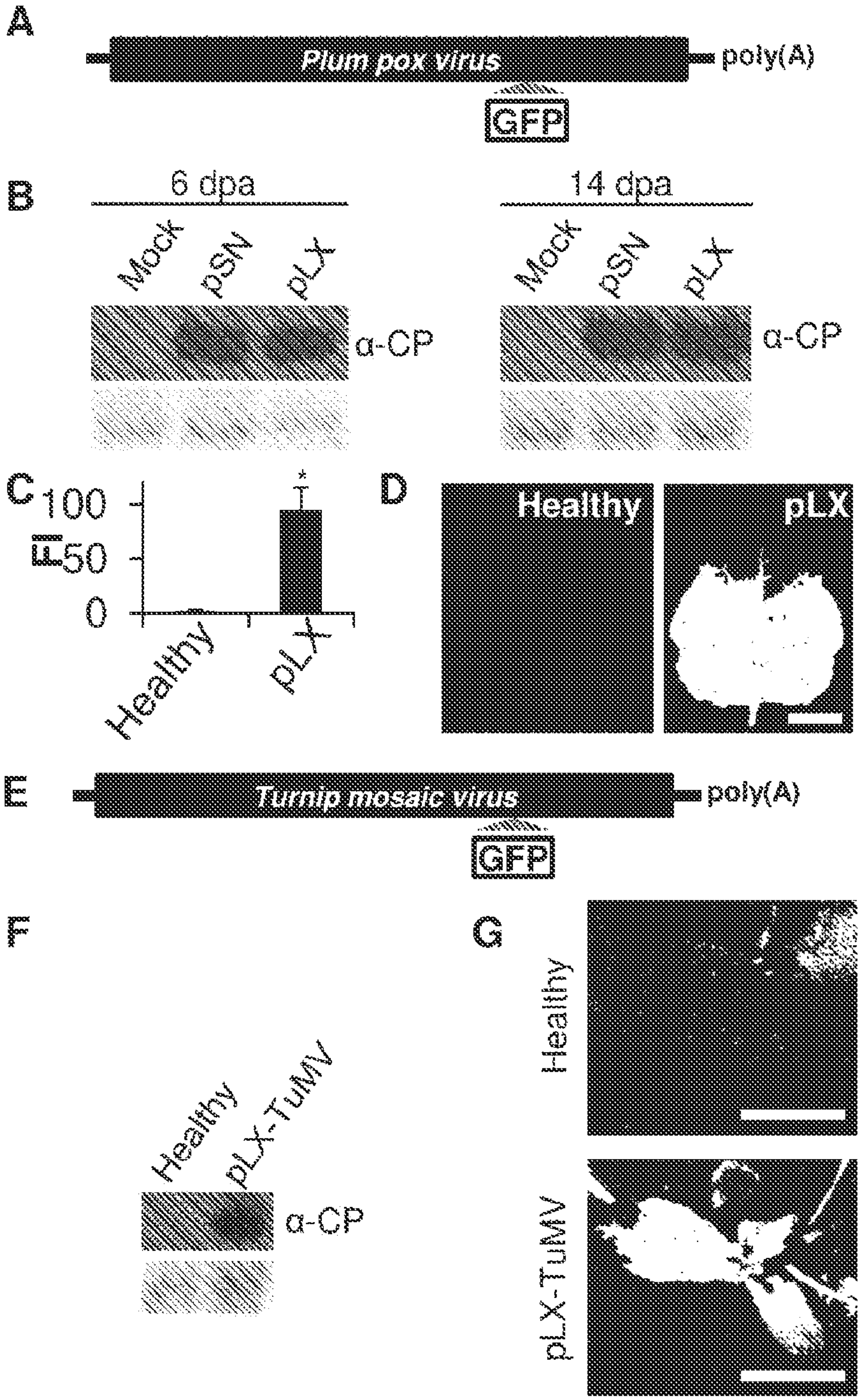

FIG. 6. Viral vector delivery and recombinant protein production in plants using the pLX vector series The pLX-PPV (pLX) (SEQ ID NO: 21) and pSN-PPV (pSN) viral vectors were delivered to *N. benthamiana* plants by agro-infiltration (panels A-D); the pLX-TuMV viral vector was delivered to *A. thaliana* plants by agro-inoculation (panels E-G). (A) Recombinant GFP was expressed in plants using a chimeric PPV clone. (B) Viral accumulation was assessed by anti-PPV coat protein (CP) immunoblot analysis of samples from the agro-infiltrated and upper uninoculated leaves, at 6 and 14 dpa, respectively. Ponceau red-stained blots are shown as loading controls. (C) At 6 dpa, GFP fluorescence intensity (FI) of the agro-infiltrated leaf patches was quantified in a 96-well plate reader. Bar indicates mean±standard deviation (SD, n=4); *p<0.001, Student's t-test. (D) At 14 dpa, the upper uninoculated leaves were imaged on a blue light transilluminator; GFP fluorescence is shown in light gray; scale bar, 2 cm. (E) Recombinant GFP was expressed in plants using a chimeric TuMV clone. (F) The pLX-TuMV (SEQ ID NO: 28) vector was delivered to *A. thaliana* plants by agro-inoculation, and data were collected at 11 days post agro-inoculation. Viral accumulation was assessed by anti-TuMV CP immunoblot analysis of upper uninoculated leaves; the Ponceau red-stained blot is shown as a loading control. (G) Upper uninoculated leaves were imaged; GFP fluorescence is shown in light gray; scale bar, 1 cm.

Figure 7:
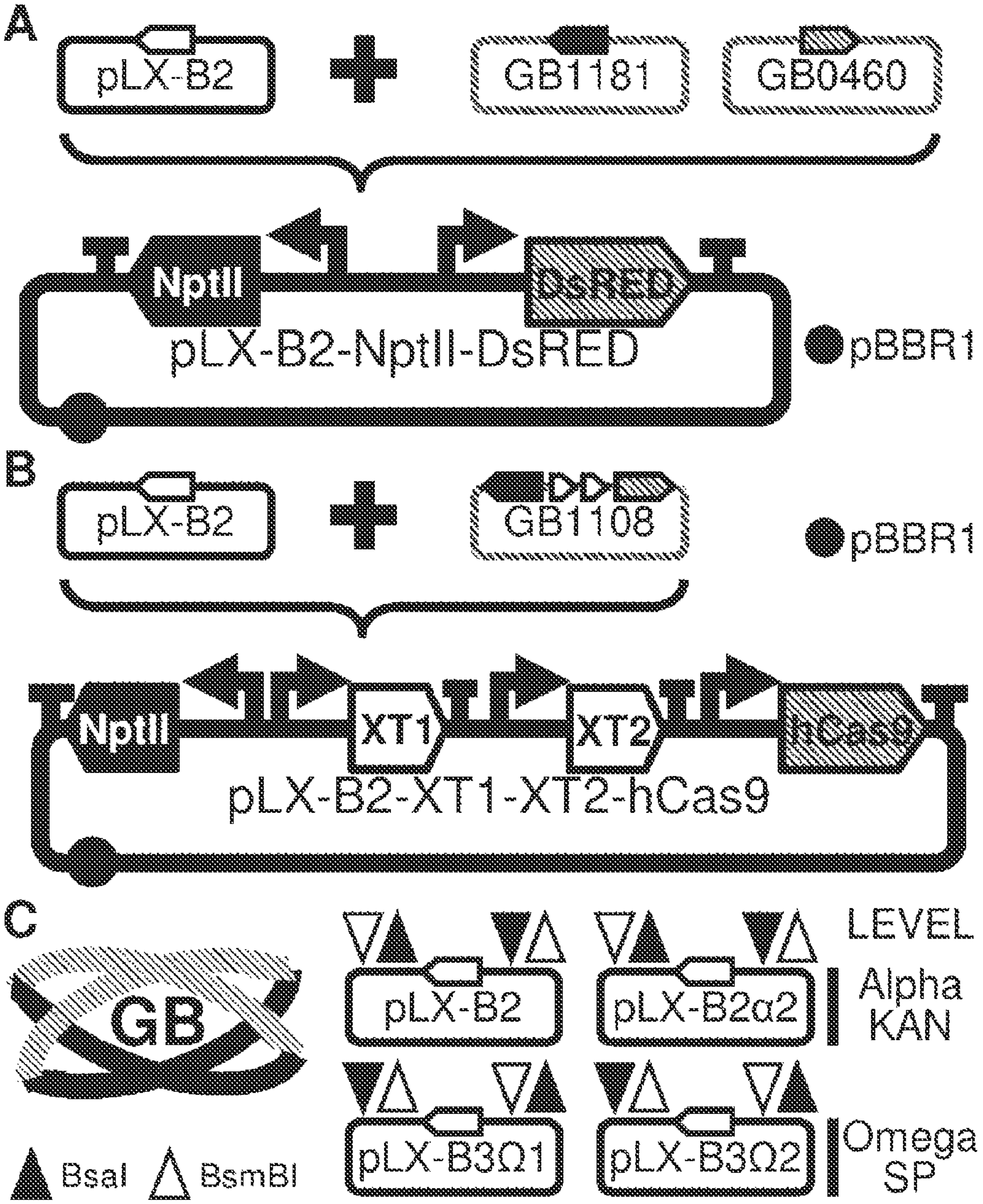

FIG. 7. Assembly of DNA parts into the pLX vectors by using synthetic biology standards (A) Standardized units for delivery to plants of the kanamycin resistance (NptII) and red fluorescent protein (DsRED) genes were assembled into the pLX-B2 vector (SEQ ID NO: 3) to generate the pLX-B2-NptII-DsRED vector (SEQ ID NO: 20). (B) The pLX-B2-XT1-XT2-hCas9 vector (SEQ ID NO: 19) was assembled for delivery of standardized units: a kanamycin resistance gene (NptII), human codon-optimized *Streptococcus pyogenes* Cas9 gene (hCas9), and sgRNA targeting the *N. benthamiana* Niben101Scf04205Ctg025 (XT1) and Niben101Scf04551Ctg021 (XT2) endogenous genes. (C) Scheme of the pLX vectors that incorporate cloning cassettes compatible with the GoldenBraid binary assembly. The alpha level kanamycin-resistant plasmids have divergent BsaI and convergent BsmBI sites; the omega level spectinomycin-resistant plasmids have divergent BsmBI and convergent BsaI sites. All plasmids include the pBBR1 origin and the lacZα reporter.

Figure 8:
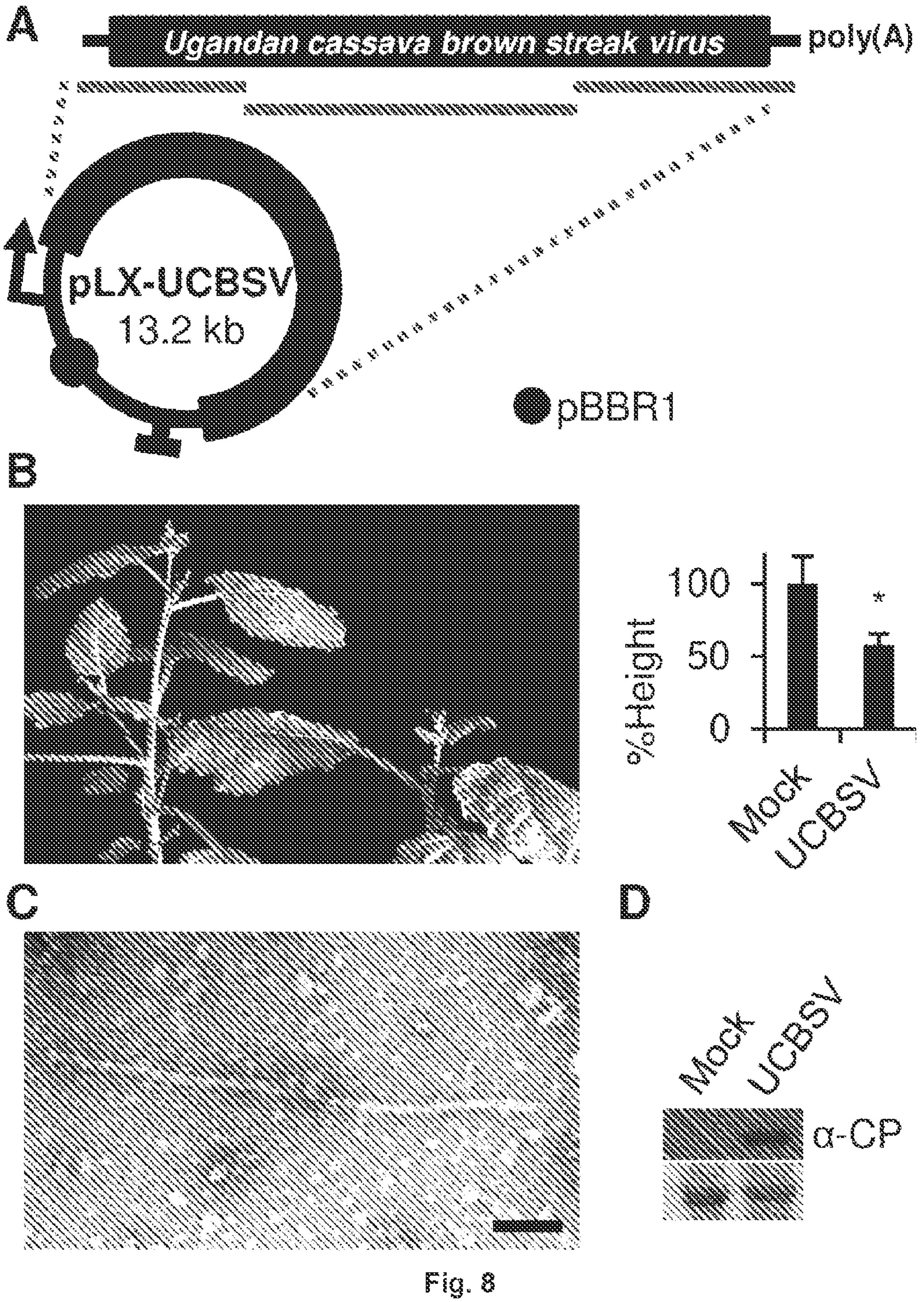

FIG. 8. Assembly of large transcription units by overlap-based cloning methods, and virus agro-inoculation using the pLX vector series (A) Use of a pLX vector to generate an infectious cDNA clone of an RNA virus. Three RT-FOR fragments (gray boxes) spanning the entire Ugandan cassava brown streak virus (UCBSV) genome were cloned in a linearized pLX-B2-based vector by Gibson assembly. The pLX-UCBSV vector (SEQ ID NO: 22) obtained was delivered to *N. benthamiana* plants by agro-infiltration, and data were collected at 12 dpa. (B) Photographs of mock- and pLX-UCBSV-infiltrated plants (left and right, respectively). The plant relative height is plotted, mean±SD (n=4); *p=0.0059, Student's t-test. (C) Transmission electron micrograph shows particles observed in the infected plant sample; scale bar, 100 nm. (D) Viral accumulation was assessed by anti-UCBSV coat protein (CP) immunoblot analysis of samples from upper uninoculated leaves. The Ponceau red-stained blot is shown as a loading control.

Figure 9:
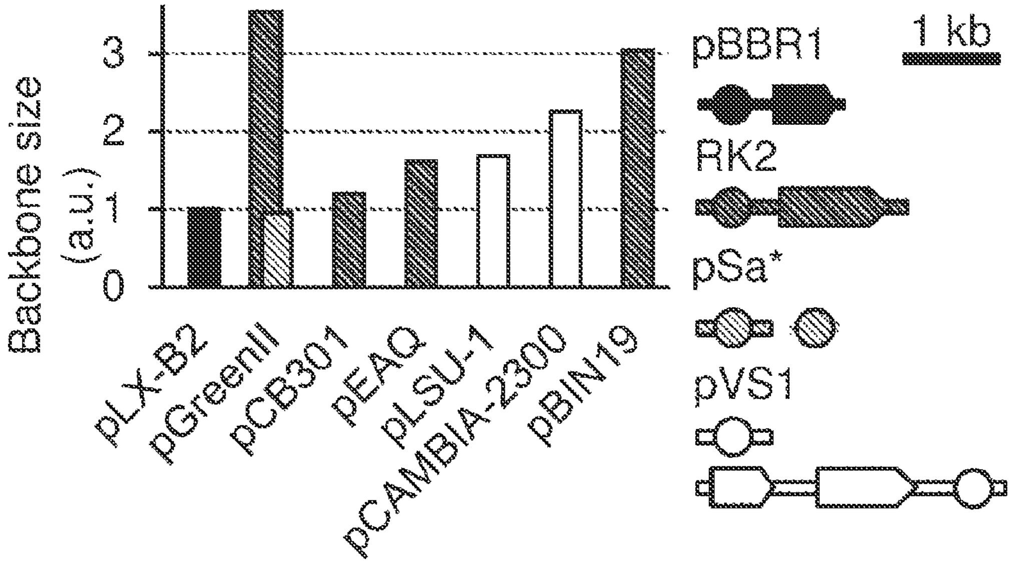

FIG. 9. Relative size comparison of the pLX-B2 backbone and selected T-DNA binary vectors Relative size comparison of the pLX-B2 backbone and selected binary vectors (T-DNA cassette sequences were not considered). Graph bars are filled according to the plasmid replication origins shown at right; the pVS1- and pSa-based binary vectors include a narrow-host-range origin for maintenance in *E. coli*; *, as the pSa origin in the pGreen-based vectors is not autonomous, the size of the RK2-based pSoup plasmid required for pGreenII maintenance in *A. tumefaciens* is also included in the graph. Glyphs according to the Synthetic Biology Open Language visual format.

Figure 10:
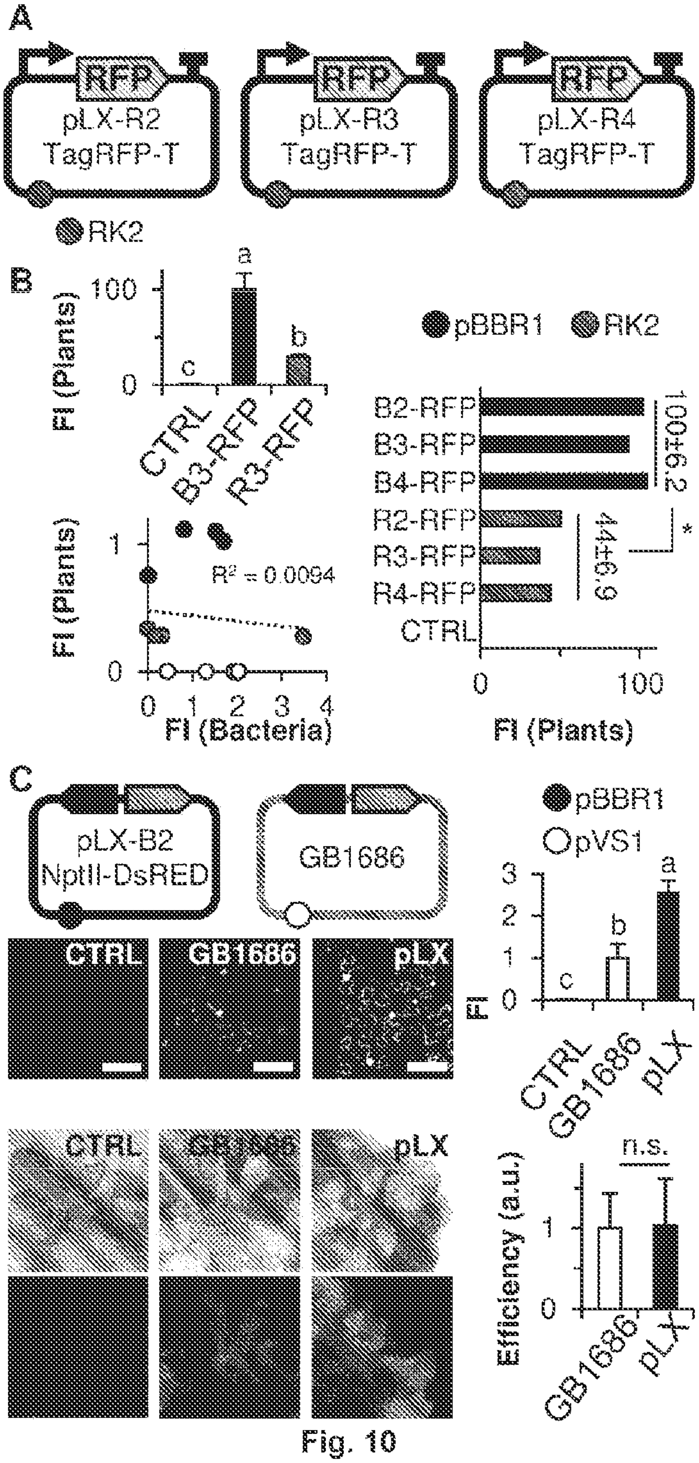

FIG. 10. Comparison in plant expression assays of the pBBR1-based pLX vectors, and T-DNA binary vectors based on the RK2 and pVS1 origins (A) The pBBR1 replication module of pLX vectors was replaced with an RK2 minimal origin to build pLX-R2 (SEQ ID NO: 6), pLX-R3 (SE ID NO: 7) and pLX-R4 (SEQ ID NO: 8) vectors. These were engineered to obtain the pLX-R2-TagRFP-T (SEQ ID NO: 16), pLX-R3-TagRFP-T (SEQ ID NO: 17) and pLX-R4-TagRFP-T (SEQ ID NO: 18) vectors for expression of the TagRFP-T gene (RFP). (B) In transient expression assays, the RFP vectors from FIG. 3 (B2-RFP indicates pLX-B2-TagRFP-T (SEQ ID NO: 13); B3-RFP, pLX-B3-TagRFP-T (SEQ ID NO: 14); B4-RFP, pLX-B4-TagRFP-T (SEQ ID NO: 15)) were compared to RK2-based pLX vectors (R2-RFP indicates pLX-R2-TagRFP-T (SEQ ID NO: 16); R3-RFP, pLX-R3-TagRFP-T (SEQ ID NO: 17); R4-RFP, pLX-R4-TagRFP-T (SEQ ID NO: 18)); CTRL, an empty control. RFP fluorescence intensity (FI) of bacterial suspensions and infiltrated plant samples (at 4 or 6 dpa) was measured in a plate reader. Bar graphs show the FI values for plant samples, mean±SD (n≥n); letters indicate $p<0.05$, one-way Anova and Tukey's HSD test; *p=0.00047, Student's t-test. Scatter plot shows linear regression analysis of FI values for plant and bacterial samples; the B3-RFP, R3-RFP, and empty control samples are shown in black, gray and white, respectively. (C) Expression of a DsRED standard cassette was compared in transient and stable expression assays. A pCAMBIA-derived vector (GB1686, SEQ ID NO: 27) and pLX-B2-NptII-DsRED (pLX, SEQ ID NO: 20) were transformed into *N. benthamiana* plants; CTRL, control. In agro-infiltrated leaf samples, cell DsRED fluorescence was imaged by confocal microscopy (bars, 100 μm) and quantified in a plate reader. FI values were plotted, mean±SD (n=4); letters indicate $p<0.05$, one-way Anova and Tukey's HSD test. In stable transformation assays, leaf samples were co-cultured with the indicated *A. tumefaciens* strains and transferred to kanamycin-containing medium. Images show plantlets imaged under an epifluorescence microscope at 40 days post inoculation. The plot shows transformation efficiencies defined as the number of kanamycin-resistant plantlets that showed DsRED fluorescence, mean±SD (n=7); n.s., p=0.91. Vector origins are indicated: pBBR1, solid circle/bars; pVS1, open circle/bars.

Figure 11:
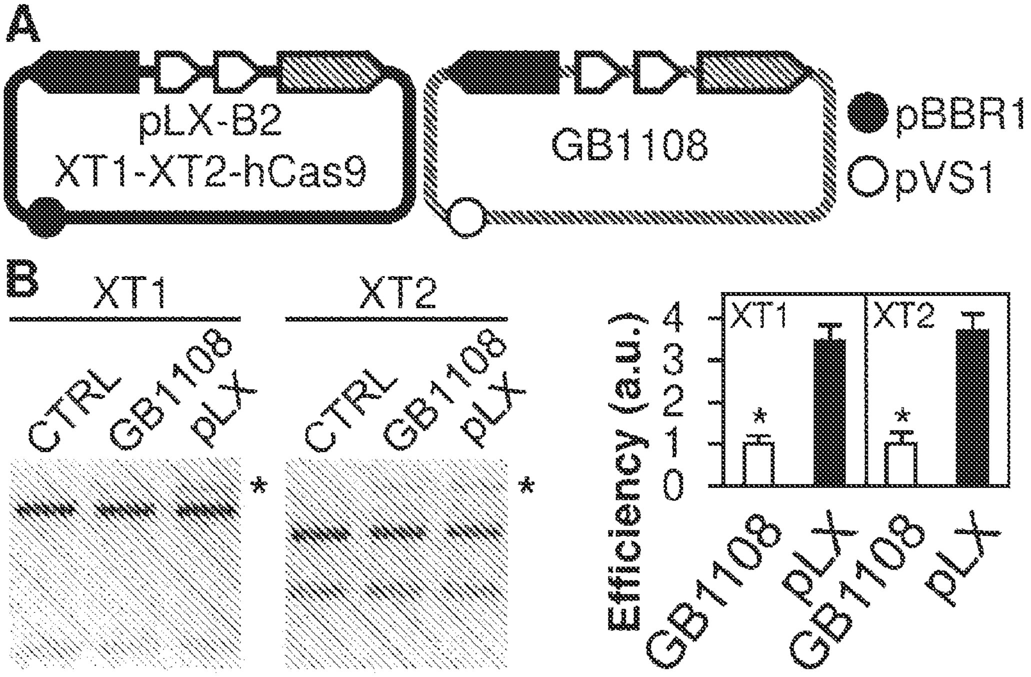

FIG. 11. Delivery of CRISPR/Cas system components, and targeted genome mutagenesis comparison of pBBR1-based pLX vectors and T-DNA binary vectors based on the pVS1 origin Targeted mutagenesis in transient expression assays by using a GoldenBraid-based CRISPR/Cas9 system. (A) *Nicotiana benthamiana* plants were infiltrated with a pCAMBIA-derived vector (GB1108) and the pLX-B2-XT1-XT2-hCas9 (pLX; SEQ ID NO: 19); the vectors bear transcription units for the human codon-optimized Cas9 (hCas9), and sgRNA targeting the Niben101Scf04205Ctg025 (XT1) and Niben101Scf04551Ctg021 (XT2) endogenous genes. (B) Gels show PCR/digestion assays; asterisks mark cleavage-resistant DNA bands; CTRL, hCas9 delivered with no sgRNA sequences. The plot shows mutagenesis efficiencies, which were estimated by quantifying the ratio of uncleaved/cleaved bands; mean±SD (n=4); *$p<0.001$. Vector origins are indicated: pBBR1, solid circle/bars; pVS1, open circle/bars.

Figure 12:
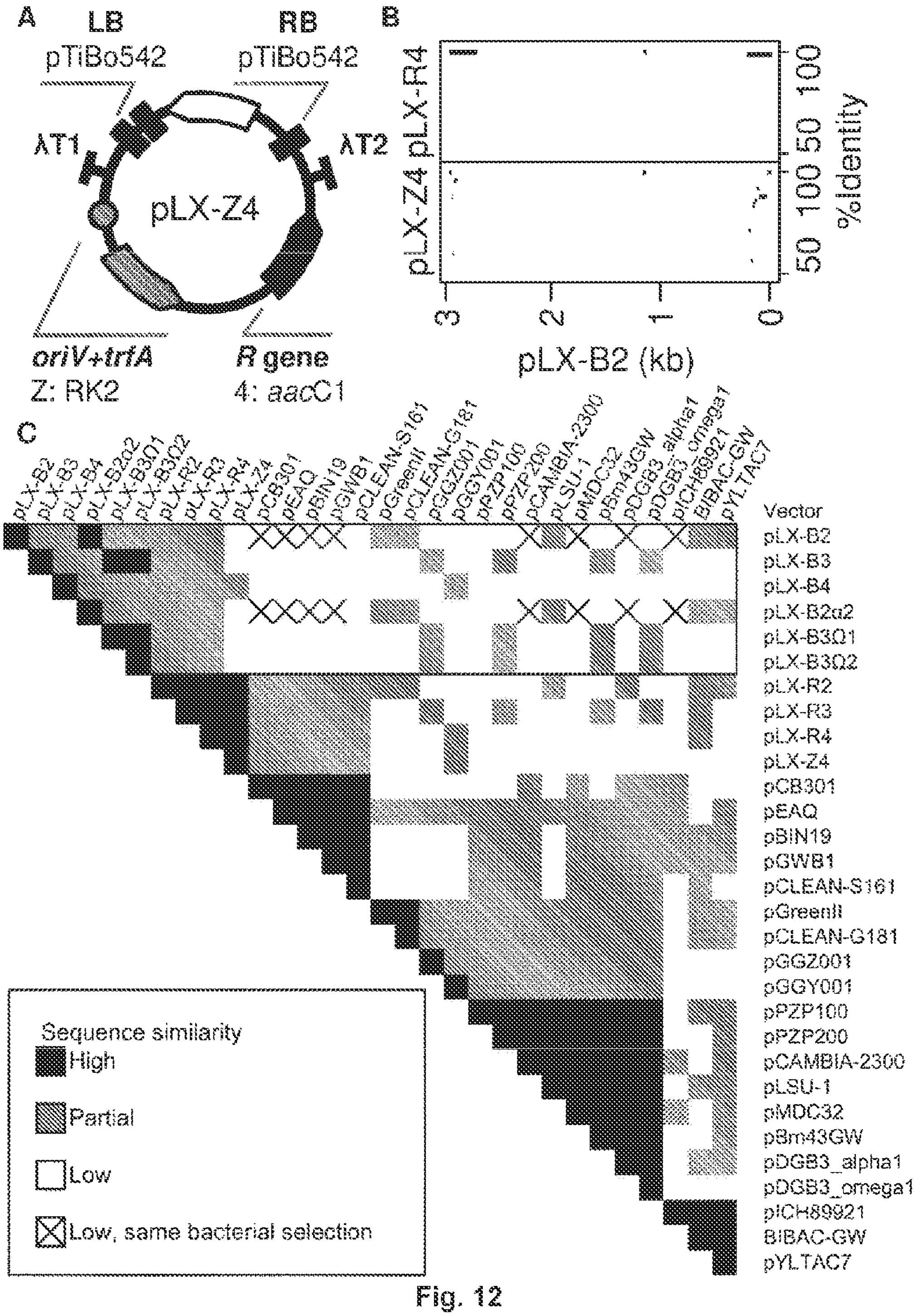

FIG. 12. Sequence similarity of the pLX vectors and reference T-DNA binary vectors (A) Representation of the new pLX binary vector compatible with the pBBR1 origin. pLX-Z4 (SEQ ID NO: 9) shares the pLX modular organization and cloning cassette shown in FIG. 2; it includes T-DNA border sequences from the succinamopine-type pTiBo542 plasmid, a second left border sequence, lambda phage terminators, a gentamicin resistance gene (aacC1), and a 2.2-kb minimal replicon from the broad host-range plasmid RK2. (B) Percent identity plots show significant DNA local alignments between the pBBR1-based pLX-B2 and RK2-based pLX-Z4 (SEQ ID NO: 9), or pLX-R4 (SEQ ID NO: 8) vectors. Cloning cassette sequences were omitted in the comparisons; plots were generated using PipMaker (Schwartz S., et al., Genome Res. 2000, 10, 577-586). (C) Sequence similarity of the new pLX and reference T-DNA binary vectors. The matrix shows outputs obtained by pairwise sequence analysis of the vector backbones. Sequence similarity was classified according to BLASTN total score values: high, >4100; partial, 800-4100; low, <800. Matrix entries of the pBBR1-based pLX vectors are boxed, and crossed entries mark vector pairs that show low sequence similarity but share selection antibiotics.

Figure 13:
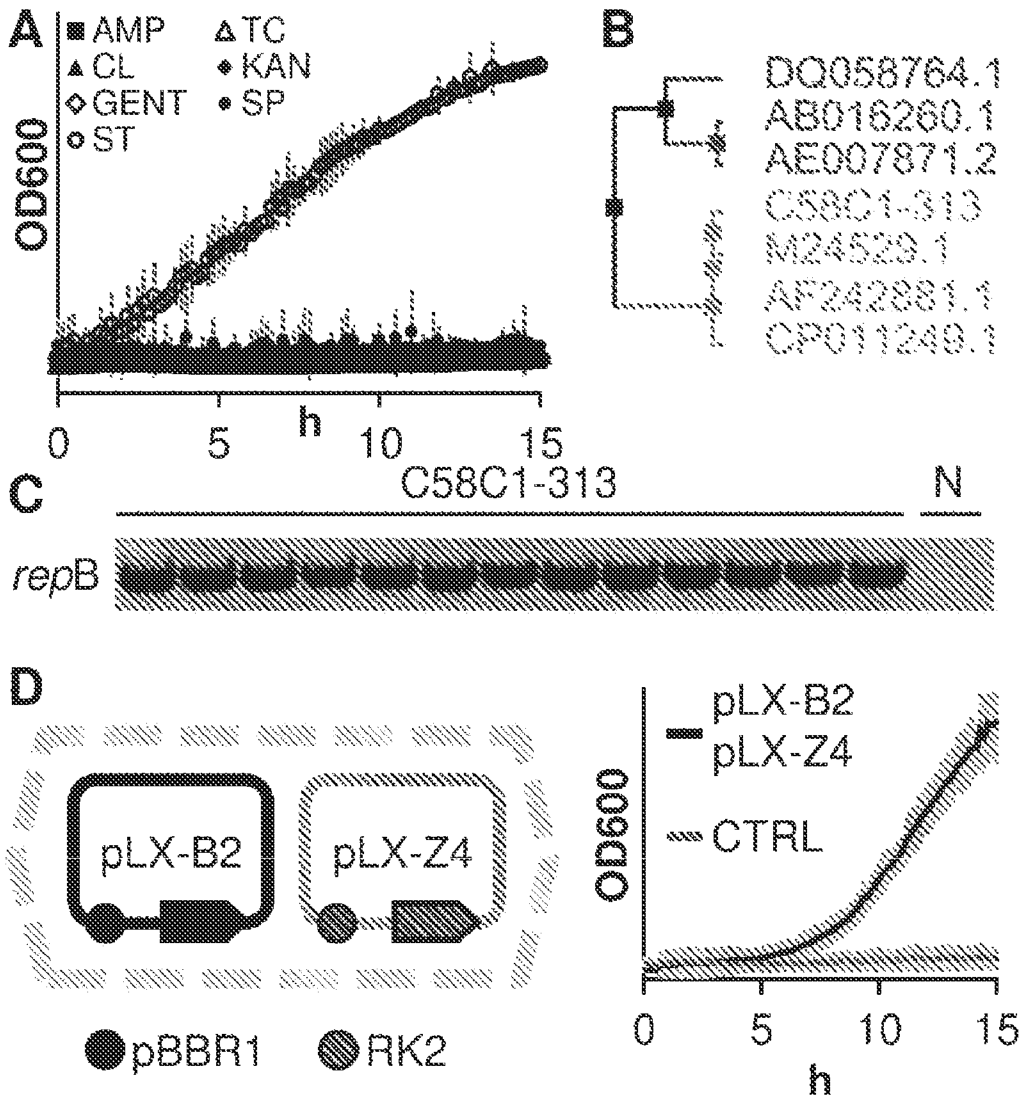

FIG. 13. Characterization of an octopine-type, disarmed strain of *A. tumefaciens* that shows sensitivity to several antibiotics, and strain usage for vector multiplexing (A) Antibiotic sensitivity of C58C1-313, an *A. tumefaciens* disarmed strain. Bacteria were inoculated into Luria-Bertani medium supplemented with rifampicin plus indicated antibiotics: AMP (ampicillin), CL (chloramphenicol), GENT (gentamicin), TC (tetracycline), KAN (kanamycin), SP (spectinomycin) and ST (streptomycin). To monitor growth curves, absorbance (OD600) was measured in a plate reader. Plot shows mean±SD (n=6); h, hours. (B) C58C1-313 harbors a pTi of the octopine type. A fragment of pTi repB gene was PCR-amplified from C58C1-313 and sequenced. A phylogenetic tree was built from an alignment of the 607-nt repB sequence from the C58C1-313 strain and deposited Ti plasmid sequences (NCBI: DQ058764.1; AB016260.1; AE007871.2; M24529.1; CP011249.1; AF242881.1). C58C1-313 clusters with the octopine-type pTi accessions. (C) Stability of pTi maintenance in the *A. tumefaciens* strain C58C1-313. C58C1-313 was plated, and the presence of pTi in individual colonies was confirmed by PCR using pTi-specific primers (repB; 724 bp); N, negative control. (D) Diagram of an *A. tumefaciens* strain (dashed hexagon) that simultaneously hosts pLX-B2- and pLX-Z4-derived vectors conferring kanamycin and gentamicin resistance, respectively. Growth curves of *A. tumefaciens* C58C1-313 that harbors no vectors (CTRL, gray), or the pLX-B2-plus pLX-Z4-derived vectors (black). Kanamycin- and gentamicin-supplemented medium was inoculated with the indicated strains, and absorbance measured in a plate reader. The plot shows mean±SD (n=6); h, hours.

Figure 14:
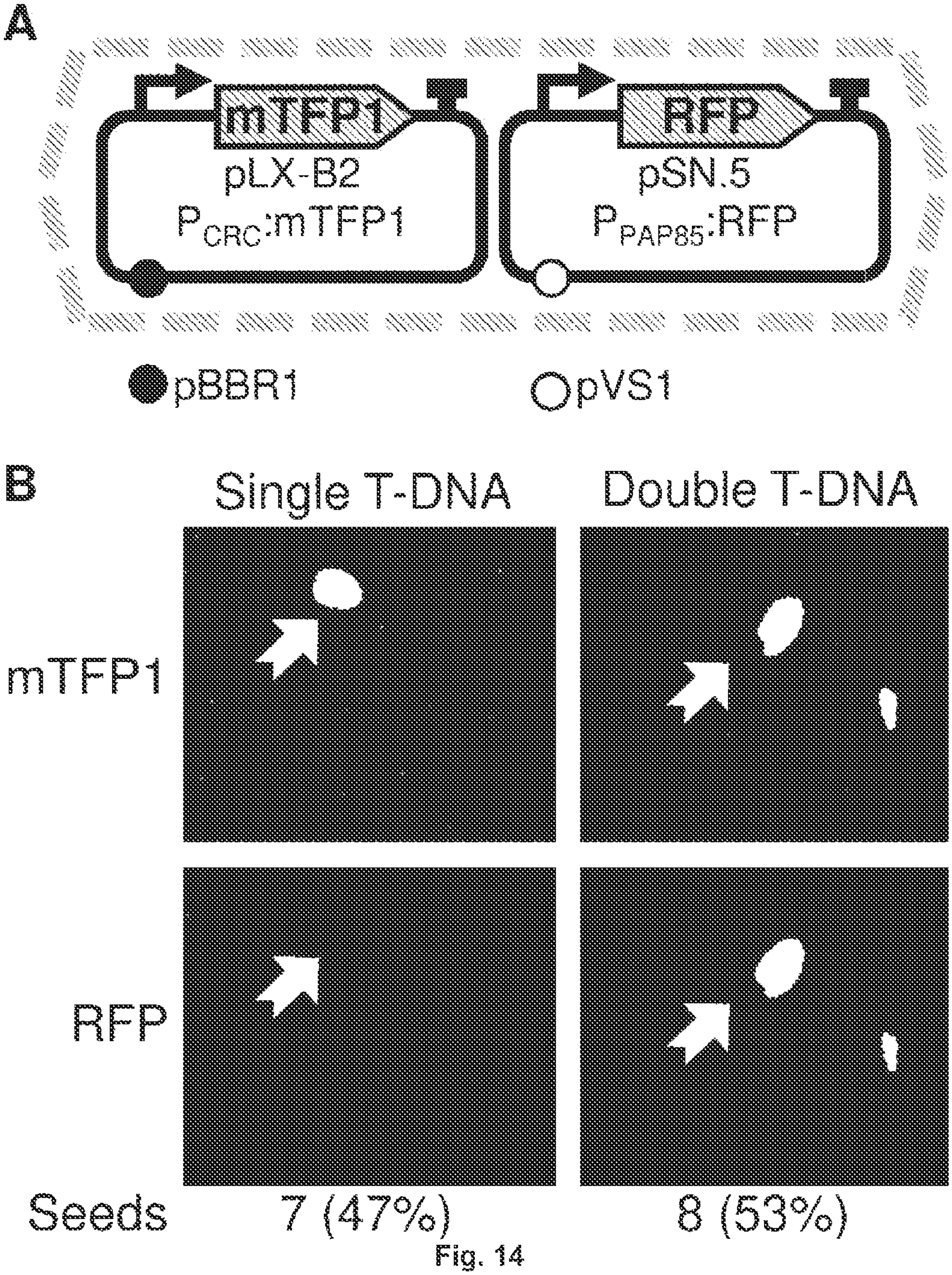

FIG. 14. Usage of the pLX vector series for multiple T-DNA delivery to plants (A) Diagram of an *A. tumefaciens* strain (dashed hexagon) that simultaneously hosts pLX-B2-derived and pCAMBIA-derived vectors conferring kanamycin and spectinomycin resistance, respectively; vector origins are indicated: pBBR1, solid circle; pVS1, open circle. Components of pLX-B2-$P_{CRC}$:mTFP1 are described in FIG. 4; in pSN.5-PPAP85:RFP, the TagRFP-T gene (RFP) is driven by the *A. thaliana* PAP85 promoter (PPAP85). The $P_{CRC}$ and $P_{PAP85}$ promoters used are active in seeds. (B) *Arabidopsis thaliana* plants were treated with the *A. tumefaciens* pLX-B2-$P_{CRC}$:mTFP1 plus pSN.5-PPAP85:RFP strain by floral dipping. The $T_1$ seeds were collected and visualized under a fluorescence stereoscope. Pictures show seeds that express mTFP1 only (Single T-DNA), or mTFP1 plus RFP (Double T-DNA); for each condition, number and percentage of obtained seeds are indicated.

Figure 15:
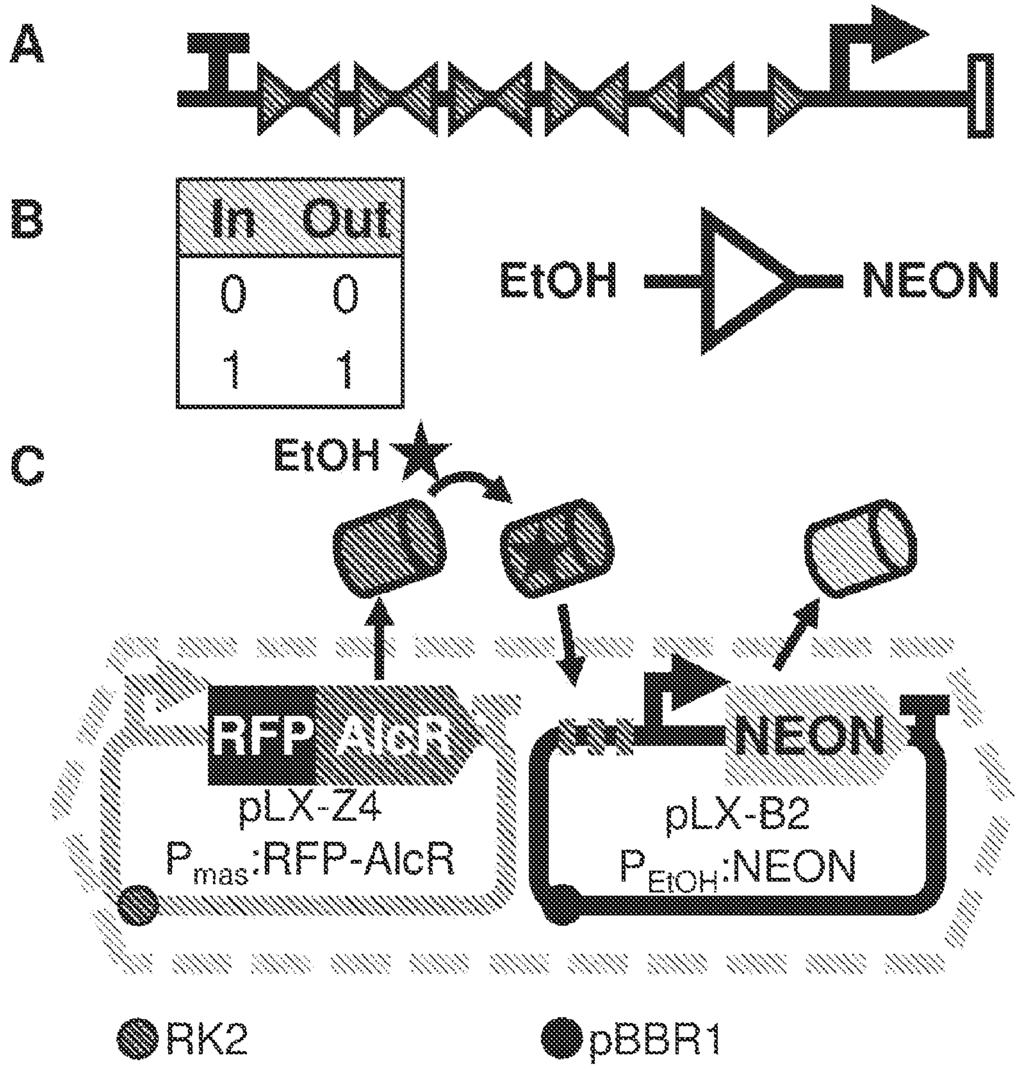

FIG. 15. Experimental design for delivery of synthetic circuit components to plants by multiplexing the pLX vectors (A) Sequence of the $P_{EtOH}$ synthetic promoter (SEQ ID NO: 35). The cauliflower mosaic virus (CaMV) 35S terminator was included to insulate against promoters that might flank the T-DNA integration sites; AlcR DNA-binding sites (triangles) derived from the *Aspergillus nidulans* alcM, alcR, aldA, alcA promoters are placed upstream of a figwort mosaic virus 34S minimal promoter (arrow); open box, starting codon of the coding sequence. (B) Buffer gate truth table. Symbol of a buffer gate that uses ethanol (EtOH) as the input, and mNeonGreen (NEON) fluorescence as the output. (C) Genetic circuit that implements the gate of the previous panel. The dashed hexagon represents a single *A. tumefaciens* strain (R-AlcR+$P_{EtOH}$:NEON) that hosts two compatible T-DNA binary vectors, pLX-Z4-$P_{mas}$:RFP-AlcR (SEQ ID NO: 24) and pLX-B2-$P_{EtOH}$:NEON (SEQ ID NO: 25), which confer gentamicin and kanamycin resistance, respectively. Once delivered to plants, the constitutive mannopine synthase promoter ($P_{mas}$) drives expression of the RFP and AlcR proteins. In the presence of EtOH (star), AlcR binds to and activates an otherwise silent synthetic promoter ($P_{EtOH}$). NEON accumulation results from the activation of the gate.

Figure 16:
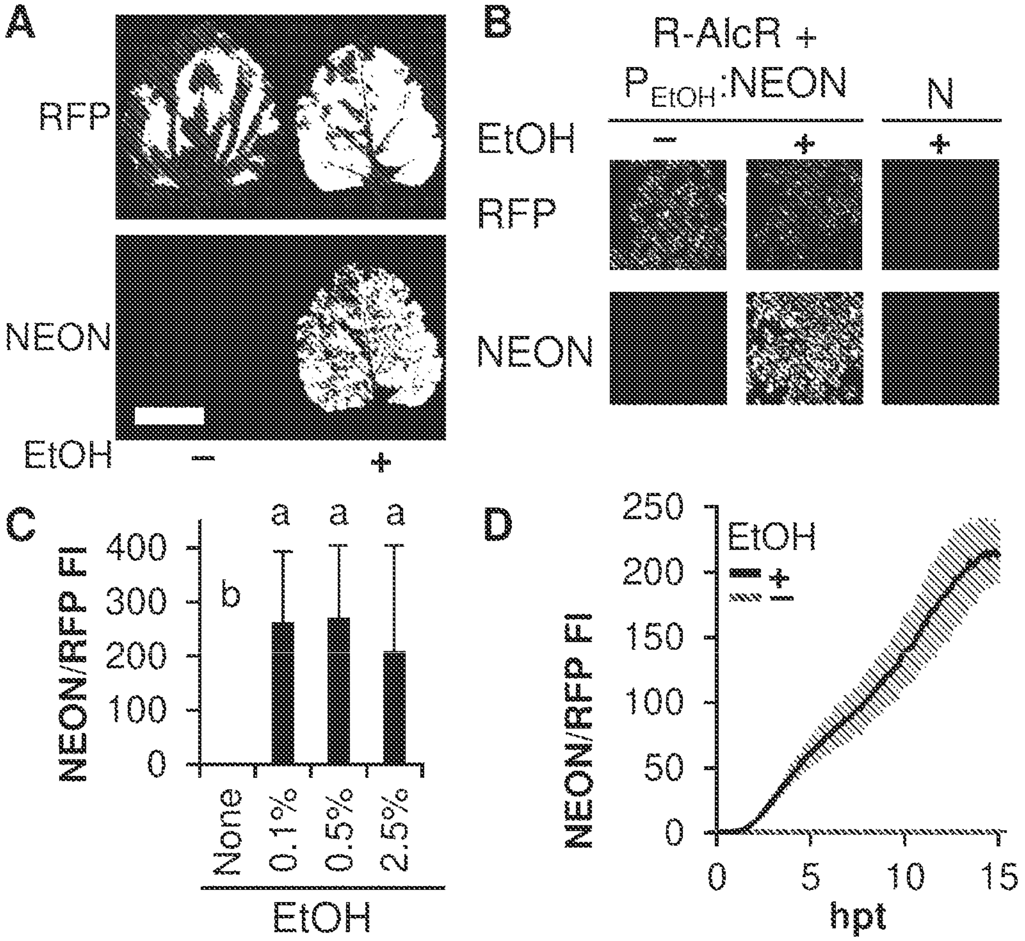

FIG. 16. Gene expression control and delivery of synthetic circuit components to plants by the pLX vectors Evaluation of a buffer gate in plants. (A) *Nicotiana benthamiana* plants were infiltrated with an *Agrobacterium* strain that harbors both pLX-Z4-$P_{mas}$:RFP-AlcR (SEQ ID NO: 24) and pLX-B2-$P_{EtOH}$:NEON (SEQ ID NO: 25) binary vectors (R-AlcR+$P_{EtOH}$:NEON). Plants were treated twice with water or EtOH. At 4 dpa, RFP and NEON fluorescence was imaged by laser scanning of leaves. Scale bar, 3 cm. (B) *Nicotiana benthamiana* leaves were untreated (N), or infiltrated with the *A. tumefaciens* R-AlcR+$P_{EtOH}$:NEON strain. Leaf disks were collected, placed in a 96-well plate and incubated in the presence or absence of EtOH. Cell RFP and NEON fluorescence was imaged by confocal microscopy at 24 h post-treatment (hpt). (C) Leaf disks from agro-infiltrated patches were placed in a 96-well plate and different amounts of inducer were added. Fluorescence intensities (FI) were measured in a plate reader at 22 hpt, and the NEON/RFP FI relative value of the non-inducer condition (None) was set to 1. Bar graph shows mean±SD (n=18). Letters indicate $p<0.01$, one-way Anova and Tukey's HSD test. (D) Kinetics of the EtOH-responsive buffer gate. Leaf disks from agro-infiltrated patches were treated with water (gray, minus) or 0.1% EtOH (black, plus), and fluorescence intensity was measured in a plate reader. NEON/RFP FI relative value of the water condition was set to 1. The plot shows mean±SD (n=5).

DETAILED DESCRIPTION OF THE INVENTION

In a first aspect, the present invention relates to a binary vector (pBBR1-based pLX vector) comprising at least three modules: (a) a T-DNA cassette module comprising at least sequences of a T-DNA right border and a T-DNA left border; (b) a replication origin module comprising a pBBR1 origin or a variant functionally equivalent thereof; and (c) at least a selectable marker module.

The terms "plasmid" and "vector", as used herein, are interchangeable and refer to an extra-chromosomal element that may carry one or more genes. Plasmids and vectors typically are circular double-stranded DNA molecules. However, plasmids and vectors may be linear or circular nucleic acids, of single- or double-stranded DNA or RNA, and may be derived from any source, in which a number of nucleotide sequences have been joined or recombined into a unique construct that is capable of introducing a promoter fragment and a coding polynucleotide sequence along with any appropriate 3' untranslated sequence into a cell. In the examples, plasmids and vectors may comprise autonomously replicating sequences, genome integrating sequences, and/or phage or nucleotide sequences.

The term "viral vector" refers to a vector that comprises viral genome sequences that can launch viral infections, and are useful for rapid, high-level delivery of exogenous sequences to eukaryotic cells.

The terms "Ti plasmid", "Ri plasmid", "pTi" and "pRi", as used herein, are interchangeable, and refer to a large plasmid contained in the wild-type *Agrobacterium* sp.; pTi comprises a T-DNA (transfer DNA) that is introduced into plants, a virulence region (vir region), etc. T-DNA is a DNA fragment inserted into the genome of a plant cell, and in wild-type *Agrobacterium* sp. comprises genes for the synthesis of opines and plant growth regulators. The vir region is a region that encodes virulence proteins, a protein group required for integration of the T-DNA into plants, and it comprises genes such as virA, virB, virC, virD1, virD2, virD3, virG or virJ.

The term "disarmed Ti plasmid" refers to a plasmid produced by removing the T-DNA region from a wild-type Ti plasmid and that encodes virulence proteins, or to a functionally equivalent artificial or natural plasmid, such as and without limitation, the p42a plasmid of *Rhizobium etli* (Lacroix B. & Citovsky V., PLoS Pathog. 2016, 12, 3, e1005502). Thus, a disarmed Ti plasmid lacks the T-DNA region, and is able to mediate the DNA transfer to eukaryotic cells and their subsequent genetic modification.

The term "border sequence", e.g., right border (RB) or left border (LB), refers to a directly repeated nucleic acid sequence defining an end of the T-DNA region. Border sequences may be from a Ti plasmid, or may be other bacterial, plant-derived, or synthetic sequences that function similarly. In a preferred embodiment of the pBBR1-based pLX vector of the invention, the LB and RB are independently selected from the group consisting of a T-DNA border from a nopaline-, an octopine-, a succinamopine-type Ti plasmid, or any combination thereof. In a preferred embodiment, the T-DNA borders are selected from octopine- or succinamopine-type Ti plasmids from *A. tumefaciens*, and include a second left border of the nopaline type.

The terms "binary vector" and "T-DNA binary vector", as used herein, are interchangeable. They refer to a plasmid that has an origin of replication (on) that permits maintenance of the vector in a wide range of bacteria including *E. coli* and *Agrobacterium* sp., and that comprises a T-DNA cassette, and a marker for selection and maintenance in bacteria. In some embodiments, the binary vector may include a selectable marker for selection in eukaryotic organisms, preferably for selection in plants.

The terms "T-DNA cassette" and "T-DNA cloning cassette", as used herein, are interchangeable and refer to a T-DNA region that comprises at least the RB and LB sequences, and features that allow insertion of a sequence of interest between the RB and LB sequences in a way that the sequence of interest can be transferred to eukaryotic cells.

In a more preferred embodiment, the pBBR1-based pLX binary vector of the present invention is characterized in that the T-DNA cassette comprises one T-DNA right border and two T-DNA left border sequences. In a more preferred embodiment, the right border comprises a nucleotide sequence that is at least 80%, 85%, 90%, 95%, 96%, 97%, 98% or 99% identical to SEQ ID NO: 102 or SEQ ID NO: 115. In a more preferred embodiment, the left border comprises a nucleotide sequence that is at least 80%, 85%, 90%, 95%, 96%, 97%, 98% or 99%, identical to SEQ ID NO: 103, SEQ ID NO: 104 or SEQ ID NO: 116. In a more preferred embodiment, the right border comprises the SEQ ID NO: 102 and the left borders comprise the SEQ ID NO: 103 and SEQ ID NO: 104. In a more preferred embodiment, the right border consists of SEQ ID NO: 102 and the left borders consist of SEQ ID NO: 103 and SEQ ID NO: 104.

In a further preferred embodiment, the pBBR1-based pLX binary vector is characterized in that the T-DNA region also comprises at least two transcription terminators. Transcription terminators useful in the present invention are known in the art (i.e., in Chen Y. J., et al., Nat Methods. 2013, 10, 7, 659-664). In a more preferred embodiment, the transcription terminators comprise a nucleotide sequence that is at least 80%, 85%, 90%, 95%, 96%, 97%, 98% or 99% identical to any of the sequences selected from the list consisting of: SEQ ID NO: 108, 109, 110, 111, or any combinations thereof, more preferably, SEQ ID NO: 108 and 109. In a more preferred embodiment, the transcription terminators are selected from sequences comprising the SEQ ID NO: 108, 109, 110, 111 or any combinations thereof, more preferably, SEQ ID NO: 108 and 109. In a more preferred embodiment, the transcription terminators consist of any of the sequences selected from SEQ ID NO: 108, 109, 110, 111, or any combinations thereof, more preferably, SEQ ID NO: 108 and 109.

"Homology", "identity" or "similarity" refer to the sequence similarity between two nucleic acid or amino acid sequences. Homology can be determined by comparing a position in each sequence, which may be aligned for comparison purposes. When a position in the compared sequence is occupied by the same base or amino acid, then the molecules are identical at that position. A degree of homology or similarity or identity between nucleic acid sequences is a function of the number of identical or matching nucleotides at positions shared by the nucleic acid sequences. A degree of identity of amino acid sequences is a function of the number of identical amino acids at positions shared by the amino acid sequences. A degree of homology or similarity of amino acid sequences is a function of the number of amino acids, i.e., structurally related, at positions shared by the amino acid sequences. The degree of homology, identity, and/or similarity can be determined by the use of algorithms, programs and methods, such as and without limitations Clustal, Wilbur-Lipman, GAG, GAP, BLAST, BLASTN, BLASTP, EMBOSS Needle, FASTA, Smith Waterman or BLOSUM.

In a more preferred embodiment, the pBBR1-based pLX vector of the invention is characterized in that the T-DNA borders flank a sequence of interest. The nucleic acid sequence(s) of interest is operatively linked to sequences required for DNA transfer to a target eukaryotic cell.

The term "operatively linked" or "operably associated" refer to a functional linkage between a regulatory sequence and a coding sequence, or a functional linkage between two regulatory sequences. The term "construct" refers to units or components so described that are assembled and operatively linked thus in a relationship that permits them to function in their intended manner. By placing a coding sequence under regulatory control of a promoter or another regulatory sequence means positioning the coding sequence such that the expression of the coding sequence is controlled by the regulatory sequence. The term "transcription unit" refers to a construct including promoter, coding and terminator sequences that are operatively linked to permit the expression or delivery of the sequence of interest in the intended manner.

The sequence of interest, although often a gene sequence, can actually be any nucleic acid sequence whether or not it produces a protein, an RNA, an antisense molecule or regulatory sequence or the like.

A "transgene" refers to a sequence of interest independently of whether this sequence has been introduced exogenously or has been manipulated; in both cases, the sequence defined as "transgene" has not been shown to occur naturally. The terms "endogenous gene", "endogenous sequence", "wild-type gene" or "wild-type sequence" refer to a native gene in its natural location in the genome of an organism.

Sequences of interest or transgenes may include functional elements that affect developmental processes, fertility, abiotic and biotic stress resistance, or that confer new phenotypes, and the like. Other transgenes include sequences useful to produce edible vaccines for humans or animals (e.g., U.S. Pat. Nos. 6,136,320; 6,395,964), to alter fatty acid content or change amino acid composition of crops (e.g., U.S. Pat. No. 6,664,445), to introduce enzymes in pathways to synthesize metabolites such as vitamin A and vitamin E, to increase iron concentration, to control fruit ripening, to reduce allergenic properties of e.g., wheat and nuts, to absorb and store toxic and hazardous substances and to assist contaminated soil cleanup, to alter fiber content of woods, to enhance resistance to diseases, bacteria, fungi, nematodes, herbicides, viruses and insects, or to increase salt tolerance and drought resistance, amongst others.

In a typical vector, the sequence of interest is operatively linked to a promoter. A "promoter" is a sequence of nucleotides from which transcription of a downstream, operatively linked DNA may be initiated. The product of a sequence of interest may be expressed constitutively, after induction, in specific tissues or at certain development stages. Regulatory elements to effect such expression are well known in the art. Many examples of regulatory elements may be found in the Patent Lens document "Promoters used to regulate gene expression" version 1.0, October 2003 (incorporated in its entirety). Other promoters can be identified through a variety of assays. Enhancer elements or other regulatory elements can be included in addition to a promoter. "Minimal promoter" sequences usually require an enhancer element for activity, such as the so-called 35S minimal promoter from cauliflower mosaic virus (CaMV), or the 34S minimal promoter from figwort mosaic virus.

In a more preferred embodiment, the pBBR1-based vector of the invention is characterized in that the T-DNA cassette module also comprises a cloning cassette. More preferably, the T-DNA cloning cassette comprises restriction endonuclease and primer annealing sites; and in a more preferred embodiment, these sites are compatible with high-throughput, Type IIS restriction endonuclease- and/or overlap-based DNA assembly methods, such as and without limitations, Golden Gate, GoldenBraid, Modular Cloning (MoClo), one- or two-step Gibson assembly (Gibson D. G., et al., Nat. Methods 2009, 6, 343-345), Sequence and Ligation Independent Cloning (SLIC), GeneArt seamless cloning and assembly (Thermo Fisher Scientific), NEBuilder HiFi DNA assembly (New England BioLabs), Cold Fusion cloning (System Biosciences), or In-fusion cloning (Clontech).

In another preferred embodiment, a T-DNA cloning cassette also comprises a selectable, screenable marker or reporter elements for identifying insertion of the sequence of interest. The marker or reporter element is a gene or an operon that confers a visual phenotype or negative selection, such as, and without limitations, the lacZa, ccdB, sacB, a luciferase or a fluorescent protein gene, or a canthaxanthin biosynthesis operon. Additionally, the screenable marker or reporter element included in the T-DNA cassette can be selected from the list mentioned below for the selectable marker module of the binary vector of the present invention.

In a further preferred embodiment, the replication origin module of the pBBR1-based pLX vector of the invention comprises a pBBR1 origin comprising the pBBR1-oriV and -rep regions, or a variant functionally equivalent thereof. In a further preferred embodiment, the pBBR1 origin comprises a nucleotide sequence that is at least 80%, 85%, 90%, 95%, 96%, 97%, 98% or 99% identical to SEQ ID NO: 105, more preferably the pBBR1 origin comprises the SEQ ID NO: 105, and more preferably the pBBR1 origin consists of SEQ ID NO: 105.

As used herein, the term "functionally equivalent variant" refers to any variant in which the nucleotide sequence encodes an amino acid sequence comprising conservative or non-conservative alterations in the amino acid sequence resulting in silent changes that preserve the functionality of the molecule including, for example, deletions, additions, and substitutions. Such altered molecules may be desirable where they provide certain advantages in their use. As used herein, conservative substitution involves the substitution of one or more amino acids within the sequence of the corresponding peptide with another amino acid having similar polarity and hydrophobicity/hydrophilicity characteristics resulting in a functionally equivalent molecule. Such conservative substitutions include but are not limited to substitutions within the following groups of amino acids: glycine, alanine; valine, isoleucine, leucine; aspartic acid, glutamic acid; asparagine, glutamine; serine, threonine; lysine, arginine; phenylalanine, tyrosine; and methionine, norleucine. The skilled person in the art will understand that mutations in the nucleotide sequence encoding a peptide, which give rise to conservative amino acid substitutions in positions that are non-critical for the functionality of the peptide, are evolutionarily neutral mutations that do not affect its global structure or its functionality.

The term "replication origin" (ori) refers to a cis-acting sequence essential for replication. Origin sequences that permit the plasmid replication or maintenance in a wide range of bacteria have been described (U.S. Pat. Nos. 4,940,838; 5,149,645; 6,165,780; 6,265,638, incorporated in its entirety). In a preferred embodiment, the origin of replication is a wide-host-range origin or a broad-host-range origin, terms that are interchangeable in the present invention. As used herein, "wide-host-range" or "broad-host-range" means that the vector replicates in at least two bacterial species, preferably in *Agrobacterium* sp. and *E. coli*. The host range is conferred by an origin of replication. When a nucleic acid molecule is integrated into the bacterial chromosome or other self-replicating bacterial DNA molecules, an origin is not necessary. Thus, when suitably modified and engineered, these bacteria may be used for transferring nucleic acid sequences into eukaryotic cells, and especially into plant cells.

In another preferred embodiment, the pBBR1-based pLX vector also comprises a selectable or a screenable marker module for identifying host cell transformants, preferably bacterial transformants. Well-known selectable markers are genes that confer resistance to drugs (such as antibiotics selected from the list consisting of: neomycin, ampicillin, carbenicillin, chloramphenicol, kanamycin, tetracycline, gentamicin, spectinomycin, bleomycin, phleomycin, streptomycin, erythromycin, blasticidin, and hygromycin), herbicide resistance genes, and the like. Other selection systems can alternatively be used, including genes encoding resistance to other toxic compounds, such as potassium tellurite resistance genes, genes encoding products required for growth of the cells in positive selection systems. Examples of these "positive selection" systems are abundant (e.g., U.S. Pat. No. 5,994,629). "Negative selection" systems can also be used. Alternatively, a screenable marker or reporter gene may be employed to allow selection of transformed cells based on a visual phenotype, e.g. a β-glucuronidase, a luciferase or a fluorescent protein gene. The selectable marker is also typically operably linked to regulatory elements necessary for gene transcription, e.g., a constitutive or inducible promoter and a terminator sequence. Elements that enhance efficiency of transcription are optionally included. In a preferred embodiment, the selectable marker module comprises a gene that confers resistance to a drug, and is selected from the group consisting of neomycin, ampicillin, carbenicillin, chloramphenicol, kanamycin, tetracycline, gentamicin, spectinomycin, bleomycin, phleomycin, streptomycin, erythromycin, blasticidin and hygromycin resistance genes.

In a more preferred embodiment, the pBBR1-based pLX vector is selected from the list consisting of: SEQ ID NO: 3 (pLX-B2), SEQ ID NO: 4 (pLX-B3), SEQ ID NO: 5 (pLX-B4), SEQ ID NO: 10 (pLX-B2α2), SEQ ID NO: 11 (pLX-B3Q1), SEQ ID NO: 12 (pLX-B3Q2), SEQ ID NO: 13, SEQ ID NO: 14, SEQ ID NO: 15, SEQ ID NO: 19, SEQ ID NO: 20, SEQ ID NO: 21, SEQ ID NO: 22, SEQ ID NO: 23, SEQ ID NO: 25, and SEQ ID NO: 28.

Furthermore, a pBBR1-based pLX vector of the present invention can be used as a single binary vector, which has autonomous replication, or in a binary vector system, which includes a combination of binary vectors that have replication and bacterial selection mechanisms allowing a mutual and autonomous coexistence with each other.

As used herein, the phrase "binary vector system" refers to binary vectors that are capable of replicating in both *E. coli* and *A. tumefaciens*, and host unlinked T-DNA cassettes. In a binary vector system, vectors are multiplexed and employed for delivery of multiple T-DNA cassettes to eukaryotic cells or organisms, preferably to plants.

In a more preferred embodiment, the binary vectors and vectors of the binary vector system of the present invention have a minimal size between 2 to 20 kb, preferably between 2.5 to 3.8 kb, more preferably have a size below 3.8 kb.

Another aspect of the present invention refers to a binary vector system comprising the pBBR1-based pLX plasmid according to the present disclosure and another binary vector (second binary vector) known in the art and compatible with a first binary vector of the present invention. In a more preferred embodiment of the binary vector system of the present invention, the second binary vector is an RK2-based pLX plasmid as described herein.

Another aspect of the present invention, the RK2-based pLX plasmid, according to the present disclosure refers to a binary vector comprising at least three modules: (a) a T-DNA cassette module comprising at least a T-DNA right border and a T-DNA left border; (b) a replication origin module comprising an origin compatible with the pBBR1 origin, preferably selected from the list consisting of origins of the IncQ, IncW, IncU, pRi, pVS1 and IncP-α plasmid incompatibility groups, wherein more preferably is an origin of the IncP-α plasmid incompatibility group, and wherein more preferably, the replication origin is the RK2 origin, or a variant functionally equivalent thereof; and (c) at least a selectable marker module.

In a preferred embodiment, the RK2-based pLX vector of the invention comprises a T-DNA cassette comprising one T-DNA right border and two T-DNA left borders; preferably comprising the T-DNA border sequences mentioned above.

In a more preferred embodiment, the right border comprises the SEQ ID NO: 115 and the left borders comprise the SEQ ID NO: 116 and SEQ ID NO: 104. In a more preferred embodiment, the right border consists of SEQ ID NO: 115, and the left borders consist of the SEQ ID NO: 104 and SEQ ID NO: 116.

In a further preferred embodiment, the RK2-based pLX vector is characterized in that the T-DNA cassette is flanked by at least two transcription terminators, preferably the transcription terminators that are disclosed above. In a more preferred embodiment, the transcription terminators comprise the SEQ ID NO: 110 and 111, more preferably the transcription terminators consist of SEQ ID NO: 110 and 111.

In a more preferred embodiment, the RK2-based pLX vector of the invention is characterized in that the T-DNA borders flank a sequence of interest. The nucleic acid sequence(s) of interest is operatively linked to sequences required for the DNA transfer to a target eukaryotic cell. In a more preferred embodiment, the sequences of interest are mentioned above.

In a more preferred embodiment, the RK2-based vector of the invention is characterized in that the T-DNA cassette module also comprises a cloning cassette; more preferably, the T-DNA cloning cassette comprises the selectable, screenable marker or reporter elements mentioned above. In a further preferred embodiment, the T-DNA cassette comprises restriction endonuclease and primer annealing sites; in a more preferred embodiment, these sites are compatible with high-throughput, Type IIS restriction endonuclease- and overlap-based assembly methods as mentioned above.

In a further preferred embodiment, the replication origin of the RK2-based pLX vector of the invention comprises an RK2 replication origin comprising the RK2-oriV and -trfA regions, or a variant functionally equivalent thereof. In a more preferred embodiment the RK2 origin comprises a nucleotide sequence that is at least 80%, 85%, 90%, 95%, 96%, 97%, 98% or 99% identical to SEQ ID NO: 106 or SEQ ID NO: 107, more preferably the RK2 origin comprises the SEQ ID NO: 106 or SEQ ID NO: 107, and more preferably the RK2 origin consists of SEQ ID NO: 106 or SEQ ID NO: 107.

In another preferred embodiment, the selectable marker module of the RK2-based pLX binary vector comprises a selectable or a screenable marker gene mentioned above.

In a more preferred embodiment, the selectable marker gene of the RK2-based pLX binary vector differs from the selectable marker gene of the pBBR1-based pLX vector, so as to facilitate simultaneous selection of both plasmids.

In a more preferred embodiment, the RK2-based pLX vector is selected from the list consisting of: SEQ ID NO: 6 (pLX-R2), SEQ ID NO: 7 (pLX-R3), SEQ ID NO: 8 (pLX-R4), SEQ ID NO: 9 (pLX-Z4), SEQ ID NO: 16, SEQ ID NO: 17, SEQ ID NO: 18 and SEQ ID NO: 24.

In another preferred embodiment, the backbone of the RK2-based pLX vector has no regions with >28 nucleotide identity to the pBBR1-based pLX vector of the present invention.

Consequently, the binary vector system of the present invention comprises the pBBR1-based pLX plasmid and, preferably, the RK2-based pLX plasmid according to the present disclosure.

Another aspect of the present invention relates to methods to assemble synthetic, genomic, metagenomic, and/or cDNA sequences of interest into the binary vector or the binary vector system disclosed in the present invention.

Another aspect of the present invention is related to a host cell comprising the pBBR1-based pLX vector, the RK2-based pLX vector, or the binary vector system of the present invention.

In accordance with the present invention, the term "host cell" refers to a cell which has been transformed, or is capable of being transformed, by an exogenous DNA sequence, preferably by the binary vector or the binary vector system of the present invention. A host cell can be used, for example, for expression of a nucleic acid of interest, propagation of plasmid vectors and/or delivery of a sequence of interest to eukaryotic cells.

In a preferred embodiment, the host cell of the present invention is a bacterial cell, preferably selected from *Agrobacterium* sp. and *E. coli* cells. In a more preferred embodiment, the host cell is preferably of a species of the Rhizobiaceae family, more preferably is an *Agrobacterium* sp. bacterium, especially preferably an *Agrobacterium* strain that comprises a disarmed Ti plasmid.

Alternatively, genome sequences of *Agrobacterium* sp. and other bacterial species can be compared. Genes that are missing in the latter bacteria and are important for delivery and transformation of T-DNA into eukaryotic cells may be individually picked from the *Agrobacterium* genome and inserted into the desired bacterial genome by any means, or expressed on a plasmid. Similarly, bacteria can be used to transform a eukaryotic organism or cell under a variety of test conditions, such as temperature, pH, nutrient additives and the like. The best conditions can be quickly determined and then tested to transform plant cells or other eukaryotic cells as mentioned above. Furthermore, host bacterial species may naturally interact in specific ways with a number of eukaryotic organisms, such as plants. These bacterial-plant interactions are very different from the way *Agrobacterium* naturally interacts with plants. Thus, tissues and cells that can be transformed by *Agrobacterium* sp. or by the use of other bacteria may be different.

In general, plasmids are transferred through a direct transfer method to the bacteria (host cell) of this invention. By transferring either single or multiple binary vectors as described herein, transformation competent bacteria are generated. These bacteria can be used to transform a eukaryotic cell or organism, such as a yeast, a fungus, a plant, an insect or an animal.

The term "eukaryotic cell" refers to either individual cells or cell aggregates (such as tissues or organs, parts of tissues or organs) and to entire organisms, comprising a yeast, a fungus, an alga, a plant, an insect or an animal.

In a more preferred embodiment, the term "plant cell" refers to individual cells or cell aggregates, organized plant tissues, organs, or entire plants, such as and without limitation, protoplasts, calli, cell cultures, meristems and meristematic tissues, leaves, shoots, roots, flowers, ovules, pollen and pollen tubes, seeds, embryos, hypocotyls, cotyledons, seedlings and mature plants.

Eukaryotic cells may be transformed within the context of this invention. Generally, eukaryotic cells to be transformed are cultured before transformation, or cells may be transformed in situ. In some embodiments, cells are cultured in the presence of additives to render them more susceptible to transformation. Transformants can be easily detected by their phenotypic changes, e.g., growth on a medium including drugs/herbicides/toxic compounds or lacking an essential growth component on which the untransformed cells cannot grow. In other embodiments, cells are transformed without prior culturing.

Briefly, in an exemplary transformation protocol to generate transformed plants, plant cells are transformed by their co-cultivation with a culture of bacteria containing the binary vector or the binary vector system described herein. After co-cultivation for a few days, bacteria are removed, for example by washing and treatment with antibiotics, and plant cells are transferred to post-cultivation medium plates generally containing an antibiotic to inhibit or kill bacterial growth and optionally a selective agent, such as that described in U.S. Pat. No. 5,994,629. Plant cells are further incubated for several days. The expression of the transgene may be tested at this time. After further incubation for several weeks in selective medium, plant cells are transferred to regeneration medium and placed in the light. Shoots obtained are transferred to rooting medium and resulting plants are further propagated.

Alternative methods to transform plant cells include dipping whole flowers into a suspension of bacteria, growing the plants further into seed formation, harvesting the seeds and germinating them in the presence of a selection agent that allows the growth of the transformed seedlings only. Alternatively, germinated seeds may be treated with a selection agent that only the transformed plants tolerate. Alternatively, seeds may be visually selected by detection of fluorescent proteins that only the transformed seeds accumulate.

Cell transformation by *Agrobacterium* is independent of stable transgene integration into host genomes, and the use of transient expression systems or autonomously replicating RNA/DNA units (viral vectors) can bypass the need for gene integration, if desired. In this sense, the terms "infiltration" and "agro-infiltration" refer to a transient transformation method that relies on mechanical introduction of cultures of host cells comprising at least one binary vector, into eukaryotic organisms or their organs, preferably entire plants, seedlings or leaves. Scale-up is achieved, for example, through the use of vacuum infiltration. The term "agro-inoculation" refers to the delivery of viral vectors by *Agrobacterium*-mediated transient transformation.

Plants that are especially desirable to transform include corn, rice, wheat, soybean, alfalfa and other leguminous plants, potato, tomato, tobacco, *Nicotiana benthamiana*, and so on.

Another aspect of the present invention refers to a cell culture comprising the host cells of the present invention.

Another aspect of the present invention relates to a method for delivering at least one nucleotide sequence of interest into at least one plant cell, comprising: (a) inserting the nucleotide sequence of interest into the T-DNA cassette of the pBBR1-based pLX vector, the RK2-based pLX vector, or the binary vector system of the present invention; (b) introducing the pBBR1-based pLX vector, the RK2-based pLX vector, or the binary vector system obtained in step (a) into at least one bacterial host cell according to the present invention; and (c) contacting the host cell of step (b) with a plant cell.

In a preferred embodiment, the method for delivering at least one nucleotide sequence of interest into at least one plant cell is characterized in that the bacterial host cell is an *Agrobacterium* sp. cell, more preferably, the *Agrobacterium* cell comprises a disarmed Ti plasmid.

In addition to the numerous technologies for transforming plants or plant cells, the type of cell, tissue, organ that is contacted with foreign constructs may vary as well. Almost all plant tissues may be transformed during dedifferentiation using appropriate techniques within the skill of the art. One skilled in the field of plant transformation will understand that multiple methodologies are available for the production of transformed plants, and that they may be modified and specialized to accommodate biological differences between various plant species. Regardless of the transformation technique employed, the nucleotide sequence of interest can be incorporated into the binary vector or the binary vector system of the present invention, and adapted to express the nucleotide sequence of interest in a plant cell by including in the vector a plant promoter. In addition to plant promoters, promoters from a variety of sources can be used to efficiently express foreign genes in plant cells. For example, promoters of bacterial origin, such as the octopine synthase promoter, nopaline synthase promoter, and mannopine synthase promoter; promoters of viral origin, such as the 35S and 19S promoters of CaMV, a promoter from sugarcane bacilliform virus, and the like may be used. Plant-derived promoters include, but are not limited to, the ribulose-1,5-bisphosphate carboxylase (RuBisCO) small subunit promoter, beta-conglycinin promoter, cruciferin promoter, phaseolin promoter, alcohol dehydrogenase promoter, heat-shock promoters, actin depolymerization factor promoter, and tissue-specific promoters. Promoters may also contain certain enhancer sequence elements that may improve the transcription efficiency. Typical enhancers include, but are not limited to, the alcohol dehydrogenase 1 (ADH1)-intron 1 and ADH1-intron 6. Constitutive promoters may be used. Constitutive promoters direct continuous gene expression in nearly all cell types and at nearly all times (e.g., the actin promoter, ubiquitin promoter, CaMV 35S promoter). Tissue-specific promoters are responsible for gene expression in specific cell, tissue, or organ types. Examples of other promoters that may be used include those that are active during a certain stage of the plant's development, or in specific plant tissues and organs. Examples of such promoters include, but are not limited to, promoters that are root-, pollen-, embryo-, corn silk-, cotton fiber-, seed endosperm-, and phloem-specific promoters. In a further embodiment, the promoter is an inducible promoter. An inducible promoter is "switched on" or increases expression of genes in response to a specific signal, such as physical stimuli (e.g., temperature, heat-shock gene promoters; light, the RuBisCO promoter); hormones (e.g., glucocorticoid); antibiotics (e.g., tetracycline); metabolites or chemical compounds (e.g., ethanol); and stresses (e.g., drought). Other desirable transcription and translation elements that function in plants also may be used, such as, for example, 5' untranslated leader sequences, RNA transcription termination sequences and poly-adenylate addition signal sequences. Any additional element known in the art and functional in plants may be used.

The biological transformation method described herein can be used to introduce one or more sequences of interest (transgene) into eukaryotic cells, wherein the eukaryotic cell is selected from the group consisting of a yeast cell, a fungal cell, a plant cell, an insect cell and an animal cell; preferably, the eukaryotic cell is a plant cell.

*Agrobacterium* is an extremely advantageous agent for eukaryotic transformation; alternatively, the binary vector or the vector system disclosed in the present invention can be introduced into eukaryotic cells using any physical methods, such as particle or microprojectile bombardment, electroporation, or other forms of direct DNA uptake such as liposome mediated DNA uptake, or the vortexing method. In a preferred embodiment, physical methods for the transformation of plant cells are reviewed in Oard J. H., Biotech. Adv. 1991, 9, 1-11.

The present invention furthermore relates to a transformed plant system, to a regenerated cell or a regenerated plant therefrom, to their progeny or seeds therefrom generated in accordance with the methods described hereinabove.

In a particular embodiment of the present invention, this transformed plant system is characterized by single or multiple modifications of the plant cell genome, epigenome, transcriptome or metabolome, and in that it may or may not comprise any sequence segments of the abovementioned vector, vector system or of their T-DNA cassettes. In this sense, a component of the Clustered regularly interspaced short palindromic repeats (CRISPR)/CRISPR-associated protein (Cas) systems from bacteria and archaea can be used to target specific sequences in eukaryotic and in plant genomes (Murovec J., et al., Plant Biotechnol. J. 2017, doi:10.1111/pbi.12736). This document features a method for modifying the genomic material in a eukaryotic cell, preferably in a plant cell, based on the use of the binary vectors of the invention together with components of the CRISPR/Cas systems; the method provides a relatively simple, effective tool for generating modifications in genomic DNA at selected sites, with no need for transgene integration or maintenance in eukaryotic cell genomes. The CRISPR/Cas systems and their derivatives can be used for, without limitation, targeted mutagenesis, gene targeting, gene replacement, targeted deletion, targeted inversion, targeted translocation, and/or targeted insertion at single or multiple genome site(s). CRISPR/Cas system applications also include epigenetic and transcription regulation, cellular imaging and pathogen targeting. This technology can be used to accelerate the rate of functional genetic studies in eukaryotes, preferably in plants, and to engineer plants with improved characteristics, including enhanced nutritional quality, increased resistance to disease and stress, and heightened production of commercially valuable compounds.

In another aspect, the present invention relates to a method for in vitro delivering at least one nucleotide sequence of interest into at least one eukaryotic cell or organism, comprising: (a) inserting at least one nucleotide sequence of interest into the binary vector or into the binary vector system of the invention; and (b) introducing the binary vector or the binary vector system, of step (a) into at least one eukaryotic cell or organism.

In a preferred embodiment of the method for in vitro delivering at least one nucleotide sequence of interest into at least one eukaryotic cell or organism, the eukaryotic organism is selected from the group consisting of yeasts, fungi, insects and animals.

Another aspect of the present invention relates to a method for transforming eukaryotic cells comprising the step of introducing into the eukaryotic cell the pBBR1-based pLX vector, the RK2-based pLX vector, the binary vector system or the host cell disclosed in the present invention.

Another aspect the present invention relates to a method for obtaining a genetically-engineered plant cell or plant comprising the step of introducing into a plant cell the binary vector, preferably the pBBR1-based pLX vector or the RK2-based pLX vector, the binary vector system, or the bacterial host cell of the invention.

In another aspect, the present invention relates to a genetically-engineered plant cell or plant obtainable by the methods disclosed above.

Another aspect the present invention relates to a method for obtaining in vitro a genetically-engineered eukaryotic cell or organism, comprising the step of introducing into a eukaryotic cell or organism the binary vector, preferably the pBBR1-based or the RK2-based binary vectors, or the binary vector system described herein. In a preferred embodiment, the eukaryotic cell or organism is selected from the group consisting of a yeast, a fungal, an insect and an animal.

In another aspect, the present invention relates to a genetically-engineered eukaryotic cell or organism obtainable by the methods disclosed above.

Another aspect of the present invention relates to the use in vitro or ex vivo of the binary vector, preferably the pBBR1-based pLX binary vector, the RK2-based pLX binary vector, the binary vector system, the bacterial host cell, the culture cells, the genetically-engineered plant cell or plant obtainable by the methods disclosed above, or the genetically-engineered eukaryotic cell or organism obtainable by the methods disclosed above: (a) for site-specific gene knockout; (b) for site-specific genome editing; (c) for DNA sequence-specific interference; (d) for site-specific epigenome editing; (e) for site-specific transcription modulation; or (1 for multiplex genomic engineering; and provided that the use does not comprise a process for modifying the germ line genetic identity of human beings.

In another aspect, the disclosure provides a kit comprising one or more of the components described herein. In some embodiments, the kit comprises the binary vector, the binary vector system, the host cell or the culture cell disclosed herein, and instructions for using the kit. The components or elements may be provided individually or in combinations, and may be provided in any suitable container, such as a vial, a bottle, or a tube. By "kit" as used herein, it refers to a product containing the different reagents necessary to carry out the methods of the invention packaged, allowing transport and storage. Suitable materials for packaging kit components include glass, plastic (polyethylene, polypropylene, polycarbonate, and the like), bottles, vials, paper, envelopes, and the like. Additionally, kits invention may contain instructions for simultaneous, sequential or separate use of the different components found in the kit. Such instructions may be in the form of printed material or in the form of an electronic device capable of storing instructions so that they can be read by a subject, such as electronic storage media (magnetic disks, tapes and the like), optical media (CD-ROM, DVD) and the like. Additionally or alternatively, the media can contain Internet addresses that provide such instructions.

Unless otherwise defined, all technical and scientific terms used herein have the same meaning as commonly understood by one of ordinary skill in the art to which this invention belongs. Methods and materials similar or equivalent to those described herein can be used in the practice of the present invention. Throughout the description and claims the word "comprise", "include" and their variations are not intended to exclude other technical features, additives, components, or steps. Additional objects, advantages and features of the invention will become apparent to those skilled in the art upon examination of the description or may be learned by practice of the invention. The following examples, drawings and sequence listing are provided by way of illustration and are not intended to be limiting of the present invention.

EXAMPLES

The following examples are offered to illustrate, but not to limit, the claimed invention. It is understood that the examples and embodiments described herein are for illustrative purposes only, and persons skilled in the art will recognize various reagents or parameters that can be altered without departing from the spirit of the invention or the scope of the appended claims.

Materials and Methods

DNA Constructs

Unless otherwise indicated, standard molecular cloning methods were used (Sambrook J. & Russel D. W., Molecular cloning: a laboratory manual—3rd edition. Cold Spring Harbor Laboratory Press. 2001). DNA constructs were generated using chemically synthesized and available parts (Table 1). The Ugandan cassava brown streak virus isolate Ke_125 was obtained from DSMZ (PV-0912). Nucleic acids were purified using silica column-based purification kits. Alternatively, genomic DNA from plant samples was extracted following the procedure described by Edwards and collaborators (Edwards K., et al., Nucleic Acids Res. 1991, 19, 1349). PCR reactions were performed with Phusion High-Fidelity DNA polymerase (Fermentas or New England BioLabs), and DnpI-treated to remove plasmid templates, if required. The T-DNA synthetic cassettes T-DNA_1 (SEQ ID NO: 1), for the pLX-B-series and pLX-R series, and T-DNA_2 (SEQ ID NO: 2), for pLX-Z4, were obtained from GeneArt. Overlapping DNA fragments were gel purified and joined using homemade one-step isothermal (Gibson D. G., et al., Nat. Methods. 2009, 6, 343-345) or NEBuilder HiFi (New England BioLabs) DNA assembly master mixes. One-step digestion-ligation reactions were done using Type IIS restriction endonucleases (BsaI or BsmBI, New England BioLabs) and T4 DNA ligase (Promega), as described (Sarrion-Perdigones A., et al., Plant Physiol. 2013, 162, 1618-1631).

Complete details of the plasmids disclosed in the present invention are reported in Table 1.

TABLE 1

| Plasmid name | Origin(s) | Reference |
|---|---|---|
| pSEVA431 | pBBR1 | http://seva.cnb.csic.es/ |
| pSEVA631 | pBBR1 | http://seva.cnb.csic.es/ |
| pSEVA221 | RK2 | http://seva.cnb.csic.es/ |
| pSN.5-TagRFP-T | pVS1 + ColE1 | Pasin F., et al., Plant Methods. 2014, 10, 22 |
| pSN.5-mTFP1 | pVS1 + ColE1 | Pasin F., et al., Plant Methods. 2014, 10, 22 |
| pSN.5-mNeon | pVS1 + ColE1 | Pasin F., et al., Plant Methods. 2014, 10, 22 |
| pGGF003 | pUC | Lampropoulos A., et al., PLoS One. 2013, 8, e83043 |
| pGGC011 | pUC | Lampropoulos A., et al., PLoS One. 2013, 8, e83043 |
| p35Tunos-vec01-NAT1 | pUC | Touriño A., et al., Span. J. Agric. Res. 2008, 6, 48-58 |
| pSN-PPV | RK2 | Pasin F., et al., PLoS Pathog. 2014, 10, e1003985 |
| pSN-PPV-TagRFP-T2A | RK2 | Pasin F., et al., PLoS Pathog. 2014, 10, e1003985 |
| pSN2-ccdB | pVS1 + ColE1 | Pasin F., et al., PLoS Pathog. 2014, 10, e1003985 |
| GB0639 | pVS1 + ColE1 | Vazquez-Vilar M., et al., Plant Methods. 2016, 12, 1-12 |
| GB1108 | pVS1 + ColE1 | Vazquez-Vilar M., et al., Plant Methods. 2016, 12, 1-12 |

TABLE 1-continued

| Plasmid name | Origin(s) | Reference |
|---|---|---|
| GB1181 | pVS1 + ColE1 | Vazquez-Vilar M., et al., Plant Methods. 2016, 12, 1-12 |
| GB0460 | pSa + pUC | Sarrion-Perdigones A., et al., Plant Physiol. 2013, 162, 1618-1631. |
| pDGB3_alpha1 | pVS1 + ColE1 | Vazquez-Vilar M., et al., Nucleic Acids Res. 2017, 45, 2196-2209 |
| pLX-B2 (SEQ ID NO: 3) | pBBR1 | Present disclosure |
| pLX-B3 (SEQ ID NO: 4) | pBBR1 | Present disclosure |
| pLX-B4 (SEQ ID NO: 5) | pBBR1 | Present disclosure |
| pLX-R2 (SEQ ID NO: 6) | RK2 | Present disclosure |
| pLX-R3 (SEQ ID NO: 7) | RK2 | Present disclosure |
| pLX-R4 (SEQ ID NO: 8) | RK2 | Present disclosure |
| pLX-Z4 (SEQ ID NO: 9) | RK2 | Present disclosure |
| pLX-B2α2 (SEQ ID NO: 10) | pBBR1 | Present disclosure |
| pLX-B3Ω1 (SEQ ID NO: 11) | pBBR1 | Present disclosure |
| pLX-B3Ω2 (SEQ ID NO: 12) | pBBR1 | Present disclosure |
| pLX-B2-TagRFP-T (SEQ ID NO: 13) | pBBR1 | Present disclosure |
| pLX-B3-TagRFP-T (SEQ ID NO: 14) | pBBR1 | Present disclosure |
| pLX-B4-TagRFP-T (SEQ ID NO: 15) | pBBR1 | Present disclosure |
| pLX-R2-TagRFP-T (SEQ ID NO: 16) | RK2 | Present disclosure |
| pLX-R3-TagRFP-T (SEQ ID NO: 17) | RK2 | Present disclosure |
| pLX-R4-TagRFP-T (SEQ ID NO: 18) | RK2 | Present disclosure |
| pLX-B2-XT1-XT2-hCas9 (SEQ ID NO: 19) | pBBR1 | Present disclosure |
| pLX-B2-NptII-DsRED (SEQ ID NO: 20) | pBBR1 | Present disclosure |
| pLX-PPV (SEQ ID NO: 21) | pBBR1 | Present disclosure |
| pLX-UCBSV (SEQ ID NO: 22) | pBBR1 | Present disclosure |
| pLX-B2-$P_{CRC}$:mTFP1 (SEQ ID NO: 23) | pBBR1 | Present disclosure |
| pLX-Z4-$P_{mas}$:RFP-AlcR (SEQ ID NO: 24) | RK2 | Present disclosure |
| pLX-B2-$P_{EtOH}$:NEON (SEQ ID NO: 25) | pBBR1 | Present disclosure |
| pSN.5-$P_{PAP85}$:RFP (SEQ ID NO: 26) | pVS1 + ColE1 | Present disclosure |
| GB1686 (SEQ ID NO: 27) | pVS1 + ColE1 | Present disclosure |
| pLX-TuMV (SEQ ID NO: 28) | pBBR1 | Present disclosure |

The details of the plasmid of the present invention are the following:

pLX-B2 (SEQ ID NO: 3) is a T-DNA binary vector according to the present invention (pBBR1-based pLX vector) and comprises the replication origin from the pBBR1 plasmid (SEQ ID NO: 105). The following parts were joined by Gibson assembly: (i) pBBR1 origin (SEQ ID NO: 105), amplified from pSEVA631 using the X198_F/X199_R primers (SEQ ID NO: 42/SEQ ID NO: 43); (ii) nptI gene, from pSEVA221 using X192_F/X193_R (SEQ ID NO: 36/SEQ ID NO: 37); (iii) T-DNA_1 synthetic cassette (SEQ ID NO: 1).

pLX-B3 (SEQ ID NO: 4) is a T-DNA binary vector according to the present invention (pBBR1-based pLX vector) and comprises the replication origin from the pBBR1 plasmid (SEQ ID NO: 105). The following parts were joined by Gibson assembly: (i) pBBR1 origin (SEQ ID NO: 105) amplified from pSEVA631 using the X198_F/X199_R primers (SEQ ID NO: 42/SEQ ID NO: 43); (ii) aadA gene, from pSEVA431 using X194_F/X195_R (SEQ ID NO: 38/SEQ ID NO: 39); (iii) T-DNA_1 synthetic cassette (SEQ ID NO: 1).

pLX-B4 (SEQ ID NO: 5) is a T-DNA binary vector according to the present invention (pBBR1-based pLX vector) and comprises the replication origin from the pBBR1 plasmid (SEQ ID NO: 105). The following parts were joined by Gibson assembly: (i) pBBR1 origin (SEQ ID NO: 105), amplified from pSEVA631 using the X198_F/X199_R primers (SEQ ID NO: 42/SEQ ID NO: 43); (ii) aacC1 gene, from pSEVA631 using X196_F/X197_R (SEQ ID NO: 40/SEQ ID NO: 41); (iii) T-DNA_1 synthetic cassette (SEQ ID NO: 1).

pLX-R2 (SEQ ID NO: 6) is a T-DNA binary vector according to the present invention (RK2-based pLX vector) and comprises the replication origin from the RK2 plasmid (SEQ ID NO: 106). The following parts were joined by Gibson assembly: (i) RK2 origin (SEQ ID NO: 106), amplified from pSEVA221 using the X200_F/X201_R primers (SEQ ID NO: 44/SEQ ID NO: 45); (ii) nptI gene, from pSEVA221 using X192_F/X193_R (SEQ ID NO: 36/SEQ ID NO: 37); (iii) T-DNA_1 synthetic cassette (SEQ ID NO: 1).

pLX-R3 (SEQ ID NO: 7) is a T-DNA binary vector according to the present invention (RK2-based pLX vector) and comprises the replication origin from the RK2 plasmid (SEQ ID NO: 106). The following parts were joined by Gibson assembly: (i) RK2 origin (SEQ ID NO: 106), amplified from pSEVA221 using the X200_F/X201_R primers (SEQ ID NO: 44/SEQ ID NO: 45); (ii) aadA gene, from pSEVA431 using X194_F/X195_R (SEQ ID NO: 38/SEQ ID NO: 39); (iii) T-DNA_1 synthetic cassette (SEQ ID NO: 1).

pLX-R4 (SEQ ID NO: 8) is a T-DNA binary vector according to the present invention (RK2-based pLX vector) and comprises the replication origin from the RK2 plasmid (SEQ ID NO: 106). The following parts were joined by Gibson assembly: (i) RK2 origin (SEQ ID NO: 106), amplified from pSEVA221 using the X200_F/X201_R primers (SEQ ID NO: 44/SEQ ID NO: 45); (ii) aacC1 gene, from pSEVA631 using X196_F/X197_R (SEQ ID NO: 40/SEQ ID NO: 41); (iii) T-DNA_1 synthetic cassette (SEQ ID NO: 1).

pLX-Z4 (SEQ ID NO: 9) is a T-DNA binary vector according to the present invention (pLX-R4 derivative with the T-DNA_2 cassette (SEQ ID NO: 2), and no BsmBI sites in RK2-trfA and aacC1 genes) and that comprises the replication origin from the RK2 plasmid (SEQ ID NO: 107). The following parts were joined by Gibson assembly: (i) aacC1-3', amplified from pLX-R4 (SEQ ID NO: 8) using the X295_F/X296_R primers (SEQ ID NO: 73/SEQ ID NO: 74); (ii) aacC1_RK2, from pLX-R4 (SEQ ID NO: 8) using X297_F/X298_R (SEQ ID NO: 75/SEQ ID NO: 76); (iii) RK2_5', from pLX-R4 (SEQ ID NO: 8) using X299_F/X300_R (SEQ ID NO: 77/SEQ ID NO: 78); (iv) T-DNA_2 synthetic cassette (SEQ ID NO: 2).

pLX-B2α2 (SEQ ID NO: 10) is a pLX-B2 derivative with the GoldenBraid alpha2 cloning cassette (Sarrion-Perdigones A., et al., Plant Physiol. 2013, 162, 1618-1631) and comprises the replication origin from the pBBR1 plasmid (SEQ ID NO: 105). The following parts were joined by Gibson assembly: (i) backbone, amplified from pLX-B2 (SEQ ID NO: 3) using the X210_R/X321_F primers (SEQ ID NO: 46/SEQ ID NO: 89); (ii) lacZα cloning cassette, amplified using X322_F/X323_R (SEQ ID NO: 90/SEQ ID NO: 91).

pLX-B3Ω1 (SEQ ID NO: 11) is a pLX-B3 derivative with the GoldenBraid omega1 cloning cassette (Sarrion-Perdigones A., et al., Plant Physiol. 2013, 162, 1618-1631) and comprises the replication origin from the pBBR1 plasmid (SEQ ID NO: 105). The following parts were joined by Gibson assembly: (i) backbone, amplified from pLX-B3 (SEQ ID NO: 4) using the X324_R/X325_F primers (SEQ ID NO: 92/SEQ ID NO: 93); (ii) lacZα cloning cassette, amplified using X326_F/X327_R (SEQ ID NO: 94/SEQ ID NO: 95).

pLX-B3Ω2 (SEQ ID NO: 12) is a pLX-B3 derivative with the GoldenBraid omega2 cloning cassette (Sarrion-Perdigones A., et al., Plant Physiol. 2013, 162, 1618-1631) and comprises the replication origin from the pBBR1 plasmid (SEQ ID NO: 105). The following parts were joined by Gibson assembly: (i) backbone, amplified from pLX-B3 (SEQ ID NO: 4) using the X324_R/X325_F primers (SEQ ID NO: 92/SEQ ID NO: 93); (ii) lacZα cloning cassette, amplified using X328_F/X329_R (SEQ ID NO: 96/SEQ ID NO: 34).

pLX-B2-TagRFP-T (SEQ ID NO: 13) is a pLX-B2 derivative with the CaMV 35S promoter, TagRFP-T and nopaline synthase terminator transcription unit ($P_{35S}$:RFP:$T_{nos}$). The following parts were joined by Gibson assembly: (i) backbone, amplified from pLX-B2 (SEQ ID NO: 3) using the X210_R/X211_F primers (SEQ ID NO: 46/SEQ ID NO: 47); (ii) $P_{35S}$:RFP:$T_{nos}$, from pSN.5-TagRFP-T using X218_F/X219_R (SEQ ID NO: 51/SEQ ID NO: 52).

pLX-B3-TagRFP-T (SEQ ID NO: 14) is a pLX-B3 derivative with $P_{35S}$:RFP:$T_{nos}$. The following parts were joined by Gibson assembly: (i) backbone, amplified from pLX-B3 (SEQ ID NO: 4) using the X210_R/X211_F primers (SEQ ID NO: 46/SEQ ID NO: 47); (ii) $P_{35S}$:RFP:$T_{nos}$, from pSN.5-TagRFP-T using X218_F/X219_R (SEQ ID NO: 51/SEQ ID NO: 52).

pLX-B4-TagRFP-T (SEQ ID NO: 15) is a pLX-B4 derivative with $P_{35S}$:RFP:$T_{nos}$. The following parts were joined by Gibson assembly: (i) backbone, amplified from pLX-B4 (SEQ ID NO: 5) using the X210_R/X211_F primers (SEQ ID NO: 46/SEQ ID NO: 47); (ii) $P_{35S}$:RFP:$T_{nos}$, from pSN.5-TagRFP-T using X218_F/X219_R (SEQ ID NO: 51/SEQ ID NO: 52).

pLX-R2-TagRFP-T (SEQ ID NO: 16) is a pLX-R2 derivative with $P_{35S}$:RFP:$T_{nos}$. The following parts were joined by Gibson assembly: (i) backbone, amplified from pLX-R2 (SEQ ID NO: 6) using the X210_R/X211_F primers (SEQ ID NO: 46/SEQ ID NO: 47); (ii) $P_{35S}$:RFP:$T_{nos}$, from pSN.5-TagRFP-T using X218_F/X219_R (SEQ ID NO: 51/SEQ ID NO: 52).

pLX-R3-TagRFP-T (SEQ ID NO: 17) is a pLX-R3 derivative with $P_{35S}$:RFP:$T_{nos}$. The following parts were joined by Gibson assembly: (i) backbone, amplified from pLX-R3 (SEQ ID NO: 7) using the X210_R/X211_F primers (SEQ ID NO: 46/SEQ ID NO: 47); (ii) $P_{35S}$:RFP:$T_{nos}$, from pSN.5-TagRFP-T using X218_F/X219_R (SEQ ID NO: 51/SEQ ID NO: 52).

pLX-R4-TagRFP-T (SEQ ID NO: 18) is a pLX-R4 derivative with $P_{35S}$:RFP:$T_{nos}$. The following parts were joined by Gibson assembly: (i) backbone, amplified from pLX-R4 (SEQ ID NO: 8) using the X210_R/X211_F primers (SEQ ID NO: 46/SEQ ID NO: 47); (ii) $P_{35S}$:RFP:$T_{nos}$, from pSN.5-TagRFP-T using X218_F/X219_R (SEQ ID NO: 51/SEQ ID NO: 52).

pLX-B2-XT1-XT2-hCas9 (SEQ ID NO: 19) is a pLX-B2 derivative with the XT1 sgRNA, XT2 sgRNA, and hCas9 transcription units. Transcription units were transferred from the GB1108 vector to pLX-B2 performing a restriction-ligation reaction that included BsmBI (New England BioLabs) and T4 DNA ligase (Promega). The reaction mixture was subjected to 30 cycles of 7 min each (3 min at 37° C. and 4 min at 16° C.). Clones were selected onto kanamycin medium plates, and by restriction enzyme assays.

pLX-B2-NptII-DsRED (SEQ ID NO: 20) is a pLX-B2 derivative with the $P_{nos}$:NptII:$T_{nos}$ and $P_{35S}$:DsRED:$T_{35S}$ transcription units. Transcription units were transferred from the GB0460 and GB1181 vectors to pLX-B2 performing a restriction-ligation reaction that included BsaI (New England BioLabs) and T4 DNA ligase (Promega). The reaction mixture was subjected to 30 cycles of 7 min each (3 min at 37° C. and 4 min at 16° C.). Clones were selected onto kanamycin medium plates, and by restriction enzyme assays.

pLX-PPV (SEQ ID NO: 21) is a pLX-B2 derivative with a GFP-tagged plum pox virus cDNA clone cassette ($P_{35S}$:PPV:$T_{nos}$). ScaI/XbaI-digested pSN-PPV was mixed with ScaI/NheI-digested pLX-B2. The fragments were ligated using T4 DNA ligase (New England BioLabs).

pLX-UCBSV (SEQ ID NO: 22) is a pLX-B2 derivative with a cDNA clone cassette of Ugandan cassava brown streak virus ($P_{35S}$:UCBSV:$T_{nos}$). Total RNA purified from plants infected with the UCBSV isolate Ke_125 (PV-0912, DSMZ) was used in a cDNA synthesis reaction. This included X122_R (SEQ ID NO: 32), X123_R (SEQ ID NO: 33), random primers and commercial kit components (High Capacity cDNA reverse transcription kit, Applied Biosystems). The cDNA sample was used in PCR reactions: (i) 5UTR-P3, using the X240_F/X241_R primers (SEQ ID NO: 59/SEQ ID NO: 60); (ii) P3-NIb, using X242_F/X243_R (SEQ ID NO: 61/SEQ ID NO: 62); (iii) NIb-3UTR, using X244_F/X245_R (SEQ ID NO: 63/SEQ ID NO: 64). The pLX-B2 backbone with P35s and $T_{nos}$ was amplified from pLX-PPV using X238_R/X239_F (SEQ ID NO: 57/SEQ ID NO: 58). The RT- and PCR fragments were joined by Gibson assembly. The sequence of the UCBSV cDNA clone was determined by Sanger sequencing using the 1989_F (SEQ ID NO: 29), X241_R (SEQ ID NO: 60), X244_F (SEQ ID NO: 63), X245_R (SEQ ID NO: 64), X253_R (SEQ ID NO: 65), X254_F (SEQ ID NO: 66), X255_R (SEQ ID NO: 67), X256_F (SEQ ID NO: 68), X257_F (SEQ ID NO: 69), X258_F (SEQ ID NO: 70), X259_R (SEQ ID NO: 71), X260_R (SEQ ID NO: 72) primers.

pLX-B2-$P_{CRC}$:mTFP1 (SEQ ID NO: 23) is a pLX-B2 derivative with a transcription unit ($P_{CRC}$:mTFP1:$T_{CRC}$) including an *A. thaliana* seed promoter of the cruciferin C gene (AT4G28520), a cyan fluorescent protein (mTFP1) and AT4G28520 terminator. The following parts were joined by Gibson assembly: (i) backbone, amplified from pLX-B2 using the X210_R/X211_F primers (SEQ ID NO: 46/SEQ ID NO: 47); (ii) $P_{CRC}$, from *A. thaliana* Col-0 genomic DNA using X220_F/X221_R (SEQ ID NO: 53/SEQ ID NO: 54); (iii) mTFP1, from pSN.5-mTFP1 using X212_F/X213_R (SEQ ID NO: 48/SEQ ID NO: 49); (iv) $T_{CRC}$, from *A. thaliana* Col-0 genomic DNA using X222_F/X223_R (SEQ ID NO: 55/SEQ ID NO: 56).

pLX-Z4-$P_{mas}$:RFP-AlcR (SEQ ID NO: 24) is a pLX-Z4 derivative with the TagRFP-T, Thosea asigna virus 2A peptide (Donnelly M. L. L., et al., J. Gen. Virol. 2001, 82, 1027-1041), *A. nidulans* AlcR coding sequences flanked by the mannopine synthase promoter and terminator ($P_{mas}$:RFP-2A-AlcR:$T_{mas}$). The following parts were joined by Gibson assembly: (i) backbone, amplified from pLX-Z4 using X210_R/X211_F primers (SEQ ID NO: 46/SEQ ID NO: 47); (ii) $P_{mas}$, from pGGF003 using X301_F/X302_R (SEQ ID NO: 79/SEQ ID NO: 80); (iii) RFP-2A, from pSN-PPV-TagRFP-T2A using X216_F/X303_R (SEQ ID NO: 50/SEQ ID NO: 81); (iv) AlcR_5', from pGGC011 using X304_F/X305_R (SEQ ID NO: 82/SEQ ID NO: 83); (v) AlcR_3', from pGGC011 using X306_F/X307_R (SEQ ID NO: 84/SEQ ID NO: 85); (vi) $T_{mas}$, from pGGF003 using X308_F/X309_R (SEQ ID NO: 86/SEQ ID NO: 87).

pLX-B2-$P_{EtOH}$:NEON (SEQ ID NO: 25) is a pLX-B2 derivative with the mNeonGreen sequence under an ethanol-responsive synthetic promoter ($P_{EtOH}$:NEON:$T_{nos}$). The following parts were joined by Gibson assembly: (i) backbone, amplified from pLX-B2 using the X210_R/X211_F primers (SEQ ID NO: 46/SEQ ID NO: 47); (ii) NEON:$T_{nos}$, from pSN.5-mNeon using X310_F/X219_R (SEQ ID NO: 88/SEQ ID NO: 52); (iii) $P_{EtOH}$ synthetic fragment (SEQ ID NO: 35).

pSN.5-PPAP85:RFP (SEQ ID NO: 26) is a pSN2-ccdB derivative with the *A. thaliana* AT3G22640 seed promoter, RFP and nopaline synthase terminator transcription unit ($P_{PAP85}$:RFP:$T_{nos}$). To generate the pSN.5-PPAP85:RFP vector the following parts were joined by Gibson assembly: (i) backbone, XbaI/PmlI-digested pSN2-ccdB; (ii) PPAP85, from *A. thaliana* Col-0 genomic DNA using X228_F/X229_R (SEQ ID NO: 98/SEQ ID NO: 99); (iii) RFP:$T_{nos}$, from pSN.5-TagRFP-T using X216_F/X80_R (SEQ ID NO: 50/SEQ ID NO: 97).

GB1686 (SEQ ID NO: 27) is a pDGB3_alpha1 derivative with the $P_{nos}$:NptII:$T_{nos}$ and $P_{35S}$:DsRED:$T_{35S}$ transcription units. Transcription units were transferred from the GB0460 and GB1181 vectors to pDGB3_alpha1 performing a restriction-ligation reaction that included BsaI (New England BioLabs) and T4 DNA ligase (Promega). The reaction mixture was subjected to 30 cycles of 7 min each (3 min at 37° C. and 4 min at 16° C.). Clones were selected onto kanamycin medium plates, and by restriction enzyme assays.

pLX-TuMV (SEQ ID NO: 28) is a pLX-B2 derivative with the $P_{35S}$:TuMV:$T_{nos}$ cassette from p35Tunos-vec01-NAT1. To generate the pLX-TuMV vector the following parts were joined by Gibson assembly: (i) backbone, amplified from pLX-PPV using X333_R/X334_F primers (SEQ ID NO: 100/SEQ ID NO: 101); (ii) XmaI/SalI-digested p35Tunos-vec01-NAT1.

The primers were synthesized by Sigma-Aldrich, and their sequences are listed in Table 2.

TABLE 2

Table 2. List of the primers, and assembly linkers

| ID | Sequence | SEQ ID NO: |
|---|---|---|
| 1989_F | GATTGATGTGATTTCTCCACTGACG | 29 |
| 2050_F | GCCATTGTCCGAAATCTCACG | 30 |

TABLE 2-continued

Table 2. List of the primers, and assembly linkers

| ID | Sequence | SEQ ID NO: |
|---|---|---|
| 2051_R | CTGGAAATGCGATTCTCTTAGC | 31 |
| X122_R | CGTCAATCGTTAGAGC | 32 |
| X123 R | CGACCTTGCACTTCA | 33 |
| X329_R | CGCATCCTTGTCCGGTCTCCAGCGAGAGACGTCACTC ATTAG | 34 |
| X192_F | CGACTTGCGACATGCGGTCCTTTGCAATCAACTATTA GAAAAATTCATCC | 36 |
| X193_R | AACCGCATAACCGCCAATCCGATCTTGTGTCTCAAAA TCTCTGATGTTAC | 37 |
| X194_F | CGACTTGCGACATGCGGTCCTTTGTTATTTGCCGACT ACCTTGGTGA | 38 |
| X195_R | AACCGCATAACCGCCAATCCGATCGAACCTTGACCGA ACGCAGC | 39 |
| X196_F | CGACTTGCGACATGCGGTCCTTTGCAATTTACCCAAC AACTCCGC | 40 |
| X197_R | AACCGCATAACCGCCAATCCGATCTTGACATAAGCCT GTTCGGTTC | 41 |
| X198_F | GATCGGATTGGCGGTTATGCGGTTCTACCGGCGCGG CAG | 42 |
| X199_R | GGAAGACCACCGAACTGATGATGGCCCCCTACGGGC TTGCTCTC | 43 |
| X200_F | GATCGGATTGGCGGTTATGCGGTTGCGATGCAGGTG GCTGCTGA | 44 |
| X201_R | GGAAGACCACCGAACTGATGATGGGTAGAAAAGATCA AAGGATCTTCTTG | 45 |
| X210_R | TGAGACGGTTTCGACCAGG | 46 |
| X211_F | GTCAGGAGACGGGACAAGGA | 47 |
| X212_F | ATGGTTTCTAAAGGTGAAGAGAC | 48 |
| X213_R | TTATGCTCCTTTATCGTCGTC | 19 |
| X216_F | ATGGTTTCAAAGGGAGAAGAG | 50 |
| X218_F | GTAGCCTGGTCGAAACCGTCTCACCAGTACGCACGAT TCAAGG | 51 |
| X219_R | CGCATCCTTGTCCCGTCTCCTGACGAGATCGAGTAAC ATAGATGACACC | 52 |
| X220_F | GTAGCCTGGTCGAAACCGTCTCATAACGAACGCTCAT GCTAAG | 53 |
| X221_R | TTGTAGTCTCTTCACCTTTAGAAACCATTTTCTTTTTGT TTGTTGTGAG | 54 |
| X222_F | GGATGACGACGATAAAGGAGCATAATGCACTGGAGG TCAAGGAAG | 55 |
| X223_R | CGCATCCTTGTCCCGTCTCCTGACATAGCTCGATAGA ATCATTTGCT | 56 |
| X238_R | GTCATATTTATTTTTCCTCTCCAAATGAAATGAACTTCC | 57 |
| X239_F | GAAATACACCTTATAAAAGTACAAAAAAAAAAAAAAAA AAAAAAAAATGC | 58 |
| X240_F | GTTCATTTCATTTGGAGAGGAAAAATAAATATGACATA AGAATACATAA | 59 |

TABLE 2-continued

Table 2. List of the primers, and assembly linkers

| ID | Sequence | SEQ ID NO: |
|---|---|---|
| X241_R | CTCTTCCTTTCGACCTTGCACTTCA | 60 |
| X242_F | TTGAAGTGCAAGGTCGAAAGGAAGAG | 61 |
| X243_R | AAAGAAGTATCAAACCTACTACCATCACAATC | 62 |
| X244_F | GATTGTGATGGTAGTAGGTTTGATACTTCTT | 63 |
| X245_R | TTTTTTTTTTTTTGTACTTTTATAAGGTGTATTTCTACAC CAAACAAAAGGATATGG | 64 |
| X253_R | CTTTCGTAACAGCTTGCTTTCTCA | 65 |
| X254_F | CTTTGGTTTAGACAAGCAATGTGTG | 66 |
| X255_R | CCACTATTATTTCCACGATGCTTC | 67 |
| X256_F | CAGAGGTGAAGTCTATTCTTGGCAT | 68 |
| X257_F | AGTTTGGTGGAGTTTTGGATAGC | 69 |
| X258_F | ATACACACGCTTGAGATAATGGATG | 70 |
| X259_R | ATCGCCACTGATACAATTCAAAAG | 71 |
| X260_R | AGGACCAAAATTCTCATAAGTCTCTCT | 72 |
| X295_F | CAATTTACCCAACAACTCCGC | 73 |
| X296_R | TGAGTTCGGCGATGTAGCCACCT | 74 |
| X297_F | GGTGGCTACATCGCCGAACTCA | 75 |
| X298_R | CGTTCGCGTCGGCTAGAACAGGAG | 76 |
| X299_F | TGTTCTAGCCGACGCGAACGCT | 77 |
| X300_R | GTAGAAAAGATCAAAGGATCTTCTTG | 78 |
| X301_F | GTAGCCTGGTCGAAACCGTCTCATTTTTCAAATCAGT GCGCAAGA | 79 |
| X302_R | CAGCTCTTCTCCCTTTGAAACCATTGTTGTTACCCGAT TTGGTG | 80 |
| X303_R | TGGCCCTGGATTTTCCTCAA | 81 |
| X304_F | TTGAGGAAAATCCAGGGCCAATGGCAGATACACGCC GAC | 82 |
| X305_R | TCCAGCACAGATTGCGTGAGAGAA | 83 |
| X306_F | CTCTCACGCAATCTGTGCTGGATG | 84 |
| X307_R | AGCTACAAGAAGCTGTCAACTTTCCCA | 85 |
| X308_F | GGAAAGTTGACAGCTTCTTGTAGCTCTTGGACTCCCA TGTTGG | 86 |
| X309_R | GCATCCTTGTCCCGTCTCCTGACGATAATTTATTTGAA AATTCATAAG | 87 |
| X310_F | CAACATTACAATTACTATTTACAATTACAATGGTGAGC AAGGGAGAGGAG | 88 |
| X321_F | GAGACGGGACAAGGATGCG | 89 |
| X322_F | CCTGGTCGAAACCGTCTCAGTCAGGAGAGAGACCAA AAGCAAAAAC | 90 |
| X323_R | CGCATCCTTGTCCCGTCTCCAGCGAGAGACCTCACTC ATTAG | 91 |
| X324_R | TGAGACCGTTTCGACCAGG | 92 |

TABLE 2-continued

Table 2. List of the primers, and assembly linkers

| ID | Sequence | SEQ ID NO: |
|---|---|---|
| X325_F | GAGACCGGACAAGGATGCG | 93 |
| X326_F | CCTGGTCGAAACGGTCTCAGGAGAGAGACGAAAAGC AAAAAC | 94 |
| X327_R | CGCATCCTTGTCCGGTCTCCTGACAGCGAGAGACGT CACTCATTAG | 95 |
| X328_F | CCTGGTCGAAACGGTCTCAGTCAGGAGAGAGACGAA AAGCAAAAAC | 96 |
| X80_R | CTCAATGCTGCTGCCTTCATCTGGATATGAGCTTCAC | 97 |
| X228_F | CCTCGAGTACGTAGGATCCATTTAAATTCCTTCAAGAG AGCAAACCATT | 98 |
| X229 R | ATCAGCTCTTCTCCCTTTGAAACCATTTTTTCTTGTTGT TTTGTTG | 99 |
| X333_R | CGTGTCGTGCTCCACCATGTTCACGAAGATT | 100 |
| X334_F | AAAAAAAAAAATCGGTTCCCCCTAGAGCAGATCGTTC AAACATTTGGCA | 101 |
| Linker_1 | CCATCATCAGTTCGGTGGTCTTCC | 112 |
| Linker_2 | CGACTTGCGACATGCGGTCCTTTG | 113 |
| Linker_3 | GATCGGATTGGCGGTTATGCGGTT | 114 |

Bacterial Growth Conditions

The *E. coli* DH10B strain was used for cloning and plasmid propagation. To increase plasmid miniprep yields, 10 mL cultures were grown in 50 mL tubes at 30 or 37° C. Overnight cultures were pelleted by centrifugation and processed using commercial minicolumn kits (FavorPrep Plasmid Extraction Mini Kit, Favorgen; Wizard Plus SV Minipreps, Promega). Double volumes of resuspension (50 mM Tris-HCl pH 7.5, 10 mM EDTA, 100 μg/mL RNase A), lysis (0.2 M NaOH, 1% SDS) and neutralization (4.09 M guanidine hydrochloride, 0.759 M potassium acetate, 2.12 M glacial acetic acid) kit solutions were used to improve clearing of bacterial lysates and final plasmid yields. Bacteria were grown in Luria-Bertani medium and antibiotics used at final concentrations of 100 mg/L ampicillin, 15 mg/L chloramphenicol, 20 mg/L gentamicin, 50 mg/L kanamycin, 50 mg/L rifampicin, 100 mg/L spectinomycin, 100 mg/L streptomycin, and 10 mg/L tetracycline. Growth curves were measured in 96-well plates, by recording OD600 absorbance values at 10-minute intervals in a plate reader (Infinite M200, Tecan). Maintenance of pTi in the *A. tumefaciens* C58C1-313 strain was evaluated by PCR amplification of a repB fragment using the 2050_F/2051_R primers (SEQ ID NO: 30/SEQ ID NO: 31).

Plant Transformation and Agro-Inoculation

The T-DNA binary vectors (See Table 1) were transformed into *A. tumefaciens* cells by the freeze-thawing or electroporation methods. In transient expression and agro-inoculation assays, *A. tumefaciens* suspensions were mechanically infiltrated into *N. benthamiana* and *A. thaliana* leaves as described (Pasin F., et al., Plant Methods. 2014, 10, 22). The floral dip method was used to stably transform germ line cells of *A. thaliana* (Clough S. J. & Bent A. F., Plant J. 1998, 16, 735-743). Stable transformation of *N. benthamiana* leaf disks was carried as described (Horsch R. B. & Klee H. J., Proc. Natl. Acad. Sci. USA 1986, 83, 4428-4432).

Protein Detection

Plant samples that express fluorescent proteins were visualized under an epifluorescence stereoscope, confocal microscope, or imaged in a laser scanner (Pasin F., et al., Plant Methods. 2014, 10, 22). Fluorescence was measured by placing leaf discs in 96-well flat-bottom plates; in kinetics studies, plates were sealed with optical adhesive films (4311971, Applied Biosystems). The fluorescence signal was acquired in filter-based (VICTOR X5, PerkinElmer) or monochromator-based plate readers (Infinite M200, Tecan), as reported (Pasin F., et al., Plant Methods. 2014, 10, 22). Total protein extracts were resolved by SDS-PAGE, and immunodetection was done using rabbit anti-tRFP (AB234, Evrogen), anti-UCBSV CP (AS-0912, DSMZ), anti-PPV CP and anti-TuMV CP sera as the primary antibodies. For the electron microscopy, plant extracts were incubated with collodion-coated carbon-stabilized copper grids, which were negative stained with 2% uranyl acetate. Grids were observed in a transmission electron microscope (JEM 1011, Jeol).

Targeted Genome Mutagenesis

The CRISPR/Cas constructs were transiently expressed in *N. benthamiana* leaves. To estimate the mutagenesis efficiency, PCR/restriction enzyme assays were done as described (Vazquez-Vilar M., et al., Plant Methods. 2016, 12, 1-12). Briefly, genomic DNA was purified from infiltrated leave samples and used in PCR reactions to amplify DNA fragments spanning the sites targeted by the CRISPR/Cas constructs. The resulting PCR products were purified, and used in DNA digestion reactions that included restriction enzymes whose target sequences overlap predicted editing sites. Intensities of cleaved and cleavage-resistant bands were estimated using the ImageJ software (https://imagej.nih.gov/ij/).

Example 1. Construction of T-DNA Binary Vectors by Assembly of Modular Parts, and Cloning Features of a pBBR1-Based pLX Vector In the design of new T-DNA binary vectors, the inventors chose basic principles: (a) reduced size; (b) stability; (c) a broad-host-range replication origin for maintenance in *E. coli* and *A. tumefaciens*; (d) an origin compatible with the most commonly used T-DNA binary vectors; (e) consistency with current standards for plant synthetic biology; and (f) the possibility to adopt overlap-dependent cloning methods for construct assembly.

Figure 1:
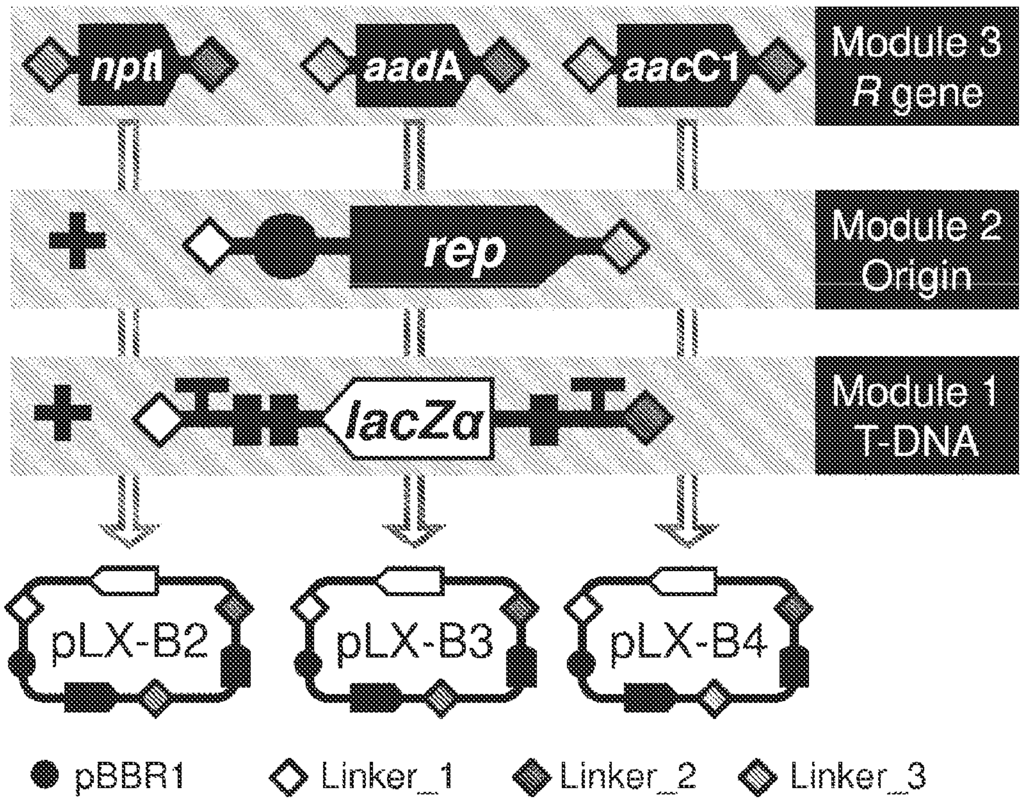
FIG. 1. Construction of T-DNA binary vectors by assembly of modular parts

Therefore, to construct the pLX binary vectors of the present invention, modular parts were assembled by overlap-based cloning methods. Sequences of synthetic orthogonal overlapping junctions known as assembly linker were designed to allow combinatorial assembly of DNA modules (Table 2). Module 1, 2, and 3 refer to the T-DNA cassette, the pBBR1 origin and a selectable marker (resistance (R) genes such as nptI, aadA, and aacC1), respectively (FIG. 1). Each module includes one or several DNA parts, which are flanked by two diverse assembly linkers that are shown as diamonds in FIG. 1. Parts from the three modules were obtained by PCR or chemical synthesis, and were joined by one-step isothermal DNA assembly to generate the pLX-B2 (SEQ ID NO: 3), pLX-B3 (SEQ ID NO: 4) and pLX-B4 (SEQ ID NO: 5) binary vectors (FIG. 1, Table 3). Details for the generation of the pLX-B2, pLX-B3 and pLX-B4 plasmid are disclosed above.

assembly of single and multiple eukaryotic transcription units from libraries of standard DNA parts. Parts or transcription units can be assembled from plasmid libraries into the pLX vectors using the BsaI-based Golden Gate, and GoldenBraid standards (FIG. 2C). The T-DNA cassette hosts divergent primer annealing regions with no sequence similarity and secondary structures (arrows, FIG. 2B). These allow linearization of the small pLX backbones by inverse PCR, and subsequent use in the cloning of multiple overlapping fragments by Gibson assembly (FIG. 2C). The pLX vectors with compatible replicons can be multiplexed into *Agrobacterium* cells for multiple T-DNA delivery (Multiplexing; FIG. 2C). Therefore, the binary vectors of the present invention comprise features that make them compatible with Type IIS restriction endonuclease- and overlap-based assembly methods, and with the delivery of multiple T-DNA cassettes by the multiplexing of binary vectors with compatible origins (Table 3).

Example 2. Transgene Expression in Plants Using the pLX Vector Series

To demonstrate that the binary vectors of the present invention can be used to deliver DNA constructs to eukaryotic cells, specifically to plant cells by *Agrobacterium tumefaciens*-mediated transformation, a transcription unit ($P_{35S}$:RFP:$T_{nos}$) that comprises sequences of the cauliflower mosaic virus 35S promoter, the red fluorescent protein (RFP, as a reporter; FIG. 3A), and the nopaline synthase terminator was assembled into the pLX vectors of the present invention to obtain pLX-B2-TagRFP-T (SEQ ID NO: 13), pLX-B3-TagRFP-T (SEQ ID NO: 14) and pLX-B4-TagRFP-T (SEQ ID NO: 15)(FIG. 3A). Details for the generation of the

TABLE 3

Table 3. Binary T-DNA vectors of the present invention

| Vector | Size bp | Origin | T-DNA* | Bacterial selection | Cassette | Cloning features§ Golden Gate | Golden Braid | Gibson assembly | Multiplexing |
|---|---|---|---|---|---|---|---|---|---|
| pLX-B2 | 3287 | pBBR1 | octopine | KAN | alpha1 | ■ | ■ | ■ | ■ |
| pLX-B3 | 3349 | pBBR1 | octopine | SP | alpha1 | ■ | — | ■ | n.t. |
| pLX-B4 | 3165 | pBBR1 | octopine | GENT | alpha1 | ■ | — | ■ | n.t. |
| pLX-B2α2 | 3287 | pBBR1 | octopine | KAN | alpha2 | ■ | ■ | ■ | n.t. |
| pLX-B3Ω1 | 3349 | pBBR1 | octopine | SP | omega1 | — | ■ | ■ | n.t. |
| pLX-B3Ω2 | 3349 | pBBR1 | octopine | SP | omega2 | — | ■ | ■ | n.t. |
| pLX-Z4 | 3740 | RK2 | succinamopine | GENT | alpha1 | ■ | — | ■ | ■ |

*pTi type of right and left border source, all vectors include a second left border of the nopaline type: §cloning cassette nomenclature according to GoldenBraid standards (Sarrion-Perdigones A., et al., Plant Physiol. 2013, 162, 1618-1631): solid square, suitable; open square, not suitable; n.t., not tested.

The pLX binary vectors of the present invention facilitate flexible experimental designs since their replication is autonomous in both *E. coli* and *A. tumefaciens*. Additional features of the pLX binary vectors include diverse selectable markers, a T-DNA with borders from an octopine-type pTi and a second left border sequence that was shown to reduce the backbone transfer (FIG. 2A). Bacterial synthetic terminators based on different scaffolds (T1, SEQ ID NO: 108; and T2, SEQ ID NO: 109) were included to increase plasmid stability.

For cloning purposes, the T-DNA cassette hosts the *E. coli* lacZα reporter gene flanked by Type IIS restriction endonuclease sites (FIG. 2B). Sequences of BsaI- or BsmBI-produced overhangs comply with the syntax proposed for plant synthetic biology; the pLX vectors are thus suitable for vectors are disclosed above. Transient expression of RFP in *Nicotiana benthamiana* leaves was evaluated by *A. tumefaciens*-mediated delivery. At 6 dpa, leaves infiltrated with pLX-B2-TagRFP-T (SEQ ID NO: 13), pLX-B3-TagRFP-T (SEQ ID NO: 14) and pLX-B4-TagRFP-T (SEQ ID NO: 15) showed bright RFP fluorescence, which was absent in the control sample (FIG. 3B). Consistent with genuine plant expression, confocal images showed that the RFP fluorescent protein signal distributes in the cytosol and nucleoplasm of plant cells (FIG. 3C). The RFP accumulation in leaf samples was confirmed by immunoblot analysis of total protein extracts (FIG. 3D).

For some applications, stable integration of T-DNA cassettes into eukaryotic cell genomes is desirable. To prove the suitability of the pLX vectors to mediate stable transgene integration into plant genomes, the inventors used *Arabidopsis thaliana* as a model plant and the pLX-B2-$P_{CRC}$:mTFP1 vector (SEQ ID NO: 23) (FIG. 4A). Details for its synthesis are disclosed above.

The construct was inserted in *A. tumefaciens* and transformed into plants by floral dipping. Consistent with mTFP1 expression, bright cyan fluorescence was detectable in seed collected from the *Agrobacterium*-treated plants ($T_1$ seeds). The mTFP1-expressing seeds were selected under an epifluorescence stereoscope, and sown to soil. The stable transgene integration in germ-line cells was confirmed by PCR analysis of the $T_1$ plants: the promoter of the endogenous cruciferin C gene was amplified ($P_{CRC}$) from transformed and untransformed plants, whereas the mTFP1 sequence could be amplified only from plants derived from the cyan fluorescent seeds. Diverse fluorescence phenotypes of the T2 seeds were consistent with the transgene integration into the plant genome and its segregation across generations (FIG. 4B).

The present invention shows that T-DNA cassettes from the pLX vectors can be delivered to plants, and the pLX vectors can be used to transiently express or stably integrate transgenes into eukaryotic cell genomes. The inventors generated transgenic plants that are "marker-free", since they do not include genes that confer resistance to antibiotics, herbicides, or other chemical compounds used in transgenic plant selection.

Example 3. Stable Maintenance of T-DNA Cassettes in the pLX Binary Plasmid Series of the Invention cDNA copies of RNA virus genomes can be inserted into plasmids to generate viral infectious clones; these often show instability problems and sequence deletions that arise during the clone propagation in bacteria. To test the stability of the pLX binary vectors of the present invention in challenging conditions, the inventors transferred the entire cDNA sequence of potyvirus genomes into a pLX vector. The vectors generated were propagated in *Escherichia coli*, and the bacteria were subjected to several growth cycles. Vector stability was evaluated by restriction enzyme digestion assays.

The whole cDNA sequence of an RNA virus was obtained from a pBIN19-based vector, pSN-PPV (Pasin F., et al., PLoS Pathog. 2014, 10, e1003985), which contains the cauliflower mosaic virus 35S promoter, a cDNA copy of the plum pox virus (PPV) genome and the nopaline synthase terminator ($P_{35S}$:PPV:$T_{nos}$) sequences. As disclosed above, the inventors generated pLX-PPV (SEQ ID NO: 21), a pLX-B2 derivative with the $P_{35S}$:PPV:$T_{nos}$ cassette from pSN-PPV (FIG. 5A). The pLX-PPV vector obtained (SEQ ID NO: 21) has the pBBR1 origin (SEQ ID NO: 105), and is 38% and 9.3 kb smaller than pSN-PPV. Purified plasmids from two independent clones of pLX-PPV (In, #A and #B) were EcoRI digested and resolved by agarose gel (FIG. 5B). Compared to the pSN-PPV digestion profile, pLX-PPV clones showed all the bands corresponding to the viral cDNA cassette of pSN-PPV. High molecular weight DNA bands were consistent with differences in the pSN-PPV and pLX-PPV backbones, pBIN19 and pLX-B2, respectively. The new pLX-PPV #A and #B clones (pLX-PPV, In) were transformed in *E. coli* cells to evaluate the plasmid stability. For each transformation, eight individual colonies were picked and subjected to six growth cycles (24 h, 37° C.). Purified plasmids were digested with EcoRI and resolved by agarose gel electrophoresis (pLX-PPV, Out; FIG. 5B). The pLX-PPV plasmid showed no instability, since digestion profiles of the input and output plasmids were identical.

To further confirm the results, the entire cDNA sequence from a different RNA virus was obtained from a pUC-based vector, p35Tunos-vec01-NAT1, which contains the cauliflower mosaic virus 35S promoter, a cDNA copy of the turnip mosaic virus (TuMV) genome and the nopaline synthase terminator ($P_{35S}$:TuMV:$T_{nos}$) sequences (Touriño A., et al., Span. J. Agric. Res. 2008, 6, 48-58). The p35Tunos-vec01-NAT1 vector cannot replicate in *A. tumefaciens*, and does not include T-DNA borders for its transformation to plants. The inventors generated pLX-TuMV (SEQ ID NO: 28), a pLX-B2 derivative with the $P_{35S}$:TuMV:$T_{nos}$ cassette from p35Tunos-vec01-NAT1 (FIG. 5C). The pLX-TuMV vector (SEQ ID NO: 28) obtained as disclosed above, is only slightly larger (3%, and 0.4 kb) than p35Tunos-vec01-NAT1, but includes the pBBR1 origin (SEQ ID NO: 105) and T-DNA borders suitable for its delivery to plants by *Agrobacterium*-mediated transformation. The new pLX-TuMV vector (SEQ ID NO: 28) (pLX-TuMV, In) was transformed in *E. coli* cells to evaluate the plasmid stability. For each transformation, ten individual colonies were picked and subjected to six growth cycles (24 h, 37° C.). Purified plasmids were digested with EcoRI and resolved by agarose gel electrophoresis (pLX-TuMV, Out; FIG. 5D). In agreement with the pLX-PPV results, the newly generated pLX-TuMV plasmid showed no instability, since digestion profiles of the input and output plasmids were identical.

The present example shows that pLX vectors of the present invention can host >10 kb T-DNA cassettes, and that they can be used to generate clones that contain viral genome sequences. cDNA copies of RNA virus genomes have been reported to cause plasmid instability and loss of partial or entire insert sequences. In contrast, the pLX vectors that host cDNA genome copies of plant RNA viruses showed no instability when propagated in the bacterium *E. coli.*

Example 4. Viral Agro-Inoculation and Delivery of Exogenous Sequences to Plants Using pLX-Based Viral Vectors The pLX-PPV (SEQ ID NO: 21) and pLX-TuMV (SEQ ID NO: 28) binary vectors from Example 3, if properly expressed in plants, would initiate an infection of a chimeric PPV or TuMV, respectively. These chimeric viruses would host in their genome the GFP coding sequence (FIG. 6A, 6E), and GFP fluorescence could be measured and visualized to confirm exogenous sequence expression in plants by viral expression vectors.

An *A. tumefaciens* strain hosting pLX-PPV (pLX) (SEQ ID NO: 21) was infiltrated to *N. benthamiana* plants; a pSN-PPV strain (pSN) (Pasin F., et al., PLoS Pathog. 2014, 10, e1003985) was used as a positive control. The PPV infection and viral accumulation were confirmed by coat protein immunoblot analyses of samples from the agro-infiltrated and upper uninoculated leaves (6 dpa and 14 dpa, respectively; FIG. 6B). The accumulation of recombinant GFP in infected plant samples was confirmed by measuring the fluorescence intensity (FIG. 6C), and by imaging of upper uninoculated leaves (FIG. 6D). To further confirm the results, an *A. tumefaciens* strain hosting pLX-TuMV (SEQ ID NO: 28) was agro-inoculated to *A. thaliana* plants. In agreement with the pLX-PPV results, the TuMV infection and viral accumulation in upper uninoculated leaf samples were confirmed by immunoblot analysis of the TuMV coat protein (FIG. 6F). Bright green fluorescence signal was detectable in inoculated plants (FIG. 6G), confirming the accumulation of recombinant GFP.

Therefore, the present example shows that the pLX binary vectors of the present invention can be used to engineer viral infectious clones and viral vectors. These can be delivered by agro-inoculation, and used to introduce exogenous sequences and express recombinant proteins into plants.

Example 5. Assembly of Transcription Units into the pLX Vectors of the Invention Using Plant Synthetic Biology Standards To demonstrate pLX vector compatibility with plant synthetic biology standards, DNA parts from public libraries were assembled into the pLX binary vectors of the present invention.

The GB1181 and GB0460 plasmids that contain standardized units for plant delivery of the kanamycin resistance (NptII) and red fluorescent protein (DsRED) genes, respectively, were obtained from a public repository (https://gbcloning.upv.es/). As disclosed above, the inventors assembled the standardized units into the pLX-B2 vector (SEQ ID NO: 3) to generate pLX-B2-NptII-DsRED (SEQ ID NO: 20) (FIG. 7A). The pLX-B2-NptII-DsRED vector (SEQ ID NO: 20) obtained is a pLX-B2 derivative with the pBBR1 origin (SEQ ID NO: 105) and two transcription units for plant expression of NptII and DsRED.

To further confirm the results, the inventors transferred the GB1108 (https://gbcloning.upv.es/) standardized units into the pLX-B2 vector (SEQ ID NO: 3) to generate pLX-B2-XT1-XT2-hCas9 (SEQ ID NO: 19) (FIG. 7B). The pLX-B2-XT1-XT2-hCas9 vector (SEQ ID NO: 19) obtained is a pLX-B2 derivative with the pBBR1 origin (SEQ ID NO: 105) and four transcription units for plant expression of NptII, a human codon-optimized *Streptococcus pyogenes* Cas9 gene (hCas9), and single-guide RNA targeting the *N. benthamiana* Niben101Scf04205Ctg025 (XT1) and Niben101Scf04551Ctg021 (XT2) endogenous genes. Details for the generation of pLX-B2-XT1-XT2-hCas9 vector are disclosed above. To improve flexibility of the binary vectors of the present invention and facilitate the reuse of assembled DNA parts, the inventors generated the pLX-B2α2 (SEQ ID NO: 10), pLX-B3Ω1 (SEQ ID NO: 11) and pLX-B3Ω2 vectors (SEQ ID NO: 12) including the GoldenBraid cloning cassettes (Sarrion-Perdigones A., et al., Plant Physiol. 2013, 162, 1618-1631) (FIG. 7C, Table 3). The pLX-B2α2 (SEQ ID NO: 10) vector is a pLX-B2 derivative with the alpha2 cloning cassette; pLX-B3Ω1 (SEQ ID NO: 11) is a pLX-B3 derivative with the omega1 cloning cassette; and pLX-B3Ω2 (SEQ ID NO: 12) is a pLX-B3 derivative with the omega2 cloning cassette; details for their generation are disclosed above. The pLX-B2α2, pLX-B3Ω1 and pLX-B3Ω2 vectors include the replication origin from the pBBR1 plasmid (SEQ ID NO: 105) and, together with the pLX-B2 plasmid of the present invention, comprise a minimal set of two alpha and two omega level cloning cassettes with convergent and divergent BsaI and BsmBI sites (Table 3). Following the GoldenBraid standards (Sarrion-Perdigones A., et al., Plant Physiol. 2013, 162, 1618-1631), these cloning cassettes allow reuse of assembled parts and building of large multigenic constructs.

Therefore, based on the pLX binary vectors described in the present invention, the inventors generated the pLX-B2α2 (SEQ ID NO: 10), pLX-B3Ω1 (SEQ ID NO: 11) and pLX-B3Ω2 (SEQ ID NO: 12) vectors (Table 3) that include cloning cassettes facilitating combinatorial assembly of pre-made DNA elements and transcription units into multigene constructs.

Example 6. Direct Cloning and Assembly of Large T-DNA Constructs into the pLX Vector Series without Intermediate Plasmids This example demonstrates that the pLX binary vectors of the present invention can be used to assemble large T-DNA constructs with no intermediate subcloning steps.

The inventors sought to use the vectors of the present invention to generate an infectious clone of the Ugandan cassava brown streak virus (UCBSV), a plant virus, since: (a) the UCBSV genome is a large RNA molecule of 9.1 kb; (b) a cDNA copy of UCBSV genome is not available in public parts libraries; (c) the cDNA copy of UCBSV genome would contain several Type IIS restriction endonuclease sites, whose removal is required for parts domestication and Golden Gate/GoldenBraid cloning; (d) mutagenesis of the UCBSV genome sequence (e.g., to remove BsaI/BsmBI sites) is not desirable, as its effects on virus viability are unknown; (e) correct assembly of the UCBSV genome into a pLX vector can be easily evaluated in plants; (f) UCBSV is a major threat to the staple food crop cassava, and an UCBSV infectious clone would have commercial applications as it facilitates screens for plant genetic resistance.

The inventors generated the pLX-UCBSV vector (SEQ ID NO: 22), a pLX-B2 derivative with a Ugandan cassava brown streak virus cDNA clone cassette ($P_{35S}$:UCBSV:$T_{nos}$), by one-step assembly of three RT-PCR fragments that spanned the entire 9.1-kb UCBSV genome (FIG. 8A). Details for the generation of the pLX-UCBSV vector are disclosed above.

An *A. tumefaciens* strain that contains pLX-UCBSV (SEQ ID NO: 22) was infiltrated to *N. benthamiana* plants. At 12 dpa, the agro-inoculated plants showed reduced height (FIG. 8B). In upper uninoculated leaves, the inventors detected filamentous particles typical of potyvirid virions (FIG. 8C), and confirmed accumulation of the UCBSV coat protein by immunoblot analysis (FIG. 8D). These results demonstrated that a cDNA copy of UCBSV was assembled into a pLX vectors to obtain pLX-UCBSV (SEQ ID NO: 22), which is an infectious clone of UCBSV that can be delivered to plants by *Agrobacterium*-mediated inoculation.

Thus, the inventors assembled large T-DNA constructs into the pLX binary vectors of the present invention and this assembly did not require the use of restriction enzymes, parts domestication, intermediate plasmids and subcloning steps.

Example 7. Comparison of a pBBR1-Based pLX Vector of the Present Invention Versus RK2 and pVS1 Binary Vectors Briefly, vectors that use the replicon from the RK2 plasmid include pBIN19, and its smaller derivatives pEAQ and pCB301 (FIG. 9). Due to its reduced size, pCB301 is classified as a mini binary vector. The pVS1 origin is used in the pPZP series, and its derivatives of the pCAMBIA and pLSU series. The pCAMBIA vectors are among those most commonly used by plant scientists (http://www.cambia.org/daisy/cambia/585.html). A pSa minimal replicon includes the ori and RepA regions. These were split and used in the pGreen/pSoup dual-plasmid system: pGreen is a T-DNA binary vector that hosts the pSa-ori sequence, and its replication in *A. tumefaciens* is not autonomous since it lacks the pSa-RepA gene. The pGreen maintenance in *A. tumefaciens* requires the simultaneous presence of the helper plasmid pSoup, which provides the pSa-RepA gene and allows replication of the pGreen binary vector (FIG. 9). On the one hand, removal of the RepA gene allowed pGreen size to be kept to a minimum, and on the other, it sacrificed plasmid replication autonomy and promoted instability under non-selective conditions.

To demonstrate that the pLX-binary vectors of the present invention can be classified as mini binary vectors and additionally are useful for driving high transient expression in plants, the inventors compared the pLX binary vectors to the binary vectors mentioned above, which are known in the art.

Firstly, backbone sizes of pLX-B2 (SEQ ID NO: 3) and of the mentioned binary vectors known in the art were compared (FIG. 9). The pBBR1-based backbone of the pLX vectors of the present invention is substantially smaller than the widely used pBIN- and pCAMBIA-based vectors (pBIN19, pCAMBIA-2300; FIG. 9). The pLX-B2 (SEQ ID NO: 3) backbone size equals to those of the pGreen-based vectors, which are not autonomous and require pSoup for their replication in *A. tumefaciens*. In contrast, the pLX vectors facilitate flexible experimental designs since their replication is autonomous in both *E. coli* and *A. tumefaciens*.

pLX-B2 (SEQ ID NO: 3) can be classified as a mini binary vector since its size is below the one of pCB301, an RK2-based vector. Although larger than pBBR1, the RK2 replicon is relatively small and has previously been used to generate autonomous, mini binary vectors. To compare the performance of the pBBR1 and RK2 replicons, the inventors replaced the pBBR1 replication module (SEQ ID NO: 105) of the pLX vectors by an RK2 minimal origin (SEQ ID NO: 106) to build pLX-R2 (SEQ ID NO: 6), pLX-R3 (SEQ ID NO: 7) and pLX-R4 (SEQ ID NO: 8). A transcription unit ($P_{35S}$:RFP:$T_{nos}$) that contains sequences of the cauliflower mosaic virus 35S promoter, RFP, and nopaline synthase terminator was inserted into the pLX-R2, pLX-R3 and pLX-R4 vectors to obtain pLX-R2-TagRFP-T (SEQ ID NO: 16), pLX-R3-TagRFP-T (SEQ ID NO: 17) and pLX-R4-TagRFP-T (SEQ ID NO: 18), respectively (FIG. 10A). Details for the generation of these vectors are disclosed above.

Transient expression of RFP in *N. benthamiana* leaves was evaluated by *A. tumefaciens*-mediated delivery of the pLX vectors including the pBBR1 (FIG. 3A) or RK2 origins (FIG. 10A). Compared to RK2, the use of the pBBR1-based pLX vectors led to significantly higher RFP accumulation in plant transient expression assays (FIG. 10B). The result was independent of the resistance genes used for plasmid selection, and did not correlate significantly with the *A. tumefaciens* fluorescence that might derive from undesired RFP accumulation in bacteria (FIG. 10B).

The pCAMBIA plasmids have the pVS1 origin, and among the most commonly used T-DNA binary vectors. To compare the pLX and pCAMBIA vectors, the inventors assembled standardized units for plant delivery of the kanamycin resistance (NptII) and red fluorescent protein (DsRED) genes into the pLX-B2 (SEQ ID NO: 3) and pCAMBIA-derived vectors to obtain pLX-B2-NptII-DsRED (SEQ ID NO: 20) and GB1686 (SEQ ID NO: 27), respectively (FIG. 7A, 10C). *Agrobacterium* strains that contain pLX-B2-NptII-DsRED (pLX) (SEQ ID NO: 20) or GB1686 (SEQ ID NO: 27) were used in transient and stable transformation of *N. benthamiana* plants. Compared to GB1686, the pLX-B2 backbone significantly enhanced the DsRED accumulation in transient expression assays. In stable transformation assays, a similar number of kanamycin-resistant plantlets that showed DsRED fluorescence were obtained (FIG. 10C). The result indicates that the pLX- and pCAMBIA-based vectors tested have equal stable transformation efficiencies (FIG. 10C).

Therefore, whereas stable transformation efficiencies of the present invention and commercially available vectors are similar, transient expression yields obtained by the use of the pBBR1-based binary vectors of the present invention are higher than those obtained by use of the RK2- and pVS1-based binary vectors.

Example 8. CRISPR/Cas Delivery and High Efficiency of Plant Genome Editing Using the pLX Vector Series of the Present Invention To demonstrate that the binary vectors of the present invention can be used for CRISPR/Cas construct delivery and targeted genome mutagenesis, transient expression of components of a CRISPR/Cas system was evaluated. The pLX-B2-XT1-XT2-hCas9 (pLX) (SEQ ID NO: 19) vector and GB1108, a pCAMBIA-derived vector that has the pVS1 origin and comprises transcription units identical to those of pLX-B2-XT1-XT2-hCas9 (SEQ ID NO: 19) were delivered to *N. benthamiana* leaves by *A. tumefaciens* (FIG. 7C, 11A). The hCas9 gene was delivered with no sgRNA sequences as a control (CTRL). In infiltrated samples, BsmBI- and SpeI-site loss was predicted to occur in the XT1 and XT2 edited loci, respectively. The mutagenesis was confirmed by the appearance of cleavage-resistant bands in PCR/digestion assays (FIG. 11B). Compared to pDGB3, and consistent with the DsRED transient expression results, the pLX vector showed greater mutagenesis efficiency (FIG. 11B).

Therefore, genome mutagenesis obtained by the binary vectors of the present invention is higher than that obtained by use of a pVS1-based binary vector.

Example 9. Multiplexing of T-DNA Binary Vectors Using the pLX Vector Series of the Present Invention To demonstrate that the vectors generated in Example 1 can be multiplexed with compatible T-DNA binary vectors into *A. tumefaciens* cells and delivered to plants, the inventors designed the pLX-Z4 plasmid (SEQ ID NO: 9). pLX-Z4 is a novel T-DNA vector of low sequence similarity, and compatible with the pLX-B2 (SEQ ID NO: 3) and pLX-B3 (SEQ ID NO: 4) plasmids (FIG. 12, Table 3). pLX-B4 (SEQ ID NO: 5) and pLX-Z4 (SEQ ID NO: 9) are not compatible, since their selection relies on the same antibiotic, gentamicin. Additional features of pLX-Z4 (SEQ ID NO: 9) include small size, autonomous replication, and compatibility with Type IIS endonuclease-based and overlap-dependent cloning. The pLX-Z4 obtained as disclosed above is an improved pLX-R4 derivative with the T-DNA_2 cassette (SEQ ID NO: 2), and no BsmBI sites in the RK2-trfA and aacC1 genes. It incorporates the RK2 replication origin (SEQ ID NO: 107), lambda phage terminators (λ T1, SEQ ID NO: 110; and λ T2, SEQ ID NO: 111), and T-DNA border sequences from a succinamopine-type pTi, pTiBo542, and a second left border sequence (FIG. 12A). For cloning purposes, the pLX-Z4 T-DNA cassette includes the lacZα reporter, divergent BsaI and convergent BsmBI sites, and primer annealing regions with no sequence similarity and secondary structures and that allow the backbone linearization by inverse PCR. pLX-B2 (SEQ ID NO: 3) shows minimal sequence similarity with the pLX-Z4 backbone (SEQ ID NO: 9) (FIG. 12B). More extensive sequence analyses predicted that the pBBR1-based pLX vectors described in Examples 1 and 5 could be multiplexed with pLX-Z4, and a wide array of binary vectors commonly used by plant scientists (FIG. 12C).

To facilitate vector multiplexing, the inventors characterized a disarmed *A. tumefaciens* strain (C58C1-313) that is sensitive to antibiotics commonly used in the plasmid selection: C58C1-313 growth is inhibited by the presence of ampicillin, chloramphenicol, gentamicin, tetracycline, kanamycin, or spectinomycin (FIG. 13A). A pTi-repB fragment was amplified from the C58C1-313 cells using the 2050_F (SEQ ID NO: 30)/2051_R (SEQ ID NO: 31) primers, and sequenced. Phylogenetic analysis showed that C58C1-313 hosts an octopine-type Ti plasmid, which is stably retained (FIG. 13B, C). Thus, C58C1-313 is a disarmed *A. tumefaciens* strain of the octopine type that is suitable for the simultaneous use of multiple plasmids, since it shows sensitivity to several antibiotics. To confirm the results, the C58C1-313 strain was sequentially transformed with the pLX-B2 and pLX-Z4 derivatives disclosed in the present invention, which include, respectively, the pBBR1 origin (SEQ ID NO: 105) and the kanamycin resistance gene or the RK2 origin (SEQ ID NO: 107) and the gentamicin resistance gene (FIG. 13D). A C58C1-313 strain that simultaneously hosts the pLX-B2 and pLX-Z4 derivatives showed resistance to kanamycin and gentamicin, and grew in a medium supplemented with these antibiotics (FIG. 13D). In the same conditions, growth of C58C1-313, a strain that harbors no vectors, was inhibited (CTRL; FIG. 13D).

In Example 2, the pLX-B2-$P_{CRC}$:mTFP1 vector (SEQ ID NO: 23) including the pBBR1 origin (SEQ ID NO: 105), and kanamycin resistance was used to drive seed expression of the cyan fluorescent mTFP1. Under epifluorescence stereoscopes, cyan and red fluorescence can be imaged with no signal overlap. The inventors generated the pSN.5-$P_{PAP85}$:RFP vector (SEQ ID NO: 26) (FIG. 14A), a pCAMBIA derivative with the pVS1 origin, spectinomycin resistance and a transcription unit ($P_{PAP85}$:RFP:$T_{nos}$) that contains an *A. thaliana* seed-specific promoter from a seed storage protein gene (PAP85; λT3G22640), RFP and nopaline synthase terminator sequences. Details for the generation of the pSN.5-$P_{PAP85}$:RFP vector are disclosed above.

To show that vectors of the present invention (Example 1) can be multiplexed with commercially available binary vectors, the inventors used a two-vector/one-strain system to transform *A. thaliana*. The pLX-B2-$P_{CRC}$:mTFP1 (SEQ ID NO: 23) and pSN.5-$P_{PAP85}$:RFP (SEQ ID NO: 26) T-DNA binary vectors were inserted in *A. tumefaciens* C58C1-313 (FIG. 14A), and transformed into plants by floral dipping. Consistent with the Example 2 results and the mTFP1 expression, cyan fluorescence was detectable in seed collected from the *Agrobacterium*-treated plants (FIG. 14B); 53% of the mTFP1-expressing seeds also showed red fluorescence derived by RFP expression (FIG. 14B).

These results indicate that the binary vectors of the present invention can be multiplexed with compatible vectors, and used in a two-vector/one-strain system to deliver multiple and diverse T-DNA cassettes to plant cells.

Example 10. Gene Expression Control and Delivery of Synthetic Circuit Components to Plants by Multiplexing of Binary Vectors The inventors used a chemical expression switch to test whether the binary vectors of the present invention and the multiplexing strategy described in Example 9 could be applied to deliver synthetic circuit components to plants and to regulate gene expression. Ethanol was chosen as a chemical inducer of the expression switch because of its potential in fundamental research and commercial biotechnology applications.

$P_{EtOH}$ (SEQ ID NO: 35), a novel synthetic promoter that is activated by *Aspergillus nidulans* AlcR in the presence of ethanol, was designed. The $P_{EtOH}$ promoter (SEQ ID NO: 35) includes multiple AlcR DNA-binding sites derived from the *A. nidulans* alcM, alcR, aldA, alcA promoters, and a figwort mosaic virus 34S minimal promoter (FIG. 15A). An ethanol-responsive buffer gate was designed to sense ethanol as the input, and to produce a bright green fluorescent protein (NEON, output; FIG. 15B). To evaluate the two-vector/one-bacterial strain system for the delivery of synthetic circuit components, the gate elements were distributed into the gentamicin-selectable pLX-Z4-$P_{mas}$:RFP-AlcR (SEQ ID NO: 24) and the kanamycin-selectable pLX-B2-$P_{EtOH}$:NEON (SEQ ID NO: 25) vectors, which have the RK2 and pBBR1 origins respectively (FIG. 15C). pLX-Z4-$P_{mas}$:RFP-AlcR (SEQ ID NO: 24) codes for RFP (used as an expression control) and the *A. nidulans* AlcR transcription factor under the mannopine synthase promoter ($P_{mas}$), which directs constitutive expression in plants; whereas pLX-B2-$P_{EtOH}$:NEON (SEQ ID NO: 25) encodes the NEON sequence under $P_{EtOH}$, a synthetic promoter activated by AlcR in the presence of the inducer (FIG. 15C). Details for the vector generation are disclosed above.

The plasmids were introduced sequentially into *A. tumefaciens* C58C1-313, and selected using a gentamicin plus kanamycin medium to obtain the R-AlcR+$P_{EtOH}$:NEON strain. The R-AlcR+$P_{EtOH}$:NEON strain was infiltrated into *N. benthamiana* leaves, and plants were treated with water or ethanol. As anticipated, while the RFP fluorescence was visible in both conditions, the NEON fluorescence was significantly increased in the presence of the gate inducer (FIG. 16A). Circuit modeling requires quantitative characterization of genetic parts. To test whether the two-vector/one-strain expression system is compatible with medium-throughput analyses, leaf disks were collected from the R-AlcR+$P_{EtOH}$:NEON-infiltrated leaves, and placed in 96-well plates to evaluated the gate responses. At 24 h post-treatment (hpt), the gate function was maintained in leaf disks, since the NEON fluorescence was detected only in the presence of the gate input (FIG. 16B). Quantification of the output fluorescence intensity in intact leaf disks showed appropriate gate responsiveness and sensitivity, since 0.1% ethanol was sufficient to trigger >200-fold induction (FIG. 16C). NEON detection requires no lysis or substrate addition steps, which allowed measuring the gate kinetics in a continuous-read assay. In the conditions tested and compared to the water control, the ratio of NEON/RFP fluorescence intensity was significantly increased at 1.5 hpt and reached a plateau at 15 hpt (FIG. 16D).

The results show that the pBBR1-based and RK2-based pLX binary vectors of the present invention can be used to control gene expression in plants, and be coupled in a two-plasmid/one-strain system to allow multiple T-DNA delivery from *A. tumefaciens*. The binary vector system of the present invention is suitable for delivery of genetic circuit components, and their quantitative characterization in a medium-throughput scale.

The invention claimed is:

1. A binary vector comprising a nucleic acid sequence comprising in this order:

(a) a T-DNA right border comprising a nucleotide sequence selected from the group consisting of SEQ ID NO: 102 and SEQ ID NO: 115; and (b) a sequence portion connecting item (a) with the following item (c); and (c) a bacterial terminator; and (d) an origin of replication that is functional in at least one bacterial species; and (e) a bacterial terminator; and (f) a sequence portion connecting item (e) with the following item (g); and (g) a T-DNA left border comprising a nucleotide sequence selected from the group consisting of SEQ ID NO: 103, SEQ ID NO: 104 and SEQ ID NO: 116; and wherein the bacterial terminator comprises a nucleotide sequence selected from the group consisting of SEQ ID NO: 108, SEQ ID NO: 109, SEQ ID NO: 110 and SEQ ID NO: 111; and wherein the sequence of item (b) and item (f) has a size of less than 200 nucleotides.

2. A binary vector according to claim 1, wherein the origin of replication comprises a nucleotide sequence selected from the group consisting of SEQ ID NO: 105, SEQ ID NO: 106, and SEQ ID NO: 107.

3. A binary vector according to claim 2 comprising a nucleotide sequence selected from the group consisting of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, and SEQ ID NO: 28.

4. A method for obtaining a binary vector comprising at least one nucleotide sequence of interest, said method comprising operably linking at least one nucleotide sequence of interest to the sequence of at least one binary vector according to claim 1.

5. A binary vector obtained from the method according to claim 4.

6. A host cell comprising one or more binary vector(s) according to claim 1.

7. A method for delivering at least one nucleotide sequence of interest in at least one eukaryotic cell or organism comprising:

(a) operably linking at least one nucleotide sequence of interest to the sequence of at least one binary vector according to claim 1; and (b) contacting with or introducing into at least one eukaryotic cell or organism the item obtained from step (a); or (c) introducing the item obtained from step (a) into a host cell, and contacting with or introducing into at least one eukaryotic cell or organism the obtained host cell.

8. A eukaryotic cell or organism, regenerated cell, regenerated organism, progeny or seed obtainable by the method according to claim 7.

9. A kit comprising:

(a) a binary vector according to claim 1; and (b) instructions for using the kit.

10. A kit comprising:

(a) the host cell according to claim 6; and (b) instructions for using the kit.

11. A binary vector system comprising:

(a) a binary vector according to claim 1; and (b) one or more binary vector(s).

12. A binary vector system comprising:

(a) a first binary vector comprising an origin of replication comprising the nucleotide sequence of SEQ ID NO: 105; and (b) a second binary vector comprising an origin of replication comprising a nucleotide sequence selected from the group consisting of SEQ ID NO: 106 and SEQ ID NO: 107; and wherein item (a) and item (b) further comprise a T-DNA right border comprising a nucleotide sequence selected from the group consisting of SEQ ID NO: 102 and SEQ ID NO: 115; and a T-DNA left border comprising a nucleotide sequence selected from the group consisting of SEQ ID NO: 103, SEQ ID NO: 104 and SEQ ID NO: 116.

13. A binary vector system according to claim 12 comprising:

(a) a first binary vector comprising a nucleotide sequence selected from the group consisting of SEQ ID NO: 3, SEQ ID NO: 4, SEQ ID NO: 5, SEQ ID NO: 10, SEQ ID NO: 11, SEQ ID NO: 12, SEQ ID NO: 13, SEQ ID NO: 14, SEQ ID NO: 15, SEQ ID NO: 19, SEQ ID NO: 20, SEQ ID NO: 21, SEQ ID NO: 22, SEQ ID NO: 23, SEQ ID NO: 25 and SEQ ID NO: 28; and (b) a second binary vector comprising a nucleotide sequence selected from the group consisting of SEQ ID NO: 6, SEQ ID NO: 7, SEQ ID NO: 8, SEQ ID NO: 9, SEQ ID NO: 16, SEQ ID NO: 17, SEQ ID NO: 18 and SEQ ID NO: 24.

14. A method for obtaining a binary vector system comprising at least one nucleotide sequence of interest, said method comprising operably linking at least one nucleotide sequence of interest to the sequence of at least one binary vector of the binary vector system according to claim 12.

15. A binary vector system obtained from the method according to claim 14.

16. A host cell comprising the binary vector system according to claim 12.

17. A method for delivering at least one nucleotide sequence of interest in at least one eukaryotic cell or organism comprising:

(a) operably linking at least one nucleotide sequence of interest to the sequence of at least one binary vector of the binary vector system according to claim 12; and (b) contacting with or introducing into at least one eukaryotic cell or organism the item obtained from step (a); or (c) introducing the item obtained from step (a) into a host cell, and contacting with or introducing into at least one eukaryotic cell or organism the obtained host cell.

18. A eukaryotic cell or organism, regenerated cell, regenerated organism, progeny or seed obtainable by the method according to claim 17.

19. A kit comprising:

(a) a binary vector system according to claim 12; and (b) instructions for using the kit.

20. A kit comprising:

(a) the host cell according to claim 16; and (b) instructions for using the kit.

* * * * *

SEQUENCE LISTING

```
Sequence total quantity: 116
SEQ ID NO: 1            moltype = DNA  length = 814
FEATURE                 Location/Qualifiers
misc_feature            1..814
                        note = Synthetic T_DNA_1 cassette
misc_feature            73..221
                        note = T-DNA border
primer_bind             241..259
                        note = Annealing region of Gibson assembly primer X210_R
misc_binding            253..258
                        bound_moiety = BsmBI binding site
                        note = BsmBI binding site
misc_binding            265..270
                        bound_moiety = BsaI binding site
                        note = BsaI binding site
gene                    299..475
                        note = LacZ alpha
misc_binding            580..585
                        bound_moiety = BsaI binding site
                        note = BsaI binding site
primer_bind             591..610
                        note = Annealing region of Gibson assembly primer X211_F
misc_binding            596..601
                        bound_moiety = BsmBI binding site
                        note = BsmBI binding site
misc_feature            629..740
                        note = T-DNA border
source                  1..814
                        mol_type = other DNA
                        organism = synthetic construct
regulatory              25..72
                        note = Bacterial transcriptional terminators
                        regulatory_class = terminator
regulatory              741..781
                        note = Bacterial transcriptional terminators
                        regulatory_class = terminator
SEQUENCE: 1
ccatcatcag ttcggtggtc ttccgacgaa caataaggcc gcaaatcgcg gccttttta  60
ttgataacaa aaccggctca gttctgcgta gaaaccaaca tgcaagctcc accgggtgca  120
aagcggcagc ggcggcagga tatattcaat tgtaaatggc ttcatgtccg ggaaatctac  180
tggtggcagg atatattgtg gtgtaaacaa tggagaaaaa gattaattaa gtactagtag  240
cctggtcgaa accgtctcag gagagagacc aaaagcaaaa acccgccgaa gcgggttact  300
agcgccattc gccattcaga gagcggagct gctgcgacgg acgatcggta cgcgcctctt  360
cgctattacg ccaactggcg aaaggtggat gtgctgcaag gcgattaagt tgggtaacgc  420
cagggttttc ccagtcacga cgttgtagta ccacggcaag gctatctgta atcattgttg  480
tactccggtt aggacggatt gggaactggc taactcaaaa tccacacatt atacgagccg  540
gaagcataaa gtgtaaagcc tggggtgcct aatgagtgag gtctctcgct gtcaggagac  600
gggacaagga tgcgagctag cctgcaggaa ttgttgattt tgtgatgact gatggcagga  660
tatatgcggt tgtaattcat ttttattgtc taaatttctg tatttgtttg tttgttcggt  720
tgtaaatttt tttggaagaa caagaaaaga aaaaacaccc gttagggtgt ttttagttag  780
tgtggcgcgc cgacttgcga catgcggtcc tttg                             814

SEQ ID NO: 2            moltype = DNA  length = 750
FEATURE                 Location/Qualifiers
misc_feature            1..750
                        note = Synthetic T_DNA_2 cassette
regulatory              37..68
                        note = Bacterial transcriptional terminator
                        regulatory_class = terminator
misc_feature            69..156
                        note = T-DNA border
primer_bind             169..187
                        note = Annealing region of Gibson assembly primer X210_R
misc_binding            181..186
                        bound_moiety = BsmBI binding site
                        note = BsmBI binding site
misc_binding            193..198
                        bound_moiety = BsaI binding site
                        note = BsaI binding site
gene                    227..403
                        note = LacZ alpha
misc_binding            508..513
                        bound_moiety = BsaI binding site
                        note = BsaI binding site
primer_bind             519..538
                        note = Annealing region of Gibson assembly primer X211_F
misc_binding            524..529
                        bound_moiety = BsmBI binding site
```

-continued

```
                         note = BsmBI binding site
misc_feature             551..666
                         note = T-DNA border
regulatory               667..719
                         note = Bacterial transcriptional terminator
                         regulatory_class = terminator
source                   1..750
                         mol_type = other DNA
                         organism = synthetic construct
SEQUENCE: 2
aaaaggatct caagaagatc ctttgatctt ttctacaggc ctgctggtaa tcgcaggcct  60
ttttattttg gcaggatata ttgtggtgta aacacttacc gcacctctgc agcagcggca  120
ggatatatgg cagtgtaaac tccattttcg aacgcgttaa ttaagtagcc tggtcgaaac  180
cgtctcagga gagagaccaa aagcaaaaac ccgccgaagc gggttactag cgccattcgc  240
cattcagaga gcggagctgc tgcgacggac gatcggtacg cgcctcttcg ctattacgcc  300
aactggcgaa aggtggatgt gctgcaaggc gattaagttg ggtaacgcca gggttttccc  360
agtcacgacg ttgtagtacc acggcaaggc tatctgtaat cattgttgta ctccggttag  420
gacggattgg gaactggcta actcaaaatc cacacattat acgagccgga agcataaagt  480
gtaaagcctg gggtgcctaa tgagtgaggt ctctcgctgt caggagacgg gacaaggatg  540
cgcctgcagg ttgttgatga tgtgatgact gatggcagga tatatgtggt tgtaattcat  600
ttctaccgtg taatttactg tatttttttg tttgttcgtt cgtttgtaaa aatatttttt  660
ggaagcaaaa aattagcgca agaagacaaa aatcaccttg cgctaatgct ctgttacagg  720
cgcgccaatt tacccaacaa ctccgcggcc                                    750

SEQ ID NO: 3             moltype = DNA  length = 3287
FEATURE                  Location/Qualifiers
misc_feature             1..3287
                         note = pLX-B2
source                   1..3287
                         mol_type = other DNA
                         organism = synthetic construct
SEQUENCE: 3
ccatcatcag ttcggtggtc ttccgacgaa caataaggcc gcaaatcgcg gccttttta  60
ttgataacaa aaccggctca gttctgcgta gaaaccaaca tgcaagctcc accgggtgca  120
aagcggcagc ggcggcagga tatattcaat tgtaaatggc ttcatgtccg ggaaatctac  180
tggtggcagg atatattgtg gtgtaaacaa tggagaaaaa gattaattaa gtactagtag  240
cctggtcgaa accgtctcag gagagagacc aaaagcaaaa acccgccgaa gcgggttact  300
agcgccattc gccattcaga gagcggagct gctgcgacgg acgatcggta cgcgcctctt  360
cgctattacg ccaactggcg aaaggtggat gtgctgcaag gcgattaagt tgggtaacgc  420
cagggttttc ccagtcacga cgttgtagta ccacggcaag gctatctgta atcattgttg  480
tactccggtt aggacggatt gggaactggc taactcaaaa tccacacatt atacgagccg  540
gaagcataaa gtgtaaagcc tggggtgcct aatgagtgag gtctctcgct gtcaggagac  600
gggacaagga tgcgagctag cctgcaggaa ttgttgattt tgtgatgact gatggcagga  660
tatatgcggt tgtaattcat ttttattgtc taaatttctg tatttgtttg tttgttcggt  720
tgtaaatttt tttggaagaa caagaaaaga aaaaacaccc gttagggtgt ttttagttag  780
tgtggcgcgc cgacttgcga catgcggtcc tttgcaatca actattagaa aaattcatcc  840
agcatcagat gaaattgcag tttgttcata tccggattat caatgccata tttctgaaac  900
agacgttttt gcaggctcgg gctaaattcg cccaggcagt tccacagaat ggccagatcc  960
tgataacgat ccgcaatgcc cacacggccc acatcaatgc agccaatcag tttgccttca  1020
tcgaaaatca ggttatccag gctaaaatcg ccgtgggtca ccacgctatc cgggctaaac  1080
ggcagcagtt tatgcatttc tttccacacc tgttccaccg gccagccgtt acgttcatca  1140
tcaaaatcgc tcgcatccac caggccgttg ttcatacggc tctgcgcctg ggccagacga  1200
aacacacgat cgctgttaaa cgggcagttg cacaccggaa tgctatgcag acgacgcaga  1260
aacacggcca gcgcatccac aatgttttcg ccgctatccg gatattcttc cagcacctga  1320
aacgcggttt tgcccggaat cgcggtggtc agcagccacg catcatccgg ggtgcgaata  1380
aaatgtttaa tggtcggcag cggcataaat tcggtcagcc agttcagacg caccatttca  1440
tcggtcacat cgttcgccac gctgcctttg ccatgtttca gaaacagttc cggcgcatcc  1500
ggtttgccat acagacgata aatggtcgcg ccgctctgac ccacgttatc acgcgcccat  1560
ttatagccat acagatccgc atccatgttg ctgttcagac gcggacggct acagctcgtt  1620
tcacgctgaa tatggctcat aacacccctt gtattactgt ttatgtaagc agacagtttt  1680
attgttcatg atgatatatt tttatcttgt gcaatgtaac atcagagatt ttgagacaca  1740
agatcggatt ggcggttatg cggttctacc ggcgcggcag cgttacccgt gtcggcggct  1800
ccaacggctc gccatcgtcc agaaaacacg gctcatcggg catcggcagg cgctgctgcc  1860
cgcgccgttc ccattcctcc gtttcggtca aggctggcag gtctggttcc atgcccggaa  1920
tgccgggctg gctgggcggc tcctcgccgg ggccggtcgg tagttgctgc tcgcccggat  1980
acagggtcgg gatgcggcgc aggtcgccat gccccaacag cgattcgtcc tggtcgtcgt  2040
gatcaaccac cacggcggca ctgaacaccg acaggcgcaa ctggtcgcgg ggctggcccc  2100
acgccacgcg gtcattgacc acgtaggccg acacggtgcc ggggccgttg agcttcacga  2160
cggagatcca gcgctcggcc accaagtcct tgactgcgta ttggaccgtc cgcaaagaac  2220
gtccgatgag cttggaaagt gtcttctggc tgaccaccac ggcgttctgg tggcccatct  2280
gcgccacgag gtgatgcagc agcattgccg ccgtgggttt cctcgcaata agcccggccc  2340
acgcctcatg cgctttgcgt tccgtttgca cccagtgacc gggcttgttc ttggcttgaa  2400
tgccgatttc tctggactgc gtggccatgc ttatctccat gcggtagggg tgccgcacgg  2460
ttgcggcacc atgcgcaatc agctgcaact tttcggcagc gcgacaacaa ttatgcgttg  2520
cgtaaaagtg gcagtcaatt acagattttc tttaacctac gcaatgagct attgcggggg  2580
gtgccgcaat gagctgttgc gtacccccct tttttaagtt gttgattttt aagtctttcg  2640
catttcgccc tatatctagt tctttggtgc ccaaagaagg gcacccctgc ggggttcccc  2700
cacgccttcg gcgcggctcc ccctccggca aaaagtggcc cctccggggc ttgttgatcg  2760
actgcgcggc cttcggcctt gcccaaggtg gcgctgcccc cttggaaccc ccgcactcgc  2820
```

-continued

```
cgccgtgagg ctcgggggc aggcgggcgg gcttcgccct tcgactgccc ccactcgcat  2880
aggcttgggt cgttccaggc gcgtcaaggc caagccgctg cgcggtcgct gcgcgagcct  2940
tgacccgcct tccacttggt gtccaaccgg caagcgaagc gcgcaggccg caggccggag  3000
gcttttcccc agagaaaatt aaaaaaattg atggggcaag gccgcaggcc gcgcagttgg  3060
agccggtggg tatgtggtcg aaggctgggt agccggtggg caatccctgt ggtcaagctc  3120
gtgggcaggc gcagcctgtc catcagcttg tccagcaggg ttgtccacgg gccgagcgaa  3180
gcgagccagc cggtggccgc tcgcggccat cgtccacata tccacgggct ggcaagggag  3240
cgcagcgacc gcgcagggcg aagcccggag agcaagcccg taggggg               3287

SEQ ID NO: 4           moltype = DNA  length = 3349
FEATURE                Location/Qualifiers
misc_feature           1..3349
                       note = pLX-B3
source                 1..3349
                       mol_type = other DNA
                       organism = synthetic construct
SEQUENCE: 4
ccatcatcag ttcggtggtc ttccgacgaa caataaggcc gcaaatcgcg gcctttttta  60
ttgataacaa aaccggctca gttctgcgta gaaaccaaca tgcaagctcc accgggtgca  120
aagcggcagc ggcggcagga tatattcaat tgtaaatggc ttcatgtccg ggaaatctac  180
tggtggcagg atatattgtg gtgtaaacaa tggagaaaaa gattaattaa gtactagtag  240
cctggtcgaa accgtctcag gagagagacc aaaagcaaaa acccgccgaa gcgggttact  300
agcgccattc gccattcaga gagcggagct gctgcgacgg acgatcggta cgcgcctctt  360
cgctattacg ccaactggcg aaaggtggat gtgctgcaag gcgattaagt tgggtaacgc  420
cagggttttc ccagtcacga cgttgtagta ccacggcaag gctatctgta atcattgttg  480
tactccggtt aggacggatt gggaactggc taactcaaaa tccacacatt atacgagccg  540
gaagcataaa gtgtaaagcc tggggtgcct aatgagtgag gtctctcgct gtcaggagac  600
gggacaagga tgcgagctag cctgcaggaa ttgttgattt tgtgatgact gatggcagga  660
tatatgcggt tgtaattcat ttttattgtc taaatttctg tatttgtttg tttgttcggt  720
tgtaaatttt tttggaagaa caagaaaaga aaaaacaccc gttagggtgt ttttagttag  780
tgtggcgcgc cgacttgcga catgcggtcc tttgttattt gccgactacc ttggtgatct  840
cgcctttcac gtagtggaca aattcttcca actgatctgc gcgcgaggcc aagcgatctt  900
cttcttgtcc aagataagcc tgtctagctt caagtatgac gggctgatac tgggccggca  960
ggcgctccat tgcccagtcg gcagcgacat ccttcggcgc gattttgccg gttactgcgc  1020
tgtaccaaat gcgggacaac gtaagcacta catttcgctc atcgccagcc cagtcgggcg  1080
gcgagttcca tagcgttaag gtttcattta gcgcctcaaa tagatcctgt tcaggaaccg  1140
gatcaaagag ttcctccgcc gctggaccta ccaaggcaac gctatgttct cttgcttttg  1200
tcagcaagat agccagatca atgtcgatcg tggctggctc gaagatacct gcaagaatgt  1260
cattgcgctg ccattctcca aattgcagtt cgcgcttagc tggataacgc cacggaatga  1320
tgtcgtcgtg cacaacaatg gtgacttcta cagcgcggag aatctcgctc tctccagggg  1380
aagccgaagt ttccaaaagg tcgttgatca aagctcgccg cgttgtttca tcaagcctta  1440
cggtcaccgt aaccagcaaa tcaatatcac tgtgtggctt caggccgcca tccactgcgg  1500
agccgtacaa atgtacggcc agcaacgtcg gttcgagatg gcgctcgatg acgccaacta  1560
cctctgatag ttgagtcgat acttcggcga tcaccgcttc cctcatgatg tttaactttg  1620
ttttagggcg actgccctgc tgcgtaacat cgttgctgct ccataacatc aaacatcgac  1680
ccacggcgta acgcgcttgc tgcttggatg cccgaggcat agactgtacc ccaaaaaaac  1740
agtcataaca agccatgaaa accgccactg cgccgttacc accgctgcgt tcggtcaagg  1800
ttcgatcgga ttggcggtta tgcggttcta ccggcgcggc agcgttaccc gtgtcggcgg  1860
ctccaacggc tcgccatcgt ccagaaaaca cggctcatcg ggcatcggca ggcgctgctg  1920
cccgcgccgt tcccattcct ccgtttcggt caaggctggc aggtctggtt ccatgcccgg  1980
aatgccgggc tggctgggcg gctcctcgcc ggggccggtc ggtagttgct gctcgcccgg  2040
atacagggtc gggatgcggc gcaggtcgcc atgccccaac agcgattcgt cctggtcgtc  2100
gtgatcaacc accacggcgg cactgaacac cgacaggcgc aactggtcgc ggggctggcc  2160
ccacgccacg cggtcattga ccacgtaggc cgacacggtg ccggggccgt tgagcttcac  2220
gacggagatc cagcgctcgg ccaccaagtc cttgactgcg tattggaccg tccgcaaaga  2280
acgtccgatg agcttggaaa gtgtcttctg gctgaccacc acggcgttct ggtggcccat  2340
ctgcgccacg aggtgatgca gcagcattgc cgccgtgggt ttcctcgcaa taagcccggc  2400
ccacgcctca tgcgctttgc gttccgtttg cacccagtga ccgggcttgt tcttggcttg  2460
aatgccgatt tctctggact gcgtggccat gcttatctcc atgcggtagg ggtgccgcac  2520
ggttgcggca ccatgcgcaa tcagctgcaa cttttcggca gcgcgacaac aattatgcgt  2580
tgcgtaaaag tggcagtcaa ttacagattt tctttaacct acgcaatgag ctattgcggg  2640
gggtgccgca atgagctgtt gcgtaccccc ctttttaag ttgttgattt ttaagtcttt  2700
cgcatttcgc cctatatcta gttctttggt gcccaaagaa gggcacccct gcggggttcc  2760
cccacgcctt cggcgcggct cccccctccgg caaaaagtgg cccctccggg gcttgttgat  2820
cgactgcgcg gccttcggcc ttgcccaagg tggcgctgcc cccttggaac ccccgcactc  2880
gccgccgtga ggctcggggg gcaggcgggc gggcttcgcc cttcgactgc cccccactcgc  2940
ataggcttgg gtcgttccag gcgcgtcaag gccaagccgc tgcgcggtcg ctgcgcgagc  3000
cttgacccgc cttccacttg gtgtccaacc ggcaagcgaa gcgcgcaggc cgcaggccgg  3060
aggcttttcc ccagagaaaa ttaaaaaaat tgatggggca aggccgcagg ccgcgcagtt  3120
ggagccggtg ggtatgtggt cgaaggctgg gtagccggtg ggcaatccct gtggtcaagc  3180
tcgtgggcag gcgcagcctg tccatcagct tgtccagcag ggttgtccac gggccgagcg  3240
aagcgagcca gccggtggcc gctcgcggcc atcgtccaca tatccacggg ctggcaaggg  3300
agcgcagcga ccgcgcaggg cgaagcccgg agagcaagcc cgtagggggg             3349

SEQ ID NO: 5           moltype = DNA  length = 3165
FEATURE                Location/Qualifiers
misc_feature           1..3165
                       note = pLX-B4
source                 1..3165
```

-continued

```
                        mol_type = other DNA
                        organism = synthetic construct
SEQUENCE: 5
ccatcatcag ttcggtggtc ttccgacgaa caataaggcc gcaaatcgcg gcctttttta  60
ttgataacaa aaccggctca gttctgcgta gaaaccaaca tgcaagctcc accgggtgca  120
aagcggcagc ggcggcagga tatattcaat tgtaaatggc ttcatgtccg ggaaatctac  180
tggtggcagg atatattgtg gtgtaaacaa tggagaaaaa gattaattaa gtactagtag  240
cctggtcgaa accgtctcag gagagagacc aaaagcaaaa acccgccgaa gcgggttact  300
agcgccattc gccattcaga gagcggagct gctgcgacgg acgatcggta cgcgcctctt  360
cgctattacg ccaactggcg aaaggtggat gtgctgcaag gcgattaagt tgggtaacgc  420
cagggttttc ccagtcacga cgttgtagta ccacggcaag gctatctgta atcattgttg  480
tactccggtt aggacggatt gggaactggc taactcaaaa tccacacatt atacgagccg  540
gaagcataaa gtgtaaagcc tggggtgcct aatgagtgag gtctctcgct gtcaggagac  600
gggacaagga tgcgagctag cctgcaggaa ttgttgattt tgtgatgact gatggcagga  660
tatatgcggt tgtaattcat ttttattgtc taaatttctg tatttgtttg tttgttcggt  720
tgtaaatttt tttggaagaa caagaaaaga aaaaacaccc gttagggtgt ttttagttag  780
tgtggcgcgc cgacttgcga catgcggtcc tttgcaattt acccaacaac tccgcggccg  840
ggaagccgat ctcggcttga acgaattgtt aggtggcggt acttgggtcg atatcaaagt  900
gcatcacttc ttcccgtatg cccaactttg tatagagagc cactgcggga tcgtcaccgt  960
aatctgcttg cacgtagatc acataagcac caagcgcgtt ggcctcatgc ttgaggagat  1020
tgatgagcgc ggtggcaatg ccctgcctcc ggtgctctcc ggagactgcg agatcataga  1080
tatagatctc actacgcggc tgctcaaact tgggcagaac gtaagccgcg agagcgccaa  1140
caaccgcttc ttggtcgaag gcagcaagcg cgatgaatgt cttactacgg agcaagttcc  1200
cgaggtaatc ggagtccggc tgatgttggg agtaggtggc tacgtctccg aactcacgac  1260
cgaaaagatc aagagcagcc cgcatggatt tgacttggtc agggccgagc ctacatgtgc  1320
gaatgatgcc catacttgag ccacctaact ttgttttagg gcgactgccc tgctgcgtaa  1380
catcgttgct gctgcgtaac atcgttgctg ctccataaca tcaaacatcg acccacggcg  1440
taacgcgctt gctgcttgga tgcccgaggc ataggctgta caaaaaaaca gtcataacaa  1500
gccatgaaaa ccgccactgc gccgttacca ccgctgcgtt cggtcaaggt tctggaccag  1560
ttgcgtgagc gcatacgcta cttgcattac agtttacgaa ccgaacaggc ttatgtcaag  1620
atcggattgg cggttatgcg gttctaccgg cgcggcagcg ttacccgtgt cggcggctcc  1680
aacggctcgc catcgtccag aaaacacggc tcatcgggca tcggcaggcg ctgctgcccg  1740
cgccgttccc attcctccgt ttcggtcaag gctggcaggt ctggttccat gcccggaatg  1800
ccgggctggc tgggcggctc ctcgccgggg ccggtcggta gttgctgctc gcccggatac  1860
agggtcggga tgcggcgcag gtcgccatgc cccaacagcg attcgtcctg gtcgtcgtga  1920
tcaaccacca cggcggcact gaacaccgac aggcgcaact ggtcgcgggg ctggccccac  1980
gccacgcggt cattgaccac gtaggccgac acggtgccgg ggccgttgag cttcacgacg  2040
gagatccagc gctcggccac caagtccttg actgcgtatt ggaccgtccg caaagaacgt  2100
ccgatgagct tggaaagtgt cttctggctg accaccacgg cgttctggtg gcccatctgc  2160
gccacgaggt gatgcagcag cattgccgcc gtgggtttcc tcgcaataag cccggcccac  2220
gcctcatgcg ctttgcgttc cgtttgcacc cagtgaccgg gcttgttctt ggcttgaatg  2280
ccgatttctc tggactgcgt ggccatgctt atctccatgc ggtaggggtg ccgcacggtt  2340
gcggcaccat gcgcaatcag ctgcaacttt tcggcagcgc gacaacaatt atgcgttgcg  2400
taaaagtggc agtcaattac agattttctt taacctacgc aatgagctat tgcggggggt  2460
gccgcaatga gctgttgcgt accccccttt tttaagttgt tgatttttaa gtctttcgca  2520
tttcgcccta tatctagttc tttggtgccc aaagaagggc acccctgcgg ggttcccccca  2580
cgccttcggc gcggctcccc ctccggcaaa aagtggcccc tccggggctt gttgatcgac  2640
tgcgcggcct tcggccttgc ccaaggtggc gctgccccct tggaaccccc gcactcgccg  2700
ccgtgaggct cggggggcag gcgggcgggc ttcgcccttc gactgccccc actcgcatag  2760
gcttgggtcg ttccaggcgc gtcaaggcca agccgctgcg cggtcgctgc gcgagccttg  2820
acccgccttc cacttggtgt ccaaccggca agcgaagcgc gcaggccgca ggccggaggc  2880
ttttccccag agaaaattaa aaaaattgat ggggcaaggc cgcaggccgc gcagttggag  2940
ccggtgggta tgtggtcgaa ggctgggtag ccggtgggca atccctgtgg tcaagctcgt  3000
gggcaggcgc agcctgtcca tcagcttgtc cagcagggtt gtccacgggc cgagcgaagc  3060
gagccagccg gtggccgctc gcggccatcg tccacatatc cacgggctgg caagggagcg  3120
cagcgaccgc gcagggcgaa gcccggagag caagcccgta ggggg                  3165

SEQ ID NO: 6            moltype = DNA  length = 3987
FEATURE                 Location/Qualifiers
misc_feature            1..3987
                        note = pLX-R2
source                  1..3987
                        mol_type = other DNA
                        organism = synthetic construct
SEQUENCE: 6
ccatcatcag ttcggtggtc ttccgacgaa caataaggcc gcaaatcgcg gcctttttta  60
ttgataacaa aaccggctca gttctgcgta gaaaccaaca tgcaagctcc accgggtgca  120
aagcggcagc ggcggcagga tatattcaat tgtaaatggc ttcatgtccg ggaaatctac  180
tggtggcagg atatattgtg gtgtaaacaa tggagaaaaa gattaattaa gtactagtag  240
cctggtcgaa accgtctcag gagagagacc aaaagcaaaa acccgccgaa gcgggttact  300
agcgccattc gccattcaga gagcggagct gctgcgacgg acgatcggta cgcgcctctt  360
cgctattacg ccaactggcg aaaggtggat gtgctgcaag gcgattaagt tgggtaacgc  420
cagggttttc ccagtcacga cgttgtagta ccacggcaag gctatctgta atcattgttg  480
tactccggtt aggacggatt gggaactggc taactcaaaa tccacacatt atacgagccg  540
gaagcataaa gtgtaaagcc tggggtgcct aatgagtgag gtctctcgct gtcaggagac  600
gggacaagga tgcgagctag cctgcaggaa ttgttgattt tgtgatgact gatggcagga  660
tatatgcggt tgtaattcat ttttattgtc taaatttctg tatttgtttg tttgttcggt  720
tgtaaatttt tttggaagaa caagaaaaga aaaaacaccc gttagggtgt ttttagttag  780
tgtggcgcgc cgacttgcga catgcggtcc tttgcaatca actattagaa aaattcatcc  840
```

-continued

```
agcatcagat gaaattgcag tttgttcata tccggattat caatgccata tttctgaaac  900
agacgttttt gcaggctcgg gctaaattcg cccaggcagt tccacagaat ggccagatcc  960
tgataacgat ccgcaatgcc cacacggccc acatcaatgc agccaatcag tttgccttca  1020
tcgaaaatca ggttatccag gctaaaatcg ccgtgggtca ccacgctatc cgggctaaac  1080
ggcagcagtt tatgcatttc tttccacacc tgttccaccg gccagccgtt acgttcatca  1140
tcaaaatcgc tcgcatccac caggccgttg ttcatacggc tctgcgcctg ggccagacga  1200
aacacacgat cgctgttaaa cgggcagttg cacaccggaa tgctatgcag acgacgcaga  1260
aacacggcca gcgcatccac aatgttttcg ccgctatccg gatattcttc cagcacctga  1320
aacgcggttt tgcccggaat cgcggtggtc agcagccacg catcatccgg ggtgcgaata  1380
aaatgtttaa tggtcggcag cggcataaat tcggtcagcc agttcagacg caccatttca  1440
tcggtcacat cgttcgccac gctgcctttg ccatgtttca gaaacagttc cggcgcatcc  1500
ggtttgccat acagacgata aatggtcgcg ccgctctgac ccacgttatc acgcgcccat  1560
ttatagccat acagatccgc atccatgttg ctgttcagac gcggacggct acagctcgtt  1620
tcacgctgaa tatggctcat aacacccctt gtattactgt ttatgtaagc agacagtttt  1680
attgttcatg atgatatatt tttatcttgt gcaatgtaac atcagagatt ttgagacaca  1740
agatcggatt ggcggttatg cggttgcgat gcaggtggct gctgaacccc cagccggaac  1800
tgaccccaca aggccctagc gtttgcaatg caccaggtca tcattgaccc aggcgtgttc  1860
caccaggccg ctgcctcgca actcttcgca ggcttcgccg acctgctcgc gccacttctt  1920
cacgcgggtg gaatccgatc cgcacatgag gcggaaggtt tccagcttga gcgggtacgg  1980
ctcccggtgc gagctgaaat agtcgaacat ccgtcgggcc gtcggcgaca gcttgcggta  2040
cttctcccat atgaatttcg tgtagtggtc gccagcaaac agcacgacga tttcctcgtc  2100
gatcaggacc tggcaacggg acgttttctt gccacggtcc aggacgcgga agcggtgcag  2160
cagcgacacc gattccaggt gcccaacgcg gtcggacgtg aagcccatcg ccgtcgcctg  2220
taggcgcgac aggcattcct cggccttcgt gtaataccgg ccattgatcg accagcccag  2280
gtcctggcaa agctcgtaga acgtgaaggt gatcggctcg ccgatagggg tgcgcttcgc  2340
gtactccaac acctgctgcc acaccagttc gtcatcgtcg gcccgcagct cgacgccggt  2400
gtaggtgatc ttcacgtcct tgttgacgtg gaaaatgacc ttgttttgca gcgcctcgcg  2460
cgggattttc ttgttgcgcg tggtgaacag ggcagagcgg gccgtgtcgt ttggcatcgc  2520
tcgcatcgtg tccggccacg gcgcaatatc gaacaaggaa agctgcattt ccttgatctg  2580
ctgcttcgtg tgtttcagca acgcggcctg cttggcttcg ctgacctgtt ttgccaggtc  2640
ctcgccggcg gtttttcgct tcttggtcgt catagttcct cgcgtgtcga tggtcatcga  2700
cttcgccaaa cctgccgcct cctgttcgag acgacgcgaa cgctccacgg cggccgatgg  2760
cgcgggcagg gcagggggag ccagttgcac gctgtcgcgc tcgatcttgg ccgtagcttg  2820
ctggactatc gagccgacgg actggaaggt ttcgcggggc gcacgcatga cggtgcggct  2880
tgcgatggtt tcggcatcct cggcggaaaa ccccgcgtcg atcagttctt gcctgtatgc  2940
cttccggtca aacgtccgat tcattcaccc tccttgcggg attgccccgg aattaattcc  3000
ccggatcgat ccgtcgatct tgatcccctg cgccatcaga tccttggcgg caagaaagcc  3060
atccagttta ctttgcaggg cttcccaacc ttaccagagg gcgccccagc tggcaattcc  3120
ggttcgcttg ctgtccataa aaccgcccag tctagctatc gccatgtaag cccactgcaa  3180
gctacctgct ttctctttgc gcttgcgttt tcccttgtcc agatagccca gtagctgaca  3240
ttcatccggg gtcagcaccg tttctgcgga ctggctttct acgtggctgc catttttggg  3300
gtgaggccgt tcgcggccga ggggcgcagc ccctgggggg atgggaggcc cgcgttagcg  3360
ggccgggagg gttcgagaag ggggggcacc ccccttcggc gtgcgcggtc acgcgcacag  3420
ggcgcagccc tggttaaaaa caaggtttat aaatattggt ttaaaagcag gttaaaagac  3480
aggttagcgg tggccgaaaa acgggcggaa acccttgcaa atgctggatt ttctgcctgt  3540
ggacagcccc tcaaatgtca ataggtgcgc ccctcatctg tcagcactct gcccctcaag  3600
tgtcaaggat cgcgcccctc atctgtcagt agtcgcgccc ctcaagtgtc aataccgcag  3660
ggcacttatc cccaggcttg tccacatcat ctgtgggaaa ctcgcgtaaa atcaggcgtt  3720
ttcgccgatt tgcgaggctg gccagctcca cgtcgccggc cgaaatcgag cctgcccctc  3780
atctgtcaac gccgcgccgg gtgagtcggc ccctcaagtg tcaacgtccg cccctcatct  3840
gtcagtgagg gccaagtttt ccgcgaggta tccacaacgc cggcggccct acatggctct  3900
gctgtagtga gtgggttgcg ctccggcagc ggtcctgatc cccgcagaa aaaaaggatc  3960
tcaagaagat cctttgatct tttctac                                    3987

SEQ ID NO: 7            moltype = DNA  length = 4049
FEATURE                 Location/Qualifiers
misc_feature            1..4049
                        note = pLX-R3
source                  1..4049
                        mol_type = other DNA
                        organism = synthetic construct
SEQUENCE: 7
ccatcatcag ttcggtggtc ttccgacgaa caataaggcc gcaaatcgcg gcctttttta  60
ttgataacaa aaccggctca gttctgcgta gaaaccaaca tgcaagctcc accgggtgca  120
aagcggcagc ggcggcagga tatattcaat tgtaaatggc ttcatgtccg ggaaatctac  180
tggtggcagg atatattgtg gtgtaaacaa tggagaaaaa gattaattaa gtactagtag  240
cctggtcgaa accgtctcag gagagagacc aaaagcaaaa acccgccgaa gcgggttact  300
agcgccattc gccattcaga gagcggagct gctgcgacgg acgatcggta cgcgcctctt  360
cgctattacg ccaactggcg aaaggtggat gtgctgcaag gcgattaagt tgggtaacgc  420
cagggttttc ccagtcacga cgttgtagta ccacggcaag gctatctgta atcattgttg  480
tactccggtt aggacggatt gggaactggc taactcaaaa tccacacatt atacgagccg  540
gaagcataaa gtgtaaagcc tggggtgcct aatgagtgag gtctctcgct gtcaggagac  600
gggacaagga tgcgagctag cctgcaggaa ttgttgattt tgtgatgact gatggcagga  660
tatatgcggt tgtaattcat ttttattgtc taaatttctg tatttgtttg tttgttcggt  720
tgtaaatttt tttggaagaa caagaaaaga aaaaacaccc gttagggtgt ttttagttag  780
tgtggcgcgc cgacttgcga catgcggtcc tttgttattt gccgactacc ttggtgatct  840
cgcctttcac gtagtggaca aattcttcca actgatctgc gcgcgaggcc aagcgatctt  900
cttcttgtcc aagataagcc tgtctagctt caagtatgac gggctgatac tgggccggca  960
ggcgctccat tgcccagtcg gcagcgacat ccttcggcgc gattttgccg gttactgcgc  1020
```

-continued

```
tgtaccaaat gcgggacaac gtaagcacta catttcgctc atcgccagcc cagtcgggcg  1080
gcgagttcca tagcgttaag gtttcattta gcgcctcaaa tagatcctgt tcaggaaccg  1140
gatcaaagag ttcctccgcc gctggaccta ccaaggcaac gctatgttct cttgcttttg  1200
tcagcaagat agccagatca atgtcgatcg tggctggctc gaagatacct gcaagaatgt  1260
cattgcgctg ccattctcca aattgcagtt cgcgcttagc tggataacgc cacggaatga  1320
tgtcgtcgtg cacaacaatg gtgacttcta cagcgcggag aatctcgctc tctccagggg  1380
aagccgaagt ttccaaaagg tcgttgatca aagctcgccg cgttgtttca tcaagcctta  1440
cggtcaccgt aaccagcaaa tcaatatcac tgtgtggctt caggccgcca tccactgcgg  1500
agccgtacaa atgtacggcc agcaacgtcg gttcgagatg gcgctcgatg acgccaacta  1560
cctctgatag ttgagtcgat acttcggcga tcaccgcttc cctcatgatg tttaactttg  1620
ttttagggcg actgccctgc tgcgtaacat cgttgctgct ccataacatc aaacatcgac  1680
ccacggcgta acgcgcttgc tgcttggatg cccgaggcat agactgtacc ccaaaaaaac  1740
agtcataaca agccatgaaa accgccactg cgccgttacc accgctgcgt tcggtcaagg  1800
ttcgatcgga ttggcggtta tgcggttgcg atgcaggtgg ctgctgaacc cccagccgga  1860
actgacccca caaggcccta gcgtttgcaa tgcaccaggt catcattgac ccaggcgtgt  1920
tccaccaggc cgctgcctcg caactcttcg caggcttcgc cgacctgctc gcgccacttc  1980
ttcacgcggg tggaatccga tccgcacatg aggcggaagg tttccagctt gagcgggtac  2040
ggctcccggt gcgagctgaa atagtcgaac atccgtcggg ccgtcggcga cagcttgcgg  2100
tacttctccc atatgaattt cgtgtagtgg tcgccagcaa acagcacgac gatttcctcg  2160
tcgatcagga cctggcaacg ggacgttttc ttgccacggt ccaggacgcg gaagcggtgc  2220
agcagcgaca ccgattccag gtgcccaacg cggtcggacg tgaagcccat cgccgtcgcc  2280
tgtaggcgcg acaggcattc ctcggccttc gtgtaatacc ggccattgat cgaccagccc  2340
aggtcctggc aaagctcgta gaacgtgaag gtgatcggct cgccgatagg ggtgcgcttc  2400
gcgtactcca acacctgctg ccacaccagt tcgtcatcgt cggcccgcag ctcgacgccg  2460
gtgtaggtga tcttcacgtc cttgttgacg tggaaaatga ccttgttttg cagcgcctcg  2520
cgcgggattt tcttgttgcg cgtggtgaac agggcagagc gggccgtgtc gtttggcatc  2580
gctcgcatcg tgtccggcca cggcgcaata tcgaacaagg aaagctgcat ttccttgatc  2640
tgctgcttcg tgtgtttcag caacgcggcc tgcttggctt cgctgacctg ttttgccagg  2700
tcctcgccgg cggtttttcg cttcttggtc gtcatagttc ctcgcgtgtc gatggtcatc  2760
gacttcgcca aacctgccgc ctcctgttcg agacgacgcg aacgctccac ggcggccgat  2820
ggcgcgggca gggcaggggg agccagttgc acgctgtcgc gctcgatctt ggccgtagct  2880
tgctggacta tcgagccgac ggactggaag gtttcgcggg gcgcacgcat gacggtgcgg  2940
cttgcgatgg tttcggcatc ctcggcggaa aaccccgcgt cgatcagttc ttgcctgtat  3000
gccttccggt caaacgtccg attcattcac cctccttgcg ggattgcccc ggaattaatt  3060
ccccggatcg atccgtcgat cttgatcccc tgcgccatca gatccttggc ggcaagaaag  3120
ccatccagtt tactttgcag ggcttcccaa ccttaccaga gggcgcccca gctggcaatt  3180
ccggttcgct tgctgtccat aaaaccgccc agtctagcta tcgccatgta agcccactgc  3240
aagctacctg ctttctcttt gcgcttgcgt tttcccttgt ccagatagcc cagtagctga  3300
cattcatccg gggtcagcac cgtttctgcg gactggcttt ctacgtggct gccatttttg  3360
gggtgaggcc gttcgcggcc gaggggcgca gcccctgggg ggatgggagg cccgcgttag  3420
cgggccggga gggttcgaga agggggggca cccccccttcg gcgtgcgcgg tcacgcgcac  3480
agggcgcagc cctggttaaa aacaaggttt ataaatattg gtttaaaagc aggttaaaag  3540
acaggttagc ggtggccgaa aaacgggcgg aaacccttgc aaatgctgga ttttctgcct  3600
gtggacagcc cctcaaatgt caataggtgc gcccctcatc tgtcagcact ctgcccctca  3660
agtgtcaagg atcgcgcccc tcatctgtca gtagtcgcgc ccctcaagtg tcaataccgc  3720
agggcactta tccccaggct tgtccacatc atctgtggga aactcgcgta aaatcaggcg  3780
ttttcgccga tttgcgaggc tggccagctc cacgtcgccg gccgaaatcg agcctgcccc  3840
tcatctgtca acgccgcgcc gggtgagtcg gcccctcaag tgtcaacgtc cgcccctcat  3900
ctgtcagtga gggccaagtt ttccgcgagg tatccacaac gccggcggcc ctacatggct  3960
ctgctgtagt gagtgggttg cgctccggca gcggtcctga tcccccgcag aaaaaaagga  4020
tctcaagaag atcctttgat cttttctac                                  4049
```

```
SEQ ID NO: 8           moltype = DNA  length = 3865
FEATURE                Location/Qualifiers
misc_feature           1..3865
                       note = pLX-R4
source                 1..3865
                       mol_type = other DNA
                       organism = synthetic construct
SEQUENCE: 8
ccatcatcag ttcggtggtc ttccgacgaa caataaggcc gcaaatcgcg gcctttttta  60
ttgataacaa aaccggctca gttctgcgta gaaaccaaca tgcaagctcc accgggtgca  120
aagcggcagc ggcggcagga tatattcaat tgtaaatggc ttcatgtccg ggaaatctac  180
tggtggcagg atatattgtg gtgtaaacaa tggagaaaaa gattaattaa gtactagtag  240
cctggtcgaa accgtctcag gagagagacc aaaagcaaaa acccgccgaa gcgggttact  300
agcgccattc gccattcaga gagcggagct gctgcgacgg acgatcggta cgcgcctctt  360
cgctattacg ccaactggcg aaaggtggat gtgctgcaag gcgattaagt tgggtaacgc  420
cagggttttc ccagtcacga cgttgtagta ccacggcaag gctatctgta atcattgttg  480
tactccggtt aggacggatt gggaactggc taactcaaaa tccacacatt atacgagccg  540
gaagcataaa gtgtaaagcc tggggtgcct aatgagtgag gtctctcgct gtcaggagac  600
gggacaagga tgcgagctag cctgcaggaa ttgttgattt tgtgatgact gatggcagga  660
tatatgcggt tgtaattcat ttttattgtc taaatttctg tatttgtttg tttgttcggt  720
tgtaaatttt tttggaagaa caagaaaaga aaaaacaccc gttagggtgt ttttagttag  780
tgtggcgcgc cgacttgcga catgcggtcc tttgcaattt acccaacaac tccgcggccg  840
ggaagccgat ctcggcttga acgaattgtt aggtggcggt acttgggtcg atatcaaagt  900
gcatcacttc ttcccgtatg cccaactttg tatagagagc cactgcggga tcgtcaccgt  960
aatctgcttg cacgtagatc acataagcac caagcgcgtt ggcctcatgc ttgaggagat  1020
tgatgagcgc ggtggcaatg ccctgcctcc ggtgctctcc ggagactgcg agatcataga  1080
tatagatctc actacgcggc tgctcaaact tgggcagaac gtaagccgcg agagcgccaa  1140
```

```
caaccgcttc ttggtcgaag gcagcaagcg cgatgaatgt cttactacgg agcaagttcc  1200
cgaggtaatc ggagtccggc tgatgttggg agtaggtggc tacgtctccg aactcacgac  1260
cgaaaagatc aagagcagcc cgcatggatt tgacttggtc agggccgagc ctacatgtgc  1320
gaatgatgcc catacttgag ccacctaact ttgttttagg gcgactgccc tgctgcgtaa  1380
catcgttgct gctgcgtaac atcgttgctg ctccataaca tcaaacatcg acccacggcg  1440
taacgcgctt gctgcttgga tgcccgaggc ataggctgta caaaaaaaca gtcataacaa  1500
gccatgaaaa ccgccactgc gccgttacca ccgctgcgtt cggtcaaggt tctggaccag  1560
ttgcgtgagc gcatacgcta cttgcattac agtttacgaa ccgaacaggc ttatgtcaag  1620
atcggattgg cggttatgcg gttgcgatgc aggtggctgc tgaaccccca gccggaactg  1680
accccacaag gccctagcgt ttgcaatgca ccaggtcatc attgacccag gcgtgttcca  1740
ccaggccgct gcctcgcaac tcttcgcagg cttcgccgac ctgctcgcgc cacttcttca  1800
cgcgggtgga atccgatccg cacatgaggc ggaaggtttc cagcttgagc gggtacggct  1860
cccggtgcga gctgaaatag tcgaacatcc gtcgggccgt cggcgacagc ttgcggtact  1920
tctcccatat gaatttcgtg tagtggtcgc cagcaaacag cacgacgatt tcctcgtcga  1980
tcaggacctg gcaacgggac gtttcttgc cacggtccag gacgcggaag cggtgcagca  2040
gcgacaccga ttccaggtgc ccaacgcggt cggacgtgaa gcccatcgcc gtcgcctgta  2100
ggcgcgacag gcattcctcg gccttcgtgt aataccggcc attgatcgac cagcccaggt  2160
cctggcaaag ctcgtagaac gtgaaggtga tcggctcgcc gataggggtg cgcttcgcgt  2220
actccaacac ctgctgccac accagttcgt catcgtcggc ccgcagctcg acgccggtgt  2280
aggtgatctt cacgtccttg ttgacgtgga aaatgacctt gttttgcagc gcctcgcgcg  2340
ggattttctt gttgcgcgtg gtgaacaggg cagagcgggc cgtgtcgttt ggcatcgctc  2400
gcatcgtgtc cggccacggc gcaatatcga acaaggaaag ctgcatttcc ttgatctgct  2460
gcttcgtgtg tttcagcaac gcggcctgct tggcttcgct gacctgtttt gccaggtcct  2520
cgccggcggt ttttcgcttc ttggtcgtca tagttcctcg cgtgtcgatg gtcatcgact  2580
tcgccaaacc tgccgcctcc tgttcgagac gacgcgaacg ctccacggcg gccgatggcg  2640
cgggcagggc agggggagcc agttgcacgc tgtcgcgctc gatcttggcc gtagcttgct  2700
ggactatcga gccgacggac tggaaggttt cgcggggcgc acgcatgacg gtgcggcttg  2760
cgatggtttc ggcatcctcg gcggaaaacc ccgcgtcgat cagttcttgc ctgtatgcct  2820
tccggtcaaa cgtccgattc attcaccctc cttgcgggat tgccccggaa ttaattcccc  2880
ggatcgatcc gtcgatcttg atcccctgcg ccatcagatc cttggcggca agaaagccat  2940
ccagtttact ttgcagggct tcccaacctt accagagggc gccccagctg gcaattccgg  3000
ttcgcttgct gtccataaaa ccgcccagtc tagctatcgc catgtaagcc cactgcaagc  3060
tacctgcttt ctctttgcgc ttgcgttttc ccttgtccag atagcccagt agctgacatt  3120
catccggggt cagcaccgtt tctgcggact ggctttctac gtggctgcca tttttggggt  3180
gaggccgttc gcggccgagg ggcgcagccc ctgggggat gggaggcccg cgttagcggg  3240
ccgggagggt tcgagaaggg ggggcacccc ccttcggcgt gcgcggtcac gcgcacaggg  3300
cgcagccctg gttaaaaaca aggtttataa atattggttt aaaagcaggt taaaagacag  3360
gttagcggtg gccgaaaaac gggcggaaac ccttgcaaat gctggatttt ctgcctgtgg  3420
acagcccctc aaatgtcaat aggtgcgccc ctcatctgtc agcactctgc ccctcaagtg  3480
tcaaggatcg cgcccctcat ctgtcagtag tcgcgcccct caagtgtcaa taccgcaggg  3540
cacttatccc caggcttgtc cacatcatct gtgggaaact cgcgtaaaat caggcgtttt  3600
cgccgatttg cgaggctggc cagctccacg tcgccggccg aaatcgagcc tgcccctcat  3660
ctgtcaacgc cgcgccgggt gagtcggccc ctcaagtgtc aacgtccgcc cctcatctgt  3720
cagtgagggc caagttttcc gcgaggtatc cacaacgccg gcggccctac atggctctgc  3780
tgtagtgagt gggttgcgct ccggcagcgg tcctgatccc ccgcagaaaa aaaggatctc  3840
aagaagatcc tttgatcttt tctac                                          3865

SEQ ID NO: 9           moltype = DNA  length = 3740
FEATURE                Location/Qualifiers
misc_feature           1..3740
                       note = pLX-Z4
source                 1..3740
                       mol_type = other DNA
                       organism = synthetic construct
SEQUENCE: 9
caagaagatc ctttgatctt ttctacaggc ctgctggtaa tcgcaggcct ttttattttg  60
gcaggatata ttgtggtgta aacacttacc gcacctctgc agcagcggca ggatatatgg  120
cagtgtaaac tccatttcg aacgcgttaa ttaagtagcc tggtcgaaac cgtctcagga  180
gagagaccaa aagcaaaaac ccgccgaagc gggttactag cgccattcgc cattcagaga  240
gcggagctgc tgcgacggac gatcggtacg cgcctcttcg ctattacgcc aactggcgaa  300
aggtggatgt gctgcaaggc gattaagttg ggtaacgcca gggttttccc agtcacgacg  360
ttgtagtacc acggcaaggc tatctgtaat cattgttgta ctccggttag gacggattgg  420
gaactggcta actcaaaatc cacacattat acgagccgga agcataaagt gtaaagcctg  480
gggtgcctaa tgagtgaggt ctctcgctgt caggagacgg gacaaggatg cgcctgcagg  540
ttgttgatga tgtgatgact gatggcagga tatatgtggt tgtaattcat ttctaccgtg  600
taatttactg tattttttg tttgttcgtt cgtttgtaaa aatattttt ggaagcaaaa  660
aattagcgca agaagacaaa aatcaccttg cgctaatgct ctgttacagg cgcgccaatt  720
tacccaacaa ctccgcggcc gggaagccga tctcggcttg aacgaattgt taggtggcgg  780
tacttgggtc gatatcaaag tgcatcactt cttcccgtat gcccaacttt gtatagagag  840
ccactgcggg atcgtcaccg taatctgctt gcacgtagat cacataagca ccaagcgcgt  900
tggcctcatg cttgaggaga ttgatgagcg cggtggcaat gccctgcctc cggtgctctc  960
cggagactgc gagatcatag atatagatct cactacgcgg ctgctcaaac ttgggcagaa  1020
cgtaagccgc gagagcgcca acaaccgctt cttggtcgaa ggcagcaagc gcgatgaatg  1080
tcttactacg gagcaagttc ccgaggtaat cggagtccgg ctgatgttgg gagtaggtgg  1140
ctacatcgcc gaactcacga ccgaaaagat caagagcagc ccgcatggat ttgacttggt  1200
cagggccgag cctacatgtg cgaatgatgc ccatacttga gccacctaac tttgttttag  1260
ggcgactgcc ctgctgcgta acatcgttgc tgctgcgtaa catcgttgct gctccataac  1320
atcaaacatc gacccacggc gtaacgcgct tgctgcttgg atgcccgagg cataggctgt  1380
acaaaaaaac agtcataaca agccatgaaa accgccactg cgccgttacc accgctgcgt  1440
```

-continued

```
tcggtcaagg ttctggacca gttgcgtgag cgcatacgct acttgcatta cagtttacga  1500
accgaacagg cttatgtcaa gatcggattg gcggttatgc ggttgcgatg caggtggctg  1560
ctgaaccccc agccggaact gaccccacaa ggccctagcg tttgcaatgc accaggtcat  1620
cattgaccca ggcgtgttcc accaggccgc tgcctcgcaa ctcttcgcag gcttcgccga  1680
cctgctcgcg ccacttcttc acgcgggtgg aatccgatcc gcacatgagg cggaaggttt  1740
ccagcttgag cgggtacggc tcccggtgcg agctgaaata gtcgaacatc cgtcgggccg  1800
tcggcgacag cttgcggtac ttctcccata tgaatttcgt gtagtggtcg ccagcaaaca  1860
gcacgacgat ttcctcgtcg atcaggacct ggcaacggga cgttttcttg ccacggtcca  1920
ggacgcggaa gcggtgcagc agcgacaccg attccaggtg cccaacgcgg tcggacgtga  1980
agcccatcgc cgtcgcctgt aggcgcgaca ggcattcctc ggccttcgtg taataccggc  2040
cattgatcga ccagcccagg tcctggcaaa gctcgtagaa cgtgaaggtg atcggctcgc  2100
cgataggggt gcgcttcgcg tactccaaca cctgctgcca caccagttcg tcatcgtcgg  2160
cccgcagctc gacgccggtg taggtgatct tcacgtcctt gttgacgtgg aaaatgacct  2220
tgttttgcag cgcctcgcgc gggattttct tgttgcgcgt ggtgaacagg gcagagcggg  2280
ccgtgtcgtt tggcatcgct cgcatcgtgt ccggccacgg cgcaatatcg aacaaggaaa  2340
gctgcatttc cttgatctgc tgcttcgtgt gtttcagcaa cgcggcctgc ttggcttcgc  2400
tgacctgttt tgccaggtcc tcgccggcgg tttttcgctt cttggtcgtc atagttcctc  2460
gcgtgtcgat ggtcatcgac ttcgccaaac ctgccgcctc ctgttctagc cgacgcgaac  2520
gctccacggc ggccgatggc gcgggcaggg cagggggagc cagttgcacg ctgtcgcgct  2580
cgatcttggc cgtagcttgc tggactatcg agccgacgga ctggaaggtt tcgcggggcg  2640
cacgcatgac ggtgcggctt gcgatggttt cggcatcctc ggcggaaaac cccgcgtcga  2700
tcagttcttg cctgtatgcc ttccggtcaa acgtccgatt cattcaccct ccttgcggga  2760
ttgccccgga attaattccc cggatcgatc cgtcgatctt gatcccctgc gccatcagat  2820
ccttggcggc aagaaagcca tccagtttac tttgcagggc ttcccaacct taccagaggg  2880
cgccccagct ggcaattccg gttcgcttgc tgtccataaa accgcccagt ctagctatcg  2940
ccatgtaagc ccactgcaag ctacctgctt tctctttgcg cttgcgtttt cccttgtcca  3000
gatagcccag tagctgacat tcatccgggg tcagcaccgt ttctgcggac tggctttcta  3060
cgtggctgcc atttttgggg tgaggccgtt cgcggccgag gggcgcagcc cctgggggga  3120
tgggaggccc gcgttagcgg gccgggaggg ttcgagaagg gggggcaccc cccttcggcg  3180
tgcgcggtca cgcgcacagg gcgcagccct ggttaaaaac aaggtttata aatattggtt  3240
taaaagcagg ttaaaagaca ggttagcggt ggccgaaaaa cgggcggaaa cccttgcaaa  3300
tgctggattt tctgcctgtg gacagcccct caaatgtcaa taggtgcgcc cctcatctgt  3360
cagcactctg cccctcaagt gtcaaggatc gcgcccctca tctgtcagta gtcgcgcccc  3420
tcaagtgtca ataccgcagg gcacttatcc ccaggcttgt ccacatcatc tgtgggaaac  3480
tcgcgtaaaa tcaggcgttt tcgccgattt gcgaggctgg ccagctccac gtcgccggcc  3540
gaaatcgagc ctgcccctca tctgtcaacg ccgcgccggg tgagtcggcc cctcaagtgt  3600
caacgtccgc ccctcatctg tcagtgaggg ccaagttttc cgcgaggtat ccacaacgcc  3660
ggcggcccta catggctctg ctgtagtgag tgggttgcgc tccggcagcg gtcctgatcc  3720
cccgcagaaa aaaaggatct                                         3740

SEQ ID NO: 10          moltype = DNA  length = 3287
FEATURE                Location/Qualifiers
misc_feature           1..3287
                       note = pLX-B2alpha2
source                 1..3287
                       mol_type = other DNA
                       organism = synthetic construct
SEQUENCE: 10
ccatcatcag ttcggtggtc ttccgacgaa caataaggcc gcaaatcgcg gccttttta  60
ttgataacaa aaccggctca gttctgcgta gaaaccaaca tgcaagctcc accgggtgca  120
aagcggcagc ggcggcagga tatattcaat tgtaaatggc ttcatgtccg ggaaatctac  180
tggtggcagg atatattgtg gtgtaaacaa tggagaaaaa gattaattaa gtactagtag  240
cctggtcgaa accgtctcag tcaggagaga gaccaaaagc aaaaacccgc cgaagcgggt  300
tactagcgcc attcgccatt cagagagcgg agctgctgcg acggacgatc ggtacgcgcc  360
tcttcgctat tacgccaact ggcgaaaggt ggatgtgctg caaggcgatt aagttgggta  420
acgccagggt tttcccagtc acgacgttgt agtaccacgg caaggctatc tgtaatcatt  480
gttgtactcc ggttaggacg gattgggaac tggctaactc aaaatccaca cattatacga  540
gccggaagca taaagtgtaa agcctggggt gcctaatgag tgaggtctct cgctggagac  600
gggacaagga tgcgagctag cctgcaggaa ttgttgattt tgtgatgact gatggcagga  660
tatatgcggt tgtaattcat ttttattgtc taaatttctg tatttgtttg tttgttcggt  720
tgtaaatttt tttggaagaa caagaaaaga aaaaacaccc gttagggtgt ttttagttag  780
tgtggcgcgc cgacttgcga catgcggtcc tttgcaatca actattagaa aaattcatcc  840
agcatcagat gaaattgcag tttgttcata tccggattat caatgccata tttctgaaac  900
agacgttttt gcaggctcgg gctaaattcg cccaggcagt tccacagaat ggccagatcc  960
tgataacgat ccgcaatgcc cacacggccc acatcaatgc agccaatcag tttgccttca  1020
tcgaaaatca ggttatccag gctaaaatcg ccgtgggtca ccacgctatc cgggctaaac  1080
ggcagcagtt tatgcatttc tttccacacc tgttccaccg gccagccgtt acgttcatca  1140
tcaaaatcgc tcgcatccac caggccgttg ttcatacggc tctgcgcctg ggccagacga  1200
aacacacgat cgctgttaaa cgggcagttg cacaccggaa tgctatgcag acgacgcaga  1260
aacacggcca gcgcatccac aatgttttcg ccgctatccg gatattcttc cagcacctga  1320
aacgcggttt tgcccggaat cgcggtggtc agcagccacg catcatccgg ggtgcgaata  1380
aaatgtttaa tggtcggcag cggcataaat tcggtcagcc agttcagacg caccatttca  1440
tcggtcacat cgttcgccac gctgcctttg ccatgtttca gaaacagttc cggcgcatcc  1500
ggtttgccat acagacgata aatggtcgcg ccgctctgac ccacgttatc acgcgcccat  1560
ttatagccat acagatccgc atccatgttg ctgttcagac gcggacggct acagctcgtt  1620
tcacgctgaa tatggctcat aacacccctt gtattactgt ttatgtaagc agacagtttt  1680
attgttcatg atgatatatt tttatcttgt gcaatgtaac atcagagatt ttgagacaca  1740
agatcggatt ggcggttatg cggttctacc ggcgcggcag cgttacccgt gtcggcggct  1800
ccaacggctc gccatcgtcc agaaaacacg gctcatcggg catcggcagg cgctgctgcc  1860
```

```
cgcgccgttc ccattcctcc gtttcggtca aggctggcag gtctggttcc atgcccggaa  1920
tgccgggctg gctgggcggc tcctcgccgg ggccggtcgg tagttgctgc tcgcccggat  1980
acagggtcgg gatgcggcgc aggtcgccat gccccaacag cgattcgtcc tggtcgtcgt  2040
gatcaaccac cacggcggca ctgaacaccg acaggcgcaa ctggtcgcgg ggctggcccc  2100
acgccacgcg gtcattgacc acgtaggccg acacggtgcc ggggccgttg agcttcacga  2160
cggagatcca gcgctcggcc accaagtcct tgactgcgta ttggaccgtc cgcaaagaac  2220
gtccgatgag cttggaaagt gtcttctggc tgaccaccac ggcgttctgg tggcccatct  2280
gcgccacgag gtgatgcagc agcattgccg ccgtgggttt cctcgcaata agcccggccc  2340
acgcctcatg cgctttgcgt tccgtttgca cccagtgacc gggcttgttc ttggcttgaa  2400
tgccgatttc tctggactgc gtggccatgc ttatctccat gcggtagggg tgccgcacgg  2460
ttgcggcacc atgcgcaatc agctgcaact tttcggcagc gcgacaacaa ttatgcgttg  2520
cgtaaaagtg gcagtcaatt acagattttc tttaacctac gcaatgagct attgcggggg  2580
gtgccgcaat gagctgttgc gtaccccccct tttttaagtt gttgattttt aagtctttcg  2640
catttcgccc tatatctagt tctttggtgc ccaaagaagg gcacccctgc ggggttcccc  2700
cacgccttcg gcgcggctcc ccctccggca aaaagtggcc cctccggggc ttgttgatcg  2760
actgcgcggc cttcggcctt gcccaaggtg gcgctgcccc cttggaaccc ccgcactcgc  2820
cgccgtgagg ctcgggggc aggcgggcgg gcttcgccct tcgactgccc ccactcgcat  2880
aggcttgggt cgttccaggc gcgtcaaggc caagccgctg cgcggtcgct gcgcgagcct  2940
tgacccgcct tccacttggt gtccaaccgg caagcgaagc gcgcaggccg caggccggag  3000
gcttttcccc agagaaaatt aaaaaaaattg atggggcaag gccgcaggcc gcgcagttgg  3060
agccggtggg tatgtggtcg aaggctgggt agccggtggg caatccctgt ggtcaagctc  3120
gtgggcaggc gcagcctgtc catcagcttg tccagcaggg ttgtccacgg gccgagcgaa  3180
gcgagccagc cggtggccgc tcgcggccat cgtccacata tccacgggct ggcaagggag  3240
cgcagcgacc gcgcagggcg aagcccggag agcaagcccg taggggg              3287

SEQ ID NO: 11          moltype = DNA  length = 3349
FEATURE                Location/Qualifiers
misc_feature           1..3349
                       note = pLX-B3omega1
source                 1..3349
                       mol_type = other DNA
                       organism = synthetic construct
SEQUENCE: 11
ccatcatcag ttcggtggtc ttccgacgaa caataaggcc gcaaatcgcg gcctttttta  60
ttgataacaa aaccggctca gttctgcgta gaaaccaaca tgcaagctcc accgggtgca  120
aagcggcagc ggcggcagga tatattcaat tgtaaatggc ttcatgtccg ggaaatctac  180
tggtggcagg atatattgtg gtgtaaacaa tggagaaaaa gattaattaa gtactagtag  240
cctggtcgaa acggtctcag gagagagacg aaaagcaaaa acccgccgaa gcgggttact  300
agcgccattc gccattcaga gagcggagct gctgcgacgg acgatcggta cgcgcctctt  360
cgctattacg ccaactggcg aaaggtggat gtgctgcaag gcgattaagt tgggtaacgc  420
cagggttttc ccagtcacga cgttgtagta ccacggcaag gctatctgta atcattgttg  480
tactccggtt aggacggatt gggaactggc taactcaaaa tccacacatt atacgagccg  540
gaagcataaa gtgtaaagcc tggggtgcct aatgagtgac gtctctcgct gtcaggagac  600
cggacaagga tgcgagctag cctgcaggaa ttgttgattt tgtgatgact gatggcagga  660
tatatgcggt tgtaattcat ttttattgtc taaatttctg tatttgtttg tttgttcggt  720
tgtaaatttt tttggaagaa caagaaaaga aaaaacaccc gttagggtgt ttttagttag  780
tgtggcgcgc cgacttgcga catgcggtcc tttgttattt gccgactacc ttggtgatct  840
cgcctttcac gtagtggaca aattcttcca actgatctgc gcgcgaggcc aagcgatctt  900
cttcttgtcc aagataagcc tgtctagctt caagtatgac gggctgatac tgggccggca  960
ggcgctccat tgcccagtcg gcagcgacat ccttcggcgc gattttgccg gttactgcgc  1020
tgtaccaaat gcgggacaac gtaagcacta catttcgctc atcgccagcc cagtcgggcg  1080
gcgagttcca tagcgttaag gtttcattta gcgcctcaaa tagatcctgt tcaggaaccg  1140
gatcaaagag ttcctccgcc gctggaccta ccaaggcaac gctatgttct cttgcttttg  1200
tcagcaagat agccagatca atgtcgatcg tggctggctc gaagatacct gcaagaatgt  1260
cattgcgctg ccattctcca aattgcagtt cgcgcttagc tggataacgc cacggaatga  1320
tgtcgtcgtg cacaacaatg gtgacttcta cagcgcggag aatctcgctc tctccagggg  1380
aagccgaagt ttccaaaagg tcgttgatca aagctcgccg cgttgtttca tcaagcctta  1440
cggtcaccgt aaccagcaaa tcaatatcac tgtgtggctt caggccgcca tccactgcgg  1500
agccgtacaa atgtacggcc agcaacgtcg gttcgagatg gcgctcgatg acgccaacta  1560
cctctgatag ttgagtcgat acttcggcga tcaccgcttc cctcatgatg tttaactttg  1620
ttttagggcg actgccctgc tgcgtaacat cgttgctgct ccataacatc aaacatcgac  1680
ccacggcgta acgcgcttgc tgcttggatg cccgaggcat agactgtacc ccaaaaaaac  1740
agtcataaca agccatgaaa accgccactg cgccgttacc accgctgcgt tcggtcaagg  1800
ttcgatcgga ttggcggtta tgcggttcta ccggcgcggc agcgttaccc gtgtcggcgg  1860
ctccaacggc tcgccatcgt ccagaaaaca cggctcatcg ggcatcggca ggcgctgctg  1920
cccgcgccgt tcccattcct ccgtttcggt caaggctggc aggtctggtt ccatgcccgg  1980
aatgccgggc tggctgggcg gctcctcgcc ggggccggtc ggtagttgct gctcgcccgg  2040
atacagggtc gggatgcggc gcaggtcgcc atgccccaac agcgattcgt cctggtcgtc  2100
gtgatcaacc accacggcgg cactgaacac cgacaggcgc aactggtcgc ggggctggcc  2160
ccacgccacg cggtcattga ccacgtaggc cgacacggtg ccggggccgt tgagcttcac  2220
gacggagatc cagcgctcgg ccaccaagtc cttgactgcg tattggaccg tccgcaaaga  2280
acgtccgatg agcttggaaa gtgtcttctg gctgaccacc acggcgttct ggtggcccat  2340
ctgcgccacg aggtgatgca gcagcattgc cgccgtgggt ttcctcgcaa taagcccggc  2400
ccacgcctca tgcgctttgc gttccgtttg cacccagtga ccgggcttgt tcttggcttg  2460
aatgccgatt tctctggact gcgtggccat gcttatctcc atgcggtagg ggtgccgcac  2520
ggttgcggca ccatgcgcaa tcagctgcaa cttttcggca gcgcgacaac aattatgcgt  2580
tgcgtaaaag tggcagtcaa ttacagattt tctttaacct acgcaatgag ctattgcggg  2640
gggtgccgca atgagctgtt gcgtaccccc ctttttaag ttgttgattt ttaagtcttt  2700
cgcatttcgc cctatatcta gttctttggt gcccaaagaa gggcacccct gcggggttcc  2760
```

-continued

```
cccacgcctt cggcgcggct ccccctccgg caaaaagtgg cccctccggg gcttgttgat  2820
cgactgcgcg gccttcggcc ttgcccaagg tggcgctgcc cccttggaac ccccgcactc  2880
gccgccgtga ggctcggggg gcaggcgggc gggcttcgcc cttcgactgc ccccactcgc  2940
ataggcttgg gtcgttccag gcgcgtcaag gccaagccgc tgcgcggtcg ctgcgcgagc  3000
cttgacccgc cttccacttg gtgtccaacc ggcaagcgaa gcgcgcaggc cgcaggccgg  3060
aggcttttcc ccagagaaaa ttaaaaaaat tgatggggca aggccgcagg ccgcgcagtt  3120
ggagccggtg ggtatgtggt cgaaggctgg gtagccggtg ggcaatccct gtggtcaagc  3180
tcgtgggcag gcgcagcctg tccatcagct tgtccagcag ggttgtccac gggccgagcg  3240
aagcgagcca gccggtggcc gctcgcggcc atcgtccaca tatccacggg ctggcaaggg  3300
agcgcagcga ccgcgcaggg cgaagcccgg agagcaagcc cgtagggggg            3349

SEQ ID NO: 12          moltype = DNA  length = 3349
FEATURE                Location/Qualifiers
misc_feature           1..3349
                       note = pLX-B3omega2
source                 1..3349
                       mol_type = other DNA
                       organism = synthetic construct
SEQUENCE: 12
ccatcatcag ttcggtggtc ttccgacgaa caataaggcc gcaaatcgcg gcctttttta  60
ttgataacaa aaccggctca gttctgcgta gaaaccaaca tgcaagctcc accgggtgca  120
aagcggcagc ggcggcagga tatattcaat tgtaaatggc ttcatgtccg ggaaatctac  180
tggtggcagg atatattgtg gtgtaaacaa tggagaaaaa gattaattaa gtactagtag  240
cctggtcgaa acggtctcag tcaggagaga gacgaaaagc aaaaacccgc cgaagcgggt  300
tactagcgcc attcgccatt cagagagcgg agctgctgcg acggacgatc ggtacgcgcc  360
tcttcgctat tacgccaact ggcgaaaggt ggatgtgctg caaggcgatt aagttgggta  420
acgccagggt tttcccagtc acgacgttgt agtaccacgg caaggctatc tgtaatcatt  480
gttgtactcc ggttaggacg gattgggaac tggctaactc aaaatccaca cattatacga  540
gccggaagca taaagtgtaa agcctggggt gcctaatgag tgacgtctct cgctggagac  600
cggacaagga tgcgagctag cctgcaggaa ttgttgattt tgtgatgact gatggcagga  660
tatatgcggt tgtaattcat ttttattgtc taaatttctg tatttgtttg tttgttcggt  720
tgtaaatttt tttggaagaa caagaaaaga aaaaacaccc gttagggtgt ttttagttag  780
tgtggcgcgc cgacttgcga catgcggtcc tttgttattt gccgactacc ttggtgatct  840
cgcctttcac gtagtggaca aattcttcca actgatctgc gcgcgaggcc aagcgatctt  900
cttcttgtcc aagataagcc tgtctagctt caagtatgac gggctgatac tgggccggca  960
ggcgctccat tgcccagtcg gcagcgacat ccttcggcgc gattttgccg gttactgcgc  1020
tgtaccaaat gcgggacaac gtaagcacta catttcgctc atcgccagcc cagtcgggcg  1080
gcgagttcca tagcgttaag gtttcattta gcgcctcaaa tagatcctgt tcaggaaccg  1140
gatcaaagag ttcctccgcc gctggaccta ccaaggcaac gctatgttct cttgcttttg  1200
tcagcaagat agccagatca atgtcgatcg tggctggctc gaagatacct gcaagaatgt  1260
cattgcgctg ccattctcca aattgcagtt cgcgcttagc tggataacgc cacggaatga  1320
tgtcgtcgtg cacaacaatg gtgacttcta cagcgcggag aatctcgctc tctccagggg  1380
aagccgaagt ttccaaaagg tcgttgatca aagctcgccg cgttgtttca tcaagcctta  1440
cggtcaccgt aaccagcaaa tcaatatcac tgtgtggctt caggccgcca tccactgcgg  1500
agccgtacaa atgtacggcc agcaacgtcg gttcgagatg gcgctcgatg acgccaacta  1560
cctctgatag ttgagtcgat acttcggcga tcaccgcttc cctcatgatg tttaactttg  1620
ttttagggcg actgccctgc tgcgtaacat cgttgctgct ccataacatc aaacatcgac  1680
ccacggcgta acgcgcttgc tgcttggatg cccgaggcat agactgtacc ccaaaaaaac  1740
agtcataaca agccatgaaa accgccactg cgccgttacc accgctgcgt tcggtcaagg  1800
ttcgatcgga ttggcggtta tgcggttcta ccggcgcggc agcgttaccc gtgtcggcgg  1860
ctccaacggc tcgccatcgt ccagaaaaca cggctcatcg ggcatcggca ggcgctgctg  1920
cccgcgccgt tcccattcct ccgtttcggt caaggctggc aggtctggtt ccatgcccgg  1980
aatgccgggc tggctgggcg gctcctcgcc ggggccggtc ggtagttgct gctcgcccgg  2040
atacagggtc gggatgcggc gcaggtcgcc atgccccaac agcgattcgt cctggtcgtc  2100
gtgatcaacc accacggcgg cactgaacac cgacaggcgc aactggtcgc ggggctggcc  2160
ccacgccacg cggtcattga ccacgtaggc cgacacggtg ccggggccgt tgagcttcac  2220
gacggagatc cagcgctcgg ccaccaagtc cttgactgcg tattggaccg tccgcaaaga  2280
acgtccgatg agcttggaaa gtgtcttctg gctgaccacc acggcgttct ggtggcccat  2340
ctgcgccacg aggtgatgca gcagcattgc cgccgtgggt ttcctcgcaa taagcccggc  2400
ccacgcctca tgcgctttgc gttccgtttg cacccagtga ccgggcttgt tcttggcttg  2460
aatgccgatt tctctggact gcgtggccat gcttatctcc atgcggtagg ggtgccgcac  2520
ggttgcggca ccatgcgcaa tcagctgcaa cttttcggca gcgcgacaac aattatgcgt  2580
tgcgtaaaag tggcagtcaa ttacagattt tctttaacct acgcaatgag ctattgcggg  2640
gggtgccgca atgagctgtt gcgtaccccc cttttttaag ttgttgattt ttaagtcttt  2700
cgcatttcgc cctatatcta gttctttggt gcccaaagaa gggcacccct gcggggttcc  2760
cccacgcctt cggcgcggct ccccctccgg caaaaagtgg cccctccggg gcttgttgat  2820
cgactgcgcg gccttcggcc ttgcccaagg tggcgctgcc cccttggaac ccccgcactc  2880
gccgccgtga ggctcggggg gcaggcgggc gggcttcgcc cttcgactgc ccccactcgc  2940
ataggcttgg gtcgttccag gcgcgtcaag gccaagccgc tgcgcggtcg ctgcgcgagc  3000
cttgacccgc cttccacttg gtgtccaacc ggcaagcgaa gcgcgcaggc cgcaggccgg  3060
aggcttttcc ccagagaaaa ttaaaaaaat tgatggggca aggccgcagg ccgcgcagtt  3120
ggagccggtg ggtatgtggt cgaaggctgg gtagccggtg ggcaatccct gtggtcaagc  3180
tcgtgggcag gcgcagcctg tccatcagct tgtccagcag ggttgtccac gggccgagcg  3240
aagcgagcca gccggtggcc gctcgcggcc atcgtccaca tatccacggg ctggcaaggg  3300
agcgcagcga ccgcgcaggg cgaagcccgg agagcaagcc cgtagggggg            3349

SEQ ID NO: 13          moltype = DNA  length = 5485
FEATURE                Location/Qualifiers
misc_feature           1..5485
```

-continued

```
                        note = pLX-B2-TagRFP-T
source                  1..5485
                        mol_type = other DNA
                        organism = synthetic construct
SEQUENCE: 13
ccatcatcag ttcggtggtc ttccgacgaa caataaggcc gcaaatcgcg gcctttttta  60
ttgataacaa aaccggctca gttctgcgta gaaaccaaca tgcaagctcc accgggtgca  120
aagcggcagc ggcggcagga tatattcaat tgtaaatggc ttcatgtccg ggaaatctac  180
tggtggcagg atatattgtg gtgtaaacaa tggagaaaaa gattaattaa gtactagtag  240
cctggtcgaa accgtctcac cagtacgcac gattcaaggc ttgcttcaca aaccaaggca  300
agtaatagag attggagtct ctaaaaaggt agttcccact gaatcaaagg ccatggagtc  360
aaagattcaa atagaggacc taacagaact cgccgtaaag actggcgaac agttcataca  420
gagtctctta cgactcaatg acaagaagaa aatcttcgtc aacatggtgg agcacgacac  480
acttgtctac tccaaaaata tcaaagatac agtctcagaa gaccaaaggg caattgagac  540
ttttcaacaa agggtaatat ccggaaacct cctcggattc cattgcccag ctatctgtca  600
ctttattgtg aagatagtgg aaaaggaagg tggctcctac aaatgccatc attgcgataa  660
aggaaaggcc atcgttgaag atgcctctgc cgacagtggt cccaaagatg gacccccacc  720
cacgaggagc atcgtggaaa aagaagacgt tccaaccacg tcttcaaagc aagtggattg  780
atgtgataac atggtggagc acgacacact tgtctactcc aaaaatatca aagatacagt  840
ctcagaagac caaagggcaa ttgagacttt tcaacaaagg gtaatatccg gaaacctcct  900
cggattccat tgcccagcta tctgtcactt tattgtgaag atagtggaaa aggaaggtgg  960
ctcctacaaa tgccatcatt gcgataaagg aaaggccatc gttgaagatc ctctgccgac  1020
agtggtccca aagatggacc cccacccacg aggagcatcg tggaaaaaga agacgttcca  1080
accacgtctt caaagcaagt ggattgatgt gatatctcca ctgacgtaag ggatgacgca  1140
caatcccact atccttcgca agacccttcc tctatataag gaagttcatt tcatttggag  1200
aggaaaatat aaaaactcaa cacaacatac aaaattttaa gcaatcaaat caatctcaag  1260
ctatcaaaat ttttcaaatc tcacttgaaa gatcaaaaat caacaaagaa aatcccttaa  1320
tttctctacc aaatttactg caagtcaaga tggtttcaaa gggagaagag ctgattaagg  1380
agaacatgca catgaagctg tacatggagg gcaccgtgaa caaccaccac ttcaagtgca  1440
catccgaggg cgaaggcaag ccctacgagg gcacccagac catgagaatc aaggtggtcg  1500
agggcggccc tctccccttc gccttcgaca tcctggctac cagcttcatg tacggcagca  1560
gaaccttcat caaccacacc cagggcatcc ccgacttctt taagcagtcc ttccctgagg  1620
gcttcacatg ggagagagtc accacatacg aagacggggg cgtgctgacc gctacccagg  1680
acaccagcct ccaggacggc tgcctcatct acaacgtcaa gatcagaggg gtgaacttcc  1740
catccaacgg ccctgtgatg cagaagaaaa cactcggctg ggaggccaac accgagatgc  1800
tgtaccccgc tgacggcggc ctggaaggca gaacagacat ggccctgaag ctcgtgggcg  1860
ggggccacct gatctgcaac ttcaagacca catacagatc caagaaaccc gctaagaacc  1920
tcaagatgcc cggcgtctac tatgtggacc acagactgga aagaatcaag gaggccgaca  1980
aagagaccta cgtcgagcag cacgaggtgg ctgtggccag atactgcgac ctccctagca  2040
aactggggca caaacttaac taatcgatca cgtgaagctc atatccagat gaaggcagca  2100
gcattgagaa atgttcaaaa tcgtttattt ggcttggatg gaaacgtcgg aacacaagaa  2160
gaggacacag agagacacac cgctggtgat gttaatcgca acatgcacaa cctcctcggt  2220
gtgaggggag tgtagtggtc tcggtatcta tcataaactc tacctgggtg agagtctaat  2280
catccagttg tttttagatt cctgttagca tccttttctc cgctttaata gcagtacatt  2340
cagtgaggtt ttacctccat atgttctagt ctgttattgt cgaacacagg cccttgtatc  2400
tgatgtagcg agtgcttcac tccattcggg ttatagttct tgtgcaagag acaaaaaaaa  2460
aaaaaaaaaa aaaaaaaaaa aaaaaaaaaa aaaaaaaaaa aaaaaaaaaa aaaaaaaaaa  2520
atgcatgcct gcagatcgtt caaacatttg gcaataaagt ttcttaagat tgaatcctgt  2580
tgccggtctt gcgatgatta tcatctaatt tctgttgaat tacgttaagc atgtaataat  2640
taacatgtaa tgcatgacgt tatttatgag atgggttttt atgattagag tcccgcaatt  2700
atacatttaa tacgcgatag aaaacaaaat atagcgcgca aactaggata aattatcgcg  2760
cgcggtgtca tctatgttac tcgatctcgt caggagacgg gacaaggatg cgagctagcc  2820
tgcaggaatt gttgattttg tgatgactga tggcaggata tatgcggttg taattcattt  2880
ttattgtcta aatttctgta tttgtttgtt tgttcggttg taaatttttt tggaagaaca  2940
agaaaagaaa aaacacccgt tagggtgttt ttagttagtg tggcgcgccg acttgcgaca  3000
tgcggtcctt tgcaatcaac tattagaaaa attcatccag catcagatga aattgcagtt  3060
tgttcatatc cggattatca atgccatatt tctgaaacag acgtttttgc aggctcgggc  3120
taaattcgcc caggcagttc cacagaatgg ccagatcctg ataacgatcc gcaatgccca  3180
cacggcccac atcaatgcag ccaatcagtt tgccttcatc gaaaatcagg ttatccaggc  3240
taaaatcgcc gtgggtcacc acgctatccg ggctaaacgg cagcagttta tgcatttctt  3300
tccacacctg ttccaccggc cagccgttac gttcatcatc aaaatcgctc gcatccacca  3360
ggccgttgtt catacggctc tgcgcctggg ccagacgaaa cacacgatcg ctgttaaacg  3420
ggcagttgca caccggaatg ctatgcagac gacgcagaaa cacggccagc gcatccacaa  3480
tgttttcgcc gctatccgga tattcttcca gcacctgaaa cgcggttttg cccggaatcg  3540
cggtggtcag cagccacgca tcatccgggg tgcgaataaa atgtttaatg gtcggcagcg  3600
gcataaattc ggtcagccag ttcagacgca ccatttcatc ggtcacatcg ttcgccacgc  3660
tgcctttgcc atgtttcaga aacagttccg gcgcatccgg tttgccatac agacgataaa  3720
tggtcgcgcc gctctgaccc acgttatcac gcgcccattt atagccatac agatccgcat  3780
ccatgttgct gttcagacgc ggacggctac agctcgtttc acgctgaata tggctcataa  3840
cacccccttgt attactgttt atgtaagcag acagttttat tgttcatgat gatatatttt  3900
tatcttgtgc aatgtaacat cagagatttt gagacacaag atcggattgg cggttatgcg  3960
gttctaccgg cgcggcagcg ttacccgtgt cggcggctcc aacggctcgc catcgtccag  4020
aaaacacggc tcatcgggca tcggcaggcg ctgctgcccg cgccgttccc attcctccgt  4080
ttcggtcaag gctggcaggt ctggttccat gcccggaatg ccgggctggc tgggcggctc  4140
ctcgccgggg ccggtcggta gttgctgctc gcccggatac agggtcggga tgcggcgcag  4200
gtcgccatgc cccaacagcg attcgtcctg gtcgtcgtga tcaaccacca cggcggcact  4260
gaacaccgac aggcgcaact ggtcgcgggg ctggccccac gccacgcggt cattgaccac  4320
gtaggccgac acggtgccgg ggccgttgag cttcacgacg gagatccagc gctcggccac  4380
caagtccttg actgcgtatt ggaccgtccg caaagaacgt ccgatgagct tggaaagtgt  4440
```

-continued

```
cttctggctg accaccacgg cgttctggtg gcccatctgc gccacgaggt gatgcagcag  4500
cattgccgcc gtgggtttcc tcgcaataag cccggcccac gcctcatgcg ctttgcgttc  4560
cgtttgcacc cagtgaccgg gcttgttctt ggcttgaatg ccgatttctc tggactgcgt  4620
ggccatgctt atctccatgc ggtaggggtg ccgcacggtt gcggcaccat gcgcaatcag  4680
ctgcaacttt tcggcagcgc gacaacaatt atgcgttgcg taaaagtggc agtcaattac  4740
agattttctt taacctacgc aatgagctat tgcggggggt gccgcaatga gctgttgcgt  4800
accccccttt tttaagttgt tgatttttaa gtctttcgca tttcgcccta tatctagttc  4860
tttggtgccc aaagaagggc acccctgcgg ggttccccca cgccttcggc gcggctcccc  4920
ctccggcaaa aagtggcccc tccggggctt gttgatcgac tgcgcggcct tcggccttgc  4980
ccaaggtggc gctgccccct tggaaccccc gcactcgccg ccgtgaggct cggggggcag  5040
gcgggcgggc ttcgcccttc gactgccccc actcgcatag gcttgggtcg ttccaggcgc  5100
gtcaaggcca agccgctgcg cggtcgctgc gcgagccttg acccgccttc cacttggtgt  5160
ccaaccggca agcgaagcgc gcaggccgca ggccggaggc ttttccccag agaaaattaa  5220
aaaaattgat ggggcaaggc cgcaggccgc gcagttggag ccggtgggta tgtggtcgaa  5280
ggctgggtag ccggtgggca atccctgtgg tcaagctcgt gggcaggcgc agcctgtcca  5340
tcagcttgtc cagcagggtt gtccacgggc cgagcgaagc gagccagccg gtggccgctc  5400
gcggccatcg tccacatatc cacgggctgg caagggagcg cagcgaccgc gcagggcgaa  5460
gcccggagag caagcccgta ggggg                                        5485

SEQ ID NO: 14          moltype = DNA  length = 5547
FEATURE                Location/Qualifiers
misc_feature           1..5547
                       note = pLX-B3-TagRFP-T
source                 1..5547
                       mol_type = other DNA
                       organism = synthetic construct
SEQUENCE: 14
ccatcatcag ttcggtggtc ttccgacgaa caataaggcc gcaaatcgcg gcctttttta  60
ttgataacaa aaccggctca gttctgcgta gaaaccaaca tgcaagctcc accgggtgca  120
aagcggcagc ggcggcagga tatattcaat tgtaaatggc ttcatgtccg ggaaatctac  180
tggtggcagg atatattgtg gtgtaaacaa tggagaaaaa gattaattaa gtactagtag  240
cctggtcgaa accgtctcac cagtacgcac gattcaaggc ttgcttcaca aaccaaggca  300
agtaatagag attggagtct ctaaaaaggt agttcccact gaatcaaagg ccatggagtc  360
aaagattcaa atagaggacc taacagaact cgccgtaaag actggcgaac agttcataca  420
gagtctctta cgactcaatg acaagaagaa aatcttcgtc aacatggtgg agcacgacac  480
acttgtctac tccaaaaata tcaaagatac agtctcagaa gaccaaaggg caattgagac  540
ttttcaacaa agggtaatat ccggaaacct cctcggattc cattgcccag ctatctgtca  600
ctttattgtg aagatagtgg aaaaggaagg tggctcctac aaatgccatc attgcgataa  660
aggaaaggcc atcgttgaag atgcctctgc cgacagtggt cccaaagatg gacccccacc  720
cacgaggagc atcgtggaaa aagaagacgt tccaaccacg tcttcaaagc aagtggattg  780
atgtgataac atggtggagc acgacacact tgtctactcc aaaaatatca aagatacagt  840
ctcagaagac caaagggcaa ttgagacttt tcaacaaagg gtaatatccg gaaacctcct  900
cggattccat tgcccagcta tctgtcactt tattgtgaag atagtggaaa aggaaggtgg  960
ctcctacaaa tgccatcatt gcgataaagg aaaggccatc gttgaagatc ctctgccgac  1020
agtggtccca aagatggacc cccacccacg aggagcatcg tggaaaaaga agacgttcca  1080
accacgtctt caaagcaagt ggattgatgt gatatctcca ctgacgtaag ggatgacgca  1140
caatcccact atccttcgca agacccttcc tctatataag gaagttcatt tcatttggag  1200
aggaaaatat aaaaactcaa cacaacatac aaaattttaa gcaatcaaat caatctcaag  1260
ctatcaaaat ttttcaaatc tcacttgaaa gatcaaaaat caacaaagaa aatcccttaa  1320
tttctctacc aaatttactg caagtcaaga tggtttcaaa gggagaagag ctgattaagg  1380
agaacatgca catgaagctg tacatggagg gcaccgtgaa caaccaccac ttcaagtgca  1440
catccgaggg cgaaggcaag ccctacgagg gcacccagac catgagaatc aaggtggtcg  1500
agggcggccc tctccccttc gccttcgaca tcctggctac cagcttcatg tacggcagca  1560
gaaccttcat caaccacacc cagggcatcc ccgacttctt taagcagtcc ttccctgagg  1620
gcttcacatg ggagagagtc accacatacg aagacggggg cgtgctgacc gctacccagg  1680
acaccagcct ccaggacggc tgcctcatct acaacgtcaa gatcagaggg gtgaacttcc  1740
catccaacgg ccctgtgatg cagaagaaaa cactcggctg ggaggccaac accgagatgc  1800
tgtaccccgc tgacggcggc ctggaaggca gaacagacat ggccctgaag ctcgtgggcg  1860
ggggccacct gatctgcaac ttcaagacca catacagatc caagaaaccc gctaagaacc  1920
tcaagatgcc cggcgtctac tatgtggacc acagactgga aagaatcaag gaggccgaca  1980
aagagaccta cgtcgagcag cacgaggtgg ctgtggccag atactgcgac ctccctagca  2040
aactggggca caaacttaac taatcgatca cgtgaagctc atatccagat gaaggcagca  2100
gcattgagaa atgttcaaaa tcgtttattt ggcttggatg gaaacgtcgg aacacaagaa  2160
gaggacacag agagacacac cgctggtgat gttaatcgca acatgcacaa cctcctcggt  2220
gtgaggggag tgtagtggtc tcggtatcta tcataaactc tacctgggtg agagtctaat  2280
catccagttg tttttagatt cctgttagca tccttttctc cgctttaata gcagtacatt  2340
cagtgaggtt ttacctccat atgttctagt ctgttattgt cgaacacagg cccttgtatc  2400
tgatgtagcg agtgcttcac tccattcggg ttatagttct tgtgcaagag acaaaaaaaa  2460
aaaaaaaaaa aaaaaaaaaa aaaaaaaaaa aaaaaaaaaa aaaaaaaaaa aaaaaaaaaa  2520
atgcatgcct gcagatcgtt caaacatttg gcaataaagt ttcttaagat tgaatcctgt  2580
tgccggtctt gcgatgatta tcatctaatt tctgttgaat tacgttaagc atgtaataat  2640
taacatgtaa tgcatgacgt tatttatgag atgggttttt atgattagag tcccgcaatt  2700
atacatttaa tacgcgatag aaaacaaaat atagcgcgca aactaggata aattatcgcg  2760
cgcggtgtca tctatgttac tcgatctcgt caggagacgg gacaaggatg cgagctagcc  2820
tgcaggaatt gttgatttg tgatgactga tggcaggata tatgcggttg taattcattt  2880
ttattgtcta aatttctgta tttgtttgtt tgttcggttg taaatttttt tggaagaaca  2940
agaaaagaaa aaacacccgt tagggtgttt ttagttagtg tggcgcgccg acttgcgaca  3000
tgcggtcctt tgttatttgc cgactacctt ggtgatctcg cctttcacgt agtggacaaa  3060
ttcttccaac tgatctgcgc gcgaggccaa gcgatcttct tcttgtccaa gataagcctg  3120
```

-continued

```
tctagcttca agtatgacgg gctgatactg ggccggcagg cgctccattg cccagtcggc  3180
agcgacatcc ttcggcgcga ttttgccggt tactgcgctg taccaaatgc gggacaacgt  3240
aagcactaca tttcgctcat cgccagccca gtcgggcggc gagttccata gcgttaaggt  3300
ttcatttagc gcctcaaata gatcctgttc aggaaccgga tcaaagagtt cctccgccgc  3360
tggacctacc aaggcaacgc tatgttctct tgcttttgtc agcaagatag ccagatcaat  3420
gtcgatcgtg gctggctcga agatacctgc aagaatgtca ttgcgctgcc attctccaaa  3480
ttgcagttcg cgcttagctg gataacgcca cggaatgatg tcgtcgtgca caacaatggt  3540
gacttctaca gcgcggagaa tctcgctctc tccaggggaa gccgaagttt ccaaaaggtc  3600
gttgatcaaa gctcgccgcg ttgtttcatc aagccttacg gtcaccgtaa ccagcaaatc  3660
aatatcactg tgtggcttca ggccgccatc cactgcggag ccgtacaaat gtacggccag  3720
caacgtcggt tcgagatggc gctcgatgac gccaactacc tctgatagtt gagtcgatac  3780
ttcggcgatc accgcttccc tcatgatgtt taactttgtt ttagggcgac tgccctgctg  3840
cgtaacatcg ttgctgctcc ataacatcaa acatcgaccc acggcgtaac gcgcttgctg  3900
cttggatgcc cgaggcatag actgtacccc aaaaaaacag tcataacaag ccatgaaaac  3960
cgccactgcg ccgttaccac cgctgcgttc ggtcaaggtt cgatcggatt ggcggttatg  4020
cggttctacc ggcgcggcag cgttacccgt gtcggcggct ccaacggctc gccatcgtcc  4080
agaaaacacg gctcatcggg catcggcagg cgctgctgcc cgcgccgttc ccattcctcc  4140
gtttcggtca aggctggcag gtctggttcc atgcccggaa tgccgggctg gctgggcggc  4200
tcctcgccgg ggccggtcgg tagttgctgc tcgcccggat acagggtcgg gatgcggcgc  4260
aggtcgccat gccccaacag cgattcgtcc tggtcgtcgt gatcaaccac cacggcggca  4320
ctgaacaccg acaggcgcaa ctggtcgcgg ggctggcccc acgccacgcg gtcattgacc  4380
acgtaggccg acacggtgcc ggggccgttg agcttcacga cggagatcca gcgctcggcc  4440
accaagtcct tgactgcgta ttggaccgtc cgcaaagaac gtccgatgag cttggaaagt  4500
gtcttctggc tgaccaccac ggcgttctgg tggcccatct gcgccacgag gtgatgcagc  4560
agcattgccg ccgtgggttt cctcgcaata agcccggccc acgcctcatg cgctttgcgt  4620
tccgtttgca cccagtgacc gggcttgttc ttggcttgaa tgccgatttc tctggactgc  4680
gtggccatgc ttatctccat gcggtagggg tgccgcacgg ttgcggcacc atgcgcaatc  4740
agctgcaact tttcggcagc gcgacaacaa ttatgcgttg cgtaaaagtg gcagtcaatt  4800
acagattttc tttaacctac gcaatgagct attgcggggg gtgccgcaat gagctgttgc  4860
gtacccccct tttttaagtt gttgattttt aagtctttcg catttcgccc tatatctagt  4920
tctttggtgc ccaaagaagg gcacccctgc ggggttcccc cacgccttcg gcgcggctcc  4980
ccctccggca aaaagtggcc cctccggggc ttgttgatcg actgcgcggc cttcggcctt  5040
gcccaaggtg gcgctgcccc cttggaaccc ccgcactcgc cgccgtgagg ctcgggggc  5100
aggcgggcgg gcttcgccct tcgactgccc ccactcgcat aggcttgggt cgttccaggc  5160
gcgtcaaggc caagccgctg cgcggtcgct gcgcgagcct tgacccgcct tccacttggt  5220
gtccaaccgg caagcgaagc gcgcaggccg caggccggag gcttttcccc agagaaaatt  5280
aaaaaaattg atggggcaag gccgcaggcc gcgcagttgg agccggtggg tatgtggtcg  5340
aaggctgggt agccggtggg caatccctgt ggtcaagctc gtgggcaggc gcagcctgtc  5400
catcagcttg tccagcaggg ttgtccacgg gccgagcgaa gcgagccagc cggtggccgc  5460
tcgcggccat cgtccacata tccacgggct ggcaagggag cgcagcgacc gcgcagggcg  5520
aagcccggag agcaagcccg taggggg                                      5547

SEQ ID NO: 15           moltype = DNA  length = 5363
FEATURE                 Location/Qualifiers
misc_feature            1..5363
                        note = pLX-B4-TagRFP-T
source                  1..5363
                        mol_type = other DNA
                        organism = synthetic construct
SEQUENCE: 15
ccatcatcag ttcggtggtc ttccgacgaa caataaggcc gcaaatcgcg gccttttta  60
ttgataacaa aaccggctca gttctgcgta gaaaccaaca tgcaagctcc accgggtgca  120
aagcggcagc ggcggcagga tatattcaat tgtaaatggc ttcatgtccg ggaaatctac  180
tggtggcagg atatattgtg gtgtaaacaa tggagaaaaa gattaattaa gtactagtag  240
cctggtcgaa accgtctcac cagtacgcac gattcaaggc ttgcttcaca aaccaaggca  300
agtaatagag attggagtct ctaaaaaggt agttcccact gaatcaaagg ccatggagtc  360
aaagattcaa atagaggacc taacagaact cgccgtaaag actggcgaac agttcataca  420
gagtctctta cgactcaatg acaagaagaa aatcttcgtc aacatggtgg agcacgacac  480
acttgtctac tccaaaaata tcaaagatac agtctcagaa gaccaaaggg caattgagac  540
ttttcaacaa agggtaatat ccggaaacct cctcggattc cattgcccag ctatctgtca  600
ctttattgtg aagatagtgg aaaaggaagg tggctcctac aaatgccatc attgcgataa  660
aggaaaggcc atcgttgaag atgcctctgc cgacagtggt cccaaagatg gacccccacc  720
cacgaggagc atcgtggaaa aagaagacgt tccaaccacg tcttcaaagc aagtggattg  780
atgtgataac atggtggagc acgacacact tgtctactcc aaaaatatca aagatacagt  840
ctcagaagac caaagggcaa ttgagacttt tcaacaaagg gtaatatccg gaaacctcct  900
cggattccat tgcccagcta tctgtcactt tattgtgaag atagtggaaa aggaaggtgg  960
ctcctacaaa tgccatcatt gcgataaagg aaaggccatc gttgaagatc ctctgccgac  1020
agtggtccca aagatggacc cccacccacg aggagcatcg tggaaaaaga agacgttcca  1080
accacgtctt caaagcaagt ggattgatgt gatatctcca ctgacgtaag ggatgacgca  1140
caatcccact atccttcgca agacccttcc tctatataag gaagttcatt tcatttggag  1200
aggaaaatat aaaaactcaa cacaacatac aaaattttaa gcaatcaaat caatctcaag  1260
ctatcaaaat ttttcaaatc tcacttgaaa gatcaaaaat caacaaagaa aatcccttaa  1320
tttctctacc aaatttactg caagtcaaga tggtttcaaa gggagaagag ctgattaagg  1380
agaacatgca catgaagctg tacatggagg gcaccgtgaa caaccaccac ttcaagtgca  1440
catccgaggg cgaaggcaag ccctacgagg gcacccagac catgagaatc aaggtggtcg  1500
agggcggccc tctccccttc gccttcgaca tcctggctac cagcttcatg tacggcagca  1560
gaaccttcat caaccacacc cagggcatcc ccgacttctt taagcagtcc ttccctgagg  1620
gcttcacatg ggagagagtc accacatacg aagacggggg cgtgctgacc gctacccagg  1680
acaccagcct ccaggacggc tgcctcatct acaacgtcaa gatcagaggg gtgaacttcc  1740
```

```
catccaacgg ccctgtgatg cagaagaaaa cactcggctg ggaggccaac accgagatgc  1800
tgtaccccgc tgacggcggc ctggaaggca gaacagacat ggccctgaag ctcgtgggcg  1860
ggggccacct gatctgcaac ttcaagacca catacagatc caagaaaccc gctaagaacc  1920
tcaagatgcc cggcgtctac tatgtggacc acagactgga aagaatcaag gaggccgaca  1980
aagagaccta cgtcgagcag cacgaggtgg ctgtggccag atactgcgac ctccctagca  2040
aactggggca caaacttaac taatcgatca cgtgaagctc atatccagat gaaggcagca  2100
gcattgagaa atgttcaaaa tcgtttattt ggcttggatg gaaacgtcgg aacacaagaa  2160
gaggacacag agagacacac cgctggtgat gttaatcgca acatgcacaa cctcctcggt  2220
gtgaggggag tgtagtggtc tcggtatcta tcataaactc tacctgggtg agagtctaat  2280
catccagttg tttttagatt cctgttagca tccttttctc cgctttaata gcagtacatt  2340
cagtgaggtt ttacctccat atgttctagt ctgttattgt cgaacacagg cccttgtatc  2400
tgatgtagcg agtgcttcac tccattcggg ttatagttct tgtgcaagag acaaaaaaaa  2460
aaaaaaaaaa aaaaaaaaaa aaaaaaaaaa aaaaaaaaaa aaaaaaaaaa aaaaaaaaaa  2520
atgcatgcct gcagatcgtt caaacatttg gcaataaagt ttcttaagat tgaatcctgt  2580
tgccggtctt gcgatgatta tcatctaatt tctgttgaat tacgttaagc atgtaataat  2640
taacatgtaa tgcatgacgt tatttatgag atgggttttt atgattagag tcccgcaatt  2700
atacatttaa tacgcgatag aaaacaaaat atagcgcgca aactaggata aattatcgcg  2760
cgcggtgtca tctatgttac tcgatctcgt caggagacgg gacaaggatg cgagctagcc  2820
tgcaggaatt gttgattttg tgatgactga tggcaggata tatgcggttg taattcattt  2880
ttattgtcta aatttctgta tttgtttgtt tgttcggttg taaatttttt tggaagaaca  2940
agaaaagaaa aaacacccgt tagggtgttt ttagttagtg tggcgcgccg acttgcgaca  3000
tgcggtcctt tgcaatttac ccaacaactc cgcggccggg aagccgatct cggcttgaac  3060
gaattgttag gtggcggtac ttgggtcgat atcaaagtgc atcacttctt cccgtatgcc  3120
caactttgta tagagagcca ctgcgggatc gtcaccgtaa tctgcttgca cgtagatcac  3180
ataagcacca agcgcgttgg cctcatgctt gaggagattg atgagcgcgg tggcaatgcc  3240
ctgcctccgg tgctctccgg agactgcgag atcatagata tagatctcac tacgcggctg  3300
ctcaaacttg ggcagaacgt aagccgcgag agcgccaaca accgcttctt ggtcgaaggc  3360
agcaagcgcg atgaatgtct tactacggag caagttcccg aggtaatcgg agtccggctg  3420
atgttgggag taggtggcta cgtctccgaa ctcacgaccg aaaagatcaa gagcagcccg  3480
catggatttg acttggtcag ggccgagcct acatgtgcga atgatgccca tacttgagcc  3540
acctaacttt gttttagggc gactgccctg ctgcgtaaca tcgttgctgc tgcgtaacat  3600
cgttgctgct ccataacatc aaacatcgac ccacggcgta acgcgcttgc tgcttggatg  3660
cccgaggcat aggctgtaca aaaaaacagt cataacaagc catgaaaacc gccactgcgc  3720
cgttaccacc gctgcgttcg gtcaaggttc tggaccagtt gcgtgagcgc atacgctact  3780
tgcattacag tttacgaacc gaacaggctt atgtcaagat cggattggcg gttatgcggt  3840
tctaccggcg cggcagcgtt acccgtgtcg gcggctccaa cggctcgcca tcgtccagaa  3900
aacacggctc atcgggcatc ggcaggcgct gctgcccgcg ccgttcccat tcctccgttt  3960
cggtcaaggc tggcaggtct ggttccatgc ccggaatgcc gggctggctg ggcggctcct  4020
cgccggggcc ggtcggtagt tgctgctcgc ccggatacag ggtcgggatg cggcgcaggt  4080
cgccatgccc caacagcgat tcgtcctggt cgtcgtgatc aaccaccacg gcggcactga  4140
acaccgacag gcgcaactgg tcgcggggct ggccccacgc cacgcggtca ttgaccacgt  4200
aggccgacac ggtgccgggg ccgttgagct tcacgacgga gatccagcgc tcggccacca  4260
agtccttgac tgcgtattgg accgtccgca aagaacgtcc gatgagcttg gaaagtgtct  4320
tctggctgac caccacggcg ttctggtggc ccatctgcgc cacgaggtga tgcagcagca  4380
ttgccgccgt gggtttcctc gcaataagcc cggcccacgc ctcatgcgct ttgcgttccg  4440
tttgcaccca gtgaccgggc ttgttcttgg cttgaatgcc gatttctctg gactgcgtgg  4500
ccatgcttat ctccatgcgg taggggtgcc gcacggttgc ggcaccatgc gcaatcagct  4560
gcaacttttc ggcagcgcga caacaattat gcgttgcgta aaagtggcag tcaattacag  4620
attttcttta acctacgcaa tgagctattg cggggggtgc cgcaatgagc tgttgcgtac  4680
ccccctttt taagttgttg atttttaagt ctttcgcatt tcgccctata tctagttctt  4740
tggtgcccaa agaagggcac ccctgcgggg ttcccccacg ccttcggcgc ggctccccct  4800
ccggcaaaaa gtggcccctc cggggcttgt tgatcgactg cgcggccttc ggccttgccc  4860
aaggtggcgc tgcccccttg gaacccccgc actcgccgcc gtgaggctcg gggggcaggc  4920
gggcgggctt cgcccttcga ctgcccccac tcgcataggc ttgggtcgtt ccaggcgcgt  4980
caaggccaag ccgctgcgcg gtcgctgcgc gagccttgac ccgccttcca cttggtgtcc  5040
aaccggcaag cgaagcgcgc aggccgcagg ccggaggctt ttccccagag aaaattaaaa  5100
aaattgatgg ggcaaggccg caggccgcgc agttggagcc ggtgggtatg tggtcgaagg  5160
ctgggtagcc ggtgggcaat ccctgtggtc aagctcgtgg gcaggcgcag cctgtccatc  5220
agcttgtcca gcagggttgt ccacgggccg agcgaagcga gccagccggt ggccgctcgc  5280
ggccatcgtc cacatatcca cgggctggca agggagcgca gcgaccgcgc agggcgaagc  5340
ccggagagca agcccgtagg ggg                                            5363
```

```
SEQ ID NO: 16          moltype = DNA  length = 6185
FEATURE                Location/Qualifiers
misc_feature           1..6185
                       note = pLX-R2-TagRFP-T
source                 1..6185
                       mol_type = other DNA
                       organism = synthetic construct
SEQUENCE: 16
ccatcatcag ttcggtggtc ttccgacgaa caataaggcc gcaaatcgcg gccttttta  60
ttgataacaa aaccggctca gttctgcgta gaaaccaaca tgcaagctcc accgggtgca  120
aagcggcagc ggcggcagga tatattcaat tgtaaatggc ttcatgtccg ggaaatctac  180
tggtggcagg atatattgtg gtgtaaacaa tggagaaaaa gattaattaa gtactagtag  240
cctggtcgaa accgtctcac cagtacgcac gattcaaggc ttgcttcaca aaccaaggca  300
agtaatagag attggagtct ctaaaaaggt agttcccact gaatcaaagg ccatggagtc  360
aaagattcaa atagaggacc taacagaact cgccgtaaag actggcgaac agttcataca  420
gagtctctta cgactcaatg acaagaagaa aatcttcgtc aacatggtgg agcacgacac  480
acttgtctac tccaaaaata tcaaagatac agtctcagaa gaccaaaggg caattgagac  540
```

-continued

```
ttttcaacaa agggtaatat ccggaaacct cctcggattc cattgcccag ctatctgtca  600
ctttattgtg aagatagtgg aaaaggaagg tggctcctac aaatgccatc attgcgataa  660
aggaaaggcc atcgttgaag atgcctctgc cgacagtggt cccaaagatg gacccccacc  720
cacgaggagc atcgtggaaa aagaagacgt tccaaccacg tcttcaaagc aagtggattg  780
atgtgataac atggtggagc acgacacact tgtctactcc aaaaatatca aagatacagt  840
ctcagaagac caaagggcaa ttgagacttt tcaacaaagg gtaatatccg gaaacctcct  900
cggattccat tgcccagcta tctgtcactt tattgtgaag atagtggaaa aggaaggtgg  960
ctcctacaaa tgccatcatt gcgataaagg aaaggccatc gttgaagatc ctctgccgac  1020
agtggtccca aagatggacc cccacccacg aggagcatcg tggaaaaaga agacgttcca  1080
accacgtctt caaagcaagt ggattgatgt gatatctcca ctgacgtaag ggatgacgca  1140
caatcccact atccttcgca agacccttcc tctatataag gaagttcatt tcatttggag  1200
aggaaaatat aaaaactcaa cacaacatac aaaattttaa gcaatcaaat caatctcaag  1260
ctatcaaaat ttttcaaatc tcacttgaaa gatcaaaaat caacaaagaa aatcccttaa  1320
tttctctacc aaatttactg caagtcaaga tggtttcaaa gggagaagag ctgattaagg  1380
agaacatgca catgaagctg tacatggagg gcaccgtgaa caaccaccac ttcaagtgca  1440
catccgaggg cgaaggcaag ccctacgagg gcacccagac catgagaatc aaggtggtcg  1500
agggcggccc tctccccttc gccttcgaca tcctggctac cagcttcatg tacggcagca  1560
gaaccttcat caaccacacc cagggcatcc ccgacttctt taagcagtcc ttccctgagg  1620
gcttcacatg ggagagagtc accacatacg aagacggggg cgtgctgacc gctacccagg  1680
acaccagcct ccaggacggc tgcctcatct acaacgtcaa gatcagaggg gtgaacttcc  1740
catccaacgg ccctgtgatg cagaagaaaa cactcggctg ggaggccaac accgagatgc  1800
tgtaccccgc tgacggcggc ctggaaggca gaacagacat ggccctgaag ctcgtgggcg  1860
gggccacct gatctgcaac ttcaagacca catacagatc caagaaaccc gctaagaacc  1920
tcaagatgcc cggcgtctac tatgtggacc acagactgga aagaatcaag gaggccgaca  1980
aagagaccta cgtcgagcag cacgaggtgg ctgtggccag atactgcgac ctccctagca  2040
aactggggca caaacttaac taatcgatca cgtgaagctc atatccagat gaaggcagca  2100
gcattgagaa atgttcaaaa tcgtttattt ggcttggatg gaaacgtcgg aacacaagaa  2160
gaggacacag agagacacac cgctggtgat gttaatcgca acatgcacaa cctcctcggt  2220
gtgaggggag tgtagtggtc tcggtatcta tcataaactc tacctgggtg agagtctaat  2280
catccagttg tttttagatt cctgttagca tccttttctc cgctttaata gcagtacatt  2340
cagtgaggtt ttacctccat atgttctagt ctgttattgt cgaacacagg cccttgtatc  2400
tgatgtagcg agtgcttcac tccattcggg ttatagttct tgtgcaagag acaaaaaaaa  2460
aaaaaaaaaa aaaaaaaaaa aaaaaaaaaa aaaaaaaaaa aaaaaaaaaa aaaaaaaaaa  2520
atgcatgcct gcagatcgtt caaacatttg gcaataaagt ttcttaagat tgaatcctgt  2580
tgccggtctt gcgatgatta tcatctaatt tctgttgaat tacgttaagc atgtaataat  2640
taacatgtaa tgcatgacgt tatttatgag atgggttttt atgattagag tcccgcaatt  2700
atacatttaa tacgcgatag aaaacaaaat atagcgcgca aactaggata aattatcgcg  2760
cgcggtgtca tctatgttac tcgatctcgt caggagacgg gacaaggatg cgagctagcc  2820
tgcaggaatt gttgattttg tgatgactga tggcaggata tatgcggttg taattcattt  2880
ttattgtcta aatttctgta tttgtttgtt tgttcggttg taaatttttt tggaagaaca  2940
agaaaagaaa aaacacccgt tagggtgttt ttagttagtg tggcgcgccg acttgcgaca  3000
tgcggtcctt tgcaatcaac tattagaaaa attcatccag catcagatga aattgcagtt  3060
tgttcatatc cggattatca atgccatatt tctgaaacag acgtttttgc aggctcgggc  3120
taaattcgcc caggcagttc cacagaatgg ccagatcctg ataacgatcc gcaatgccca  3180
cacggcccac atcaatgcag ccaatcagtt tgccttcatc gaaaatcagg ttatccaggc  3240
taaaatcgcc gtgggtcacc acgctatccg ggctaaacgg cagcagttta tgcatttctt  3300
tccacacctg ttccaccggc cagccgttac gttcatcatc aaaatcgctc gcatccacca  3360
ggccgttgtt catacggctc tgcgcctggg ccagacgaaa cacacgatcg ctgttaaacg  3420
ggcagttgca caccggaatg ctatgcagac gacgcagaaa cacggccagc gcatccacaa  3480
tgttttcgcc gctatccgga tattcttcca gcacctgaaa cgcggttttg cccggaatcg  3540
cggtggtcag cagccacgca tcatccgggg tgcgaataaa atgtttaatg gtcggcagcg  3600
gcataaattc ggtcagccag ttcagacgca ccatttcatc ggtcacatcg ttcgccacgc  3660
tgcctttgcc atgtttcaga aacagttccg gcgcatccgg tttgccatac agacgataaa  3720
tggtcgcgcc gctctgaccc acgttatcac gcgcccattt atagccatac agatccgcat  3780
ccatgttgct gttcagacgc ggacggctac agctcgtttc acgctgaata tggctcataa  3840
cacccttgt attactgttt atgtaagcag acagttttat tgttcatgat gatatatttt  3900
tatcttgtgc aatgtaacat cagagatttt gagacacaag atcggattgg cggttatgcg  3960
gttgcgatgc aggtggctgc tgaaccccca gccggaactg accccacaag gccctagcgt  4020
ttgcaatgca ccaggtcatc attgacccag gcgtgttcca ccaggccgct gcctcgcaac  4080
tcttcgcagg cttcgccgac ctgctcgcgc cacttcttca cgcgggtgga atccgatccg  4140
cacatgaggc ggaaggtttc cagcttgagc gggtacggct cccggtgcga gctgaaatag  4200
tcgaacatcc gtcgggccgt cggcgacagc ttgcggtact tctcccatat gaatttcgtg  4260
tagtggtcgc cagcaaacag cacgacgatt tcctcgtcga tcaggacctg gcaacgggac  4320
gttttcttgc cacggtccag gacgcggaag cggtgcagca gcgacaccga ttccaggtgc  4380
ccaacgcggt cggacgtgaa gcccatcgcc gtcgcctgta ggcgcgacag gcattcctcg  4440
gccttcgtgt aataccggcc attgatcgac cagcccaggt cctggcaaag ctcgtagaac  4500
gtgaaggtga tcggctcgcc gataggggtg cgcttcgcgt actccaacac ctgctgccac  4560
accagttcgt catcgtcggc ccgcagctcg acgccggtgt aggtgatctt cacgtccttg  4620
ttgacgtgga aaatgacctt gttttgcagc gcctcgcgcg ggattttctt gttgcgcgtg  4680
gtgaacaggg cagagcgggc cgtgtcgttt ggcatcgctc gcatcgtgtc cggccacggc  4740
gcaatatcga acaaggaaag ctgcatttcc ttgatctgct gcttcgtgtg tttcagcaac  4800
gcggcctgct tggcttcgct gacctgtttt gccaggtcct cgccggcggt ttttcgcttc  4860
ttggtcgtca tagttcctcg cgtgtcgatg gtcatcgact tcgccaaacc tgccgcctcc  4920
tgttcgagac gacgcgaacg ctccacggcg gccgatggcg cgggcagggc agggggagcc  4980
agttgcacgc tgtcgcgctc gatcttggcc gtagcttgct ggactatcga gccgacggac  5040
tggaaggttt cgcggggcgc acgcatgacg gtgcggcttg cgatggtttc ggcatcctcg  5100
gcggaaaacc ccgcgtcgat cagttcttgc ctgtatgcct tccggtcaaa cgtccgattc  5160
attcaccctc cttgcgggat tgccccggaa ttaattcccc ggatcgatcc gtcgatcttg  5220
atcccctgcg ccatcagatc cttggcggca agaaagccat ccagtttact ttgcagggct  5280
```

-continued

```
tcccaacctt accagagggc gccccagctg gcaattccgg ttcgcttgct gtccataaaa  5340
ccgcccagtc tagctatcgc catgtaagcc cactgcaagc tacctgcttt ctctttgcgc  5400
ttgcgttttc ccttgtccag atagcccagt agctgacatt catccggggt cagcaccgtt  5460
tctgcggact ggctttctac gtggctgcca tttttggggt gaggccgttc gcggccgagg  5520
ggcgcagccc ctggggggat gggaggcccg cgttagcggg ccgggagggt tcgagaaggg  5580
ggggcacccc ccttcggcgt gcgcggtcac gcgcacaggg cgcagccctg gttaaaaaca  5640
aggtttataa atattggttt aaaagcaggt taaaagacag gttagcggtg gccgaaaaac  5700
gggcggaaac ccttgcaaat gctggatttt ctgcctgtgg acagcccctc aaatgtcaat  5760
aggtgcgccc ctcatctgtc agcactctgc ccctcaagtg tcaaggatcg cgcccctcat  5820
ctgtcagtag tcgcgcccct caagtgtcaa taccgcaggg cacttatccc caggcttgtc  5880
cacatcatct gtgggaaact cgcgtaaaat caggcgtttt cgccgatttg cgaggctggc  5940
cagctccacg tcgccggccg aaatcgagcc tgcccctcat ctgtcaacgc cgcgccgggt  6000
gagtcggccc ctcaagtgtc aacgtccgcc cctcatctgt cagtgagggc caagttttcc  6060
gcgaggtatc cacaacgccg gcggccctac atggctctgc tgtagtgagt gggttgcgct  6120
ccggcagcgg tcctgatccc ccgcagaaaa aaaggatctc aagaagatcc tttgatcttt  6180
tctac                                                              6185

SEQ ID NO: 17          moltype = DNA  length = 6247
FEATURE                Location/Qualifiers
misc_feature           1..6247
                       note = pLX-R3-TagRFP-T
source                 1..6247
                       mol_type = other DNA
                       organism = synthetic construct
SEQUENCE: 17
ccatcatcag ttcggtggtc ttccgacgaa caataaggcc gcaaatcgcg gcctttttta  60
ttgataacaa aaccggctca gttctgcgta gaaaccaaca tgcaagctcc accgggtgca  120
aagcggcagc ggcggcagga tatattcaat tgtaaatggc ttcatgtccg ggaaatctac  180
tggtggcagg atatattgtg gtgtaaacaa tggagaaaaa gattaattaa gtactagtag  240
cctggtcgaa accgtctcac cagtacgcac gattcaaggc ttgcttcaca aaccaaggca  300
agtaatagag attggagtct ctaaaaaggt agttcccact gaatcaaagg ccatggagtc  360
aaagattcaa atagaggacc taacagaact cgccgtaaag actggcgaac agttcataca  420
gagtctctta cgactcaatg acaagaagaa aatcttcgtc aacatggtgg agcacgacac  480
acttgtctac tccaaaaata tcaaagatac agtctcagaa gaccaaaggg caattgagac  540
ttttcaacaa agggtaatat ccggaaacct cctcggattc cattgcccag ctatctgtca  600
ctttattgtg aagatagtgg aaaaggaagg tggctcctac aaatgccatc attgcgataa  660
aggaaaggcc atcgttgaag atgcctctgc cgacagtggt cccaaagatg gacccccacc  720
cacgaggagc atcgtggaaa aagaagacgt tccaaccacg tcttcaaagc aagtggattg  780
atgtgataac atggtggagc acgacacact tgtctactcc aaaaatatca aagatacagt  840
ctcagaagac caaagggcaa ttgagacttt tcaacaaagg gtaatatccg gaaacctcct  900
cggattccat tgcccagcta tctgtcactt tattgtgaag atagtggaaa aggaaggtgg  960
ctcctacaaa tgccatcatt gcgataaagg aaaggccatc gttgaagatc ctctgccgac  1020
agtggtccca aagatggacc cccacccacg aggagcatcg tggaaaaaga agacgttcca  1080
accacgtctt caaagcaagt ggattgatgt gatatctcca ctgacgtaag ggatgacgca  1140
caatcccact atccttcgca agacccttcc tctatataag gaagttcatt tcatttggag  1200
aggaaaatat aaaaactcaa cacaacatac aaaattttaa gcaatcaaat caatctcaag  1260
ctatcaaaat ttttcaaatc tcacttgaaa gatcaaaaat caacaaagaa aatcccttaa  1320
tttctctacc aaatttactg caagtcaaga tggtttcaaa gggagaagag ctgattaagg  1380
agaacatgca catgaagctg tacatggagg gcaccgtgaa caaccaccac ttcaagtgca  1440
catccgaggg cgaaggcaag ccctacgagg gcacccagac catgagaatc aaggtggtcg  1500
agggcggccc tctccccttc gccttcgaca tcctggctac cagcttcatg tacggcagca  1560
gaaccttcat caaccacacc cagggcatcc ccgacttctt taagcagtcc ttccctgagg  1620
gcttcacatg ggagagagtc accacatacg aagacggggg cgtgctgacc gctacccagg  1680
acaccagcct ccaggacggc tgcctcatct acaacgtcaa gatcagaggg gtgaacttcc  1740
catccaacgg ccctgtgatg cagaagaaaa cactcggctg ggaggccaac accgagatgc  1800
tgtaccccgc tgacggcggc ctggaaggca gaacagacat ggccctgaag ctcgtgggcg  1860
ggggccacct gatctgcaac ttcaagacca catacagatc caagaaaccc gctaagaacc  1920
tcaagatgcc cggcgtctac tatgtggacc acagactgga aagaatcaag gaggccgaca  1980
aagagaccta cgtcgagcag cacgaggtgg ctgtggccag atactgcgac ctccctagca  2040
aactggggca caaacttaac taatcgatca cgtgaagctc atatccagat gaaggcagca  2100
gcattgagaa atgttcaaaa tcgtttattt ggcttggatg gaaacgtcgg aacacaagaa  2160
gaggacacag agagacacac cgctggtgat gttaatcgca acatgcacaa cctcctcggt  2220
gtgaggggag tgtagtggtc tcggtatcta tcataaactc tacctgggtg agagtctaat  2280
catccagttg tttttagatt cctgttagca tccttttctc cgctttaata gcagtacatt  2340
cagtgaggtt ttacctccat atgttctagt ctgttattgt cgaacacagg cccttgtatc  2400
tgatgtagcg agtgcttcac tccattcggg ttatagttct tgtgcaagag acaaaaaaaa  2460
aaaaaaaaaa aaaaaaaaaa aaaaaaaaaa aaaaaaaaaa aaaaaaaaaa aaaaaaaaaa  2520
atgcatgcct gcagatcgtt caaacatttg gcaataaagt ttcttaagat tgaatcctgt  2580
tgccggtctt gcgatgatta tcatctaatt tctgttgaat tacgttaagc atgtaataat  2640
taacatgtaa tgcatgacgt tatttatgag atgggttttt atgattagag tcccgcaatt  2700
atacatttaa tacgcgatag aaaacaaaat atagcgcgca aactaggata aattatcgcg  2760
cgcggtgtca tctatgttac tcgatctcgt caggagacgg gacaaggatg cgagctagcc  2820
tgcaggaatt gttgattttg tgatgactga tggcaggata tatgcggttg taattcattt  2880
ttattgtcta aatttctgta tttgtttgtt tgttcggttg taaatttttt tggaagaaca  2940
agaaaagaaa aaacacccgt tagggtgttt ttagttagtg tggcgcgccg acttgcgaca  3000
tgcggtcctt tgttatttgc cgactacctt ggtgatctcg cctttcacgt agtggacaaa  3060
ttcttccaac tgatctgcgc gcgaggccaa gcgatcttct tcttgtccaa gataagcctg  3120
tctagcttca agtatgacgg gctgatactg ggccggcagg cgctccattg cccagtcggc  3180
agcgacatcc ttcggcgcga ttttgccggt tactgcgctg taccaaatgc gggacaacgt  3240
```

-continued

```
aagcactaca tttcgctcat cgccagccca gtcgggcggc gagttccata gcgttaaggt  3300
ttcatttagc gcctcaaata gatcctgttc aggaaccgga tcaaagagtt cctccgccgc  3360
tggacctacc aaggcaacgc tatgttctct tgcttttgtc agcaagatag ccagatcaat  3420
gtcgatcgtg gctggctcga agatacctgc aagaatgtca ttgcgctgcc attctccaaa  3480
ttgcagttcg cgcttagctg gataacgcca cggaatgatg tcgtcgtgca caacaatggt  3540
gacttctaca gcgcggagaa tctcgctctc tccaggggaa gccgaagttt ccaaaaggtc  3600
gttgatcaaa gctcgccgcg ttgtttcatc aagccttacg gtcaccgtaa ccagcaaatc  3660
aatatcactg tgtggcttca ggccgccatc cactgcggag ccgtacaaat gtacggccag  3720
caacgtcggt tcgagatggc gctcgatgac gccaactacc tctgatagtt gagtcgatac  3780
ttcggcgatc accgcttccc tcatgatgtt taactttgtt ttagggcgac tgccctgctg  3840
cgtaacatcg ttgctgctcc ataacatcaa acatcgaccc acggcgtaac gcgcttgctg  3900
cttggatgcc cgaggcatag actgtaccc aaaaaaacag tcataacaag ccatgaaaac  3960
cgccactgcg ccgttaccac cgctgcgttc ggtcaaggtt cgatcggatt ggcggttatg  4020
cggttgcgat gcaggtggct gctgaacccc cagccggaac tgaccccaca aggccctagc  4080
gtttgcaatg caccaggtca tcattgaccc aggcgtgttc caccaggccg ctgcctcgca  4140
actcttcgca ggcttcgccg acctgctcgc gccacttctt cacgcgggtg gaatccgatc  4200
cgcacatgag gcggaaggtt tccagcttga gcgggtacgg ctcccggtgc gagctgaaat  4260
agtcgaacat ccgtcgggcc gtcggcgaca gcttgcggta cttctcccat atgaatttcg  4320
tgtagtggtc gccagcaaac agcacgacga tttcctcgtc gatcaggacc tggcaacggg  4380
acgttttctt gccacggtcc aggacgcgga agcggtgcag cagcgacacc gattccaggt  4440
gcccaacgcg gtcggacgtg aagcccatcg ccgtcgcctg taggcgcgac aggcattcct  4500
cggccttcgt gtaataccgg ccattgatcg accagcccag gtcctggcaa agctcgtaga  4560
acgtgaaggt gatcggctcg ccgatagggg tgcgcttcgc gtactccaac acctgctgcc  4620
acaccagttc gtcatcgtcg gcccgcagct cgacgccggt gtaggtgatc ttcacgtcct  4680
tgttgacgtg gaaaatgacc ttgttttgca gcgcctcgcg cgggattttc ttgttgcgcg  4740
tggtgaacag ggcagagcgg gccgtgtcgt ttggcatcgc tcgcatcgtg tccggccacg  4800
gcgcaatatc gaacaaggaa agctgcattt ccttgatctg ctgcttcgtg tgtttcagca  4860
acgcggcctg cttggcttcg ctgacctgtt ttgccaggtc ctcgccggcg gtttttcgct  4920
tcttggtcgt catagttcct cgcgtgtcga tggtcatcga cttcgccaaa cctgccgcct  4980
cctgttcgag acgacgcgaa cgctccacgg cggccgatgg cgcgggcagg gcagggggag  5040
ccagttgcac gctgtcgcgc tcgatcttgg ccgtagcttg ctggactatc gagccgacgg  5100
actggaaggt ttcgcggggc gcacgcatga cggtgcggct tgcgatggtt tcggcatcct  5160
cggcggaaaa ccccgcgtcg atcagttctt gcctgtatgc cttccggtca aacgtccgat  5220
tcattcaccc tccttgcggg attgccccgg aattaattcc ccggatcgat ccgtcgatct  5280
tgatcccctg cgccatcaga tccttggcgg caagaaagcc atccagttta ctttgcaggg  5340
cttcccaacc ttaccagagg gcgccccagc tggcaattcc ggttcgcttg ctgtccataa  5400
aaccgcccag tctagctatc gccatgtaag cccactgcaa gctacctgct ttctctttgc  5460
gcttgcgttt tcccttgtcc agatagccca gtagctgaca ttcatccggg gtcagcaccg  5520
tttctgcgga ctggctttct acgtggctgc catttttggg gtgaggccgt tcgcggccga  5580
ggggcgcagc ccctgggggg atgggaggcc cgcgttagcg ggccgggagg gttcgagaag  5640
ggggggcacc ccccttcggc gtgcgcggtc acgcgcacag ggcgcagccc tggttaaaaa  5700
caaggtttat aaatattggt ttaaaagcag gttaaaagac aggttagcgg tggccgaaaa  5760
acgggcggaa acccttgcaa atgctggatt ttctgcctgt ggacagcccc tcaaatgtca  5820
ataggtgcgc ccctcatctg tcagcactct gcccctcaag tgtcaaggat cgcgcccctc  5880
atctgtcagt agtcgcgccc ctcaagtgtc aataccgcag ggcacttatc cccaggcttg  5940
tccacatcat ctgtgggaaa ctcgcgtaaa atcaggcgtt ttcgccgatt tgcgaggctg  6000
gccagctcca cgtcgccggc cgaaatcgag cctgcccctc atctgtcaac gccgcgccgg  6060
gtgagtcggc ccctcaagtg tcaacgtccg cccctcatct gtcagtgagg gccaagtttt  6120
ccgcgaggta tccacaacgc cggcggccct acatggctct gctgtagtga gtgggttgcg  6180
ctccggcagc ggtcctgatc ccccgcagaa aaaaaggatc tcaagaagat cctttgatct  6240
tttctac                                                            6247

SEQ ID NO: 18          moltype = DNA  length = 6063
FEATURE                Location/Qualifiers
misc_feature           1..6063
                       note = pLX-R4-TagRFP-T
source                 1..6063
                       mol_type = other DNA
                       organism = synthetic construct
SEQUENCE: 18
ccatcatcag ttcggtggtc ttccgacgaa caataaggcc gcaaatcgcg gcctttttta  60
ttgataacaa aaccggctca gttctgcgta gaaaccaaca tgcaagctcc accgggtgca  120
aagcggcagc ggcggcagga tatattcaat tgtaaatggc ttcatgtccg ggaaatctac  180
tggtggcagg atatattgtg gtgtaaacaa tggagaaaaa gattaattaa gtactagtag  240
cctggtcgaa accgtctcac cagtacgcac gattcaaggc ttgcttcaca aaccaaggca  300
agtaatagag attggagtct ctaaaaaggt agttcccact gaatcaaagg ccatggagtc  360
aaagattcaa atagaggacc taacagaact cgccgtaaag actggcgaac agttcataca  420
gagtctctta cgactcaatg acaagaagaa aatcttcgtc aacatggtgg agcacgacac  480
acttgtctac tccaaaaata tcaaagatac agtctcagaa gaccaaaggg caattgagac  540
ttttcaacaa agggtaatat ccggaaacct cctcggattc cattgcccag ctatctgtca  600
ctttattgtg aagatagtgg aaaaggaagg tggctcctac aaatgccatc attgcgataa  660
aggaaaggcc atcgttgaag atgcctctgc cgacagtggt cccaaagatg gacccccacc  720
cacgaggagc atcgtggaaa aagaagacgt tccaaccacg tcttcaaagc aagtggattg  780
atgtgataac atggtggagc acgacacact tgtctactcc aaaaatatca aagatacagt  840
ctcagaagac caaagggcaa ttgagacttt tcaacaaagg gtaatatccg gaaacctcct  900
cggattccat tgcccagcta tctgtcactt tattgtgaag atagtggaaa aggaaggtgg  960
ctcctacaaa tgccatcatt gcgataaagg aaaggccatc gttgaagatc ctctgccgac  1020
agtggtccca aagatggacc cccacccacg aggagcatcg tggaaaaaga agacgttcca  1080
accacgtctt caaagcaagt ggattgatgt gatatctcca ctgacgtaag ggatgacgca  1140
```

-continued

```
caatcccact atccttcgca agacccttcc tctatataag gaagttcatt tcatttggag  1200
aggaaaatat aaaaactcaa cacaacatac aaaattttaa gcaatcaaat caatctcaag  1260
ctatcaaaat ttttcaaatc tcacttgaaa gatcaaaaat caacaaagaa aatcccttaa  1320
tttctctacc aaatttactg caagtcaaga tggtttcaaa gggagaagag ctgattaagg  1380
agaacatgca catgaagctg tacatggagg gcaccgtgaa caaccaccac ttcaagtgca  1440
catccgaggg cgaaggcaag ccctacgagg gcacccagac catgagaatc aaggtggtcg  1500
agggcggccc tctccccttc gccttcgaca tcctggctac cagcttcatg tacggcagca  1560
gaaccttcat caaccacacc cagggcatcc ccgacttctt taagcagtcc ttccctgagg  1620
gcttcacatg ggagagagtc accacatacg aagacggggg cgtgctgacc gctacccagg  1680
acaccagcct ccaggacggc tgcctcatct acaacgtcaa gatcagaggg gtgaacttcc  1740
catccaacgg ccctgtgatg cagaagaaaa cactcggctg ggaggccaac accgagatgc  1800
tgtaccccgc tgacggcggc ctggaaggca gaacagacat ggccctgaag ctcgtgggcg  1860
ggggccacct gatctgcaac ttcaagacca catacagatc caagaaaccc gctaagaacc  1920
tcaagatgcc cggcgtctac tatgtggacc acagactgga aagaatcaag gaggccgaca  1980
aagagaccta cgtcgagcag cacgaggtgg ctgtggccag atactgcgac ctccctagca  2040
aactggggca caaacttaac taatcgatca cgtgaagctc atatccagat gaaggcagca  2100
gcattgagaa atgttcaaaa tcgtttattt ggcttggatg gaaacgtcgg aacacaagaa  2160
gaggacacag agagacacac cgctggtgat gttaatcgca acatgcacaa cctcctcggt  2220
gtgaggggag tgtagtggtc tcggtatcta tcataaactc tacctgggtg agagtctaat  2280
catccagttg tttttagatt cctgttagca tccttttctc cgctttaata gcagtacatt  2340
cagtgaggtt ttacctccat atgttctagt ctgttattgt cgaacacagg cccttgtatc  2400
tgatgtagcg agtgcttcac tccattcggg ttatagttct tgtgcaagag acaaaaaaaa  2460
aaaaaaaaaa aaaaaaaaaa aaaaaaaaaa aaaaaaaaaa aaaaaaaaaa aaaaaaaaaa  2520
atgcatgcct gcagatcgtt caaacatttg gcaataaagt ttcttaagat tgaatcctgt  2580
tgccggtctt gcgatgatta tcatctaatt tctgttgaat tacgttaagc atgtaataat  2640
taacatgtaa tgcatgacgt tatttatgag atgggttttt atgattagag tcccgcaatt  2700
atacatttaa tacgcgatag aaaacaaaat atagcgcgca aactaggata aattatcgcg  2760
cgcggtgtca tctatgttac tcgatctcgt caggagacgg gacaaggatg cgagctagcc  2820
tgcaggaatt gttgattttg tgatgactga tggcaggata tatgcggttg taattcattt  2880
ttattgtcta aatttctgta tttgtttgtt tgttcggttg taaatttttt tggaagaaca  2940
agaaaagaaa aaacacccgt tagggtgttt ttagttagtg tggcgcgccg acttgcgaca  3000
tgcggtcctt tgcaatttac ccaacaactc cgcggccggg aagccgatct cggcttgaac  3060
gaattgttag gtggcggtac ttgggtcgat atcaaagtgc atcacttctt cccgtatgcc  3120
caactttgta tagagagcca ctgcgggatc gtcaccgtaa tctgcttgca cgtagatcac  3180
ataagcacca agcgcgttgg cctcatgctt gaggagattg atgagcgcgg tggcaatgcc  3240
ctgcctccgg tgctctccgg agactgcgag atcatagata tagatctcac tacgcggctg  3300
ctcaaacttg ggcagaacgt aagccgcgag agcgccaaca accgcttctt ggtcgaaggc  3360
agcaagcgcg atgaatgtct tactacggag caagttcccg aggtaatcgg agtccggctg  3420
atgttgggag taggtggcta cgtctccgaa ctcacgaccg aaaagatcaa gagcagcccg  3480
catggatttg acttggtcag ggccgagcct acatgtgcga atgatgccca tacttgagcc  3540
acctaacttt gttttagggc gactgccctg ctgcgtaaca tcgttgctgc tgcgtaacat  3600
cgttgctgct ccataacatc aaacatcgac ccacggcgta acgcgcttgc tgcttggatg  3660
cccgaggcat aggctgtaca aaaaaacagt cataacaagc catgaaaacc gccactgcgc  3720
cgttaccacc gctgcgttcg gtcaaggttc tggaccagtt gcgtgagcgc atacgctact  3780
tgcattacag tttacgaacc gaacaggctt atgtcaagat cggattggcg gttatgcggt  3840
tgcgatgcag gtggctgctg aacccccagc cggaactgac cccacaaggc cctagcgttt  3900
gcaatgcacc aggtcatcat tgacccaggc gtgttccacc aggccgctgc ctcgcaactc  3960
ttcgcaggct tcgccgacct gctcgcgcca cttcttcacg cgggtggaat ccgatccgca  4020
catgaggcgg aaggtttcca gcttgagcgg gtacggctcc cggtgcgagc tgaaatagtc  4080
gaacatccgt cgggccgtcg gcgacagctt gcggtacttc tcccatatga atttcgtgta  4140
gtggtcgcca gcaaacagca cgacgatttc ctcgtcgatc aggacctggc aacgggacgt  4200
tttcttgcca cggtccagga cgcggaagcg gtgcagcagc gacaccgatt ccaggtgccc  4260
aacgcggtcg gacgtgaagc ccatcgccgt cgcctgtagg cgcgacaggc attcctcggc  4320
cttcgtgtaa taccggccat tgatcgacca gcccaggtcc tggcaaagct cgtagaacgt  4380
gaaggtgatc ggctcgccga taggggtgcg cttcgcgtac tccaacacct gctgccacac  4440
cagttcgtca tcgtcggccc gcagctcgac gccggtgtag gtgatcttca cgtccttgtt  4500
gacgtggaaa atgaccttgt tttgcagcgc ctcgcgcggg attttcttgt tgcgcgtggt  4560
gaacagggca gagcgggccg tgtcgtttgg catcgctcgc atcgtgtccg gccacggcgc  4620
aatatcgaac aaggaaagct gcatttcctt gatctgctgc ttcgtgtgtt tcagcaacgc  4680
ggcctgcttg gcttcgctga cctgttttgc caggtcctcg ccggcggttt ttcgcttctt  4740
ggtcgtcata gttcctcgcg tgtcgatggt catcgacttc gccaaacctg ccgcctcctg  4800
ttcgagacga cgcgaacgct ccacggcggc cgatggcgcg ggcagggcag gggagccag  4860
ttgcacgctg tcgcgctcga tcttggccgt agcttgctgg actatcgagc cgacggactg  4920
gaaggtttcg cggggcgcac gcatgacggt gcggcttgcg atggtttcgg catcctcggc  4980
ggaaaacccc gcgtcgatca gttcttgcct gtatgccttc cggtcaaacg tccgattcat  5040
tcaccctcct tgcgggattg ccccggaatt aattccccgg atcgatccgt cgatcttgat  5100
cccctgcgcc atcagatcct tggcggcaag aaagccatcc agtttacttt gcagggcttc  5160
ccaaccttac cagagggcgc cccagctggc aattccggtt cgcttgctgt ccataaaacc  5220
gcccagtcta gctatcgcca tgtaagccca ctgcaagcta cctgctttct ctttgcgctt  5280
gcgttttccc ttgtccagat agcccagtag ctgacattca tccggggtca gcaccgtttc  5340
tgcggactgg ctttctacgt ggctgccatt tttggggtga ggccgttcgc ggccgagggg  5400
cgcagcccct gggggggatgg gaggcccgcg ttagcgggcc gggagggttc gagaaggggg  5460
ggcacccccc ttcggcgtgc gcggtcacgc gcacagggcg cagccctggt taaaaacaag  5520
gtttataaat attggtttaa aagcaggtta aaagacaggt tagcggtggc cgaaaaacgg  5580
gcggaaaccc ttgcaaatgc tggattttct gcctgtggac agcccctcaa atgtcaatag  5640
gtgcgcccct catctgtcag cactctgccc ctcaagtgtc aaggatcgcg cccctcatct  5700
gtcagtagtc gcgcccctca agtgtcaata ccgcagggca cttatcccca ggcttgtcca  5760
catcatctgt gggaaactcg cgtaaaatca ggcgttttcg ccgatttgcg aggctggcca  5820
gctccacgtc gccggccgaa atcgagcctg cccctcatct gtcaacgccg cgccgggtga  5880
```

-continued

```
gtcggcccct caagtgtcaa cgtccgcccc tcatctgtca gtgagggcca agttttccgc  5940
gaggtatcca caacgccggc ggccctacat ggctctgctg tagtgagtgg gttgcgctcc  6000
ggcagcggtc ctgatccccc gcagaaaaaa aggatctcaa gaagatcctt tgatcttttc  6060
tac                                                                6063

SEQ ID NO: 19          moltype = DNA  length = 10749
FEATURE                Location/Qualifiers
misc_feature           1..10749
                       note = pLX-B2-XT1-XT2-hCas9
source                 1..10749
                       mol_type = other DNA
                       organism = synthetic construct
SEQUENCE: 19
ccatcatcag ttcggtggtc ttccgacgaa caataaggcc gcaaatcgcg gccttttta  60
ttgataacaa aaccggctca gttctgcgta gaaaccaaca tgcaagctcc accgggtgca  120
aagcggcagc ggcggcagga tatattcaat tgtaaatggc ttcatgtccg ggaaatctac  180
tggtggcagg atatattgtg gtgtaaacaa tggagaaaaa gattaattaa gtactagtag  240
cctggtcgaa accgtctcag gagagcgatc agcttgcatg ccggtcgatc tagtaacata  300
gatgacaccg cgcgcgataa tttatcctag tttgcgcgct atattttgtt ttctatcgcg  360
tattaaatgt ataattgcgg gactctaatc ataaaaaccc atctcataaa taacgtcatg  420
cattacatgt taattattac atgcttaacg taattcaaca gaaattatat gataatcatg  480
gcaagaccgg caacaggatt caatcttaag aaactttatt gccaaatgtt tgaacgatct  540
gcttgactct agctagagtc cgaaccccag agtcccgctc agaagaactc gtcaagaagg  600
cgatagaagg ctatgcgctg cgaatcggga gcggcgatac cgtaaagcac gaggaagcgg  660
tcagcccatt cgccgccaag ctcttcagca atatcacggg tagccaacgc tatgtcctga  720
tagcggtccg ccacacccag ccggccacag tcgatgaatc cagaaaagcg gccattttcc  780
accatgatat tcggcaagca ggcgtcgccg tgggtcacga cgagatcctc gccgtcgggc  840
atccgcgcct tgagcctggc gaacagttcg gctggcgcga gcccctgatg ctcttcgtcc  900
agatcatcct gatcgacaag accggcttcc atccgagtac gtgctcgctc gatgcggtgt  960
ttcgcttggt ggtcgaatgg gcaggtagcc ggatcaagcg tatgcagccg ccgcattgca  1020
tcagccatga tggatacttt ctcggcagga gcaaggtgag atgacaggag atcctgcccc  1080
ggcacttcgc ccaatagcag ccagtccctt cccgcttcag tgacaacgtc gagcacagct  1140
gcgcaaggaa cgcccgtcgt ggccagccac gatagccgcg ctgcctcgtc ttggagttca  1200
ttcagggcac cggacaggtc ggtcttgaca aaaagaaccg ggcgcccctg cgctgacagc  1260
cggaacacgg cggcatcaga gcagccgatt gtctgttgtg cccagtcata gccgaatagc  1320
ctctccaccc aagcggccgg agaacctgcg tgcaatccat cttgttcaat catgcctcga  1380
tcgagttgag agtgaatatg agactctaat tggataccga ggggaattta tggaacgtca  1440
gtggagcatt tttgacaaga aatatttgct agctgatagt gaccttaggc gacttttgaa  1500
cgcgcaataa tggtttctga cgtatgtgct tagctcatta aactccagaa acccgcggct  1560
gagtggctcc ttcaacgttg cggttctgtc agttccaaac gtaaaacggc ttgtcccgcg  1620
tcatcggcgg gggtcataac gtgactccct taattctcat gtatctccgt caggagcatc  1680
ttcattctta agatatgaag ataatcttca aaaggcccct gggaatctga aagaagagaa  1740
gcaggcccat ttatatggga aagaacaata gtatttctta tataggccca tttaagttga  1800
aaacaatctt caaaagtccc acatcgctta gataagaaaa cgaagctgag tttatataca  1860
gctagagtcg aagtagtgat tgaaaacacc gtcttcggag agttttagag ctagaaatag  1920
caagttaaaa taaggctagt ccgttatcaa cttgaaaaag tggcaccgag tcggtgcttt  1980
ttttctagac ccagctttct tgtacaaagt tggcattacg ctgtcaggag catcttcatt  2040
cttaagatat gaagataatc ttcaaaaggc ccctgggaat ctgaaagaag agaagcaggc  2100
ccatttatat gggaaagaac aatagtattt cttatatagg cccatttaag ttgaaaacaa  2160
tcttcaaaag tcccacatcg cttagataag aaaacgaagc tgagtttata tacagctaga  2220
gtcgaagtag tgattgaaaa ttgggaaaaa actaggtttt agagctagaa atagcaagtt  2280
aaaataaggc tagtccgtta tcaacttgaa aaagtggcac cgagtcggtg ctttttttct  2340
agacccagct ttcttgtaca aagttggcat tacgctgtca ggagactaga gccaagctga  2400
tctcctttgc cccggagatc accatggacg actttctcta tctctacgat ctaggaagaa  2460
agttcgacgg agaaggtgac gataccatgt tcaccaccga taatgagaag attagcctct  2520
tcaatttcag aaagaatgct gacccacaga tggttagaga ggcctacgcg gcaggtctga  2580
tcaagacgat ctacccgagt aataatctcc aggagatcaa ataccttccc aagaaggtta  2640
aagatgcagt caaaagattc aggactaact gcatcaagaa cacagagaaa gatatatttc  2700
tcaagatcag aagtactatt ccagtatgga cgattcaagg cttgcttcat aaaccaaggc  2760
aagtaataga gattggagtc tctaagaaag tagttcctac tgaatcaaag gccatggagt  2820
caaaaattca gatcgaggat ctaacagaac tcgccgtgaa gactggcgaa cagttcatac  2880
agagtctttt acgactcaat gacaagaaga aaatcttcgt caacatggtg gagcacgaca  2940
ctctcgtcta ctccaagaat atcaaagata cagtctcaga agaccaaagg gctattgaga  3000
cttttcaaca aagggtaata tcgggaaacc tcctcggatt ccattgccca gctatctgtc  3060
acttcatcaa aaggacagta gaaaaggaag gtggcaccta caaatgccat cattgcgata  3120
aaggaaaggc tatcgttcaa gatgcctctg ccgacagtgg tcccaaagat ggacccccac  3180
ccacgaggag catcgtggaa aaagaagacg ttccaaccac gtcttcaaag caagtggatt  3240
gatgtgatat ctccactgac gtaagggatg acgcacaatc ccactatcct tcgcaagacc  3300
cttcctctat ataaggaagt tcatttcatt tggagaggac tccggtattt ttacaacaat  3360
accacaacaa aacaaacaac aaacaacatt acaatttact attctagtcg aaatggacaa  3420
gaagtactcc attgggctcg atatcggcac aaacagcgtc ggctgggccg tcattacgga  3480
cgagtacaag gtgccgagca aaaaattcaa agttctgggc aataccgatc gccacagcat  3540
aaagaagaac ctcattggcg ccctcctgtt cgactccggg gaaacggccg aagccacgcg  3600
gctcaaaaga acagcacggc gcagatatac ccgcagaaag aatcggatct gctacctgca  3660
ggagatcttt agtaatgaga tggctaaggt ggatgactct ttcttccata ggctggagga  3720
gtcctttttg gtggaggagg ataaaaagca cgagcgccac ccaatctttg gcaatatcgt  3780
ggacgaggtg gcgtaccatg aaaagtaccc aaccatatat catctgagga agaagcttgt  3840
agacagtact gataaggctg acttgcggtt gatctatctc gcgctggcgc atatgatcaa  3900
atttcgggga cacttcctca tcgagggggga cctgaaccca gacaacagcg atgtcgacaa  3960
```

-continued

```
actctttatc caactggttc agacttacaa tcagcttttc gaagagaacc cgatcaacgc  4020
atccggagtt gacgccaaag caatcctgag cgctaggctg tccaaatccc ggcggctcga  4080
aaacctcatc gcacagctcc ctggggagaa gaagaacggc ctgtttggta atcttatcgc  4140
cctgtcactc gggctgaccc ccaactttaa atctaacttc gacctggccg aagatgccaa  4200
gcttcaactg agcaaagaca cctacgatga tgatctcgac aatctgctgg cccagatcgg  4260
cgaccagtac gcagaccttt ttttggcggc aaagaacctg tcagacgcca ttctgctgag  4320
tgatattctg cgagtgaaca cggagatcac caaagctccg ctgagcgcta gtatgatcaa  4380
gcgctatgat gagcaccacc aagacttgac tttgctgaag gcccttgtca gacagcaact  4440
gcctgagaag tacaaggaaa ttttcttcga tcagtctaaa aatggctacg ccggatacat  4500
tgacggcgga gcaagccagg aggaatttta caaatttatt aagcccatct tggaaaaaat  4560
ggacggcacc gaggagctgc tggtaaagct taacagagaa gatctgttgc gcaaacagcg  4620
cactttcgac aatggaagca tcccccacca gattcacctg ggcgaactgc acgctatcct  4680
caggcggcaa gaggatttct acccctttt gaaagataac agggaaaaga ttgagaaaat  4740
cctcacattt cggataccct actatgtagg cccctcgcc cggggaaatt ccagattcgc  4800
gtggatgact cgcaaatcag aagagactat cactccctgg aacttcgagg aagtcgtgga  4860
taagggggcc tctgcccagt ccttcatcga aaggatgact aactttgata aaaatctgcc  4920
taacgaaaag gtgcttccta aacactctct gctgtacgag tacttcacag tttataacga  4980
gctcaccaag gtcaaatacg tcacagaagg gatgagaaag ccagcattcc tgtctggaga  5040
gcagaagaaa gctatcgtgg acctcctctt caagacgaac cggaaagtta ccgtgaaaca  5100
gctcaaagaa gattatttca aaaagattga atgtttcgac tctgttgaaa tcagcggagt  5160
ggaggatcgc ttcaacgcat ccctgggaac gtatcacgat ctcctgaaaa tcattaaaga  5220
caaggacttc ctggacaatg aggagaacga ggacattctt gaggacattg tcctcaccct  5280
tacgttgttt gaagataggg agatgattga agaacgcttg aaaacttacg ctcatctctt  5340
cgacgacaaa gtcatgaaac agctcaagag gcgccgatat acaggatggg ggcggctgtc  5400
aagaaaactg atcaatggga tccgagacaa gcagagtgga aagacaatcc tggattttct  5460
taagtccgat ggatttgcca accggaactt catgcagttg atccatgatg actctctcac  5520
ctttaaggag gacatccaga aagcacaagt ttctggccag gggacagtc tccacgagca  5580
catcgctaat cttgcaggta gcccagctat caaaaaggga atactgcaga ccgttaaggt  5640
cgtggatgaa ctcgtcaaag taatgggaag gcataagccc gagaatatcg ttatcgagat  5700
ggcccgagag aaccaaacta cccagaaggg acagaagaac agtagggaaa ggatgaagag  5760
gattgaagag ggtataaaag aactggggtc ccaaatcctt aaggaacacc cagttgaaaa  5820
cacccagctt cagaatgaga agctctacct gtactacctg cagaacggca gggacatgta  5880
cgtggatcag gaactggaca tcaatcggct ctccgactac gacgtggatc atatcgtgcc  5940
ccagtctttt ctcaaagatg attctattga taataaagtg ttgacaagat ccgataaaaa  6000
tagagggaag agtgataacg tcccctcaga agaagttgtc aagaaaatga aaaattattg  6060
gcggcagctg ctgaacgcca aactgatcac acaacggaag ttcgataatc tgactaaggc  6120
tgaacgaggt ggcctgtctg agttggataa agccggcttc atcaaaaggc agcttgttga  6180
gacacgccag atcaccaagc acgtggccca aattctcgat tcacgcatga acaccaagta  6240
cgatgaaaat gacaaactga ttcgagaggt gaaagttatt actctgaagt ctaagctggt  6300
ttcagatttc agaaaggact ttcagtttta taaggtgaga gagatcaaca attaccacca  6360
tgcgcatgat gcctacctga atgcagtggt aggcactgca cttatcaaaa aatatcccaa  6420
gcttgaatct gaatttgttt acggagacta taaagtgtac gatgttagga aaatgatcgc  6480
aaagtctgag caggaaatag gcaaggccac cgctaagtac ttcttttaca gcaatattat  6540
gaatttttc aagaccgaga ttacactggc caatggagag attcggaagc gaccacttat  6600
cgaaacaaac ggagaaacag gagaaatcgt gtgggacaag ggtagggatt tcgcgacagt  6660
ccggaaggtc ctgtccatgc cgcaggtgaa catcgttaaa aagaccgaag tacagaccgg  6720
aggcttctcc aaggaaagta tcctcccgaa aaggaacagc gacaagctga tcgcacgcaa  6780
aaaagattgg gaccccaaga aatacggcgg attcgattct cctacagtcg cttacagtgt  6840
actggttgtg gccaaagtgg agaaagggaa gtctaaaaaa ctcaaaagcg tcaaggaact  6900
gctgggcatc acaatcatgg agcgatcaag cttcgaaaaa aaccccatcg actttctcga  6960
ggcgaaagga tataaagagg tcaaaaaaga cctcatcatt aagcttccca agtactctct  7020
ctttgagctt gaaaacggcc ggaaacgaat gctcgctagt gcgggcgagc tgcagaaagg  7080
taacgagctg gcactgccct ctaaatacgt taatttcttg tatctggcca gccactatga  7140
aaagctcaaa ggatctcccg aagataatga gcagaagcag ctgttcgtgg aacaacacaa  7200
acactacctt gatgagatca tcgagcaaat aagcgaattc tccaaaagag tgatcctcgc  7260
cgacgctaac ctcgataagg tgctttctgc ttacaataag cacagggata agcccatcag  7320
ggagcaggca gaaaacatta tccacttgtt tactctgacc aacttgggcg cgcctgcagc  7380
cttcaagtac ttcgacacca ccatagacag aaagcggtac acctctacaa aggaggtcct  7440
ggacgccaca ctgattcatc agtcaattac ggggctctat gaaacaagaa tcgacctctc  7500
tcagctcggt ggagacagca gggctgaccc caagaagaag aggaaggtgt gagcttggaa  7560
tggatcttcg atcccgatcg ttcaaacatt tggcaataaa gtttcttaag attgaatcct  7620
gttgccggtc ttgcgacgat tatcatataa tttctgttga attacgttaa gcatgtaata  7680
attaacatgt aatgcatgac gttatttatg agatgggttt ttatgattag agtcccgcaa  7740
ttatacattt aatacgcgat agaaaacaaa atatagcgcg caaactagga taaattatcg  7800
cgcdcggtgt catctatgtt actagatcgg gaattgccaa gctaattctt gaagacgaaa  7860
gggcctcgtg atacgcctat ttttataggt taatgtcatg ataataatgg tttcttagac  7920
gtcaggtggc acttttcggg gaaatgtgcg cggaacccct atttgtttat ttttctaaat  7980
acattcaaat atgtatccgc tcatgagaca ataaccctga taaatgcttc aataatggga  8040
ccgactcgcg ctgtcaggag acgggacaag gatgcgagct agcctgcagg aattgttgat  8100
tttgtgatga ctgatggcag gatatatgcg gttgtaattc atttttattg tctaaatttc  8160
tgtatttgtt tgtttgttcg gttgtaaatt tttttggaag aacaagaaaa gaaaaaacac  8220
ccgttagggt gtttttagtt agtgtggcgc gccgacttgc gacatgcggt cctttgcaat  8280
caactattag aaaaattcat ccagcatcag atgaaattgc agtttgttca tatccggatt  8340
atcaatgcca tatttctgaa acagacgttt ttgcaggctc gggctaaatt cgcccaggca  8400
gttccacaga atggccagat cctgataacg atccgcaatg cccacacggc ccacatcaat  8460
gcagccaatc agtttgcctt catcgaaaat caggttatcc aggctaaaat cgccgtgggt  8520
caccacgcta tccgggctaa acggcagcag tttatgcatt tctttccaca cctgttccac  8580
cggccagccg ttacgttcat catcaaaatc gctcgcatcc accaggccgt tgttcatacg  8640
gctctgcgcc tgggccagac gaaacacacg atcgctgtta aacggcagt tgcacaccgg  8700
```

```
aatgctatgc agacgacgca gaaacacggc cagcgcatcc acaatgtttt cgccgctatc  8760
cggatattct tccagcacct gaaacgcggt tttgcccgga atcgcggtgg tcagcagcca  8820
cgcatcatcc ggggtgcgaa taaaatgttt aatggtcggc agcggcataa attcggtcag  8880
ccagttcaga cgcaccattt catcggtcac atcgttcgcc acgctgcctt tgccatgttt  8940
cagaaacagt tccggcgcat ccggtttgcc atacagacga taaatggtcg cgccgctctg  9000
acccacgtta tcacgcgccc atttatagcc atacagatcc gcatccatgt tgctgttcag  9060
acgcggacgg ctacagctcg tttcacgctg aatatggctc ataacacccc ttgtattact  9120
gtttatgtaa gcagacagtt ttattgttca tgatgatata tttttatctt gtgcaatgta  9180
acatcagaga ttttgagaca caagatcgga ttggcggtta tgcggttcta ccggcgcggc  9240
agcgttaccc gtgtcggcgg ctccaacggc tcgccatcgt ccagaaaaca cggctcatcg  9300
ggcatcggca ggcgctgctg cccgcgccgt tcccattcct ccgtttcggt caaggctggc  9360
aggtctggtt ccatgcccgg aatgccgggc tggctgggcg gctcctcgcc ggggccggtc  9420
ggtagttgct gctcgcccgg atacagggtc gggatgcggc gcaggtcgcc atgccccaac  9480
agcgattcgt cctggtcgtc gtgatcaacc accacggcgg cactgaacac cgacaggcgc  9540
aactggtcgc ggggctggcc ccacgccacg cggtcattga ccacgtaggc cgacacggtg  9600
ccggggccgt tgagcttcac gacggagatc cagcgctcgg ccaccaagtc cttgactgcg  9660
tattggaccg tccgcaaaga acgtccgatg agcttggaaa gtgtcttctg gctgaccacc  9720
acggcgttct ggtggcccat ctgcgccacg aggtgatgca gcagcattgc cgccgtgggt  9780
ttcctcgcaa taagcccggc ccacgcctca tgcgctttgc gttccgtttg cacccagtga  9840
ccgggcttgt tcttggcttg aatgccgatt tctctggact gcgtggccat gcttatctcc  9900
atgcggtagg ggtgccgcac ggttgcggca ccatgcgcaa tcagctgcaa cttttcggca  9960
gcgcgacaac aattatgcgt tgcgtaaaag tggcagtcaa ttacagattt tctttaacct  10020
acgcaatgag ctattgcggg gggtgccgca atgagctgtt gcgtaccccc ctttttttaag  10080
ttgttgattt ttaagtcttt cgcatttcgc cctatatcta gttctttggt gcccaaagaa  10140
gggcacccct gcggggttcc cccacgcctt cggcgcggct ccccctccgg caaaaagtgg  10200
cccctccggg gcttgttgat cgactgcgcg gccttcggcc ttgcccaagg tggcgctgcc  10260
cccttggaac cccgcactc gccgccgtga ggctcggggg gcaggcgggc gggcttcgcc  10320
cttcgactgc ccccactcgc ataggcttgg gtcgttccag gcgcgtcaag gccaagccgc  10380
tgcgcggtcg ctgcgcgagc cttgacccgc cttccacttg gtgtccaacc ggcaagcgaa  10440
gcgcgcaggc cgcaggccgg aggcttttcc ccagagaaaa ttaaaaaaat tgatggggca  10500
aggccgcagg ccgcgcagtt ggagccggtg ggtatgtggt cgaaggctgg gtagccggtg  10560
ggcaatccct gtggtcaagc tcgtgggcag gcgcagcctg tccatcagct tgtccagcag  10620
ggttgtccac gggccgagcg aagcgagcca gccggtggcc gctcgcggcc atcgtccaca  10680
tatccacggg ctggcaaggg agcgcagcga ccgcgcaggg cgaagcccgg agagcaagcc  10740
cgtagggg                                                           10749

SEQ ID NO: 20           moltype = DNA  length = 6637
FEATURE                 Location/Qualifiers
misc_feature            1..6637
                        note = pLX-B2-NptII-DsRED
source                  1..6637
                        mol_type = other DNA
                        organism = synthetic construct
SEQUENCE: 20
ccatcatcag ttcggtggtc ttccgacgaa caataaggcc gcaaatcgcg gcctttttta  60
ttgataacaa aaccggctca gttctgcgta gaaaccaaca tgcaagctcc accgggtgca  120
aagcggcagc ggcggcagga tatattcaat tgtaaatggc ttcatgtccg ggaaatctac  180
tggtggcagg atatattgtg gtgtaaacaa tggagaaaaa gattaattaa gtactagtag  240
cctggtcgaa accgtctcag gagagcgatc agcttgcatg ccggtcgatc tagtaacata  300
gatgacaccg cgcgcgataa tttatcctag tttgcgcgct atattttgtt ttctatcgcg  360
tattaaatgt ataattgcgg gactctaatc ataaaaaccc atctcataaa taacgtcatg  420
cattacatgt taattattac atgcttaacg taattcaaca gaaattatat gataatcatg  480
gcaagaccgg caacaggatt caatcttaag aaactttatt gccaaatgtt tgaacgatct  540
gcttgactct agctagagtc cgaaccccag agtcccgctc agaagaactc gtcaagaagg  600
cgatagaagg ctatgcgctg cgaatcggga gcggcgatac cgtaaagcac gaggaagcgg  660
tcagcccatt cgccgccaag ctcttcagca atatcacggg tagccaacgc tatgtcctga  720
tagcggtccg ccacacccag ccggccacag tcgatgaatc cagaaaagcg gccattttcc  780
accatgatat tcggcaagca ggcgtcgccg tgggtcacga cgagatcctc gccgtcgggc  840
atccgcgcct tgagcctggc gaacagttcg gctggcgcga gcccctgatg ctcttcgtcc  900
agatcatcct gatcgacaag accggcttcc atccgagtac gtgctcgctc gatgcggtgt  960
ttcgcttggt ggtcgaatgg gcaggtagcc ggatcaagcg tatgcagccg ccgcattgca  1020
tcagccatga tggatacttt ctcggcagga gcaaggtgag atgacaggag atcctgcccc  1080
ggcacttcgc ccaatagcag ccagtccctt cccgcttcag tgacaacgtc gagcacagct  1140
gcgcaaggaa cgcccgtcgt ggccagccac gatagccgcg ctgcctcgtc ttggagttca  1200
ttcagggcac cggacaggtc ggtcttgaca aaaagaaccg ggcgcccctg cgctgacagc  1260
cggaacacgg cggcatcaga gcagccgatt gtctgttgtg cccagtcata gccgaatagc  1320
ctctccaccc aagcggccgg agaacctgcg tgcaatccat cttgttcaat catgcctcga  1380
tcgagttgag agtgaatatg agactctaat tggataccga ggggaattta tggaacgtca  1440
gtggagcatt tttgacaaga aatatttgct agctgatagt gaccttaggc gacttttgaa  1500
cgcgcaataa tggtttctga cgtatgtgct tagctcatta aactccagaa acccgcggct  1560
gagtggctcc ttcaacgttg cggttctgtc agttccaaac gtaaaacggc ttgtcccgcg  1620
tcatcggcgg gggtcataac gtgactccct taattctcat gtatctcctg acagcgaaat  1680
gattgatgaa gaacaatggt ggatgaagaa caaagaagga gggagctttt gttcaagatg  1740
aacaaagaac aatagtggat gaagaacaaa gtgaaaaaaa taaaaaaaaa tgtatggtta  1800
aataaagagt aaagttacca ttgagactcc gtcaggagac tagagccaag ctgatctcct  1860
ttgccccgga gatcaccatg gacgactttc tctatctcta cgatctagga agaaagttcg  1920
acggagaagg tgacgatacc atgttcacca ccgataatga gaagattagc ctcttcaatt  1980
tcagaaagaa tgctgaccca cagatggtta gagaggccta cgcggcaggt ctgatcaaga  2040
cgatctaccc gagtaataat ctccaggaga tcaaatacct tcccaagaag gttaaagatg  2100
```

-continued

```
cagtcaaaag attcaggact aactgcatca agaacacaga gaaagatata tttctcaaga  2160
tcagaagtac tattccagta tggacgattc aaggcttgct tcataaacca aggcaagtaa  2220
tagagattgg agtctctaag aaagtagttc ctactgaatc aaaggccatg gagtcaaaaa  2280
ttcagatcga ggatctaaca gaactcgccg tgaagactgg cgaacagttc atacagagtc  2340
ttttacgact caatgacaag aagaaaatct tcgtcaacat ggtggagcac gacactctcg  2400
tctactccaa gaatatcaaa gatacagtct cagaagacca aagggctatt gagacttttc  2460
aacaaagggt aatatcggga aacctcctcg gattccattg cccagctatc tgtcacttca  2520
tcaaaaggac agtagaaaag gaaggtggca cctacaaatg ccatcattgc gataaaggaa  2580
aggctatcgt tcaagatgcc tctgccgaca gtggtcccaa agatggaccc ccacccacga  2640
ggagcatcgt ggaaaaagaa gacgttccaa ccacgtcttc aaagcaagtg gattgatgtg  2700
atatctccac tgacgtaagg gatgacgcac aatcccacta tccttcgcaa gacccttcct  2760
ctatataagg aagttcattt catttggaga ggactccggt atttttacaa caataccaca  2820
acaaaacaaa caacaaacaa cattacaatt tactattcta gtcgaaatgg cctcctccga  2880
gaacgtcatc accgagttca tgcgcttcaa ggtgcgcatg gagggcaccg tgaacggcca  2940
cgagttcgag atcgagggcg agggcgaggg ccgcccctac gagggccaca acaccgtgaa  3000
gctgaaggtg accaagggcg gccccctgcc cttcgcctgg gacatcctgt ccccccagtt  3060
ccagtacggc tccaaggtgt acgtgaagca ccccgccgac atccccgact acaagaagct  3120
gtccttcccc gagggcttca agtgggagcg cgtgatgaac ttcgaggacg gcggcgtggc  3180
gaccgtgacc caggactcct ccctgcagga cggctgcttc atctacaagg tgaagttcat  3240
cggcgtgaac ttcccctccg acggccccgt gatgcagaag aagacgatgg gctgggaggc  3300
ctccaccgag cgcctgtacc cccgcgacgg cgtgctgaag ggcgagacac acaaggccct  3360
gaagctgaag gacggcggcc actacctggt ggagttcaag tccatctaca tggccaagaa  3420
gcccgtgcag ctgcccggct actactacgt ggacgccaag ctggacatca cctcccacaa  3480
cgaggactac accatcgtgg agcagtacga gcgcaccgag ggccgccacc acctgttcct  3540
gtaggcttcg gccatgctag agtccgcaaa aatcaccagt ctctctctac aaatctatct  3600
ctctctattt ttctccagaa taatgtgtga gtagttccca gataagggaa ttagggttct  3660
tatagggttt cgctcatgtg ttgagcatat aagaaaccct tagtatgtat ttgtatttgt  3720
aaaatacttc tatcaataaa atttctaatt cctaaaacca aaatccagtg acctcgctgt  3780
caggagtctc aatggtaact ttactcttta tttaaccata cattttttt tattttttc  3840
actttgttct tcatccacta ttgttctttg ttcatcttga acaaaagctc cctccttctt  3900
tgttcttcat ccaccattgt tcttcatcaa tcatttcgct gtcaggagac gggacaagga  3960
tgcgagctag cctgcaggaa ttgttgattt tgtgatgact gatggcagga tatatgcggt  4020
tgtaattcat ttttattgtc taaatttctg tatttgtttg tttgttcggt tgtaaatttt  4080
tttggaagaa caagaaaaga aaaaacaccc gttagggtgt ttttagttag tgtggcgcgc  4140
cgacttgcga catgcggtcc tttgcaatta attattagaa aaattcatcc agcatcagat  4200
gaaattgcag tttgttcata tccggattat caatgccata tttctgaaac agacgttttt  4260
gcaggctcgg gctaaattcg cccaggcagt tccacagaat ggccagatcc tgataacgat  4320
ccgcaatgcc cacacggccc acatcaatgc agccaatcag tttgccttca tcgaaaatca  4380
ggttatccag gctaaaatcg ccgtgggtca ccacgctatc cgggctaaac ggcagcagtt  4440
tatgcatttc tttccacacc tgttccaccg gccagccgtt acgttcatca tcaaaatcgc  4500
tcgcatccac caggccgttg ttcatacggc tctgcgcctg ggccagacga aacacacgat  4560
cgctgttaaa cgggcagttg cacaccggaa tgctatgcag acgacgcaga aacacggcca  4620
gcgcatccac aatgttttcg ccgctatccg gatattcttc cagcacctga aacgcggttt  4680
tgcccggaat cgcggtggtc agcagccacg catcatccgg ggtgcgaata aaatgtttaa  4740
tggtcggcag cggcataaat tcggtcagcc agttcagacg caccatttca tcggtcacat  4800
cgttcgccac gctgcctttg ccatgtttca gaaacagttc cggcgcatcc ggtttgccat  4860
acagacgata aatggtcgcg ccgctctgac ccacgttatc acgcgcccat ttatagccat  4920
acagatccgc atccatgttg ctgttcagac gcggacggct acagctcgtt tcacgctgaa  4980
tatggctcat aacacccctt gtattactgt ttatgtaagc agacagtttt attgttcatg  5040
atgatatatt tttatcttgt gcaatgtaac atcagagatt ttgagacaca agatcggatt  5100
ggcggttatg cggttctacc ggcgcggcag cgttacccgt gtcggcggct ccaacggctc  5160
gccatcgtcc agaaaacacg gctcatcggg catcggcagg cgctgctgcc cgcgccgttc  5220
ccattcctcc gtttcggtca aggctggcag gtctggttcc atgcccggaa tgccgggctg  5280
gctgggcggc tcctcgccgg ggccggtcgg tagttgctgc tcgcccggat acagggtcgg  5340
gatgcggcgc aggtcgccat gccccaacag cgattcgtcc tggtcgtcgt gatcaaccac  5400
cacggcggca ctgaacaccg acaggcgcaa ctggtcgcgg ggctggcccc acgccacgcg  5460
gtcattgacc acgtaggccg acacggtgcc ggggccgttg agcttcacga cggagatcca  5520
gcgctcggcc accaagtcct tgactgcgta ttggaccgtc cgcaaagaac gtccgatgag  5580
cttggaaagt gtcttctggc tgaccaccac ggcgttctgg tggcccatct gcgccacgag  5640
gtgatgcagc agcattgccg ccgtgggttt cctcgcaata agcccggccc acgcctcatg  5700
cgctttgcgt tccgtttgca cccagtgacc gggcttgttc ttggcttgaa tgccgatttc  5760
tctggactgc gtggccatgc ttatctccat gcggtagggg tgccgcacgg ttgcggcacc  5820
atgcgcaatc agctgcaact ttttcggcagc gcgacaacaa ttatgcgttg cgtaaaagtg  5880
gcagtcaatt acagatttc tttaacctac gcaatgagct attgcggggg gtgccgcaat  5940
gagctgttgc gtacccccct tttttaagtt gttgattttt aagtctttcg catttcgccc  6000
tatatctagt tctttggtgc ccaaagaagg gcacccctgc ggggttcccc cacgccttcg  6060
gcgcggctcc ccctccggca aaaagtggcc cctccggggc ttgttgatcg actgcgcggc  6120
cttcggcctt gcccaaggtg gcgctgcccc cttggaaccc ccgcactcgc cgccgtgagg  6180
ctcggggggc aggcgggcgg gcttcgccct tcgactgccc ccactcgcat aggcttgggt  6240
cgttccaggc gcgtcaaggc caagccgctg cgcggtcgct gcgcgagcct tgacccgcct  6300
tccacttggt gtccaaccgg caagcgaagc gcgcaggccg caggccggag gcttttcccc  6360
agagaaaatt aaaaaaattg atggggcaag gccgcaggcc gcgcagttgg agccggtggg  6420
tatgtggtcg aaggctgggt agccggtggg caatccctgt ggtcaagctc gtgggcaggc  6480
gcagcctgtc catcagcttg tccagcaggg ttgtccacgg gccgagcgaa gcgagccagc  6540
cggtggccgc tcgcggccat cgtccacata tccacgggct ggcaagggag cgcagcgacc  6600
gcgcagggcg aagcccggag agcaagcccg taggggg                          6637
```

SEQ ID NO: 21 moltype = DNA length = 14938
FEATURE Location/Qualifiers

-continued

```
misc_feature            1..14938
                        note = pLX-PPV
source                  1..14938
                        mol_type = other DNA
                        organism = synthetic construct
SEQUENCE: 21
ccatcatcag ttcggtggtc ttccgacgaa caataaggcc gcaaatcgcg gcctttttta  60
ttgataacaa aaccggctca gttctgcgta gaaaccaaca tgcaagctcc accgggtgca  120
aagcggcagc ggcggcagga tatattcaat tgtaaatggc ttcatgtccg ggaaatctac  180
tggtggcagg atatattgtg gtgtaaacaa tggagaaaaa gattaattaa gtactagtcc  240
agtacgcacg attcaaggct tgcttcacaa accaaggcaa gtaatagaga ttggagtctc  300
taaaaaggta gttcccactg aatcaaaggc catggagtca aagattcaaa tagaggacct  360
aacagaactc gccgtaaaga ctggcgaaca gttcatacag agtctcttac gactcaatga  420
caagaagaaa atcttcgtca acatggtgga gcacgacaca cttgtctact ccaaaaatat  480
caaagataca gtctcagaag accaaagggc aattgagact tttcaacaaa gggtaatatc  540
cggaaacctc ctcggattcc attgcccagc tatctgtcac tttattgtga agatagtgga  600
aaaggaaggt ggctcctaca aatgccatca ttgcgataaa ggaaaggcca tcgttgaaga  660
tgcctctgcc gacagtggtc ccaaagatgg acccccaccc acgaggagca tcgtggaaaa  720
agaagacgtt ccaaccacgt cttcaaagca agtggattga tgtgataaca tggtggagca  780
cgacacactt gtctactcca aaaatatcaa agatacagtc tcagaagacc aaagggcaat  840
tgagactttt caacaaaggg taatatccgg aaacctcctc ggattccatt gcccagctat  900
ctgtcacttt attgtgaaga tagtggaaaa ggaaggtggc tcctacaaat gccatcattg  960
cgataaagga aaggccatcg ttgaagatcc tctgccgaca gtggtcccaa agatggaccc  1020
ccacccacga ggagcatcgt ggaaaaagaa gacgttccaa ccacgtcttc aaagcaagtg  1080
gattgatgtg atatctccac tgacgtaagg gatgacgcac aatcccacta tccttcgcaa  1140
gacccttcct ctatataagg aagttcattt catttggaga ggaaaatata aaaactcaac  1200
acaacataca aaattttatg caatcaaatc aatctcaagc tatcaaaatt tttcaaatct  1260
cacttgaaag atcaaaaatc aacaaagaaa atcccttaat ttctctacca aatttactgc  1320
aagtcaagat gtcaaccatt gtatttggct cattcacttg ccacctcgat gcagctatcc  1380
accaggataa tgcagacaga ttggcaaagg cctggacccg tccagagaac caccaagtca  1440
gtaacgtgca tctactgtgc cgaagagcgg caaaaagtct cataaacaca tatgagagtg  1500
caacagctag tgcttggaaa gggctggaag agaagttgca acctatgttt gctaagcgtg  1560
agtttagcaa aacagtcaca aagagagaag ggcttcggtg cttcaaagaa agctctgaga  1620
agtttattga aaagaagctc aggaaacagt atcaagagga gcgtgagaga ttccaatttc  1680
tcaacggtcc ggatgcaata gtcaaccaaa tcagtgttga caaatgtgaa gcttcagtac  1740
gggtgccatt ccctcatatt attgagaaac ctagctttgc aacaccatca atgaaaaaga  1800
aggtggtgtt tactaaggtt aggatgtccg aggcatcact acaacttttt atgaggaggg  1860
ttgctgcaaa cgccaaggca aatggtcaaa aagttgagat catagggcgt aagcgtgtag  1920
tcggtaacta cacaacgaaa agtcgcttga catactttcg cacacatgtt cggcacttgg  1980
atggttcaaa accacgctat gatcttgtgt tggacgaggc aaccaagaag attctgcaac  2040
tgtttgcaaa cacaagcggt ttccaccatg tccacaagaa aggggaggta acaccaggaa  2100
tgagcggatt tgtggtaaat cccatgaatc tatcggaccc aatgcaagtg tatgacacgg  2160
atctttttat agttcgtgga aaacacaact ctattcttgt tgactcacgg tgtaaggttt  2220
ctaaagaaca gagcaatgag ataatccact actctgaccc aggcaaacaa ttttgggatg  2280
gtttcaccaa ttcatttatg cagtgcaagc tacgcgaaac tgatcatcag tgcacatctg  2340
acctggacgt gaaggagtgt ggttatgtcg cagcacttgt gtgccaagcg ataatccctt  2400
gcggaaaaat cacatgtctg caatgtgctc aaaagtattc ttacatgtca caacaggaaa  2460
tacgtgatag attttcgaca gtaattgagc agcatgagaa aacagtgatg gataactatc  2520
cacaattttc acatgttctc gcttttctaa agagatatcg tgaactaatg cgcgtggaaa  2580
atcagaatta tgaagctttc aaggatatca cgcacatgat aggcgagcgt aaagaagcac  2640
ctttttccca tctcaacaaa atcaatgaat taatcattaa gggtggtatg atgagcgcac  2700
aagactacat agaagcctcg gatcatctgc gcgaactagc gcgatatcag aagaatcgca  2760
cggagaacat taggagcgga tctataaagg ctttcaggaa taaaatctca tcaaaagcac  2820
atgtcaatat gcagcttatg tgtgacaatc aacttgatac taatggcaat ttcgtgtggg  2880
gacagagaga gtatcatgct aaacgcttct ttaggaatta cttcgatgtg atcgatgtta  2940
gcgagggcta cagacgtcat attgttcgtg aaaatcctaa aggtatccgc aaattggcca  3000
ttggcaacct tgttatgtca acaaatctgg cagcactacg taagcagctt ttgggtgaag  3060
agtgcattca ttttgaggtc tcaaaggaat gcactagcaa gcgaggggaa aactttgtat  3120
accaatgttg ctgtgtcaca cacgaagacg gtacaccact ggagtctgaa ataataagtc  3180
caacaaagaa tcatttagtt gttgggaact caggtgattc gaagtatgtg gatttgccca  3240
cagcaaaagg aggtgcaatg ttcatagcaa aggcaggtta ttgttacatt aacattttcc  3300
ttgctatgct gatcaacata aatgaagatg aagcaaaaag tttcacaaag acagtgcgtg  3360
acactcttgt acctaagctt ggaacatggc catcgatgat ggacttagct acagcttgcc  3420
actttctcgc aattctctac ccagaaactc ggaatgctga acttccacga atactcgttg  3480
atcatgaagc aaaaaatctt catgtagttg actcattcgg atcactgtca actggaatgc  3540
atgttttgaa agcgaacaca atcaatcagc ttattagctt tgcgagtgat acattggatt  3600
caaatatgaa aacatacctg gttggaggtc ttgaagtgga taagtgtgac gaattcaaaa  3660
atgtcaagct cttgatcaga agcatttaca agccacaaat catggagcag gtgcttaagg  3720
aagaaccata tttattgctc atgagcgttt tgtcacctgg cgtcttgatg gcgctgttca  3780
atagtggttc attggagaaa gccacacaat attggatcac acgatctcat agcttggcag  3840
cgatcacatc aatgttatca tcacttgcag ccaaagtttc actcgcaagt acactgaatg  3900
cacagatgag tgtcattgac gaacatgcag cagttctatg tgatagtgtt tttgttggaa  3960
cgaagccata cgcatcctac atgatggcag tgaaaacttt ggaaaggatg aaagcacgga  4020
cggaatccga tcacacttta aatgacttag gattctcggt actcagacag gcaacacccc  4080
acttggtgga aaaaagttat ctgcaggtaa gtttctgctt ctacctttga tatatatata  4140
ataattatca ttaattagta gtaatataat atttcaaata tttttttcaa aataaaagaa  4200
tgtagtatat agcaattgct ttctgtagt ttataagtgt gtatatttta atttataact  4260
tttctaatat atgaccaaaa tttgttgata tgcaggaatt ggagcaagct tggaaagagt  4320
taagctggtc ggaaaaattc tctgcaatct tggaatcgca gcggtggcga aaacatatac  4380
```

-continued

```
caaaaccttt catcccaaaa gacggcgcag atttaggagg caggtacgac atctccgttc  4440
ggtcattact tggcaaccag tacaaacgcc tgagagacgt agtccgacgg aaaagagacg  4500
atgtggtttg ctatacacac cagtcgatgg ggaagctatt ttgcaaagcc atcggaattt  4560
ccacaagttt tcttccaagc actcttaaaa tgtttgacat gctcatcgtg ttcagtctct  4620
tgctttcaat aggagccaca tgcaactcaa tgatcaatga gcataaacat cttaagcaac  4680
ttgccgctga tcgggaagat aagaaaagat tcaaaagatt gcaagtctta cacacgaggt  4740
tatcagagaa agttggttgc acaccaacag cagatgaatt cctggagtat gtgggaggtg  4800
aaaaccctga tttactgaaa catgcagagg atctaattgg ggatggtcaa gttgttgttc  4860
atcaaagcaa gagagactca caagcaaatt tggaacgggt tgtagcattt gtagctcttg  4920
ttatgatgct gtttgactcg gagcgaagtg acggcgtgta caagattctc aataaactca  4980
aaggcattat ggggagtgtc gaccaggctg ttcagcatca gagcttggac gatatagaag  5040
atatactgga tgagaagaag ctcacagtcg attttgtact gcaaagtaac gaagttgcac  5100
caactgtccc atttgactca acttttgaga aatggtggac gaatcaactt gagacaggaa  5160
atgtgattcc acactacagg actgaaggac atttccttga attcacacga gaaaatgcag  5220
cgcacattgc gaatgaagtc atgcatggct cacatcaaga tatcctaatt cgtggagcag  5280
ttggatcggg caaatcaact ggattgccat tccacttaag caagaagggc cacgtcctgc  5340
taattgaacc caccaggccg ctagctgaga atgtgtgcaa gcagttgcga ggtcaaccat  5400
tcaatgtcaa tcctacactg cgcatgcgtg ggatgagcac ctttggatca actccaatca  5460
ctgtgatgac aagcggttac gcactgcact tcttggcaaa caatccaact tatttggaca  5520
actataagtg catcattttt gacgaatgtc acgtgcatga cgcatcagca atggcattta  5580
gatgtcttct ttcggagtat tcatacccgg gaaagatact gaaggtctca gcgacacccc  5640
ctggacatga agttgatttc aaaacacaga aggaggtgaa ggtcattgtt gaagaatctt  5700
tgtcattcca gcagtttgtc tccaatctcg gcacaggttg caatagcgat attctcaagc  5760
atggggtcaa tgtgttggtc tatgtcgcaa gttacaatga ggttgacaca ctaagcaaat  5820
tgctcacaga caggagcttc aaagtttcaa aagtcgatgg gcgaactatg aaaattggca  5880
atgttgagat accaacgagt ggcactcagg ctaaaccgca tttcgtggtt gcaacaaata  5940
tcattgaaaa tggagtcaca ttggacattg atgtggttgt ggacttcggt ttgaaagtcg  6000
tgcctgtatt ggacattgac aatcgtctcg ttcgatacac gaagaagagc atcagttatg  6060
gagaaaggat tcaaagattg gggcgagttg gtcgaaacaa accaggagca gcacttcgta  6120
ttggatttac agagaaagga ctcactcaaa tacctccaat aatcgcaaca gaagcagctt  6180
ttctatgttt cacttatggt ttgccagtta tgactaacgg tgtgtcaacg agcttactag  6240
cgatgtgcac tgttaagcaa gcacggacga tgcaacaatt tgaattatcc ccgttctaca  6300
cagtggcgtt ggttcgattt gacgggacaa tgcaccagga aatttttcga ttgctcaaga  6360
gctatagact gcgtgactca gaggtaatct taaacaagtt ggctatacca aacagcaacg  6420
tatgtgggtg gatgagtgtt cgtgactaca aacgacaagg ctgcaacttg gacttggatg  6480
agaacattcg tgtaccgttt tacgtgaaag acatccctga aactttgcac gagagaatat  6540
ggcaagtggt agaaacccac aaatctgatg caggatttgg aaggatctgt agttcgagtg  6600
cgtgcaaaat tgcgtatacg ttacagacag acatccactc cattcctcgg acaattaaaa  6660
tcattgacgc actgttggag caagagagaa caaagcaagc acacttcaga gctatgacca  6720
gtcaatcctg ctcaagttca aatttctctc tgtcaagcat cacctcagcc attcgctcaa  6780
aatacgccaa agaccatacg gaagaaaaca ttggtgttct ccaaacggcg aagtctcagt  6840
tgctagaatt caagaacctg aacattgatc caagttatcc tgaacttgtc cgcaactttg  6900
gcgccttaga atgtgtgcac catcaaacaa aggaaggagt ttcaaaggcg ctacaactta  6960
aggggcattg gaataagcga ctcatcactc gtgacgcaac attaatgctt ggagttcttg  7020
gtggaggggc atggatgatt ttcagttatt tgagggatag cttcaaagaa gaagttgttc  7080
accaaggctt caatcgtagg caaagacaaa aattgaaatt caggcaagcc cgagataaca  7140
gaatggccag ggaagtgtat ggtgacgatt caactatggc ggactacttt ggttctgcat  7200
attcaaagaa aggaaagagc aaaggaaaga ctagagggat gggaacgaaa acacgcaaat  7260
ttgtgaacat gtacgggtac gatcccacag actacaactt tgttcgcttt gttgatccat  7320
tgactggtca caccctggac gagaatcctc ttatggacat caacttggtg caggaacact  7380
tctcacagat tcgcaatgat tacatcggag acgacaaaat caccatgcag cacataatgt  7440
caaatccagg tattgtcgca tactatatca aggatgcgac gcagaaagcc ctcaaggtgg  7500
accttactcc acacaaccca ttgcgtgtgt gtgacaaaac tgcaactatt gcaggatttc  7560
cagagagaga gtttgaattg aggcagacag gacacccagt tttgttgaa cctaatgcaa  7620
tcccaaagat caatgaagag ggggacgaag aagttgacca cgaaagtaaa tcactgttca  7680
gaggcctgag agactataat ccaatcgcaa gctcaatatg ccaattgaat aactcatctg  7740
gtgctagaca aagtgtaatg tttggacttg gctttggggg tttaattgtc acgaatcagc  7800
atttgttcaa aaggaatgac ggagagctaa caatccgatc gcatcatggg gaattcgtag  7860
tgaaggacac aaaaactctc aaactgcttc cttgcaaagg tcgagacata gtgatcatca  7920
gattaccaaa ggatttccct ccttttccga agaggttgca gttccgcacc ccgacgactg  7980
aggacagagt ttgtttaatt ggttcaaatt tccaaacgaa gagcatttca agcaccatgt  8040
cggaaacaag cgcaacatat ccagttgata acagtcattt ctggaaacac tggattagca  8100
cgaaggatgg tcattgcgga ttacccatcg tgagcactcg agatggcagt attcttgggc  8160
tacacagtct tgcaaattca acgaacaccc agaatttcta tgcagctttc cctgacaact  8220
tcgagaccac atacttgtca aatcaagaca atgataactg gataaagcag tggcgataca  8280
acccggatga agtttgctgg ggatccctac aactcaagag ggacattcca cagagtccgt  8340
ttacaatttg taaactgcta acggatcttg atggggaatt tgtttacact cagtccaaaa  8400
ctacacattg gctcagagat agattagaag gaaatttgaa agcagttgga gcctgccctg  8460
ggcagttggt tactaagcat gtcgttaaag gcaaatgtac actctttgaa acatacctgt  8520
tgactcatcc agaggagcac gaattctttc gacctttaat gggagcatac caaaagagtg  8580
ctctaaataa ggacgcatac gtcaaagatc tgatgaagta ttcaaaacca atcgtcgttg  8640
gtgcagttga ctgtgatcaa tttgaacgtg ctgttgatgt ggtcatttcg atgctaattt  8700
ccaaaggttt tgaagaatgt aattacgtca ctgatccaga tgacatattc tcagcactta  8760
acatgaaagc agcagttggc gctttgtaca gtggaaagaa aagagactat tttaagaacg  8820
tgtcagacca ggacaaggaa agtttcgtgc gagctagttg caaacgtttg ttcatgggaa  8880
agaaaggagt gtggaatggc tctttgaagg cagaattgcg ccctaaagag aaggtagagg  8940
ctaataaaac tcgatcattc acagcagcac cgattgatac ccttctgggg ggaaaagtgt  9000
gtgttgatga cttcaataat cagttttaca gcctgaattt acattgtcca tggagcgttg  9060
ggatgacaaa attcagaggt ggttgggaca aactgcttag agcactgcca gaaggatgga  9120
```

-continued

```
tttactgtga tgccgatggc tctcaatttg acagttccct ctcaccgtac ttaatcaatg  9180
cagttctcaa tattcgtctg gcatttatgg aagaatggga cattggtgaa caaatgcttt  9240
caaacctgta cacggagatt gtatatacac caattgctac accagatggc actattgtta  9300
agaagttcaa gggcaacaat agtggtcaac cctcgacagt tgttgacaat acactcatgg  9360
ttattttggc aatgacatat tcactcctta agcttggata ccatccggat acacacgatt  9420
gcatttgtcg gtacttcgtg aatggtgatg atcttgtcct tgcagtgcac ccagcatacg  9480
agagcattta tgatgagctt caagaacact tttcccaact tggattgaat tacacattcg  9540
ccacaaagac tgaaaacaag gaagagctgt ggtttatgtc acataaaggc gttctctacg  9600
atgacatgta cattcctaag ctagagcctg agaggattgt atcaatactt gaatgggaca  9660
gatcaaatga gccaatccat cgattggagg caatttgtgc atcaatggtg gaagcgtggg  9720
gttataagga gctgctgagg gagatccgga aattttacag ttgggttctt gaacaagcac  9780
catacaatgc tctttcaaaa gatggaaaag ccccgtacat tgcggagaca gcactgaaga  9840
agctttacac tgacactgaa gcatctgaga cagaaattga gcgatatctt gaagcttttt  9900
acgacgactt taacgatgat ggtgagtcca atgtcgtagt acatcaggcc atggtgagca  9960
agggcgagga gctgttcacc ggggtggtgc ccatcctggt cgagctggac ggcgacgtaa  10020
acggccacaa gttcagcgtg tccggcgagg gcgagggcga tgccacctac ggcaagctga  10080
ccctgaagtt catctgcacc accggcaagc tgcccgtgcc ctggcccacc ctcgtgacca  10140
ccttcaccta cggcgtgcag tgcttcagcc gctaccccga ccacatgaag cagcacgact  10200
tcttcaagtc cgccatgccc gaaggctacg tccaggagcg caccatcttc ttcaaggacg  10260
acggcaacta caagacccgc gccgaggtga agttcgaggg cgacaccctg gtgaaccgca  10320
tcgagctgaa gggcatcgac ttcaaggagg acggcaacat cctggggcac aagctggagt  10380
acaactacaa cagccacaac gtctatatca tggccgacaa gcagaagaac ggcatcaagg  10440
tgaacttcaa gatccgccac aacatcgagg acggcagcgt gcagctcgcc gaccactacc  10500
agcagaacac ccccatcggc gacggccccg tgctgctgcc cgacaaccac tacctgagca  10560
cccagtccgc cctgagcaaa gaccccaacg agaagcgcga tcacatggtc ctgctggagt  10620
tcgtgaccgc cgccgggatc actcacggca tggacgagct gtacaagggt accaacgttg  10680
ttgtgcacca agctgacgaa agagaagacg aggaggaagt tgatgcaggc aagccgagtg  10740
tagttactgc accggcagca actagcccaa tacttcaacc acctccagtc atacagcctg  10800
caccccggac tacggcgtca atgctcaacc ccattttcac gccagcaaca actcaaccag  10860
caacaaaacc agtttcacag gtgtcaggac ctcaactgca aacttttgga acatatggta  10920
atgaggatgc atcacctagc aactcaaacg cgctagtcaa cacaaacaga gacagggacg  10980
tcgatgcagg atcagttgga acttttacag tgccacgttt gaaggcaatg acttcgaaac  11040
tatctctgcc aaaggtgaag ggaaaggcta ttatgaactt gaaccatttg gcacattata  11100
gtcctgcaca ggttgacttg tcaaacacga gagctccgca gtcttgtttc caaacttggt  11160
atgaaggagt taagcgagat tatgatgtca cggacgatga aatgagcatc attttaaatg  11220
gtcttatggt ttggtgcata gagaatggaa catccccgaa tatcaatgga atgtgggtga  11280
tgatggatgg ggaaacacaa gtggagtatc caataaagcc attgttggat catgcgaaac  11340
ccacttttag acaaattatg gcacatttca gtaacgtggc tgaagcgtat attgaaaaac  11400
gaaattatga aaaagcatac atgccaaggt atggaattca gcgcaacctg acagactaca  11460
gcctcgccag atatgccttt gattttacg aaatgacttc aacgacacca gtacgggcac  11520
gtgaagctca tatccagatg aaggcagcag cattgagaaa tgttcaaaat cgtttatttg  11580
gcttggatgg aaacgtcgga acacaagaag aggacacaga gagacacacc gctggtgatg  11640
ttaatcgcaa catgcacaac ctcctcggtg tgaggggagt gtagtggtct cggtatctat  11700
cataaactct acctgggtga gagtctaatc atccagttgt ttttagattc ctgttagcat  11760
ccttttctcc gctttaatag cagtacattc agtgaggttt tacctccata tgttctagtc  11820
tgttattgtc gaacacaggc ccttgtatct gatgtagcga gtgcttcact ccattcgggt  11880
tatagttctt gtgcaagaga caaaaaaaaa aaaaaaaaaa aaaaaaaaaa aaaaaaaaaa  11940
aaaaaaaaaa aaaaaaaaaa aaaaaaaaaa aaaaaaaaaa aaaaaaaaaa aaaaaaaaaa  12000
atgcatgcct gcagatcgtt caaacatttg gcaataaagt ttcttaagat tgaatcctgt  12060
tgccggtctt gcgatgatta tcatctaatt tctgttgaat tacgttaagc atgtaataat  12120
taacatgtaa tgcatgacgt tatttatgag atgggttttt atgattagag tcccgcaatt  12180
atacatttaa tacgcgatag aaaacaaaat atagcgcgca aactaggata aattatcgcg  12240
cgcggtgtca tctatgttac tagatctcta gcctgcagga attgttgatt ttgtgatgac  12300
tgatggcagg atatatgcgg ttgtaattca tttttattgt ctaaatttct gtatttgttt  12360
gtttgttcgg ttgtaaattt ttttggaaga acaagaaaag aaaaaacacc cgttagggtg  12420
tttttagtta gtgtggcgcg ccgacttgcg acatgcggtc ctttgcaatc aactattaga  12480
aaaattcatc cagcatcaga tgaaattgca gtttgttcat atccggatta tcaatgccat  12540
atttctgaaa cagacgtttt tgcaggctcg ggctaaattc gcccaggcag ttccacagaa  12600
tggccagatc ctgataacga tccgcaatgc ccacacggcc cacatcaatg cagccaatca  12660
gtttgccttc atcgaaaatc aggttatcca ggctaaaatc gccgtgggtc accacgctat  12720
ccgggctaaa cggcagcagt ttatgcattt ctttccacac ctgttccacc ggccagccgt  12780
tacgttcatc atcaaaatcg ctcgcatcca ccaggccgtt gttcatacgg ctctgcgcct  12840
gggccagacg aaacacacga tcgctgttaa acgggcagtt gcacaccgga atgctatgca  12900
gacgacgcag aaacacggcc agcgcatcca caatgttttc gccgctatcc ggatattctt  12960
ccagcacctg aaacgcggtt ttgcccggaa tcgcggtggt cagcagccac gcatcatccg  13020
gggtgcgaat aaaatgttta atggtcggca gcggcataaa ttcggtcagc cagttcagac  13080
gcaccatttc atcggtcaca tcgttcgcca cgctgccttt gccatgtttc agaaacagtt  13140
ccggcgcatc cggtttgcca tacagacgat aaatggtcgc gccgctctga cccacgttat  13200
cacgcgccca tttatagcca tacagatccg catccatgtt gctgttcaga cgcggacggc  13260
tacagctcgt ttcacgctga atatggctca taacacccct tgtattactg tttatgtaag  13320
cagacagttt tattgttcat gatgatatat ttttatcttg tgcaatgtaa catcagagat  13380
tttgagacac aagatcggat tggcggttat gcggttctac cggcgcggca gcgttacccg  13440
tgtcggcggc tccaacggct cgccatcgtc cagaaaacac ggctcatcgg gcatcggcag  13500
gcgctgctgc ccgcgccgtt cccattcctc cgtttcggtc aaggctggca ggtctggttc  13560
catgcccgga atgccgggct ggctgggcgg ctcctcgccg gggccggtcg gtagttgctg  13620
ctcgcccgga tacagggtcg ggatgcggcg caggtcgcca tgccccaaca gcgattcgtc  13680
ctggtcgtcg tgatcaacca ccacggcggc actgaacacc gacaggcgca actggtcgcg  13740
gggctggccc cacgccacgc ggtcattgac cacgtaggcc gacacggtgc cggggccgtt  13800
gagcttcacg acggagatcc agcgctcggc caccaagtcc ttgactgcgt attggaccgt  13860
```

```
ccgcaaagaa cgtccgatga gcttggaaag tgtcttctgg ctgaccacca cggcgttctg  13920
gtggcccatc tgcgccacga ggtgatgcag cagcattgcc gccgtgggtt tcctcgcaat  13980
aagcccggcc cacgcctcat gcgctttgcg ttccgtttgc acccagtgac cgggcttgtt  14040
cttggcttga atgccgattt ctctggactg cgtggccatg cttatctcca tgcggtaggg  14100
gtgccgcacg gttgcggcac catgcgcaat cagctgcaac ttttcggcag cgcgacaaca  14160
attatgcgtt gcgtaaaagt ggcagtcaat tacagatttt ctttaaccta cgcaatgagc  14220
tattgcgggg ggtgccgcaa tgagctgttg cgtacccccc tttttaagt tgttgatttt  14280
taagtctttc gcatttcgcc ctatatctag ttctttggtg cccaaagaag ggcacccctg  14340
cggggttccc ccacgccttc ggcgcggctc cccctccggc aaaaagtggc cctccgggg  14400
cttgttgatc gactgcgcgg ccttcggcct tgcccaaggt ggcgctgccc ccttggaacc  14460
cccgcactcg ccgccgtgag gctcgggggg caggcgggcg ggcttcgccc ttcgactgcc  14520
cccactcgca taggcttggg tcgttccagg cgcgtcaagg ccaagccgct gcgcggtcgc  14580
tgcgcgagcc ttgacccgcc ttccacttgg tgtccaaccg gcaagcgaag cgcgcaggcc  14640
gcaggccgga ggcttttccc cagagaaaat taaaaaaatt gatggggcaa ggccgcaggc  14700
cgcgcagttg gagccggtgg gtatgtggtc gaaggctggg tagccggtgg gcaatccctg  14760
tggtcaagct cgtgggcagg cgcagcctgt ccatcagctt gtccagcagg gttgtccacg  14820
ggccgagcga agcgagccag ccggtggccg ctcgcggcca tcgtccacat atccacgggc  14880
tggcaaggga gcgcagcgac cgcgcagggc gaagcccgga gagcaagccc gtaggggg    14938

SEQ ID NO: 22          moltype = DNA  length = 13212
FEATURE                Location/Qualifiers
misc_feature           1..13212
                       note = pLX-UCBSV
source                 1..13212
                       mol_type = other DNA
                       organism = synthetic construct
SEQUENCE: 22
ccatcatcag ttcggtggtc ttccgacgaa caataaggcc gcaaatcgcg gcctttttta  60
ttgataacaa aaccggctca gttctgcgta gaaaccaaca tgcaagctcc accgggtgca  120
aagcggcagc ggcggcagga tatattcaat tgtaaatggc ttcatgtccg ggaaatctac  180
tggtggcagg atatattgtg gtgtaaacaa tggagaaaaa gattaattaa gtactagtcc  240
agtacgcacg attcaaggct tgcttcacaa accaaggcaa gtaatagaga ttggagtctc  300
taaaaaggta gttcccactg aatcaaaggc catggagtca aagattcaaa tagaggacct  360
aacagaactc gccgtaaaga ctggcgaaca gttcatacag agtctcttac gactcaatga  420
caagaagaaa atcttcgtca acatggtgga gcacgacaca cttgtctact ccaaaaatat  480
caaagataca gtctcagaag accaaagggc aattgagact tttcaacaaa gggtaatatc  540
cggaaacctc ctcggattcc attgcccagc tatctgtcac tttattgtga agatagtgga  600
aaaggaaggt ggctcctaca aatgccatca ttgcgataaa ggaaaggcca tcgttgaaga  660
tgcctctgcc gacagtggtc ccaaagatgg acccccaccc acgaggagca tcgtggaaaa  720
agaagacgtt ccaaccacgt cttcaaagca agtggattga tgtgataaca tggtggagca  780
cgacacactt gtctactcca aaaatatcaa agatacagtc tcagaagacc aaagggcaat  840
tgagactttt caacaaaggg taatatccgg aaacctcctc ggattccatt gcccagctat  900
ctgtcacttt attgtgaaga tagtggaaaa ggaaggtggc tcctacaaat gccatcattg  960
cgataaagga aaggccatcg ttgaagatcc tctgccgaca gtggtcccaa agatggaccc  1020
ccacccacga ggagcatcgt ggaaaaagaa gacgttccaa ccacgtcttc aaagcaagtg  1080
gattgatgtg atatctccac tgacgtaagg gatgacgcac aatcccacta tccttcgcaa  1140
gacccttcct ctatataagg aagttcattt catttggaga ggaaaaataa atatgacata  1200
agaatacata aagatacatc gcatacaaac actgtgcatt caaattcgtg agaaagcaag  1260
ctgttacgaa agtttacgat atattcttat atattcatag cactgaatac ctgcagatgt  1320
cgactatcca gctattcaag actatcagat ttggttcctt tgagcctgtt aagctcgatg  1380
aaggaaacaa tattatagag aaggtcccag ttgaccttct ggcaggaaat gatggctctg  1440
gtcctgagga gcaatcagaa cagaaatacc ataggaaaga aagtggtgaa agttggcgga  1500
aagtaaccga cttatattct gtaattggaa attctgttta ctgccgcagt tacgtagcaa  1560
tgaagaactt cctcaatgac acaaagtggg gaggtctttt taaaaataag aaggggcaag  1620
aattaaaggc tgcagcaagg ctcagaaggg ctacaagcta tggattcatg tatgatccag  1680
ttgcttgtgc ctttgaatgt cctgtttgca ggacgaaagc aacagcattg gaagcattca  1740
caagcgattg tgatcattgt tttgaaatca agcacattga cgatgacagg atcgttcaga  1800
ctgaaacaaa gttttatcca ataaatccta ttgaactgga tgttgaggat aacttagtgg  1860
aagctgcatc gcttgaatgg ttgaaaggtg atgtggaaga gagagttgtg gatagggtct  1920
tactacttga ggataaggaa atccacgtca cgaagaaagc cctagtcaaa agaagagctg  1980
agacaaaact cgtggcaaat gctgctgatc ttaccaagaa attgactgag atctgttgtg  2040
agtctggaat tcctatcatt gatattgata atagtaagag gaaagccatt ccaatggtca  2100
aactcaagca tatctttggg aaagttgagt gtgatgacat gtttgaagaa gatcggtatt  2160
tcctggagca cagcaatgca gggaaaattt tccgatcatg cgagaaaatt acttatagga  2220
tgattcgtcc tggatggagt ggagcaatca ttttaagaga taatgttcag agtgaggatc  2280
atgataagtt tgattttatc aatgatattt gtgttgttca agggaagaat ctgattagtt  2340
acaaaattga gaatgccatg cgcgttaaga ctgaaacaga attggattta attgatttgt  2400
attccttcaa tctcagttgg gcgaaatcga aagataagtt cattaagcat tttgaaagtg  2460
atacaactca attagttaga tcatgttgta ctcctagtac attgtggttg tatgcacgga  2520
aagccaggtt ttacaaattt gtggatcaca tgatcttaaa gggtagtcca ataattgata  2580
ttctagttaa aatggagtat gtaggcaagc atctggacat gttcaatagt gttgaagatg  2640
tgtgtactga gtattctcat tttatgaagg agttgattag cgaaactgtt aatgacaagt  2700
cagatccaga tgtgttgcgt gttagaaatc tgattagagc gcattttgag tcagttttag  2760
aatataataa gtatgagttg atagatagga ttattgagaa aaaaacacag ttagaagcac  2820
aagaaattat gtctcgcgag ctcatcaaac atcagtacgg agagttattt tcttggcgcg  2880
aacgtttgtg tttgaaacta ggtataggtt catcaaatct ctatacgtac tgggtggaac  2940
gagaggaaaa acaatcagag aaatcgaatg taatctcttg catcatttcc aaaccgggaa  3000
tagagatgtt gatcaattgg gtctcagaag tgtgtaagag taaatatcat agtcttgtga  3060
attgtgtcga tagtggtatt ttattcttgt ggtctagaat agttcattta gcgagagttt  3120
```

-continued

```
cagtttatgg ttattggaat ctttggttta gacaagcaat gtgtgtgttg ttcatttttct  3180
tagtttcaaa tttctctggt aaaatagtta gttatcttaa gaaattaatt gtgagtgaga  3240
agaagctagc tataaagaat gaagaaggtt ttgttgaagt gcaaggtcga aaggaagagt  3300
cttttgttct aaagtggtgt gctgctgcaa ctttgtttct tagtttcctt aactatgact  3360
gggcagttgg gtgtgtttca gctattggaa agatgaaaac aatatttagc gcactaggtc  3420
cagattttat agaaaagcag gatggggatg atgatcttaa attcacaaca tttgaagttg  3480
agattcctgg agattctaga agttcaagtg cacaaacgtt tggggaatgg attgagcatt  3540
gcattaaatt caacttagtt tcaattgaac caaccacgag tggacccatg ctaactttgg  3600
agcgtgggaa agcgaatgag ttggctgacc agataaattg tttgaatgca acagacatac  3660
gtgtgcatgg tggtgttgga acgggtaagt caacagctct accatatgag ctaataaggt  3720
atggggcagt tcttgtgtgt gtgcctacga gagttctggc aaatgcattg catgagtcat  3780
tcatgagctt gtttggattt gatgtgtcat tggcttatcg gggtcgagtc agaactggtt  3840
caaaaccaat tactatcatg acatatggat atgccttgaa tcatttccat cacaatccca  3900
ggaatttagc acagtttcaa ttcataataa tggatgaggt tcacacattc cctgttcatt  3960
taaatccttt attctcattg ttgcgtgagt tgagtcctga caagaaaata atcaagacat  4020
cagcaacaca tgttggccat agtgttgatc tatcaactaa ccacaaagtt gatatacaca  4080
cgcttgagat aatggatgtc aagaaatggg ctgaattaca aggaacatct gtgtttggtg  4140
atgtgacaaa ggaacctgga aatgttttgg tgtttgttgc atcatatagg gatgttgatg  4200
tttgttcaga taagcttaag gataaaggat ttcctgtaat taaagttgat ggaagaaatt  4260
tcaggaagaa tacagaagtt cagaaaatgg tggacggaat gcaaggagag gtgaagttca  4320
ttgtcgcgac taatatcatc gaaaatggtg ttacccttga cgttgatgta gtcgttgatt  4380
ttggcgaacg cataagtcca aatttatgct cagaagatag gtgcatttta atgcagaggc  4440
aaagaatctc acaagctgaa agaaaacaaa gatttgggag agttgggaga atgaagagag  4500
gctcagtgta caaatttgga agggagacgt tgcctgattc aatgagaaat agagtggggt  4560
caacagagag tgcattaatt tgttttgctt acggtttaaa accagtagtt gatgatgtgg  4620
atatagggtc agttaggagt gtcacacaga ggcaagcttt gacagcatct atgtttgaag  4680
cgaattacat attcacagct cacttagtgg acaaacaagg tttcatgcct aggccggttt  4740
ttgagttgat gaaaagtctt ctgctacata cagatgcggt tggggtcagt agtacatatt  4800
tagctactaa tatgagtggt tggagaaggt tgaaagagta tattagaatt gacgataact  4860
cacgtcacgt gcaagaagtt caaattccat ggtactgttc agacatgagt gacgatttta  4920
ttgttaagtt aactgagtgt gttaaagctg caaagccaaa atcacagtgt ggttacaaag  4980
tagataatgt agattttcat accgtagctc ataaaataag tgtaggagag tcgaatatag  5040
atgagtcaag ggctttagtg gcaacaattt tggatgaagt caaacagtgg agagatggta  5100
ttacatacca ttcaagcaca cctaggaata agagtctgat gagtttgatg gttggatgga  5160
ttccaaggaa agcagagaaa acaaaggaaa ttcttgacaa tcggattcag cgtctcgagt  5220
tactcttgaa ccaattaaat ggagtcagag gaatcgatga ctatgaatct cttgttcggt  5280
ttttcagtga gaatcctcat tcagcggaat atcttgaatc acaatgtgct agtgattata  5340
tcgaagagaa ggttatgagt gtcaaaagaa actacgataa gtcgctaatc cttggtatgg  5400
ttggtttagc tgttgcaaca ggcacgtttg cttactggta tatgaggaga agtgctgcgg  5460
ttgaactcgt tgaaaaacaa gcgaagcaca agtataacag agataagcga acaggaagat  5520
tgatgtttga tatggatgat agagagactt atgagaattt tggtcctgaa tacacagatg  5580
atgtcatatc tgccaagatg acaaaagctc agaaagaaag agactcaaag aagaagggat  5640
ggaaagcagg taaaataaat cgacctatga gggtgtttca tcaattgtat ggagttaatc  5700
ctcttgagtt cgatgaagtt gtcatgagag ttggtaaact tgagactgaa ccgtgggatg  5760
tgaaaagaatt aaatgttgat gcaatgatga tcgaattgga tgatgattac cacattttac  5820
gggatgatcg aatgtttggg aagaaagttt ctttagcttt caagaaagaa ggggcagatg  5880
aggaaaccat tgtgaatttg actccacacc gatcaaaaat gacaagtagc atgagcttag  5940
ccccaatggg atttccagaa gaagagggta gatggaggca gacaggagca ccgctgataa  6000
ggaagatcga aaaggaagat gaagttgaag ttcaagttgc taagccagag tcaacaaatc  6060
cttacgatca tatcttggtt agacttggca gagcgcatct tgggactcgt gtattgaatt  6120
gtttctttca tgggtcaaaa tgtgttattc catatcattt agctgagaaa ggagataggg  6180
aagaatcatt ggttattgca accacgagag gacagtttga ttttggacca atgaaaaata  6240
tcaagtgcag gaaggtcaca gactatgata tcactatttg ccccactgcca aatgatgttc  6300
aaccattccg ttcaaaaatt gtaatgcgtg aaccaaagct aggagaggaa gtggttattg  6360
tgtgctttac caggatcaat gggaagatcg tgatgaaagt tagtgataag agcaccacat  6420
atcccgctgg tgggcagttt gcgcaccttt gggcgtataa atacgatggc caaccaggag  6480
attgcggagg cccaattgtt gcgacagttg atcaaaaggt ggtggggttc catagtggtg  6540
tgattagaaa tagtagagag gagaaactgc gagctgtgta cactccagta aatcaagagc  6600
ttttgaattg tatcagtggc gatatccaaa tgacggattt ttggacattc aatcctgatc  6660
ttgttgagtg gaattccgta gcaagagtgt caacattttt tcctatgaca aaagcgatta  6720
ataccatcac ggtgcaagcg aatgaaggtg aagaattaat tgatggtaac ttaatgattg  6780
ttggttatgt taaccgcgag gtttatcata atcacgtcat taaagggaaa agagagagtt  6840
tcatgagata ttgtgaacaa ttcccaaatt gtgcttttac caaggaattg cgagaccaat  6900
atcttccaag cattttgagt aagccagctt ttaggaaagg attgttgaag tacaatgagc  6960
cagttcgagt tgggtcagtg aatttctcgt gcttgatacg agcttatttg aaagtggaag  7020
aaatgtttga ggatctagga tttctggagg aagccggacc acagtgggac cctattgaaa  7080
ttttggatga tttgaataag aaagccgcaa tgggcgcatt gtatcaagga aagaagcaag  7140
actggttgaa gtccatagag cccgcagatt ttatcacggc agtgcgtgaa agtttcaaac  7200
acttggctgg tggggatgtt ggaatttgga gtggctcact caaagcagaa ttgagacctg  7260
ttgagaaagt gcttgagcag aaaacaagag tgtttactgg agctccaatt gatttgctgt  7320
tggggggaaa gattttagtt gataatttta atcatttctt ttattttaat catttgaagg  7380
ggccttggac tgtaggaatt aataaattta ataaaggttg ggatagatta gctaggtact  7440
ttaatcatag ttggaacttc atagattgtg atggtagtag gtttgatact tctttagctc  7500
ccattttgtt tcaattagtg tgccatatgc gagaaaaatt tggaaatttt gatgatattg  7560
agagggcagc tcttcgtaat ttatacacac agatagtgta tacgccaatt ttaacaattg  7620
acggatacat tactaagaag catcgtggaa ataatagtgg acaaccttct acagttgtcg  7680
acaacactat tatactaatg attgttgtgg aatattgcaa ggctgtcatg gagagtgaag  7740
gaagagtaat gcaattcaag tatatgtgta atggggatga tctgatcctc aatgttcctg  7800
atgatgaggt gagcatagtt cagagtaggt ttagagagtt gttttcagaa tgtggtttag  7860
```

-continued

```
attataattt tgatgatgtt cataagtcaa tagaaacaat tgagtatatg agccattcat  7920
tcatgctgaa agatggtgtg tatattccaa aattgaagaa agaaagaatc gttgcaattc  7980
ttgaatggga gagaggtgat gagatcatgc gaacgcggag tgctcttaat gctgcttata  8040
ttgagagtta tggatatgac gatctgatgg ttgaaattga gcggtatgca gttttctggg  8100
ctaccgataa aggttgtgag tatccattac tggatagaaa gcgtgtagaa ggactttaca  8160
aagatgatta cacagatatc aatgaagaat ggttgatagg tattttacca ccatcattcg  8220
aacattgtta tgttgacacg caaactaagg atttgagagg aagagagaag cttgagctga  8280
gaattgagag tcatgacaga acactccaaa tgcaaatgaa gttcccagtt acatttgtga  8340
caggaaattt gggaaaatta gcagaggtga agtctattct tggcattgca aatgatgtta  8400
tggccaagaa cattgattta ccagaagtgc aaggaactcc agaagaaatt gtgagaaaga  8460
aggctcaatt agcagtgaag atgactaata gtcctgtttt agtcgaagat acatgtctct  8520
gttttaatgc tttcaatgga cttcccggac catacatcaa atggtttcta aaagaattgg  8580
gtcttgatgg tgttgtcaaa atgctgtcag catttggaga taaatcagcg tacgcactat  8640
gtacattcgc atatgtgcac aatgagtcat ctgatccaat tgtgttcaaa ggagttgtga  8700
atggtgaaat tgtgccacca cgaggtaata atggctttgg ctgggatcct atctttaagc  8760
ctgatggatg tggttgtacg ttcgcggaaa tgccaagcag cattaagaat gatttttctc  8820
acagaagaag agctttagag aaagtcaaat tgtttcttga taacttgatg gtgaagcaag  8880
agaagaataa agcaagtgtg gctctaacga ttgacgttca ggccttaaat caggaggaaa  8940
tagaagcaga gatcactgct ttaaagaagc tgtggaaaga caatgggcca acaagaacgc  9000
gtagttcatt tgaggctagg aggttgagag ccccacaagt tgagcgtgta aatgagttac  9060
ttcagaaact gaaagatgaa ggattgcaaa caaagaagag gccatgtgga gaaccagatg  9120
atggggaagt ggtagatgat gacagcaatg atggtgacaa tcagagatct gaaaaggagg  9180
ttgttgacga aagccagaat aatcaacaag ttgatccaag aaagttgaaa ttcaaaatta  9240
ggggagatgg aaatgctatt agacgggatg acattgataa aattccaact aatgctcttg  9300
agatcaagaa gacgttcaag cctccaaagg tatcacagtc agcttacatt tggattccac  9360
gctctcaaag ggataatcta acccctgatg ttattcagaa tttcctggca tatatacctc  9420
catctcatgc tatagataac caacttgctt caggaattga agttgaaaat tgggcaattg  9480
aggttgctaa agcatatgga gttaatatac aggaatttta tcgcacagtt ttgccagctt  9540
ggatagtgaa ctgtatagtg aacggcacta gcgatgaaag gaaaaatgag aagtcatggc  9600
gagcagtcga gctgaattct cagggagagg atgttgatga ttttgagtat ccaatggaac  9660
caatgtacaa atttgcattg ccaactatga ggaaggttat gagaaacttt tctagccaag  9720
ctattctcat gtaccagaat agtgtcgctg caggaaaggc gtttgtgata aaagctgcta  9780
gaaatgctgg atacacaagt attgaaaaca aatggctagg tatagacttt ctcgccgaag  9840
ctcaattgtc tcaaagtcaa cttgatatca agcatcagat tctggcagca aatgttggta  9900
ggtcaaagac aaggctgttt gcattagcag ctcctgggga tgatggcaat gtagataaag  9960
aaaggcacac aacacacgat gtcagtgcaa acaggcacag ttatagtggt gccgcaattg  10020
aataaataaa atattagtgt ttctaattag gtttaagtga gattatagct tagttggaaa  10080
gctaagctat atttcaaatt tgaatttaag tacttaaata ttgtatttta ttttcaagct  10140
tggtggagtt ttggatagcc aattatattt tggttgggta agccaaaatg tatttggag  10200
atctttctcc atatcctttt gtttggtgta gaaatacacc ttataaaagt acaaaaaaaa  10260
aaaaaaaaaa aaaaatgcat gcctgcagat cgttcaaaca tttggcaata aagtttctta  10320
agattgaatc ctgttgccgg tcttgcgatg attatcatat aatttctgtt gaattacgtt  10380
aagcatgtaa taattaacat gtaatgcatg acgttattta tgagatgggt ttttatgatt  10440
agagtcccgc aattatacat ttaatacgcg atagaaaaca aaatatagcg cgcaaactag  10500
gataaattat cgcgcgcggt gtcatctatg ttactagatc tctagcctgc aggaattgtt  10560
gattttgtga tgactgatgg caggatatat gcggttgtaa ttcattttta ttgtctaaat  10620
ttctgtattt gtttgtttgt tcggttgtaa atttttttgg aagaacaaga aaagaaaaaa  10680
cacccgttag ggtgttttta gttagtgtgg cgcgccgact tgcgacatgc ggtcctttgc  10740
aatcaactat tagaaaaatt catccagcat cagatgaaat tgcagtttgt tcatatccgg  10800
attatcaatg ccatatttct gaaacagacg tttttgcagg ctcgggctaa attcgcccag  10860
gcagttccac agaatggcca gatcctgata acgatccgca atgcccacac ggcccacatc  10920
aatgcagcca atcagtttgc cttcatcgaa aatcaggtta tccaggctaa aatcgccgtg  10980
ggtcaccacg ctatccgggc taaacggcag cagtttatgc atttctttcc acacctgttc  11040
caccggccag ccgttacgtt catcatcaaa atcgctcgca tccaccaggc cgttgttcat  11100
acggctctgc gcctgggcca gacgaaacac acgatcgctg ttaaacgggc agttgcacac  11160
cggaatgcta tgcagacgac gcagaaacac ggccagcgca tccacaatgt tttcgccgct  11220
atccggatat tcttccagca cctgaaacgc ggttttgccc ggaatcgcgg tggtcagcag  11280
ccacgcatca tccggggtgc gaataaaatg tttaatggtc ggcagcggca taaattcggt  11340
cagccagttc agacgcacca tttcatcggt cacatcgttc gccacgctgc ctttgccatg  11400
tttcagaaac agttccggcg catccggttt gccatacaga cgataaatgg tcgcgccgct  11460
ctgacccacg ttatcacgcg cccatttata gccatacaga tccgcatcca tgttgctgtt  11520
cagacgcgga cggctacagc tcgtttcacg ctgaatatgg ctcataacac cccttgtatt  11580
actgtttatg taagcagaca gttttattgt tcatgatgat atatttttat cttgtgcaat  11640
gtaacatcag agattttgag acacaagatc ggattggcgg ttatgcggtt ctaccggcgc  11700
ggcagcgtta cccgtgtcgg cggctccaac ggctcgccat cgtccagaaa acacggctca  11760
tcgggcatcg gcaggcgctg ctgcccgcgc cgttcccatt cctccgtttc ggtcaaggct  11820
ggcaggtctg gttccatgcc cggaatgccg ggctggctgg gcggctcctc gccggggccg  11880
gtcggtagtt gctgctcgcc cggatacagg gtcgggatgc ggcgcaggtc gccatgcccc  11940
aacagcgatt cgtcctggtc gtcgtgatca accaccacgg cggcactgaa caccgacagg  12000
cgcaactggt cgcggggctg gccccacgcc acgcggtcat tgaccacgta ggccgacacg  12060
gtgccggggc cgttgagctt cacgacggag atccagcgct cggccaccaa gtccttgact  12120
gcgtattgga ccgtccgcaa agaacgtccg atgagcttgg aaagtgtctt ctggctgacc  12180
accacggcgt tctggtggcc catctgcgcc acgaggtgat gcagcagcat tgccgccgtg  12240
ggtttcctcg caataagccc ggcccacgcc tcatgcgctt tgcgttccgt ttgcacccag  12300
tgaccgggct tgttcttggc ttgaatgccg atttctctgg actgcgtggc catgcttatc  12360
tccatgcggt aggggtgccg cacggttgcg gcaccatgcg caatcagctg caacttttcg  12420
gcagcgcgac aacaattatg cgttgcgtaa aagtggcagt caattacaga ttttctttaa  12480
cctacgcaat gagctattgc ggggggtgcc gcaatgagct gttgcgtacc cccctttttt  12540
aagttgttga tttttaagtc tttcgcattt cgccctatat ctagttcttt ggtgcccaaa  12600
```

-continued

```
gaagggcacc cctgcggggt tcccccacgc cttcggcgcg gctccccctc cggcaaaaag  12660
tggcccctcc ggggcttgtt gatcgactgc gcggccttcg gccttgccca aggtggcgct  12720
gccccccttgg aacccccgca ctcgccgccg tgaggctcgg ggggcaggcg ggcgggcttc  12780
gcccttcgac tgcccccact cgcataggct tgggtcgttc caggcgcgtc aaggccaagc  12840
cgctgcgcgg tcgctgcgcg agccttgacc cgccttccac ttggtgtcca accggcaagc  12900
gaagcgcgca ggccgcaggc cggaggcttt tccccagaga aaattaaaaa aattgatggg  12960
gcaaggccgc aggccgcgca gttggagccg gtgggtatgt ggtcgaaggc tgggtagccg  13020
gtgggcaatc cctgtggtca agctcgtggg caggcgcagc ctgtccatca gcttgtccag  13080
cagggttgtc cacgggccga gcgaagcgag ccagccggtg gccgctcgcg gccatcgtcc  13140
acatatccac gggctggcaa gggagcgcag cgaccgcgca gggcgaagcc cggagagcaa  13200
gcccgtaggg gg                                                      13212
```

```
SEQ ID NO: 23          moltype = DNA  length = 5929
FEATURE                Location/Qualifiers
misc_feature           1..5929
                       note = pLX-B2-PcrcmTFP1
source                 1..5929
                       mol_type = other DNA
                       organism = synthetic construct
SEQUENCE: 23
ccatcatcag ttcggtggtc ttccgacgaa caataaggcc gcaaatcgcg gcctttttta  60
ttgataacaa aaccggctca gttctgcgta gaaaccaaca tgcaagctcc accgggtgca  120
aagcggcagc ggcggcagga tatattcaat tgtaaatggc ttcatgtccg ggaaatctac  180
tggtggcagg atatattgtg gtgtaaacaa tggagaaaaa gattaattaa gtactagtag  240
cctggtcgaa accgtctcat aacgaacgct catgctaagc tgcgcaaaat acttcctaat  300
caaaacagta acaacgagta attagcaaaa tccgagcaga aaactctcac ccacctccga  360
aattcacgtc ttcactaaaa ttttcgaaag gaatcgatca ataccaaccc attacacaaa  420
atacataatc aaaatggcga gaatcgtacc tggaaacttt gcttcaagtc gcagagagag  480
gaaaaggaag atcgtggaga aaggggttta gggtttaagc tcagacttct attggagtaa  540
atgggacggt gtcacatttt ccgttttgga aatgaacttt gggctcacgt tatgggctat  600
tagatatttg atgggctttc tagtaaatac aatataagtt attgggctta gtttaaataa  660
gcccatgttg gaaatatttg acacatgtct tggctactag tgctaaacat gcaaccgaac  720
agttgtcgag acaagtcgca gcatatacaa tggatcaaac acgcctagtg tcgccgcgtc  780
tcgctcatgt gtcaccttgt ttcctcgttt tttttaatt tttcataagt tcttttgttt  840
tatcttcaat acaaattttt ggctgtatct tgcaaactct tcgatcatat cgccaatata  900
cgtgaacact ggtgatctaa tttgttgtgt taattgttaa atttagattc tattctccgg  960
tttaaaagtg aattatatgt atcatggtta aaacattgta agtaagatga taataaaatg  1020
ataaatttag ttgatggata acgtgaagca aaaaatgaga tagatacatt tgattttgtc  1080
gtattttgac atatgcggag agtgagctac gcgcatgaag atcaagagac acttgctcga  1140
gctcacagag tgacgtgtaa aaagcttaga ctgaagtccc catgcaaacc taatcctacg  1200
tggctcaaac cacgagctca cttgacaata tataaactcc tcctaagtcc cgttctcttc  1260
atccatctct cacaacaaac aaaaagaaaa tggtttctaa aggtgaagag actacaatgg  1320
gagtgatcaa gcctgatatg aagatcaagc tcaagatgga agggaacgtg aacggacacg  1380
ctttcgttat tgaaggagaa ggggagggca agccttacga tggaactaac accatcaacc  1440
ttgaagtgaa agagggtgct cctctccctt tctcttacga tatcctcact accgctttcg  1500
cttacggaaa cagggctttc accaagtacc ctgatgatat ccctaactac ttcaagcagt  1560
ctttcccaga gggatactct tgggagagaa ccatgacctt cgaggataag ggaatcgtga  1620
aagtgaagtc tgatatctct atggaagagg attctttcat ctacgagatc catctcaagg  1680
gcgagaactt ccctcctaac ggacctgtga tgcagaaaaa gactaccgga tgggatgctt  1740
ctaccgagcg gatgtatgtg agagatggtg tgttgaaggg tgatgtgaag cacaagctgt  1800
tgcttgaggg tggtggacat cacagagtgg atttcaagac catctacagg gctaagaagg  1860
ctgttaagct ccctgattac cacttcgtgg atcatcgaat cgagatcctc aaccacgata  1920
aggattacaa caaagtgacc gtgtacgagt ctgctgtggc tagaaactct accgatggag  1980
gctctggtga ttacaaagac gatgacgata agggcagtgg agactataag gatgacgacg  2040
ataaaggagc ataatgcact ggaggacaag gaaggatcca agtggtcaac gacaacggac  2100
agaacgtgtt ggaccaacag gtgcagaagg gacagctcgt ggtcatccca caagggttcg  2160
catacgttgt ccagtcccac ggaaacaagt tcgagtggat ctctttcaaa actaatgaaa  2220
acgcaatgat cagcactttg gcgggtagaa cctcgctctt gagggcattg ccattggagg  2280
tcatatcaaa tggtttccag atctctcccg aggaagctag gaagatcaag ttcaacacac  2340
ttgagaccac tttgacccgc gctgccggta ggcaacaaca acagttgatc gaggagattg  2400
tcgaggctta aatcaaaacg tttttctttt tcttaataaa gtatggtcag tttgtaatca  2460
cgtcccttta cctttaacgt acgtgtaaaa tatgtgtctg cggcacctca cttgtaataa  2520
cactttcttc tcataaataa aagggaagtt tcgagttaca tactataata tagcgccagt  2580
tttttcgtct attccacaaa acataagttt gtgtccatct actgtagctt gagcttcgta  2640
tatatacttg gtctttattc ttttttttt caaaatacgg ctttctgctt tctgtgggcc  2700
taaacggagg cccaaacgaa ttaaagttcc gtcacttgga aacgttatcc tagattactc  2760
ttgcggggaa aagtgtagat tagttccaat ttttgaagtg aaaaattgtg ttggattcta  2820
tgtcgtaaca agaaatagca tggcctccaa agattattct ctctttcttt aggctttagc  2880
ttctaaagct aagctacgga aaaactgtat cattcttctc ttttttttgg cttatgatcc  2940
atataagaga gcttggaaga gctgcttttc atctcctgat cactagctca tacagttttt  3000
gtaatttatt aacgaaacta tataaaaaaa gggaagccga aaaaacaaaa caaaaaacaa  3060
ccttcatcgg ctgctcaaat gccaatcatc ccaattggtc tccattattg ttttctcgtt  3120
actactcctc catctttgat ttaataattt tttgaaaaaa gtttactat atgaatgata  3180
ttctctgtta gggaaatata aaaattgtaa gcaaatgatt ctatcgagct atgtcaggag  3240
acgggacaag gatgcgagct agcctgcagg aattgttgat tttgtgatga ctgatggcag  3300
gatatatgcg gttgtaattc atttttattg tctaaatttc tgtatttgtt tgtttgttcg  3360
gttgtaaatt tttttggaag aacaagaaaa gaaaaaacac ccgttagggt gtttttagtt  3420
agtgtggcgc gccgacttgc gacatgcggt cctttgcaat caactattag aaaaattcat  3480
ccagcatcag atgaaattgc agtttgttca tatccggatt atcaatgcca tatttctgaa  3540
```

-continued

```
acagacgttt ttgcaggctc gggctaaatt cgcccaggca gttccacaga atggccagat  3600
cctgataacg atccgcaatg cccacacggc ccacatcaat gcagccaatc agtttgcctt  3660
catcgaaaat caggttatcc aggctaaaat cgccgtgggt caccacgcta tccgggctaa  3720
acggcagcag tttatgcatt tctttccaca cctgttccac cggccagccg ttacgttcat  3780
catcaaaatc gctcgcatcc accaggccgt tgttcatacg gctctgcgcc tgggccagac  3840
gaaacacacg atcgctgtta aacgggcagt tgcacaccgg aatgctatgc agacgacgca  3900
gaaacacggc cagcgcatcc acaatgtttt cgccgctatc cggatattct tccagcacct  3960
gaaacgcggt tttgcccgga atcgcggtgg tcagcagcca cgcatcatcc ggggtgcgaa  4020
taaaatgttt aatggtcggc agcggcataa attcggtcag ccagttcaga cgcaccattt  4080
catcggtcac atcgttcgcc acgctgcctt tgccatgttt cagaaacagt tccggcgcat  4140
ccggtttgcc atacagacga taaatggtcg cgccgctctg acccacgtta tcacgcgccc  4200
atttatagcc atacagatcc gcatccatgt tgctgttcag acgcggacgg ctacagctcg  4260
tttcacgctg aatatggctc ataacacccc ttgtattact gtttatgtaa gcagacagtt  4320
ttattgttca tgatgatata tttttatctt gtgcaatgta acatcagaga ttttgagaca  4380
caagatcgga ttggcggtta tgcggttcta ccggcgcggc agcgttaccc gtgtcggcgg  4440
ctccaacggc tcgccatcgt ccagaaaaca cggctcatcg ggcatcggca ggcgctgctg  4500
cccgcgccgt tcccattcct ccgtttcggt caaggctggc aggtctggtt ccatgcccgg  4560
aatgccgggc tggctgggcg gctcctcgcc ggggccggtc ggtagttgct gctcgcccgg  4620
atacagggtc gggatgcggc gcaggtcgcc atgccccaac agcgattcgt cctggtcgtc  4680
gtgatcaacc accacggcgg cactgaacac cgacaggcgc aactggtcgc ggggctggcc  4740
ccacgccacg cggtcattga ccacgtaggc cgacacggtg ccggggccgt tgagcttcac  4800
gacggagatc cagcgctcgg ccaccaagtc cttgactgcg tattggaccg tccgcaaaga  4860
acgtccgatg agcttggaaa gtgtcttctg gctgaccacc acggcgttct ggtggcccat  4920
ctgcgccacg aggtgatgca gcagcattgc cgccgtgggt ttcctcgcaa taagcccggc  4980
ccacgcctca tgcgctttgc gttccgtttg cacccagtga ccgggcttgt tcttggcttg  5040
aatgccgatt tctctggact gcgtggccat gcttatctcc atgcggtagg ggtgccgcac  5100
ggttgcggca ccatgcgcaa tcagctgcaa cttttcggca gcgcgacaac aattatgcgt  5160
tgcgtaaaag tggcagtcaa ttacagattt tctttaacct acgcaatgag ctattgcggg  5220
gggtgccgca atgagctgtt gcgtaccccc cttttttaag ttgttgattt ttaagtcttt  5280
cgcatttcgc cctatatcta gttctttggt gcccaaagaa gggcacccct gcggggttcc  5340
cccacgcctt cggcgcggct ccccctccgg caaaaagtgg cccctccggg gcttgttgat  5400
cgactgcgcg gccttcggcc ttgcccaagg tggcgctgcc cccttggaac cccgcactc   5460
gccgccgtga ggctcggggg gcaggcgggc gggcttcgcc cttcgactgc cccactcgc   5520
ataggcttgg gtcgttccag gcgcgtcaag gccaagccgc tgcgcggtcg ctgcgcgagc  5580
cttgaccgc  cttccacttg gtgtccaacc ggcaagcgaa gcgcgcaggc cgcaggccgg  5640
aggcttttcc ccagagaaaa ttaaaaaaat tgatggggca aggccgcagg ccgcgcagtt  5700
ggagccggtg ggtatgtggt cgaaggctgg gtagccggtg ggcaatccct gtggtcaagc  5760
tcgtgggcag gcgcagcctg tccatcagct tgtccagcag ggttgtccac gggccgagcg  5820
aagcgagcca gccggtggcc gctcgcggcc atcgtccaca tatccacggg ctggcaaggg  5880
agcgcagcga ccgcgcaggg cgaagcccgg agagcaagcc cgtagggggg             5929

SEQ ID NO: 24           moltype = DNA  length = 7308
FEATURE                 Location/Qualifiers
misc_feature            1..7308
                        note = pLX-Z4-PmasRFP-ALCR
source                  1..7308
                        mol_type = other DNA
                        organism = synthetic construct
SEQUENCE: 24
caagaagatc ctttgatctt ttctacaggc ctgctggtaa tcgcaggcct ttttattttg  60
gcaggatata ttgtggtgta aacacttacc gcacctctgc agcagcggca ggatatatgg  120
cagtgtaaac tccattttcg aacgcgttaa ttaagtagcc tggtcgaaac cgtctcattt  180
ttcaaatcag tgcgcaagac gtgacgtaag tatccgagtc agtttttatt tttctactaa  240
tttggtcgtt tatttcggcg tgtaggacat ggcaaccggg cctgaatttc gcgggtattc  300
tgtttctatt ccaacttttt cttgatccgc agccattaac gacttttgaa tagatacgct  360
gacacgccaa gcctcgctag tcaaaagtgt accaaacaac gctttacagc aagaacggaa  420
tgcgcgtgac gctcgcggtg acgccatttc gccttttcag aaatggataa atagccttgc  480
ttcctattat atcttcccaa attaccaata cattacacta gcatctgaat ttcataacca  540
atctcgatac accaaatcgg gtaacaacaa tggtttcaaa gggagaagag ctgattaagg  600
agaacatgca catgaagctg tacatggagg gcaccgtgaa caaccaccac ttcaagtgca  660
catccgaggg cgaaggcaag ccctacgagg gcacccagac catgagaatc aaggtggtcg  720
agggcggccc tctccccttc gccttcgaca tcctggctac cagcttcatg tacggcagca  780
gaaccttcat caaccacacc cagggcatcc ccgacttctt taagcagtcc ttccctgagg  840
gcttcacatg ggagagagtc accacatacg aagacggggg cgtgctgacc gctacccagg  900
acaccagcct ccaggacggc tgcctcatct acaacgtcaa gatcagaggg gtgaacttcc  960
catccaacgg ccctgtgatg cagaagaaaa cactcggctg ggaggccaac accgagatgc  1020
tgtaccccgc tgacggcggc ctggaaggca gaacagacat ggccctgaag ctcgtgggcg  1080
ggggccacct gatctgcaac ttcaagacca catacagatc caagaaaccc gctaagaacc  1140
tcaagatgcc cggcgtctac tatgtggacc acagactgga aagaatcaag gaggccgaca  1200
aagagaccta cgtcgagcag cacgaggtgg ctgtggccag atactgcgac ctccctagca  1260
aactggggca caaacttaac ggaggcggag gcgggagagc agaagggaga ggaagcttgc  1320
taacctgtgg agacgttgag gaaaatccag ggccaatggc agatacacgc cgacgccaga  1380
atcatagctg cgatccctgt cgcaagggca agcgacgctg tgatgccccg gaaaatagaa  1440
acgaggccaa tgaaaacggc tgggtttcgt gttcaaattg caagcgttgg aacaaggatt  1500
gtaccttcaa ttggctctca tcccaacgct ccaaggcaaa aggggctgca cctagagcga  1560
gaacaaagaa agccaggacc gcaacaacca ccagtgaacc atcaacttca gctgcaacaa  1620
tccctacacc ggaaagtgac aatcacgatg cgcctccagt cataaactct cacgacgcgc  1680
tcccgagctg gactcagggg ctactctccc accccggcga ccttttcgat ttcagccact  1740
ctgctattcc cgcaaatgca gaagatgcgg ccaacgtgca gtcagacgca ccttttccgt  1800
```

-continued

```
gggatctagc catccccggt gatttcagca tgggccaaca gctcgagaaa cctctcagtc  1860
cgctcagttt tcaagcagtc cttcttccgc cccatagccc gaacacggat gacctcattc  1920
gcgagctgga agagcagact acagatccgg actcggttac cgatactaat agtgtacaac  1980
aggtcgctca agatggatcg ctatggtctg atcggcagtc gccgctactg cctgagaaca  2040
gtctgtgcat ggcctcagac agcacagcac ggcgatatgc ccgttccaca atgacgaaga  2100
atctgatgcg aatctaccac gatagtatgg agaatgcact gtcctgctgg ctgacagagc  2160
acaattgtcc atactccgac cagatcagct acctgccgcc caagcagcgg gcggaatggg  2220
gcccgaactg gtcaaacagg atgtgcatcc gggtgtgccg gctagatcgc gtatctacct  2280
cattacgcgg gcgcgccctg agtgcggaag aggacaaagc cgcagcccga gccctgcatc  2340
tggcgatcgt agcttttgcg tcgcaatgga cgcagcatgc gcagaggggg gctgggctaa  2400
atgttcctgc agacatagcc gccgatgaga ggtccatccg gaggaacgcc tggaatgaag  2460
cacgccatgc cttgcagcac acgacaggga ttccatcatt ccgggttata tttgcgaata  2520
tcatcttttc tctcacgcaa tctgtgctgg atgatgatga gcagcacggt atgggtgcac  2580
gtctagacaa gctactcgaa aatgacggtg cgcccgtgtt cctggaaacc gcgaaccgtc  2640
agctttatac attccgacat aagtttgcac gaatgcaacg ccgcggtaag gctttcaaca  2700
ggctcccggg aggatctgtc gcatcgacat tcgccggtat tttcgagaca ccgacgccgt  2760
cgtctgaaag cccacagctt gacccggttg tggccagtga ggagcatcgc agtacattaa  2820
gccttatgtt ctggctaggg atcatgttcg atacactaag cgctgcaatg taccagcgac  2880
cactcgtggt gtcagatgag gatagccaga tatcatcggc atctccacca aggcgcggcg  2940
ctgaaacgcc gatcaaccta gactgctggg agcccccgag acaggtcccg agcaatcaag  3000
aaaagagcga cgtatggggc gacctcttcc tccgcacctc ggactctctc ccagatcacg  3060
aatcccacac acaaatctct cagccagcgg ctcgatggcc ctgcacctac gaacaggccg  3120
ccgccgctct ctcctctgca acgcccgtca aagtcctcct ctaccgccgc gtcacgcagc  3180
tccaaaccct cctctatcgc ggcgccagcc ctgcccgcct tgaagcggcc atccagagaa  3240
cgctctacgt ttataatcac tggacagcga agtaccaacc atttatgcag gactgcgttg  3300
ctaaccacga gctcctccct tcgcgcatcc agtcttggta cgtcattcta gacggtcact  3360
ggcatctagc cgcgatgttg ctagcggacg ttttggagag catcgaccgc gattcgtact  3420
ctgatatcaa ccacatcgac cttgtaacaa agctaaggct cgataatgca ctagcagtta  3480
gtgcccttgc gcgctcttca ctccgaggcc aggagctgga cccgggcaaa gcatctccga  3540
tgtatcgcca tttccatgat tctctgaccg aggtggcatt cctggtagaa ccgtggaccg  3600
tcgttcttat tcactcgttt gccaaagctg cgtatatctt gctggactgt ttagatctgg  3660
acggccaagg aaatgcacta gcggggtacc tgcagctgcg gcaaaattgc aactactgca  3720
ttcgggcgct gcaatttctg ggcaggaagt cggatatggc ggcgctggtt gcgaaggatt  3780
tagagagagg tttgaatggg aaagttgaca gcttcttgta gctcttggac tcccatgttg  3840
gcaaaggcaa ccaaacaaac aatgaatgat ccgctcctgc atatggggcg gtttgagtat  3900
ttcaactgcc atttgggctg aattgaagac atgctcctgt cagaaattcc gtgatcttac  3960
tcaatattca gtaatctcgg ccaatatcct aaatgtgcgt ggctttatct gtctttgtat  4020
tgtttcatca attcatgtaa cgtttgcttt tcttatgaat tttcaaataa attatcgtca  4080
ggagacggga caaggatgcg cctgcaggtt gttgatgatg tgatgactga tggcaggata  4140
tatgtggttg taattcattt ctaccgtgta atttactgta ttttttttgtt tgttcgttcg  4200
tttgtaaaaa tatttttttgg aagcaaaaaa ttagcgcaag aagacaaaaa tcaccttgcg  4260
ctaatgctct gttacaggcg cgccaattta cccaacaact ccgcggccgg gaagccgatc  4320
tcggcttgaa cgaattgtta ggtggcggta cttgggtcga tatcaaagtg catcacttct  4380
tcccgtatgc ccaactttgt atagagagcc actgcgggat cgtcaccgta atctgcttgc  4440
acgtagatca cataagcacc aagcgcgttg gcctcatgct tgaggagatt gatgagcgcg  4500
gtggcaatgc cctgcctccg gtgctctccg gagactgcga gatcatagat atagatctca  4560
ctacgcggct gctcaaactt gggcagaacg taagccgcga gagcgccaac aaccgcttct  4620
tggtcgaagg cagcaagcgc gatgaatgtc ttactacgga gcaagttccc gaggtaatcg  4680
gagtccggct gatgttggga gtaggtggct acatcgccga actcacgacc gaaaagatca  4740
agagcagccc gcatggattt gacttggtca gggccgagcc tacatgtgcg aatgatgccc  4800
atacttgagc cacctaactt tgttttaggg cgactgccct gctgcgtaac atcgttgctg  4860
ctgcgtaaca tcgttgctgc tccataacat caaacatcga cccacggcgt aacgcgcttg  4920
ctgcttggat gcccgaggca taggctgtac aaaaaaacag tcataacaag ccatgaaaac  4980
cgccactgcg ccgttaccac cgctgcgttc ggtcaaggtt ctggaccagt tgcgtgagcg  5040
catacgctac ttgcattaca gtttacgaac cgaacaggct tatgtcaaga tcggattggc  5100
ggttatgcgg ttgcgatgca ggtggctgct gaaccccccag ccggaactga ccccacaagg  5160
ccctagcgtt tgcaatgcac caggtcatca ttgacccagg cgtgttccac caggccgctg  5220
cctcgcaact cttcgcaggc ttcgccgacc tgctcgcgcc acttcttcac gcgggtggaa  5280
tccgatccgc acatgaggcg gaaggtttcc agcttgagcg ggtacggctc ccggtgcgag  5340
ctgaaatagt cgaacatccg tcgggccgtc ggcgacagct tgcggtactt ctcccatatg  5400
aatttcgtgt agtggtcgcc agcaaacagc acgacgattt cctcgtcgat caggacctgg  5460
caacgggacg ttttcttgcc acggtccagg acgcggaagc ggtgcagcag cgacaccgat  5520
tccaggtgcc caacgcggtc ggacgtgaag cccatcgccg tcgcctgtag gcgcgacagg  5580
cattcctcgg ccttcgtgta ataccggcca ttgatcgacc agcccaggtc ctggcaaagc  5640
tcgtagaacg tgaaggtgat cggctcgccg ataggggtgc gcttcgcgta ctccaacacc  5700
tgctgccaca ccagttcgtc atcgtcggcc cgcagctcga cgccggtgta ggtgatcttc  5760
acgtccttgt tgacgtggaa aatgaccttg ttttgcagcg cctcgcgcgg gatttcttg  5820
ttgcgcgtgg tgaacagggc agagcgggcc gtgtcgtttg gcatcgctcg catcgtgtcc  5880
ggccacggcg caatatcgaa caaggaaagc tgcatttcct tgatctgctg cttcgtgtgt  5940
ttcagcaacg cggcctgctt ggcttcgctg acctgttttg ccaggtcctc gccggcggtt  6000
tttcgcttct tggtcgtcat agttcctcgc gtgtcgatgg tcatcgactt cgccaaacct  6060
gccgcctcct gttctagccg acgcgaacgc tccacggcgg ccgatggcgc gggcagggca  6120
gggggagcca gttgcacgct gtcgcgctcg atcttggccg tagcttgctg gactatcgag  6180
ccgacggact ggaaggtttc gcggggcgca cgcatgacgg tgcggcttgc gatggtttcg  6240
gcatcctcgg cggaaaaccc cgcgtcgatc agttcttgcc tgtatgcctt ccggtcaaac  6300
gtccgattca ttcaccctcc ttgcgggatt gccccggaat taattccccg gatcgatccg  6360
tcgatcttga tcccctgcgc catcagatcc ttggcggcaa gaaagccatc cagtttactt  6420
tgcagggctt cccaacctta ccagagggcg ccccagctgg caattccggt tcgcttgctg  6480
tccataaaac cgcccagtct agctatcgcc atgtaagccc actgcaagct acctgctttc  6540
```

-continued

```
tctttgcgct tgcgttttcc cttgtccaga tagcccagta gctgacattc atccggggtc  6600
agcaccgttt ctgcggactg gctttctacg tggctgccat tttggggtg aggccgttcg  6660
cggccgaggg gcgcagcccc tggggggatg ggaggcccgc gttagcgggc cgggagggtt  6720
cgagaagggg gggcaccccc cttcggcgtg cgcggtcacg cgcacagggc gcagccctgg  6780
ttaaaaacaa ggtttataaa tattggttta aaagcaggtt aaaagacagg ttagcggtgg  6840
ccgaaaaacg ggcggaaacc cttgcaaatg ctggattttc tgcctgtgga cagcccctca  6900
aatgtcaata ggtgcgcccc tcatctgtca gcactctgcc cctcaagtgt caaggatcgc  6960
gcccctcatc tgtcagtagt cgcgcccctc aagtgtcaat accgcagggc acttatcccc  7020
aggcttgtcc acatcatctg tgggaaactc gcgtaaaatc aggcgttttc gccgatttgc  7080
gaggctggcc agctccacgt cgccggccga aatcgagcct gcccctcatc tgtcaacgcc  7140
gcgccgggtg agtcggcccc tcaagtgtca acgtccgccc ctcatctgtc agtgagggcc  7200
aagttttccg cgaggtatcc acaacgccgg cggccctaca tggctctgct gtagtgagtg  7260
ggttgcgctc cggcagcggt cctgatcccc cgcagaaaaa aaggatct              7308
```

```
SEQ ID NO: 25          moltype = DNA  length = 5007
FEATURE                Location/Qualifiers
misc_feature           1..5007
                       note = pLX-B2-PetohmNEON
source                 1..5007
                       mol_type = other DNA
                       organism = synthetic construct
SEQUENCE: 25
ccatcatcag ttcggtggtc ttccgacgaa caataaggcc gcaaatcgcg gccttttta  60
ttgataacaa aaccggctca gttctgcgta gaaaccaaca tgcaagctcc accgggtgca  120
aagcggcagc ggcggcagga tatattcaat tgtaaatggc ttcatgtccg ggaaatctac  180
tggtggcagg atatattgtg gtgtaaacaa tggagaaaaa gattaattaa gtactagtag  240
cctggtcgaa accgtctcaa aatcaccagt ctctctctac aaatctatct ctctctataa  300
taatgtgtga gtagttccca gataagggaa ttagggttct tatagggttt cgctcatgtg  360
ttgagcatat aagaaaccct tagtatgtat ttgtatttgt aaaatacttc tatcaataaa  420
atttctaatt cctaaaacca aaatccagtg acccatgcgg agccgcattg gaggccatgc  480
ggagccgcac gcgttaacaa gagcggctcc gcttgacctc tcgggatagt tccgacctag  540
gattggatgc atgcggaacc gcacgagggc ggggcggaaa ttgacacacc actcctctcc  600
acgcaccgtt caagaggtac gcgtatagag ccgtatagag cagagacgga gcactttctg  660
gtactgtccg cacgggatgt ccgcacggag agccacaaac gagcggggcc ccgtacgtgc  720
tctcctaccc caggatcgca tccccgcata gctgaacatc tatataagaa ggcattcatt  780
cccatttgaa ggatcatcag atactgaacc aatattattt ttacaacaat taccaacaac  840
aacaaacaac aaacaacatt acaattacta tttacaatta caatggtgag caagggagag  900
gaggataaca tggcctctct cccagctaca catgagcttc acatctttgg atccatcaac  960
ggtgtggact ttgacatggt gggtcaggga accggaaatc caaatgatgg atatgaggag  1020
cttaacctta agtccaccaa gggtgacctc cagttctccc catggattct tgtccctcat  1080
atcggatatg gattccatca gtaccttcct taccctgatg gaatgtctcc gtttcaagcc  1140
gcaatggttg atggatccgg ataccaagtc catagaacaa tgcagtttga agatggtgcc  1200
tcccttactg ttaactacag atacacctac gagggaagcc acatcaaagg agaggcccag  1260
gtgaagggaa ctggtttccc tgctgacggt cctgtgatga ccaactctct taccgctgct  1320
gactggtgca ggtctaagaa aacttaccct aacgacaaaa ccatcatcag taccttttaag  1380
tggagttaca ccactggaaa tggcaagaga tacagaagca ctgctagaac cacctacacc  1440
tttgccaagc caatggctgc taactatctt aagaaccagc ctatgtacgt gttccgtaag  1500
actgagctca agcactccaa gaccgagctc aacttcaagg agtggcaaaa ggcctttacc  1560
gatgtgatgg gaatggacga gctatacaaa taagtgaagc tcatatccag atgaaggcag  1620
cagcattgag aaatgttcaa aatcgtttat ttggcttgga tggaaacgtc ggaacacaag  1680
aagaggacac agagagacac accgctggtg atgttaatcg caacatgcac aacctcctcg  1740
gtgtgagggg agtgtagtgg tctcggtatc tatcataaac tctacctggg tgagagtcta  1800
atcatccagt tgtttttaga ttcctgttag catcctttc tccgctttaa tagcagtaca  1860
ttcagtgagg ttttacctcc atatgttcta gtctgttatt gtcgaacaca ggcccttgta  1920
tctgatgtag cgagtgcttc actccattcg ggttatagtt cttgtgcaag agacaaaaaa  1980
aaaaaaaaaa aaaaaaaaaa aaaaaaaaaa aaaaaaaaaa aaaaaaaaaa aaaaaaaaaa  2040
aaatgcatgc ctgcagatcg ttcaaacatt tggcaataaa gtttcttaag attgaatcct  2100
gttgccggtc ttgcgatgat tatcatctaa tttctgttga attacgttaa gcatgtaata  2160
attaacatgt aatgcatgac gttatttatg agatgggttt ttatgattag agtcccgcaa  2220
ttatacattt aatacgcgat agaaaacaaa atatagcgcg caaactagga taaattatcg  2280
cgcgcggtgt catctatgtt actcgatctc gtcaggagac gggacaagga tgcgagctag  2340
cctgcaggaa ttgttgattt tgtgatgact gatggcagga tatatgcggt tgtaattcat  2400
ttttattgtc taaatttctg tatttgtttg tttgttcggt tgtaaatttt tttggaagaa  2460
caagaaaaga aaaaacaccc gttagggtgt ttttagttag tgtggcgcgc cgacttgcga  2520
catgcggtcc tttgcaatca actattagaa aaattcatcc agcatcagat gaaattgcag  2580
tttgttcata tccggattat caatgccata tttctgaaac agacgttttt gcaggctcgg  2640
gctaaattcg cccaggcagt tccacagaat ggccagatcc tgataacgat ccgcaatgcc  2700
cacacggccc acatcaatgc agccaatcag tttgccttca tcgaaaatca ggttatccag  2760
gctaaaatcg ccgtgggtca ccacgctatc cgggctaaac ggcagcagtt tatgcatttc  2820
tttccacacc tgttccaccg gccagccgtt acgttcatca tcaaaatcgc tcgcatccac  2880
caggccgttg ttcatacggc tctgcgcctg ggccagacga aacacacgat cgctgttaaa  2940
cgggcagttg cacaccggaa tgctatgcag acgacgcaga aacacggcca gcgcatccac  3000
aatgttttcg ccgctatccg gatattcttc cagcacctga aacgcggttt tgcccggaat  3060
cgcggtggtc agcagccacg catcatccgg ggtgcgaata aaatgtttaa tggtcggcag  3120
cggcataaat tcggtcagcc agttcagacg caccatttca tcggtcacat cgttcgccac  3180
gctgcctttg ccatgtttca gaaacagttc cggcgcatcc ggtttgccat acagacgata  3240
aatggtcgcg ccgctctgac ccacgttatc acgcgcccat ttatagccat acagatccgc  3300
atccatgttg ctgttcagac gcggacggct acagctcgtt tcacgctgaa tatggctcat  3360
aacacccctt gtattactgt ttatgtaagc agacagtttt attgttcatg atgatatatt  3420
```

-continued

```
tttatcttgt gcaatgtaac atcagagatt ttgagacaca agatcggatt ggcggttatg  3480
cggttctacc ggcgcggcag cgttacccgt gtcggcggct ccaacggctc gccatcgtcc  3540
agaaaacacg gctcatcggg catcggcagg cgctgctgcc cgcgccgttc ccattcctcc  3600
gtttcggtca aggctggcag gtctggttcc atgcccggaa tgccgggctg gctgggcggc  3660
tcctcgccgg ggccggtcgg tagttgctgc tcgcccggat acagggtcgg gatgcggcgc  3720
aggtcgccat gccccaacag cgattcgtcc tggtcgtcgt gatcaaccac cacggcggca  3780
ctgaacaccg acaggcgcaa ctggtcgcgg ggctggcccc acgccacgcg gtcattgacc  3840
acgtaggccg acacggtgcc ggggccgttg agcttcacga cggagatcca gcgctcggcc  3900
accaagtcct tgactgcgta ttggaccgtc cgcaaagaac gtccgatgag cttggaaagt  3960
gtcttctggc tgaccaccac ggcgttctgg tggcccatct gcgccacgag gtgatgcagc  4020
agcattgccg ccgtgggttt cctcgcaata agcccggccc acgcctcatg cgctttgcgt  4080
tccgtttgca cccagtgacc gggcttgttc ttggcttgaa tgccgatttc tctggactgc  4140
gtggccatgc ttatctccat gcggtagggg tgccgcacgg ttgcggcacc atgcgcaatc  4200
agctgcaact tttcggcagc gcgacaacaa ttatgcgttg cgtaaaagtg gcagtcaatt  4260
acagattttc tttaacctac gcaatgagct attgcggggg gtgccgcaat gagctgttgc  4320
gtaccccccct tttttaagtt gttgattttt aagtctttcg catttcgccc tatatctagt  4380
tctttggtgc ccaaagaagg gcacccctgc ggggttcccc cacgccttcg gcgcggctcc  4440
ccctccggca aaaagtggcc cctccggggc ttgttgatcg actgcgcggc cttcggcctt  4500
gcccaaggtg gcgctgcccc cttggaaccc ccgcactcgc cgccgtgagg ctcggggggc  4560
aggcgggcgg gcttcgccct tcgactgccc ccactcgcat aggcttgggt cgttccaggc  4620
gcgtcaaggc caagccgctg cgcggtcgct gcgcgagcct tgacccgcct tccacttggt  4680
gtccaaccgg caagcgaagc gcgcaggccg caggccggag gcttttcccc agagaaaatt  4740
aaaaaaattg atggggcaag gccgcaggcc gcgcagttgg agccggtggg tatgtggtcg  4800
aaggctgggt agccggtggg caatccctgt ggtcaagctc gtgggcaggc gcagcctgtc  4860
catcagcttg tccagcaggg ttgtccacgg gccgagcgaa gcgagccagc cggtggccgc  4920
tcgcggccat cgtccacata tccacgggct ggcaagggag cgcagcgacc gcgcagggcg  4980
aagcccggag agcaagcccg taggggg                                      5007
```

```
SEQ ID NO: 26          moltype = DNA  length = 9237
FEATURE                Location/Qualifiers
misc_feature           1..9237
                       note = pSN.5-PPAP85:RFP plasmido
source                 1..9237
                       mol_type = other DNA
                       organism = synthetic construct
SEQUENCE: 26
tggcaggata tattgtggtg taaacaaatt gacgcttaga caacttaata acacattgcg  60
gacgttttta atgtactgaa ttaacgccga attgaattcc tcgagtacgt aggatccatt  120
taaattcctt caagagagca aaccattgtt tacacgtcaa tttgaattgc gtcaaatatt  180
cgactggaat cctacaacat atttcttcta ttatatcaat aggaagcaac gaacgttcac  240
atgaagccat gcaaaaacaa attgagaaaa aaaatcagaa aatttatgac aagtggtctt  300
gcttcttata ctacgtcgtg aatggatggt aataaacaat taaatgttac ctctagtttt  360
ttttttttga gagaatggtt tttatccgta tatggcttat tacaagtttc ctcctttttc  420
gagtttggtt tgaggtctat attgaagatg agatactaaa aattgaggta aattctttag  480
tgtgaaggaa aattagtaaa tacgatacgt ttggaattgt ttactactaa aaaaaaaatt  540
gttttagacc aagccagtcc gacaaaaagg cgtgtgaatc ataagaagta tcacatgatg  600
ctagacataa aagattttc aaacatgaca aaacaaattg tgagtgtctt agtcatgcca  660
tttgaagtag aacgaaactt agtgatgaga cacgtaacat cagtgagaat caagatctaa  720
cttcggactt atcgtacgta ccacgtccac ctaagtgtta tccatatcta ctacatgtct  780
atcttcattc aattttttttt ttgcattaac ttgtaaacat agtgcataat aattagaatc  840
aagatttgaa tccaattcgc ttactaaatc ctaaatgtta aaagcataca tgtttttcaa  900
atcctacttt taggtgctaa gtttttttc taaggtagtt agagattgtt agattttata  960
tcattgaact gatcatcagt ctctatacta acttctagat ctcattgaat gtttactcaa  1020
ttttttttaa tttttgttt ggataatcgt ctgctcgtgg ttttgatgcg tacgaacact  1080
cgtcaccatg catgtcaagc tctccttcct atataaacta aaaccaccca ttattgtcct  1140
caaaaacaaa cacatcaaca aaacaacaag aaaaaatggt ttcaaaggga gaagagctga  1200
ttaaggagaa catgcacatg aagctgtaca tggagggcac cgtgaacaac caccacttca  1260
agtgcacatc cgagggcgaa ggcaagccct acgagggcac ccagaccatg agaatcaagg  1320
tggtcgaggg cggccctctc cccttcgcct tcgacatcct ggctaccagc ttcatgtacg  1380
gcagcagaac cttcatcaac cacacccagg gcatccccga cttctttaag cagtccttcc  1440
ctgagggctt cacatgggag agagtcacca catacgaaga cgggggcgtg ctgaccgcta  1500
cccaggacac cagcctccag gacggctgcc tcatctacaa cgtcaagatc agaggggtga  1560
acttcccatc caacggccct gtgatgcaga agaaaacact cggctgggag gccaacaccg  1620
agatgctgta ccccgctgac ggcggcctgg aaggcagaac agacatggcc ctgaagctcg  1680
tgggcggggg ccacctgatc tgcaacttca agaccacata cagatccaag aaacccgcta  1740
agaacctcaa gatgcccggc gtctactatg tggaccacag actggaaaga atcaaggagg  1800
ccgacaaaga gacctacgtc gagcagcacg aggtggctgt ggccagatac tgcgacctcc  1860
ctagcaaact ggggcacaaa cttaactaat cgatcacgtg aagctcatat ccagatgaag  1920
gcagcagcat tgagaaatgt tcaaaatcgt ttatttggct tggatggaaa cgtcggaaca  1980
caagaagagg acacagagag acacaccgct ggtgatgtta atcgcaacat gcacaacctc  2040
ctcggtgtga ggggagtgta gtggtctcgg tatctatcat aaactctacc tgggtgagag  2100
tctaatcatc cagttgtttt tagattcctg ttagcatcct tttctccgct ttaatagcag  2160
tacattcagt gaggttttac ctccatatgt tctagtctgt tattgtcgaa cacaggccct  2220
tgtatctgat gtagcgagtg cttcactcca ttcgggttat agttcttgtg caagagacaa  2280
aaaaaaaaaa aaaaaaaaaa aaaaaaaaaa aaaaaaaaaa aaaaaaaaaa aaaaaaaaaa  2340
aaaaaaatgc atgcctgcag atcgttcaaa catttggcaa taaagtttct taagattgaa  2400
tcctgttgcc ggtcttgcga tgattatcat ctaatttctg ttgaattacg ttaagcatgt  2460
aataattaac atgtaatgca tgacgttatt tatgagatgg gtttttatga ttagagtccc  2520
gcaattatac atttaatacg cgatagaaaa caaaatatag cgcgcaaact aggataaatt  2580
```

-continued

```
atcgcgcgcg gtgtcatcta tgttactcga tctctagctt gagcttggat cagattgtcg  2640
tttcctagct tgagcttgga tcagattgtc gtttcccgcc ttcagtttaa actatcagtg  2700
tttgacagga tatattggcg ggtaaaccta agagaaaaga gcgtttatta gaataacgga  2760
tatttaaaag ggcgtgaaaa ggtttatccg ttcgtccatt tgtatgtgca tgccaaccac  2820
agggttcccc tcgggatcaa agtactttga tccaacccct ccgctgctat agtgcagtcg  2880
gcttctgacg ttcagtgcag ccgtcttctg aaaacgacat gtcgcacaag tcctaagtta  2940
cgcgacaggc tgccgccctg cccttttcct ggcgttttct tgtcgcgtgt tttagtcgca  3000
taaagtagaa tacttgcgac tagaaccgga gacattacgc catgaacaag agcgccgccg  3060
ctggcctgct gggctatgcc cgcgtcagca ccgacgacca ggacttgacc aaccaacggg  3120
ccgaactgca cgcggccggc tgcaccaagc tgttttccga gaagatcacc ggcaccaggc  3180
gcgaccgccc ggagctggcc aggatgcttg accacctacg ccctggcgac gttgtgacag  3240
tgaccaggct agaccgcctg gcccgcagca cccgcgacct actggacatt gccgagcgca  3300
tccaggaggc cggcgcgggc ctgcgtagcc tggcagagcc gtgggccgac accaccacgc  3360
cggccggccg catggtgttg accgtgttcg ccggcattgc cgagttcgag cgttccctaa  3420
tcatcgaccg cacccggagc gggcgcgagg ccgccaaggc ccgaggcgtg aagtttggcc  3480
cccgccctac cctcaccccg gcacagatcg cgcacgcccg cgagctgatc gaccaggaag  3540
gccgcaccgt gaaagaggcg gctgcactgc ttggcgtgca tcgctcgacc ctgtaccgcg  3600
cacttgagcg cagcgaggaa gtgacgccca ccgaggccag gcggcgcggt gccttccgtg  3660
aggacgcatt gaccgaggcc gacgccctgg cggccgccga gaatgaacgc caagaggaac  3720
aagcatgaaa ccgcaccagg acggccagga cgaaccgttt ttcattaccg aagagatcga  3780
ggcggagatg atcgcggccg ggtacgtgtt cgagccgccc gcgcacgtct caaccgtgcg  3840
gctgcatgaa atcctggccg gtttgtctga tgccaagctg gcggcctggc cggccagctt  3900
ggccgctgaa gaaaccgagc gccgccgtct aaaaaggtga tgtgtatttg agtaaaacag  3960
cttgcgtcat gcggtcgctg cgtatatgat gcgatgagta aataaacaaa tacgcaaggg  4020
gaacgcatga aggttatcgc tgtacttaac cagaaaggcg ggtcaggcaa gacgaccatc  4080
gcaacccatc tagcccgcgc cctgcaactc gccggggccg atgttctgtt agtcgattcc  4140
gatccccagg gcagtgcccg cgattgggcg gccgtgcggg aagatcaacc gctaaccgtt  4200
gtcggcatcg accgcccgac gattgaccgc gacgtgaagg ccatcggccg gcgcgacttc  4260
gtagtgatcg acggagcgcc ccaggcggcg gacttggctg tgtccgcgat caaggcagcc  4320
gacttcgtgc tgattccggt gcagccaagc ccttacgaca tatgggccac cgccgacctg  4380
gtggagctgg ttaagcagcg cattgaggtc acggatggaa ggctacaagc ggcctttgtc  4440
gtgtcgcggg cgatcaaagg cacgcgcatc ggcggtgagg ttgccgaggc gctggccggg  4500
tacgagctgc ccattcttga gtcccgtatc acgcagcgcg tgagctaccc aggcactgcc  4560
gccgccggca caaccgttct tgaatcagaa cccgagggcg acgctgcccg cgaggtccag  4620
gcgctggccg ctgaaattaa atcaaaactc atttgagtta atgaggtaaa gagaaaatga  4680
gcaaaagcac aaacacgcta agtgccggcc gtccgagcgc acgcagcagc aaggctgcaa  4740
cgttggccag cctggcagac acgccagcca tgaagcgggt caactttcag ttgccggcgg  4800
aggatcacac caagctgaag atgtacgcgg tacgccaagg caagaccatt accgagctgc  4860
tatctgaata catcgcgcag ctaccagagt aaatgagcaa atgaataaat gagtagatga  4920
attttagcgg ctaaaggagg cggcatggaa aatcaagaac aaccaggcac cgacgccgtg  4980
gaatgcccca tgtgtggagg aacgggcggt tggccaggcg taagcggctg ggttgtctgc  5040
cggccctgca atggcactgg aacccccaag cccgaggaat cggcgtgacg gtcgcaaacc  5100
atccggcccg gtacaaatcg gcgcggcgct gggtgatgac ctggtggaga agttgaaggc  5160
cgcgcaggcc gcccagcggc aacgcatcga ggcagaagca cgccccggtg aatcgtggca  5220
agcggccgct gatcgaatcc gcaaagaatc ccggcaaccg ccggcagccg gtgcgccgtc  5280
gattaggaag ccgcccaagg gcgacgagca accagatttt ttcgttccga tgctctatga  5340
cgtgggcacc cgcgatagtc gcagcatcat ggacgtggcc gttttccgtc tgtcgaagcg  5400
tgaccgacga gctggcgagg tgatccgcta cgagcttcca gacgggcacg tagaggtttc  5460
cgcagggccg gccggcatgg ccagtgtgtg ggattacgac ctggtactga tggcggtttc  5520
ccatctaacc gaatccatga accgataccg ggaagggaag ggagacaagc ccggccgcgt  5580
gttccgtcca cacgttgcgg acgtactcaa gttctgccgg cgagccgatg gcggaaagca  5640
gaaagacgac ctggtagaaa cctgcattcg gttaaacacc acgcacgttg ccatgcagcg  5700
tacgaagaag gccaagaacg gccgcctggt gacggtatcc gagggtgaag ccttgattag  5760
ccgctacaag atcgtaaaga gcgaaaccgg gcggccggag tacatcgaga tcgagctagc  5820
tgattggatg taccgcgaga tcacagaagg caagaacccg gacgtgctga cggttcaccc  5880
cgattacttt ttgatcgatc ccggcatcgg ccgttttctc taccgcctgg cacgccgcgc  5940
cgcaggcaag gcagaagcca gatggttgtt caagacgatc tacgaacgca gtggcagcgc  6000
cggagagttc aagaagttct gtttcaccgt gcgcaagctg atcgggtcaa atgacctgcc  6060
ggagtacgat ttgaaggagg aggcggggca ggctggcccg atcctagtca tgcgctaccg  6120
caacctgatc gagggcgaag catccgccgg ttcctaatgt acggagcaga tgctagggca  6180
aattgcccta gcaggggaaa aaggtcgaaa aggtctcttt cctgtggata gcacgtacat  6240
tgggaaccca aagccgtaca ttgggaaccg gaacccgtac attgggaacc caaagccgta  6300
cattgggaac cggtcacaca tgtaagtgac tgatataaaa gagaaaaaag gcgatttttc  6360
cgcctaaaac tctttaaaac ttattaaaac tcttaaaacc cgcctggcct gtgcataact  6420
gtctggccag cgcacagccg aagagctgca aaaagcgcct acccttcggt cgctgcgctc  6480
cctacgcccc gccgcttcgc gtcggcctat cgcggccgct ggccgctcaa aaatggctgg  6540
cctacggcca ggcaatctac cagggcgcgg acaagccgcg ccgtcgccac tcgaccgccg  6600
gcgcccacat caaggcaccc tgcctcgcgc gtttcggtga tgacggtgaa aacctctgac  6660
acatgcagct cccggagacg gtcacagctt gtctgtaagc ggatgccggg agcagacaag  6720
cccgtcaggg cgcgtcagcg ggtgttggcg ggtgtcgggg cgcagccatg acccagtcac  6780
gtagcgatag cggagtgtat actggcttaa ctatgcggca tcagagcaga ttgtactgag  6840
agtgcaccat atgcggtgtg aaataccgca cagatgcgta aggagaaaat accgcatcag  6900
gcgctcttcc gcttcctcgc tcactgactc gctgcgctcg gtcgttcggc tgcggcgagc  6960
ggtatcagct cactcaaagg cggtaatacg gttatccaca gaatcagggg ataacgcagg  7020
aaagaacatg tgagcaaaag gccagcaaaa ggccaggaac cgtaaaaagg ccgcgttgct  7080
ggcgtttttc cataggctcc gcccccctga cgagcatcac aaaaatcgac gctcaagtca  7140
gaggtggcga aacccgacag gactataaag ataccaggcg tttccccctg gaagctccct  7200
cgtgcgctct cctgttccga ccctgccgct taccggatac ctgtccgcct ttctcccttc  7260
gggaagcgtg gcgctttctc atagctcacg ctgtaggtat ctcagttcgg tgtaggtcgt  7320
```

-continued

```
tcgctccaag ctgggctgtg tgcacgaacc ccccgttcag cccgaccgct gcgccttatc  7380
cggtaactat cgtcttgagt ccaacccggt aagacacgac ttatcgccac tggcagcagc  7440
cactggtaac aggattagca gagcgaggta tgtaggcggt gctacagagt tcttgaagtg  7500
gtggcctaac tacggctaca ctagaaggac agtatttggt atctgcgctc tgctgaagcc  7560
agttaccttc ggaaaaagag ttggtagctc ttgatccggc aaacaaacca ccgctggtag  7620
cggtggtttt tttgtttgca agcagcagat tacgcgcaga aaaaaaggat ctcaagaaga  7680
tcctttgatc ttttctacgg ggtctgacgc tcagtggaac gaaaactcac gttaagggat  7740
tttggtcatg catgatatat ctcccaattt gtgtagggct tattatgcac gcttaaaaat  7800
aataaaagca gacttgacct gatagtttgg ctgtgagcaa ttatgtgctt agtgcatcta  7860
atcgcttgag ttaacgccgg cgaagcggcg tcggcttgaa cgaatttcta gctagacatt  7920
atttgccgac taccttggtg atctcgcctt tcacgtagtg gacaaattct tccaactgat  7980
ctgcgcgcga ggccaagcga tcttcttctt gtccaagata agcctgtcta gcttcaagta  8040
tgacgggctg atactgggcc ggcaggcgct ccattgccca gtcggcagcg acatccttcg  8100
gcgcgatttt gccggttact gcgctgtacc aaatgcggga caacgtaagc actacatttc  8160
gctcatcgcc agcccagtcg ggcggcgagt tccatagcgt taaggtttca tttagcgcct  8220
caaatagatc ctgttcagga accggatcaa agagttcctc cgccgctgga cctaccaagg  8280
caacgctatg ttctcttgct tttgtcagca agatagccag atcaatgtcg atcgtggctg  8340
gctcgaagat acctgcaaga atgtcattgc gctgccattc tccaaattgc agttcgcgct  8400
tagctggata acgccacgga atgatgtcgt cgtgcacaac aatggtgact tctacagcgc  8460
ggagaatctc gctctctcca ggggaagccg aagtttccaa aaggtcgttg atcaaagctc  8520
gccgcgttgt ttcatcaagc cttacggtca ccgtaaccag caaatcaata tcactgtgtg  8580
gcttcaggcc gccatccact gcggagccgt acaaatgtac ggccagcaac gtcggttcga  8640
gatggcgctc gatgacgcca actacctctg atagttgagt cgatacttcg gcgatcaccg  8700
cttcccccat gatgtttaac tttgttttag ggcgactgcc ctgctgcgta acatcgttgc  8760
tgctccataa catcaaacat cgacccacgg cgtaacgcgc ttgctgcttg gatgcccgag  8820
gcatagactg taccccaaaa aaacatgtca taacaagaag ccatgaaaac cgccactgcg  8880
ccgttaccac cgctgcgttc ggtcaaggtt ctggaccagt tgcgtgacgg cagttacgct  8940
acttgcatta cagcttacga accgaacgag gcttatgtcc actgggttcg tgcccgaatt  9000
gatcacaggc agcaacgctc tgtcatcgtt acaatcaaca tgctaccctc cgcgagatca  9060
tccgtgtttc aaacccggca gcttagttgc cgttcttccg aatagcatcg gtaacatgag  9120
caaagtctgc cgccttacaa cggctctccc gctgacgccg tcccggactg atgggctgcc  9180
tgtatcgagt ggtgattttg tgccgagctg ccggtcgggg agctgttggc tggctgg     9237

SEQ ID NO: 27          moltype = DNA  length = 10048
FEATURE                Location/Qualifiers
misc_feature           1..10048
                       note = GB1686 plasmid
source                 1..10048
                       mol_type = other DNA
                       organism = synthetic construct
SEQUENCE: 27
ggagagcgat cagcttgcat gccggtcgat ctagtaacat agatgacacc gcgcgcgata  60
atttatccta gtttgcgcgc tatattttgt tttctatcgc gtattaaatg tataattgcg  120
ggactctaat cataaaaacc catctcataa ataacgtcat gcattacatg ttaattatta  180
catgcttaac gtaattcaac agaaattata tgataatcat ggcaagaccg gcaacaggat  240
tcaatcttaa gaaactttat tgccaaatgt ttgaacgatc tgcttgactc tagctagagt  300
ccgaacccca gagtcccgct cagaagaact cgtcaagaag gcgatagaag gctatgcgct  360
gcgaatcggg agcggcgata ccgtaaagca cgaggaagcg gtcagcccat tcgccgccaa  420
gctcttcagc aatatcacgg gtagccaacg ctatgtcctg atagcggtcc gccacaccca  480
gccggccaca gtcgatgaat ccagaaaagc ggccattttc caccatgata ttcggcaagc  540
aggcgtcgcc gtgggtcacg acgagatcct cgccgtcggg catccgcgcc ttgagcctgg  600
cgaacagttc ggctggcgcg agcccctgat gctcttcgtc cagatcatcc tgatcgacaa  660
gaccggcttc catccgagta cgtgctcgct cgatgcggtg tttcgcttgg tggtcgaatg  720
ggcaggtagc cggatcaagc gtatgcagcc gccgcattgc atcagccatg atggatactt  780
tctcggcagg agcaaggtga gatgacagga gatcctgccc cggcacttcg cccaatagca  840
gccagtccct tcccgcttca gtgacaacgt cgagcacagc tgcgcaagga acgcccgtcg  900
tggccagcca cgatagccgc gctgcctcgt cttggagttc attcagggca ccggacaggt  960
cggtcttgac aaaaagaacc gggcgcccct gcgctgacag ccggaacacg gcggcatcag  1020
agcagccgat tgtctgttgt gcccagtcat agccgaatag cctctccacc caagcggccg  1080
gagaacctgc gtgcaatcca tcttgttcaa tcatgcctcg atcgagttga gagtgaatat  1140
gagactctaa ttggataccg aggggaattt atggaacgtc agtggagcat ttttgacaag  1200
aaatatttgc tagctgatag tgaccttagg cgacttttga acgcgcaata atggtttctg  1260
acgtatgtgc ttagctcatt aaactccaga aacccgcggc tgagtggctc cttcaacgtt  1320
gcggttctgt cagttccaaa cgtaaaacgg cttgtcccgc gtcatcggcg ggggtcataa  1380
cgtgactccc ttaattctca tgtatctcct gacagcgaaa tgattgatga agaacaatgg  1440
tggatgaaga acaaagaagg agggagcttt tgttcaagat gaacaaagaa caatagtgga  1500
tgaagaacaa agtgaaaaaa ataaaaaaaa atgtatggtt aaataaagag taaagttacc  1560
attgagactc cgtcaggaga ctagagccaa gctgatctcc tttgccccgg agatcaccat  1620
ggacgacttt ctctatctct acgatctagg aagaaagttc gacggagaag gtgacgatac  1680
catgttcacc accgataatg agaagattag cctcttcaat ttcagaaaga atgctgaccc  1740
acagatggtt agagaggcct acgcggcagg tctgatcaag acgatctacc cgagtaataa  1800
tctccaggag atcaaatacc ttcccaagaa ggttaaagat gcagtcaaaa gattcaggac  1860
taactgcatc aagaacacag agaaagatat atttctcaag atcagaagta ctattccagt  1920
atggacgatt caaggcttgc ttcataaacc aaggcaagta atagagattg gagtctctaa  1980
gaaagtagtt cctactgaat caaaggccat ggagtcaaaa attcagatcg aggatctaac  2040
agaactcgcc gtgaagactg gcgaacagtt catacagagt cttttacgac tcaatgacaa  2100
gaagaaaatc ttcgtcaaca tggtggagca cgacactctc gtctactcca agaatatcaa  2160
agatacagtc tcagaagacc aaagggctat tgagactttt caacaaaggg taatatcggg  2220
aaacctcctc ggattccatt gcccagctat ctgtcacttc atcaaaagga cagtagaaaa  2280
```

-continued

```
ggaaggtggc acctacaaat gccatcattg cgataaagga aaggctatcg ttcaagatgc  2340
ctctgccgac agtggtccca aagatggacc cccacccacg aggagcatcg tggaaaaaga  2400
agacgttcca accacgtctt caaagcaagt ggattgatgt gatatctcca ctgacgtaag  2460
ggatgacgca caatcccact atccttcgca agacccttcc tctatataag gaagttcatt  2520
tcatttggag aggactccgg tatttttaca acaataccac aacaaaacaa acaacaaaca  2580
acattacaat ttactattct agtcgaaatg gcctcctccg agaacgtcat caccgagttc  2640
atgcgcttca aggtgcgcat ggagggcacc gtgaacggcc acgagttcga gatcgagggc  2700
gagggcgagg gccgccccta cgagggccac aacaccgtga agctgaaggt gaccaagggc  2760
ggccccctgc ccttcgcctg ggacatcctg tccccccagt tccagtacgg ctccaaggtg  2820
tacgtgaagc accccgccga catccccgac tacaagaagc tgtccttccc cgagggcttc  2880
aagtgggagc gcgtgatgaa cttcgaggac ggcggcgtgg cgaccgtgac ccaggactcc  2940
tccctgcagg acggctgctt catctacaag gtgaagttca tcggcgtgaa cttcccctcc  3000
gacggccccg tgatgcagaa gaagacgatg ggctgggagg cctccaccga gcgcctgtac  3060
ccccgcgacg gcgtgctgaa gggcgagaca cacaaggccc tgaagctgaa ggacggcggc  3120
cactacctgg tggagttcaa gtccatctac atggccaaga agcccgtgca gctgcccggc  3180
tactactacg tggacgccaa gctggacatc acctcccaca acgaggacta caccatcgtg  3240
gagcagtacg agcgcaccga gggccgccac cacctgttcc tgtaggcttc ggccatgcta  3300
gagtccgcaa aaatcaccag tctctctcta caaatctatc tctctctatt tttctccaga  3360
ataatgtgtg agtagttccc agataaggga attagggttc ttatagggtt tcgctcatgt  3420
gttgagcata taagaaaccc ttagtatgta tttgtatttg taaaatactt ctatcaataa  3480
aatttctaat tcctaaaacc aaaatccagt gacctcgctg tcaggagtct caatggtaac  3540
tttactcttt atttaaccat acattttttt ttattttttt cactttgttc ttcatccact  3600
attgttcttt gttcatcttg aacaaaagct ccctccttct ttgttcttca tccaccattg  3660
ttcttcatca atcatttcgc tgtcatgaga cgaattctga caggatatat tggcgggtaa  3720
acctaagaga aaagagcgtt tattagaata atcggatatt taaaagggcg tgaaaaggtt  3780
tatccgttcg tccatttgta tgtgcatgcc aaccacaggg ttcccctcgg gatcaaagta  3840
ctttgatcca acccctccgc tgctatagtg cagtcggctt ctgacgttca gtgcagccgt  3900
catctgaaaa cgacatgtcg cacaagtcct aagttacgcg acaggctgcc gccctgccct  3960
tttcctggcg ttttcttgtc gcgtgtttta gtcgcataaa gtagaatact tgcgactaga  4020
accggagaca ttacgccatg aacaagagcg ccgccgctgg cctgctgggc tatgcccgcg  4080
tcagcaccga cgaccaggac ttgaccaacc aacgggccga actgcacgcg gccggctgca  4140
ccaagctgtt ttccgagaag atcaccggca ccaggcgcga ccgcccggag ctggccagga  4200
tgcttgacca cctacgccct ggcgacgttg tgacagtgac caggctagac cgcctggccc  4260
gcagcacccg cgacctactg gacattgccg agcgcatcca ggaggccggc gcgggcctgc  4320
gtagcctggc agagccgtgg gccgacacca ccacgccggc cggccgcatg gtgttgaccg  4380
tgttcgccgg cattgccgag ttcgagcgtt ccctaatcat cgaccgcacc cggagcgggc  4440
gcgaggccgc caaggcccga ggcgtgaagt ttggcccccg ccctaccctc accccggcac  4500
agatcgcgca cgcccgcgag ctgatcgacc aggaaggccg caccgtgaaa gaggcggctg  4560
cactgcttgg cgtgcatcgc tcgaccctgt accgcgcact tgagcgcagc gaggaagtga  4620
cgcccaccga ggccaggcgg cgcggtgcct tccgtgagga cgcattgacc gaggccgacg  4680
ccctggcggc cgccgagaat gaacgccaag aggaacaagc atgaaaccgc accaggacgg  4740
ccaggacgaa ccgtttttca ttaccgaaga gatcgaggcg gagatgatcg cggccgggta  4800
cgtgttcgag ccgcccgcgc acctctcaac cgtgcggctg catgaaatcc tggccggttt  4860
gtctgatgcc aagctggcgg cctggccggc cagcttggcc gctgaagaaa ccgagcgccg  4920
ccgtctaaaa aggtgatgtg tatttgagta aaacagcttg cgtcatgcgg tcgctgcgta  4980
tatgatccga tgagtaaata aacaaatacg caaggggaac gcatgaaggt tatcgctgta  5040
cttaaccaga aaggcgggtc aggcaagacg accatcggaa cccatctagc ccgcgccctg  5100
caactcgccg gggccgatgt tctgttagtc gattccgatc cccagggcag tgcccgcgat  5160
tgggcggccg tgcgggaaga tcaaccgcta accgttgtcg gcatcgaccg cccgacgatt  5220
gaccgcgacg tgaaggccat cggccggcgc gacttcgtag tgatcgacgg agcgccccag  5280
gcggcggact tggctgtgtc cgcgatcaag gcagccgact tcgtgctgat tccggtgcag  5340
ccaagccctt acgacatatg ggccaccgcc gacctggtgg agctggttaa gcagcgcatt  5400
gaggtcacgg atggaaggct acaagcggcc tttgtcgtgt cgcgggcgat caaaggcacg  5460
cgcatcggcg gtgaggttgc cgaggcgctg gccgggtacg agctgcccat tcttgagtcc  5520
cgtatcacgc agcgcgtgag ctacccaggc actgccgccg ccggcacaac cgttcttgaa  5580
tcagaacccg agggcgacgc tgcccgcgag gtccaggcgc tggccgctga aattaaatca  5640
aaactcattt gagttaatga ggtaaagaga aaatgagcaa aagcacaaac acgctaagtg  5700
ccggccgtcc gagcgcacgc agcagcaagg ctgcaacgtt ggccagcctg gcagacacgc  5760
cagccatgaa gcgggtcaac tttcagttgc cggcggagga tcacaccaag ctgaagatgt  5820
acgcggtacg ccaaggcaag accattaccg agctgctatc tgaatagatc gcgcagctac  5880
cagagtaaat gagcaaatga ataaatgagt agatgaattt tagcggctaa aggaggcggc  5940
atggaaaatc aagaacaacc aggcaccgac gccgtggaat gccccatgtg tggaggaacg  6000
ggcggttggc caggcgtaag cggctgggtt gtctgccggc cctgcaatgg cactggaacc  6060
cccaagcccg aggaatcggc gtgacggtcg caaaccatcc ggcccggtac aaatcggcgc  6120
ggcgctgggt gatgacctgg tggagaagtt gaaggccgcg caggccgccc agcggcaacg  6180
catcgaggca gaagcacgcc ccggtgaatc gtggcaagcg gccgctgatc gaatccgcaa  6240
agaatcccgg caaccgccgg cagccggtgc gccgtcgatt aggaagccgc ccaagggcga  6300
cgagcaacca gattttttcg ttccgatgct ctatgacgtg ggcacccgcg atagtcgcag  6360
catcatggac gtggccgttt tccgtctgtc gaagcgtgac cgacgagctg gcgaggtgat  6420
ccgctacgag cttccagacg ggcacgtaga ggtttccgca gggccggccg gcatggccag  6480
tgtgtgggat tacgacctgg tactgatggc ggtttcccat ctaaccgaat ccatgaaccg  6540
ataccgggaa gggaagggag acaagcccgg ccgcgtgttc cgtccacacg ttgcggacgt  6600
actcaagttc tgccggcgag ccgatggcgg aaagcagaaa gacgacctgg tagaaacctg  6660
cattcggtta aacaccacgc acgttgccat gcagcgtacg aagaaggcca agaacggccg  6720
cctggtgacg gtatccgagg gtgaagcctt gattagccgc tacaagatcg taaagagcga  6780
aaccgggcgg ccggagtaca tcgagatcga gctagctgat tggatgtacc gcgagatcac  6840
agaaggcaag aacccggacg tgctgacggt tcaccccgat tactttttga tcgatcccgg  6900
catcggccgt tttctctacc gcctggcacg ccgcgccgca ggcaaggcag aagccagatg  6960
gttgttcaag acgatctacg aacgcagtgg cagcgccgga gagttcaaga agttctgttt  7020
```

```
caccgtgcgc aagctgatcg ggtcaaatga cctgccggag tacgatttga aggaggaggc  7080
ggggcaggct ggcccgatcc tagtcatgcg ctaccgcaac ctgatcgagg gcgaagcatc  7140
cgccggttcc taatgtacgg agcagatgct agggcaaatt gccctagcag gggaaaaagg  7200
tcgaaaagga ctctttcctg tggatagcac gtacattggg aacccaaagc cgtacattgg  7260
gaaccggaac ccgtacattg ggaacccaaa gccgtacatt gggaaccggt cacacatgta  7320
agtgactgat ataaaagaga aaaaaggcga tttttccgcc taaaactctt taaaacttat  7380
taaaactctt aaaacccgcc tggcctgtgc ataactgtct ggccagcgca cagccgaaga  7440
gctgcaaaaa gcgcctaccc ttcggtcgct gcgctcccta cgccccgccg cttcgcgtcg  7500
gcctatcgcg gccgctggcc gctcaaaaat ggctggccta cggccaggca atctaccagg  7560
gcgcggacaa gccgcgccgt cgccactcga ccgccggcgc ccacatcaag gcaccctgcc  7620
tcgcgcgttt cggtgatgac ggtgaaaacc tctgacacat gcagctcccg gtgacggtca  7680
cagcttgtct gtaagcggat gccgggagca gacaagcccg tcagggcgcg tcagcgggtg  7740
ttggcgggtg tcggggcgca gccatgaccc agtcacgtag cgatagcgga gtgtatactg  7800
gcttaactat gcggcatcag agcagattgt actgagagtg caccatatgc ggtgtgaaat  7860
accgcacaga tgcgtaagga gaaaataccg catcaggcgc tcttccgctt cctcgctcac  7920
tgactcgctg cgctcggtcg ttcggctgcg gcgagcggta tcagctcact caaaggcggt  7980
aatacggtta tccacagaat caggggataa cgcaggaaag aacatgtgag caaaaggcca  8040
gcaaaaggcc aggaaccgta aaaaggccgc gttgctggcg tttttccata ggctccgccc  8100
ccctgacgag catcacaaaa atcgacgctc aagtcagagg tggcgaaacc cgacaggact  8160
ataaagatac caggcgtttc cccctggaag ctccctcgtg cgctctcctg ttccgaccct  8220
gccgcttacc ggatacctgt ccgcctttct cccttcggga agcgtggcgc tttctcatag  8280
ctcacgctgt aggtatctca gttcggtgta ggtcgttcgc tccaagctgg gctgtgtgca  8340
cgaacccccc gttcagcccg accgctgcgc cttatccggt aactatcgtc ttgagtccaa  8400
cccggtaaga cacgacttat cgccactggc agcagccact ggtaacagga ttagcagagc  8460
gaggtatgta ggcggtgcta cagagttctt gaagtggtgg cctaactacg gctacactag  8520
aaggacagta tttggtatct gcgctctgct gaagccagtt accttcggaa aaagagttgg  8580
tagctcttga tccggcaaac aaaccaccgc tggtagcggt ggtttttttg tttgcaagca  8640
gcagattacg cgcagaaaaa aaggatctca agaagatcct ttgatctttt ctacggggtc  8700
tgacgctcag tggaacgaaa actcacgtta agggattttg gtcatgcatt ctaggtgatt  8760
agaaaaactc atcgagcatc aaatgaaact gcaatttatt catatcagga ttatcaatac  8820
catatttttg aaaaagccgt ttctgtaatg aaggagaaaa ctcaccgagg cagttccata  8880
ggatggcaag atcctggtat cggtctgcga ttccgactcg tccaacatca atacaaccta  8940
ttaatttccc ctcgtcaaaa ataaggttat caagtgagaa atcaccatga gtgacgactg  9000
aatccggtga gaatggcaaa agtttatgca tttctttcca gacttgttca acaggccagc  9060
cattacgctc gtcatcaaaa tcactcgcat caaccaaacc gttattcatt cgtgattgcg  9120
cctgagcgag tcgaaatacg cgatcgctgt taaaaggaca attacaaaca ggaatcgaat  9180
gcaaccggcg caggaacact gccagcgcat caacaatatt ttcacctgaa tcaggatatt  9240
cttctaatac ctggaatgct gttttccctg ggatcgcagt ggtgagtaac catgcatcat  9300
caggagtacg gataaaatgc ttgatggtcg gaagaggcat aaattccgtc agccagttta  9360
gtctgaccat ctcatctgta acatcattgg caacgctacc tttgccatgt ttcagaaaca  9420
actctggcgc atcgggcttc ccatacaatc ggtagattgt cgcacctgat tgcccgacat  9480
tatcgcgagc ccatttatac ccatataaat cagcatccat gttggaattt aatcgcggcc  9540
ttgagcaaga cgtttcccgt tgaatatggc tcataacaga acttattatt tccttcctct  9600
tttctacagt atttaaagat accccaagaa gctaattata acaagacgaa ctccaattca  9660
ctgttccttg cattctaaaa ccttaaatac cagaaaacag ctttttcaaa gttgttttca  9720
aagttggcgt ataacatagt atcgacggag ccgattttga aaccgcggtg atcacaggca  9780
gcaacgctct gtcatcgtta caatcaacat gctaccctcc gcgagatcat ccgtgtttca  9840
aacccggcag cttagttgcc gttcttccga atagcatcgg taacatgagc aaagtctgcc  9900
gccttacaac ggctctcccg ctgacgccgt cccggactga tgggctgcct gtatcgagtg  9960
gtgattttgt gccgagctgc cggtcgggga gctgttggct ggctggtggc aggatatatt  10020
gtggtgtaaa cataacgaat tcgtctca                                    10048
```

```
SEQ ID NO: 28          moltype = DNA  length = 14427
FEATURE                Location/Qualifiers
misc_feature           1..14427
                       note = pLX-TuMV plasmid
source                 1..14427
                       mol_type = other DNA
                       organism = synthetic construct
SEQUENCE: 28
gaacatggtg gagcacgaca cgctcgtcta ctccaagaat atcaaagata cagtctcaga  60
agaccagagg gctattgaga cttttcaaca aagggtaata tcgggaaacc tcctcggatt  120
ccattgccca gctatctgtc acttcatcga aaggacagta gaaaaggaag atggcttcta  180
caaatgccat cattgcgata aaggaaaggc tatcgttcaa gatgcctcta ccgacagtgg  240
tcccaaagat ggacccccac ccacgaggaa catcgtggaa aaagaagacg ttccaaccac  300
gtcttcaaag caagtggatt gatgtgatat ctccactgac gtaagggatg acgcacaatc  360
ccactatcct tcgcaagacc cttcctctat ataaggaagt tcatttcatt tggagaggaa  420
aaaatataaa aactcaacat aacatacaca aaacgattaa agcaaacaca aatctttcaa  480
agcattcaag caatcaaaga ttctcaaatc tttcatcgtt atcaaagcaa tcaccaacag  540
caaaccaaat ggcagcagtt acattcgcat cagctatcac caacgccatc accagcaaac  600
cagcactcac cggaatggtg cagtttggga gtttcccacc aatgccattg cgatccacca  660
ccgtcaccac agtcgccact tcagtggcgc aacctaaact gtacacagtg cagtttggaa  720
gccttgaccc agtagtcgtc aagagtggag cagggtccct tgctaaggca acacgccagc  780
agcctaacgt tgaaatagac gttagcctca gtgaagccgc agctctggag gttgcgaaac  840
ctagatcgaa tgccgtgttg aggatgcacg aggaagcaaa caaggagaga gcactctttt  900
tggactggga ggctagtttg aagagaagct cgtatggaat tgctgaggac gagaaggttg  960
taatgacaac tcatggcgtc agcaagatag tgcccagaag ttcaagggca atgaagctaa  1020
agcgcgcaag ggagaggcgt agagcgcagc aaccaattat attaaagtgg gagcccaaat  1080
tgagcgggat ctcaatcgga ggagggctct ctgcgagcgt aatcgaagca gaagaggttc  1140
```

-continued

```
gcacaaagtg gccgcttcat aagacaccgt caatgaagaa gaggacggtg cacagaatat  1200
gcaagatgaa cgaccaagga gttgacatgt tgacacgatc cctggttaag attttcaaga  1260
ctaagagtgc caacattgaa tacatcggaa agaagtcgat taaggtcgat ttcatcagaa  1320
aagaacgaac gaaattcgca agaatccaag tagcacactt actcgggaag agagcacagc  1380
gcgacttgtt aactggaatg gaagaaaacc attttattga cattctcagt aagtactcag  1440
gtaacaaaac aaccataaat cctggagtag tttgcgcagg ttggagtggc atagtcgttg  1500
gaaatggaat tctaacccag aaacgaagca gaagtccatc agaggccttt gtaattagag  1560
gtgagcacga aggcaagttg tacgatgcca ggatcaaagt cacgaggaca atgagtcaca  1620
agattgtgca ctttagtgca gcaggagcca acttctggaa aggcttcgac agatgctttc  1680
tcgcataccg tagtgacaat cgcgagcata catgctattc agggctagat gtcactgagt  1740
gcggcgaggt ggcagcactg atgtgtttgg ctatgttccc atgcggaaag ataacctgcc  1800
ctgactgtgt aacagatagt gagctatccc aaggacaagc aagcggacca tctatgaagc  1860
acaggttgac acagctacgc gatgtcatca agtcaagcta cccacgcttc aagcatgcag  1920
tgcagatact agataggtat gagcaatcac tgagcagtgc aaacgagaac taccaagatt  1980
tcgcagaaat ccagagcata agcgatggag ttgaaaaagc tgcattccca cacgtcaaca  2040
agctaaacgc aatattgatc aaaggggcca cagtaacagg agaggaattc tcgcaggcta  2100
cgaagcactt gctcgagata gcacgatacc tgaagaacag aaccgagaac attgagaagg  2160
gttcactgaa gtcctttcgc aacaagattt cccagaaagc gcacatcaac ccaacactaa  2220
tgtgtgacaa ccagctcgat agaaatggaa atttcatatg gggtgagaga ggataccatg  2280
caaaacgatt cttcagcaac tactttgaaa taatcgatcc aaagaaaggc tacacccaat  2340
acgagacaag agcggtacca aatgggtcac ggaaacttgc aatcggcaaa ctaatagtcc  2400
caacgaactt cgaagtttta agggaacaga tgaaaggcga accggtagaa ccatacccag  2460
taacagtcga gtgtgtgagc aagttacagg gtgacttcgt ccatgcatgt tgttgtgtca  2520
caacagaatc aggcgaccca gtcttgtctg agatcaaaat gccaaccaaa caccatctag  2580
tgattggtaa cagcggtgat ccaaagtaca tagatctccc tgagatcgag gagaataaaa  2640
tgtacatagc gaaagaaggt tattgttaca tcaatatctt cctagccatg ttggtaaatg  2700
tcaaggagtc gcaggcaaag gagttcacga aagttgttag ggacaaacta gttggcgaac  2760
ttggcaagtg gcccactctg ttagatgtag caaccgcttg ttatttcctg aaagtatttt  2820
acccagacgt tgctaacgcc gaattgccac gcatgctagt ggaccataag acaaagataa  2880
ttcatgtcgt tgattcatat gggtcactgt caactggata tcatgtcctt aagacaaaca  2940
ctgtggaaca actcatcaaa ttcacgagat gtaatttgga gtcaagcttg aaacactacc  3000
gcgttggagg aacagaatgg gaggacactc atggatccag caacatagat aatccacagt  3060
ggtgcatcaa gaggctcata aaaggagtct acaaaccaaa gcaactgaaa gaagacatgt  3120
tggcaaaccc tttcttacca ctatatgctc tactgtcacc aggtgtcatc ctggcatttt  3180
acaatagtgg ctctctagag tacttgatga accattacat cagggtggac agcaacgtcg  3240
ccgttttgtt ggtcgttttg aaatctctag cgaagaaggt gtcaactagt cagagtgtgt  3300
tagcccagct tcaaatcatt gaacgaagtc taccagaact catcgaagca aaggctaatg  3360
ttaatgggcc agatgacgca gccactcgcg cgtgtaacag attcatgggc atgcttctgc  3420
atatggcaga accaaactgg gagcttgcgg atggtggata cacaattctg agggatcata  3480
gcatctccat tttggaaaaa agttatctac aaatcttgga cgaagcatgg aacgagttaa  3540
gttggtcgga gcgctgtgct ataagatact actcgtcaaa gcaagcaatc tttacacaga  3600
aagatttgcc aatgaaaagc gaagccgatt taggcggcag atacagcgtg tcagtcatgt  3660
catcttacga acggagtaag caatgtatga aaagcgtgca ctctagtata ggtaatagat  3720
tacgtagtag tatgtcttgg actagtagca aggtgtcgaa tagtgtgtgt aggactatta  3780
actatttagt accagatgtg ttcaagttta tgaatgtact cgtttgtatc agcttactaa  3840
tcaagatgac tgccgaggcg aatcacatcg tcaccacgca aagaaggctc aaactagatg  3900
tcgaggagac agagcgcagg aaaatagaat gggagcttgc attccaccat gccattctga  3960
cgcagagtgc aggtcaacac ccaacgatag acgagttcag agcgtacatc gccgacaagg  4020
caccacatct aagtgagcat atcgagcctg aagaaaaggc ggtggttcat caagcgaaga  4080
gacaatccga gcaagaactc gagcgtataa tagcatttgt tgcattggtg ctcatgatgt  4140
tcgatgcaga acgaagcgac tgtgtcacaa agattctcaa caagcttaag ggactagtcg  4200
ccactgtgga acctacagtc taccatcaga ctctcaatga tatagaggat gacttgagtg  4260
agaggaacct cttcgtcgat tttgagctta gcagcgatgg agatatgctc caacagcttc  4320
cagccgaaaa gacatttgcc tcatggtgga gtcatcaact aagcagagga ttcacaatcc  4380
cacactacag gacagaaggg aagttcatga ctttcaccag agcaactgcc acggaagtcg  4440
cgggtaaaat agcacacgag agtgacaaag acatattact aatgggagca gtaggatcag  4500
gtaagtcaac tggcttgcca tatcatctct ccagaaaagg gaacgtatta ctccttgagc  4560
cgactcggcc acttgcagaa aacgtacaca agcagttgtc gcaggcaccg ttccatcaga  4620
acacaactct taggatgcgc ggactaacag cattcgggtc ggcaccaatc tcagtgatga  4680
ccagtggttt tgcactcaat tactttgcaa acaacagaat gcgaattgaa gaatttgact  4740
ttgtcatatt tgatgaatgt cacgttcatg acgccaatgc aatggcgatg agatgtttgc  4800
tacatgagtg tgactattct ggcaaaatta tcaaagtttc agccacacca ccaggtcgag  4860
aagttgagtt ctccactcaa taccccgtgt cgataagcac agaagacaca ctatcgtttc  4920
aggattttgt gaacgcacag ggtagtggaa gcaattgtga tgtgatttca aaaggagaca  4980
atatcctcgt gtatgtagca agctacaatg aggtagacgc gctttcaaaa cttctaattg  5040
aaagagactt caaagtcacg aaggttgatg gaagaacgat gaaagttgga aacatcgaga  5100
tcaccacaag tggaacacct agtaagaagc acttcatagt tgcaaccaac atcatagaga  5160
acggtgttac tctagacatc gatgtggttg ctgattttgg aacgaaggta ctcccatatc  5220
ttgatacaga cagcagaatg ctgagcacaa ctaagacaag catcaattat ggggaacgta  5280
tccaaaggct aggaagagtc ggaaggcaca agccaggtca cgctctgcga ataggtcaca  5340
cagagaaggg gttgagcgaa gttccaagtt gtattgcaac agaagcagct ttaaagtgct  5400
tcacttatgg gcttccagtg atcaccaaca acgtctcgac aagtattctt ggtaatgtaa  5460
cggtaaagca ggcacgaaca atgtctgtat ttgagataac accgttctac acaagccaag  5520
tggtgagata tgatggctcc atgcatccac aggtgcacgc actcttaaag agattcaaac  5580
tcagagactc tgagattgtt ttgaataaat tagccatacc tcaccgagga gtgaacgctt  5640
ggctcacagc tagtgagtat gcacgacttg gcgcgaatgt tgaagatagg cgtgacgttc  5700
gaattccttt tatgtgtcgc gacatcccag aaaaacttca tctagacatg tgggatgtga  5760
ttgttaaatt caaaggtgat gcaggttttg gtcggctttc aagcgccagt gcgagcaagg  5820
tagcttatac tctacagacg gacgtcaact ccatacagcg aacagtcact atcatagata  5880
```

-continued

```
cactaatcgc tgaggagaga aggaagcagg aatacttcaa gacggtaacc tccaactgtg  5940
tctcttcttc gaacttctca ctgcagagca taacaaatgc gataaaatct cgtatgatga  6000
aagatcacac gtgcgagaac atatcagtgc ttgaaggagc gaagtcacag ttactcgagt  6060
ttagaaacct gaatgctgat cactcatttg ctacaaaaac cgatggaata tctcggcatt  6120
tcatgagtga gtatggagct cttgaggcag ttcaccatca aaacaccagc gacatgagca  6180
aattcctcaa gcttaagggc aaatggaata aaacgctaat cacgcgagat gtgctggtac  6240
tttgtggagt tcttggaggt ggattgtgga tggttattca gcacctgcgg tcaaagatgt  6300
ccgaacccgt aacccatgaa gcgaaaggta agaggcaaag gcagaaacta aaatttcgca  6360
atgcccgaga caacaaaatg ggtagagaag tgtacggaga tgatgatacc atagagcatt  6420
tcttcggtga tgcctacaca aagaaaggga agagcaaggg taggacacgt ggtatcggac  6480
acaaaaacag gaagttcatc aacatgtatg ggtttgatcc tgaagatttc tctgcagttc  6540
gtttcgtgga tccactcaca ggagcgacgt tggacgacaa cccgctcaca gacatcaccc  6600
ttgtgcaaga gcacttcggc aacataagaa tggacttact cggggaggat gagctggact  6660
caaatgaaat acgtgtgaat aagactattc aagcctacta catgaacaat aaaacaggca  6720
aggctttgaa ggtggatctg acaccacaca tacctctcaa ggtgtgtgat cttcacgcaa  6780
ccattgctgg attcccagag cgagaaaacg agctgaggca gactggaaag gctcagccca  6840
tcaacataga cgaagtgcca agagctaaca acgaactcgt cccagtggac cacgagagta  6900
actccatgtt cagagggttg cgtgactaca acccaatatc aaacaacatt tgtcatctca  6960
caaatgtttc agatggagca tcaaactcgt tatatggagt cggtttcgga ccactcatat  7020
taacgaaccg acacctcttt gagcggaata acggtgaact cgtaataaaa tcacgacatg  7080
gtgagttcgt gattaaaaac acaactcagc tacacttgct accgattcca gacagagatc  7140
ttctgctaat ccggttacca aaggacgtcc caccctttcc acagaaattg ggtttcaggc  7200
aacctgagaa aggtgaacga atttgcatgg tggggtccaa tttccaaacc aagagcataa  7260
cgagtatagt ctctgagact agtacaataa tgccagtgga gaacagtcag ttttggaaac  7320
actggattag cactaaagac ggccaatgcg gaagtccaat ggtgagcacg aaagacggga  7380
aaatactcgg attacacagc ctagcgaact tccagaactc catcaattac tttgctgctt  7440
tcccagatga ttttgccgag aagtatcttc ataccattga agcacacgag tgggtcaagc  7500
actggaagta taacactagc gccatcagtt ggggctcttt gaatatacaa gcatcgcaac  7560
cgtccggctt gttcaaagta agcaagctaa tctcagacct cgacagcacg gcagtctacg  7620
cacaaaccca gcagaatcgg tggatgttcg agcagctcaa cgggaaccta aaagcgatag  7680
cacactgccc tagccagctt gtgacaaagc acacagttaa aggaaaatgt cagatgtttg  7740
acttgtatct caagttgcat gatgaagcac gagagtattt ccaaccgatg ctgggccagt  7800
atcaaaagag caaactcaat cgagaagcat atgcaaagga tcttctgaaa tatgcaacgc  7860
caatcgaagc aggaaacatc gactgtgatc tgtttgaaaa gacagttgaa atagtcgtat  7920
cagatctgcg aggttatggt ttcgaaacat gcaattatgt cactgatgag aatgacatat  7980
tcgaagctct taacatgaaa tccgcagttg gagcgttgta taaaggaaag aagaaggatt  8040
acttcgctga gttcacaccc gagatgaaag aagaaatact gaaacaaagt tgtgaacggc  8100
tcttcctagg aaagatggga gtgtggaacg gctcgctgaa ggcagagttg cgaccactag  8160
aaaaagtgga agcaaacaaa acacggacgt ttactgccgc accactagac acactgttgg  8220
gtggaaaagt ttgcgtggat gatttcaaca accagttcta tgatcacaac cttagagctc  8280
cttggagcgt tggcatgaca aagttttatt gtggttggga tcgcttgttg gagtcgttgc  8340
cagatggttg ggtgtattgc gatgctgatg gctcacagtt cgacagctcg ctatcgccat  8400
acttgatcaa cgcagtactc aacatccgct taggattcat ggaagagtgg gacatagggg  8460
aggtaatgct gagaaatttg tacaccgaaa tcgtgtatac ccctatttct acaccagatg  8520
gtacactcgt caagaagttc aaaggaaaca atagcggaca gccatcgact gttgtggaca  8580
acacgctcat ggtcatattg gcagtcaact attcactcaa gaaaagcgga attccaagtg  8640
agttgcgcga cagcatcatc agattcttcg tcaacggaga tgatttactg ctaagcgtac  8700
acccagagta tgagtatatt cttgacacta tggcagacaa ctttcgtgaa ctgggcctga  8760
agtatacttt cgactcaaga accagggaaa aaggagacct ctggtttatg tcgcaccagg  8820
ggcacaaaag agagggaatc tggattccca agctcgagcc agagcgaata gtatcgattc  8880
tagaatggga tcggtcgaaa gagccatgcc atcgactaga ggcaatctgc gcagcgatga  8940
ttgagtcgtg gggatacgac aagttaactc acgagatacg caagttctac gcgtggatga  9000
ttgaacaagc tccatttagc tccctagcac aagaagggaa agctccttac atagcggaaa  9060
cagcgctgag gaagctctac cttgataagg aaccagctca agaggatctc acccattatt  9120
tgcaagcaat ctttgaggat tatgaagatg gtgctgaggc ttgtgtttat caccaggccg  9180
gcatgagtaa aggagaagaa cttttcactg gagttgtccc aattcttgtt gaattagatg  9240
gtgatgttaa tgggcacaaa ttttctgtca gtggagaggg tgaaggtgat gcaacatacg  9300
gaaaacttac ccttaaattt atttgcacta ctggaaaact acctgttcca tggccaacac  9360
ttgtcactac tttctcttat ggtgttcaat gcttttcaag atacccagat catatgaagc  9420
ggcacgactt cttcaagagc gccatgcctg agggatacgt gcaggagagg accatctctt  9480
tcaaggacga cgggaactac aagacacgtg ctgaagtcaa gtttgaggga gacaccctcg  9540
tcaacaggat cgagcttaag ggaatcgatt tcaaggagga cggaaacatc ctcggccaca  9600
agttggaata caactacaac tcccacaacg tatacatcac ggcagacaaa caaaagaatg  9660
gaatcaaagc taacttcaaa attagacaca acattgaaga tggaagcgtt caactagcag  9720
accattatca acaaaatact ccaattggcg atggccctgt ccttttacca gacaaccatt  9780
acctgtccac acaatctgcc ctttcgaaag atcccaacga aaagagagac cacatggtcc  9840
ttcttgagtt tgtaacagct gctgggatta cacatggcat ggatgaacta tacaaagcat  9900
gcgtatacca tcaagccggc gaaacgcttg atgcagagtt gacagacgag caaaagcagg  9960
cagagaagga gaagaaggag agagagaagg cagaaaagga acgagagagg caaaagcagt  10020
tggcactcaa gaaaggcaag gatgttgcac aagaagaggg aaaacgcgac aaggaagtaa  10080
acgctggaac ctctggaact ttcagtgtac ccagactcaa gagtctgaca agcaagatgc  10140
gcgtgccaag atacgagaaa agagtggctc taaacctcga tcatctaatc ctatacacgc  10200
cggagcagac ggatctatcc aacacacgtt caacgcgaaa gcagtttgac acatggtttg  10260
aaggtgtaat ggctgattac gaactgacgg aggacaaaat gcgaatcatt ctcaatggtt  10320
taatggtctg gtgcattgag aacggaacct ccccgaacat aaacggaatg tgggtgatga  10380
tggacggcga cgatcaggtg gaattcccga tcaaaccgct cattgaccac gccaaaccca  10440
catttaggca gataatggcc catttcagtg acgtagctga agcgtacatt gaaaagcgta  10500
accaagaccg accatacatg ccacgatatg gtcttcagcg caatttaacc gacatgagct  10560
tagctcgata cgcatttgat ttctatgaaa tgacttctag gactccaata cgtgcgagag  10620
```

```
aggcacacat ccagatgaaa gcagcagcac tgcgtggcgc aaataataat ttgttcggct  10680
tggatggaaa cgttggtaca acggtagaga acacggagag gcatacgacc gaggacgtta  10740
atcggaacat gcataactta ctgggcgttc aggggttgtg aagttgtatg ctggtagact  10800
ataagtattt aagtttactc gttagtattc tcgcttatgg gaaatatgta agtttgttaa  10860
agcagccagt gtgactttgt catgtgtgtt gttgttactt tctgtatttt cgccgaacat  10920
tttattggtg ttagcgcatg tagtgaggat cgtcctcgat tgccttaaca tttgatagga  10980
tgcaagggac aaaaaaaaaa aaaaaaaaaa aaaaaaaaaa aaaaaaaaaa aaaaaaaaaa  11040
aaaaaatcgg ttccccctag agcagatcgt tcaaacattt ggcaataaag tttcttaaga  11100
ttgaatcctg ttgccggtct tgcgatgatt atcatctaat ttctgttgaa ttacgttaag  11160
catgtaataa ttaacatgta atgcatgacg ttatttatga gatgggtttt tatgattaga  11220
gtcccgcaat tatacattta atacgcgata gaaaacaaaa tatagcgcgc aaactaggat  11280
aaattatcgc gcgcggtgtc atctatgtta ctagatctct agcctgcagg aattgttgat  11340
tttgtgatga ctgatggcag gatatatgcg gttgtaattc atttttattg tctaaatttc  11400
tgtatttgtt tgtttgttcg gttgtaaatt tttttggaag aacaagaaaa gaaaaaacac  11460
ccgttagggt gtttttagtt agtgtggcgc gccgacttgc gacatgcggt cctttgcaat  11520
caactattag aaaaattcat ccagcatcag atgaaattgc agtttgttca tatccggatt  11580
atcaatgcca tatttctgaa acagacgttt ttgcaggctc gggctaaatt cgcccaggca  11640
gttccacaga atggccagat cctgataacg atccgcaatg cccacacggc ccacatcaat  11700
gcagccaatc agtttgcctt catcgaaaat caggttatcc aggctaaaat cgccgtgggt  11760
caccacgcta tccgggctaa acggcagcag tttatgcatt tctttccaca cctgttccac  11820
cggccagccg ttacgttcat catcaaaatc gctcgcatcc accaggccgt tgttcatacg  11880
gctctgcgcc tgggccagac gaaacacacg atcgctgtta aacgggcagt tgcacaccgg  11940
aatgctatgc agacgacgca gaaacacggc cagcgcatcc acaatgtttt cgccgctatc  12000
cggatattct tccagcacct gaaacgcggt tttgcccgga atcgcggtgg tcagcagcca  12060
cgcatcatcc ggggtgcgaa taaaatgttt aatggtcggc agcggcataa attcggtcag  12120
ccagttcaga cgcaccattt catcggtcac atcgttcgcc acgctgcctt tgccatgttt  12180
cagaaacagt tccggcgcat ccggtttgcc atacagacga taaatggtcg cgccgctctg  12240
acccacgtta tcacgcgccc atttatagcc atacagatcc gcatccatgt tgctgttcag  12300
acgcggacgg ctacagctcg tttcacgctg aatatggctc ataacacccc ttgtattact  12360
gtttatgtaa gcagacagtt ttattgttca tgatgatata tttttatctt gtgcaatgta  12420
acatcagaga ttttgagaca caagatcgga ttggcggtta tgcggttcta ccggcgcggc  12480
agcgttaccc gtgtcggcgg ctccaacggc tcgccatcgt ccagaaaaca cggctcatcg  12540
ggcatcggca ggcgctgctg cccgcgccgt tcccattcct ccgtttcggt caaggctggc  12600
aggtctggtt ccatgcccgg aatgccgggc tggctgggcg gctcctcgcc ggggccggtc  12660
ggtagttgct gctcgcccgg atacagggtc gggatgcggc gcaggtcgcc atgccccaac  12720
agcgattcgt cctggtcgtc gtgatcaacc accacggcgg cactgaacac cgacaggcgc  12780
aactggtcgc ggggctggcc ccacgccacg cggtcattga ccacgtaggc cgacacggtg  12840
ccggggccgt tgagcttcac gacggagatc cagcgctcgg ccaccaagtc cttgactgcg  12900
tattggaccg tccgcaaaga acgtccgatg agcttggaaa gtgtcttctg gctgaccacc  12960
acggcgttct ggtggcccat ctgcgccacg aggtgatgca gcagcattgc cgccgtgggt  13020
ttcctcgcaa taagcccggc ccacgcctca tgcgctttgc gttccgtttg cacccagtga  13080
ccgggcttgt tcttggcttg aatgccgatt tctctggact gcgtggccat gcttatctcc  13140
atgcggtagg ggtgccgcac ggttgcggca ccatgcgcaa tcagctgcaa cttttcggca  13200
gcgcgacaac aattatgcgt tgcgtaaaag tggcagtcaa ttacagattt tctttaacct  13260
acgcaatgag ctattgcggg gggtgccgca atgagctgtt gcgtaccccc ctttttttaag  13320
ttgttgattt ttaagtcttt cgcatttcgc cctatatcta gttctttggt gcccaaagaa  13380
gggcacccct gcggggttcc cccacgcctt cggcgcggct ccccctccgg caaaaagtgg  13440
cccctccggg gcttgttgat cgactgcgcg gccttcggcc ttgcccaagg tggcgctgcc  13500
cccttggaac cccccgcactc gccgccgtga ggctcggggg gcaggcgggc gggcttcgcc  13560
cttcgactgc ccccactcgc ataggcttgg gtcgttccag gcgcgtcaag gccaagccgc  13620
tgcgcggtcg ctgcgcgagc cttgacccgc cttccacttg gtgtccaacc ggcaagcgaa  13680
gcgcgcaggc cgcaggccgg aggcttttcc ccagagaaaa ttaaaaaaat tgatggggca  13740
aggccgcagg ccgcgcagtt ggagccggtg ggtatgtggt cgaaggctgg gtagccggtg  13800
ggcaatccct gtggtcaagc tcgtgggcag gcgcagcctg tccatcagct tgtccagcag  13860
ggttgtccac gggccgagcg aagcgagcca gccggtggcc gctcgcggcc atcgtccaca  13920
tatccacggg ctggcaaggg agcgcagcga ccgcgcaggg cgaagcccgg agagcaagcc  13980
cgtagggggc catcatcagt tcggtggtct tccgacgaac aataaggccg caaatcgcgg  14040
cctttttttat tgataacaaa accggctcag ttctgcgtag aaaccaacat gcaagctcca  14100
ccgggtgcaa agcggcagcg gcggcaggat atattcaatt gtaaatggct tcatgtccgg  14160
gaaatctact ggtggcagga tatattgtgg tgtaaacaat ggagaaaaag attaattaag  14220
tactagtcca gtacgcacga ttcaaggctt gcttcacaaa ccaaggcaag taatagagat  14280
tggagtctct aaaaaggtag ttcccactga atcaaaggcc atggagtcaa agattcaaat  14340
agaggaccta acagaactcg ccgtaaagac tggcgaacag ttcatacaga gtctcttacg  14400
actcaatgac aagaagaaaa tcttcgt                                      14427

SEQ ID NO: 29          moltype = DNA  length = 25
FEATURE                Location/Qualifiers
misc_feature           1..25
                       note = Primer 1989_F
source                 1..25
                       mol_type = other DNA
                       organism = synthetic construct
SEQUENCE: 29
gattgatgtg atttctccac tgacg                                       25

SEQ ID NO: 30          moltype = DNA  length = 21
FEATURE                Location/Qualifiers
misc_feature           1..21
                       note = Primer 2050_F
```

```
source                  1..21
                        mol_type = other DNA
                        organism = synthetic construct
SEQUENCE: 30
gccattgtcc gaaatctcac g                                               21

SEQ ID NO: 31           moltype = DNA  length = 22
FEATURE                 Location/Qualifiers
misc_feature            1..22
                        note = Primer 2051_R
source                  1..22
                        mol_type = other DNA
                        organism = synthetic construct
SEQUENCE: 31
ctggaaatgc gattctctta gc                                              22

SEQ ID NO: 32           moltype = DNA  length = 16
FEATURE                 Location/Qualifiers
misc_feature            1..16
                        note = Primer X122_R
source                  1..16
                        mol_type = other DNA
                        organism = synthetic construct
SEQUENCE: 32
cgtcaatcgt tagagc                                                     16

SEQ ID NO: 33           moltype = DNA  length = 15
FEATURE                 Location/Qualifiers
misc_feature            1..15
                        note = Primer X123_R
source                  1..15
                        mol_type = other DNA
                        organism = synthetic construct
SEQUENCE: 33
cgaccttgca cttca                                                      15

SEQ ID NO: 34           moltype = DNA  length = 42
FEATURE                 Location/Qualifiers
misc_feature            1..42
                        note = Primer X329_R
source                  1..42
                        mol_type = other DNA
                        organism = synthetic construct
SEQUENCE: 34
cgcatccttg tccggtctcc agcgagagac gtcactcatt ag                        42

SEQ ID NO: 35           moltype = DNA  length = 626
FEATURE                 Location/Qualifiers
misc_feature            1..626
                        note = PEtOH synthetic promoter
source                  1..626
                        mol_type = other DNA
                        organism = synthetic construct
SEQUENCE: 35
aaatcaccag tctctctcta caaatctatc tctctctata ataatgtgtg agtagttccc  60
agataaggga attagggttc ttatagggtt tcgctcatgt gttgagcata taagaaaccc  120
ttagtatgta tttgtatttg taaaatactt ctatcaataa aatttctaat tcctaaaacc  180
aaaatccagt gacccatgcg gagccgcatt ggaggccatg cggagccgca cgcgttaaca  240
agagcggctc cgcttgacct ctcgggatag ttccgaccta ggattggatg catgcggaac  300
cgcacgaggg cggggcggaa attgacacac cactcctctc cacgcaccgt tcaagaggta  360
cgcgtataga gccgtataga gcagagacgg agcactttct ggtactgtcc gcacgggatg  420
tccgcacgga gagccacaaa cgagcggggc cccgtacgtg ctctcctacc ccaggatcgc  480
atccccgcat agctgaacat ctatataaga aggcattcat tcccatttga aggatcatca  540
gatactgaac caatattatt tttacaacaa ttaccaacaa caacaaacaa caaacaacat  600
tacaattact atttacaatt acaatg                                          626

SEQ ID NO: 36           moltype = DNA  length = 50
FEATURE                 Location/Qualifiers
misc_feature            1..50
                        note = Primer X192_F
source                  1..50
                        mol_type = other DNA
                        organism = synthetic construct
SEQUENCE: 36
cgacttgcga catgcggtcc tttgcaatca actattagaa aaattcatcc                50

SEQ ID NO: 37           moltype = DNA  length = 50
FEATURE                 Location/Qualifiers
misc_feature            1..50
```

```
                         note = Primer X193_R
source                   1..50
                         mol_type = other DNA
                         organism = synthetic construct
SEQUENCE: 37
aaccgcataa ccgccaatcc gatcttgtgt ctcaaaatct ctgatgttac            50

SEQ ID NO: 38            moltype = DNA  length = 47
FEATURE                  Location/Qualifiers
misc_feature             1..47
                         note = Primer X194_F
source                   1..47
                         mol_type = other DNA
                         organism = synthetic construct
SEQUENCE: 38
cgacttgcga catgcggtcc tttgttattt gccgactacc ttggtga               47

SEQ ID NO: 39            moltype = DNA  length = 44
FEATURE                  Location/Qualifiers
misc_feature             1..44
                         note = Primer X195_R
source                   1..44
                         mol_type = other DNA
                         organism = synthetic construct
SEQUENCE: 39
aaccgcataa ccgccaatcc gatcgaacct tgaccgaacg cagc                  44

SEQ ID NO: 40            moltype = DNA  length = 45
FEATURE                  Location/Qualifiers
misc_feature             1..45
                         note = Primer X196_F
source                   1..45
                         mol_type = other DNA
                         organism = synthetic construct
SEQUENCE: 40
cgacttgcga catgcggtcc tttgcaattt acccaacaac tccgc                 45

SEQ ID NO: 41            moltype = DNA  length = 46
FEATURE                  Location/Qualifiers
misc_feature             1..46
                         note = Primer X197_R
source                   1..46
                         mol_type = other DNA
                         organism = synthetic construct
SEQUENCE: 41
aaccgcataa ccgccaatcc gatcttgaca taagcctgtt cggttc                46

SEQ ID NO: 42            moltype = DNA  length = 39
FEATURE                  Location/Qualifiers
misc_feature             1..39
                         note = Primer X198_F
source                   1..39
                         mol_type = other DNA
                         organism = synthetic construct
SEQUENCE: 42
gatcggattg gcggttatgc ggttctaccg gcgcggcag                        39

SEQ ID NO: 43            moltype = DNA  length = 44
FEATURE                  Location/Qualifiers
misc_feature             1..44
                         note = Primer X199_R
source                   1..44
                         mol_type = other DNA
                         organism = synthetic construct
SEQUENCE: 43
ggaagaccac cgaactgatg atggccccct acgggcttgc tctc                  44

SEQ ID NO: 44            moltype = DNA  length = 44
FEATURE                  Location/Qualifiers
misc_feature             1..44
                         note = Primer X200_F
source                   1..44
                         mol_type = other DNA
                         organism = synthetic construct
SEQUENCE: 44
gatcggattg gcggttatgc ggttgcgatg caggtggctg ctga                  44

SEQ ID NO: 45            moltype = DNA  length = 50
FEATURE                  Location/Qualifiers
```

-continued

```
misc_feature           1..50
                       note = Primer X201_R
source                 1..50
                       mol_type = other DNA
                       organism = synthetic construct
SEQUENCE: 45
ggaagaccac cgaactgatg atgggtagaa aagatcaaag gatcttcttg            50

SEQ ID NO: 46          moltype = DNA  length = 19
FEATURE                Location/Qualifiers
misc_feature           1..19
                       note = Primer X210_R
source                 1..19
                       mol_type = other DNA
                       organism = synthetic construct
SEQUENCE: 46
tgagacggtt tcgaccagg                                              19

SEQ ID NO: 47          moltype = DNA  length = 20
FEATURE                Location/Qualifiers
misc_feature           1..20
                       note = Primer X211_F
source                 1..20
                       mol_type = other DNA
                       organism = synthetic construct
SEQUENCE: 47
gtcaggagac gggacaagga                                             20

SEQ ID NO: 48          moltype = DNA  length = 23
FEATURE                Location/Qualifiers
misc_feature           1..23
                       note = Primer X212_F
source                 1..23
                       mol_type = other DNA
                       organism = synthetic construct
SEQUENCE: 48
atggtttcta aaggtgaaga gac                                         23

SEQ ID NO: 49          moltype = DNA  length = 21
FEATURE                Location/Qualifiers
misc_feature           1..21
                       note = Primer X213_R
source                 1..21
                       mol_type = other DNA
                       organism = synthetic construct
SEQUENCE: 49
ttatgctcct ttatcgtcgt c                                           21

SEQ ID NO: 50          moltype = DNA  length = 21
FEATURE                Location/Qualifiers
misc_feature           1..21
                       note = Primer X216_F
source                 1..21
                       mol_type = other DNA
                       organism = synthetic construct
SEQUENCE: 50
atggtttcaa agggagaaga g                                           21

SEQ ID NO: 51          moltype = DNA  length = 43
FEATURE                Location/Qualifiers
misc_feature           1..43
                       note = Primer X218_F
source                 1..43
                       mol_type = other DNA
                       organism = synthetic construct
SEQUENCE: 51
gtagcctggt cgaaaccgtc tcaccagtac gcacgattca agg                   43

SEQ ID NO: 52          moltype = DNA  length = 49
FEATURE                Location/Qualifiers
misc_feature           1..49
                       note = Primer X219_R
source                 1..49
                       mol_type = other DNA
                       organism = synthetic construct
SEQUENCE: 52
cgcatccttg tcccgtctcc tgacgagatc gagtaacata gatgacacc             49

SEQ ID NO: 53          moltype = DNA  length = 43
```

```
FEATURE                Location/Qualifiers
misc_feature           1..43
                       note = Primer X220_F
source                 1..43
                       mol_type = other DNA
                       organism = synthetic construct
SEQUENCE: 53
gtagcctggt cgaaaccgtc tcataacgaa cgctcatgct aag                43

SEQ ID NO: 54          moltype = DNA  length = 49
FEATURE                Location/Qualifiers
misc_feature           1..49
                       note = Primer X221_R
source                 1..49
                       mol_type = other DNA
                       organism = synthetic construct
SEQUENCE: 54
ttgtagtctc ttcaccttta gaaaccattt tctttttgtt tgttgtgag          49

SEQ ID NO: 55          moltype = DNA  length = 45
FEATURE                Location/Qualifiers
misc_feature           1..45
                       note = Primer X222_F
source                 1..45
                       mol_type = other DNA
                       organism = synthetic construct
SEQUENCE: 55
ggatgacgac gataaaggag cataatgcac tggaggtcaa ggaag              45

SEQ ID NO: 56          moltype = DNA  length = 47
FEATURE                Location/Qualifiers
misc_feature           1..47
                       note = Primer X223_R
source                 1..47
                       mol_type = other DNA
                       organism = synthetic construct
SEQUENCE: 56
cgcatccttg tcccgtctcc tgacatagct cgatagaatc atttgct            47

SEQ ID NO: 57          moltype = DNA  length = 39
FEATURE                Location/Qualifiers
misc_feature           1..39
                       note = Primer X238_R
source                 1..39
                       mol_type = other DNA
                       organism = synthetic construct
SEQUENCE: 57
gtcatattta tttttcctct ccaaatgaaa tgaacttcc                     39

SEQ ID NO: 58          moltype = DNA  length = 50
FEATURE                Location/Qualifiers
misc_feature           1..50
                       note = Primer X239_F
source                 1..50
                       mol_type = other DNA
                       organism = synthetic construct
SEQUENCE: 58
gaaatacacc ttataaaagt acaaaaaaaa aaaaaaaaaa aaaaaaatgc         50

SEQ ID NO: 59          moltype = DNA  length = 49
FEATURE                Location/Qualifiers
misc_feature           1..49
                       note = Primer X240_F
source                 1..49
                       mol_type = other DNA
                       organism = synthetic construct
SEQUENCE: 59
gttcatttca tttggagagg aaaaataaat atgacataag aatacataa          49

SEQ ID NO: 60          moltype = DNA  length = 25
FEATURE                Location/Qualifiers
misc_feature           1..25
                       note = Primer X241_R
source                 1..25
                       mol_type = other DNA
                       organism = synthetic construct
SEQUENCE: 60
ctcttccttt cgaccttgca cttca                                    25
```

```
SEQ ID NO: 61              moltype = DNA  length = 26
FEATURE                    Location/Qualifiers
misc_feature               1..26
                           note = Primer X242_F
source                     1..26
                           mol_type = other DNA
                           organism = synthetic construct
SEQUENCE: 61
ttgaagtgca aggtcgaaag gaagag                                        26

SEQ ID NO: 62              moltype = DNA  length = 32
FEATURE                    Location/Qualifiers
misc_feature               1..32
                           note = Primer X243_R
source                     1..32
                           mol_type = other DNA
                           organism = synthetic construct
SEQUENCE: 62
aaagaagtat caaacctact accatcacaa tc                                 32

SEQ ID NO: 63              moltype = DNA  length = 31
FEATURE                    Location/Qualifiers
misc_feature               1..31
                           note = Primer X244_F
source                     1..31
                           mol_type = other DNA
                           organism = synthetic construct
SEQUENCE: 63
gattgtgatg gtagtaggtt tgatacttct t                                  31

SEQ ID NO: 64              moltype = DNA  length = 57
FEATURE                    Location/Qualifiers
misc_feature               1..57
                           note = Primer X245_R
source                     1..57
                           mol_type = other DNA
                           organism = synthetic construct
SEQUENCE: 64
tttttttttt tttgtacttt tataaggtgt atttctacac caaacaaaag gatatgg      57

SEQ ID NO: 65              moltype = DNA  length = 24
FEATURE                    Location/Qualifiers
misc_feature               1..24
                           note = Primer X253_R
source                     1..24
                           mol_type = other DNA
                           organism = synthetic construct
SEQUENCE: 65
ctttcgtaac agcttgcttt ctca                                          24

SEQ ID NO: 66              moltype = DNA  length = 25
FEATURE                    Location/Qualifiers
misc_feature               1..25
                           note = Primer X254_F
source                     1..25
                           mol_type = other DNA
                           organism = synthetic construct
SEQUENCE: 66
ctttggttta gacaagcaat gtgtg                                         25

SEQ ID NO: 67              moltype = DNA  length = 24
FEATURE                    Location/Qualifiers
misc_feature               1..24
                           note = Primer X255_R
source                     1..24
                           mol_type = other DNA
                           organism = synthetic construct
SEQUENCE: 67
ccactattat ttccacgatg cttc                                          24

SEQ ID NO: 68              moltype = DNA  length = 25
FEATURE                    Location/Qualifiers
misc_feature               1..25
                           note = Primer X256_F
source                     1..25
                           mol_type = other DNA
                           organism = synthetic construct
SEQUENCE: 68
cagaggtgaa gtctattctt ggcat                                         25
```

-continued

```
SEQ ID NO: 69          moltype = DNA  length = 23
FEATURE                Location/Qualifiers
misc_feature           1..23
                       note = Primer X257_F
source                 1..23
                       mol_type = other DNA
                       organism = synthetic construct
SEQUENCE: 69
agtttggtgg agttttggat agc                                          23

SEQ ID NO: 70          moltype = DNA  length = 25
FEATURE                Location/Qualifiers
misc_feature           1..25
                       note = Primer X258_F
source                 1..25
                       mol_type = other DNA
                       organism = synthetic construct
SEQUENCE: 70
atacacacgc ttgagataat ggatg                                        25

SEQ ID NO: 71          moltype = DNA  length = 24
FEATURE                Location/Qualifiers
misc_feature           1..24
                       note = Primer X259_R
source                 1..24
                       mol_type = other DNA
                       organism = synthetic construct
SEQUENCE: 71
atcgccactg atacaattca aaag                                         24

SEQ ID NO: 72          moltype = DNA  length = 27
FEATURE                Location/Qualifiers
misc_feature           1..27
                       note = Primer X260_R
source                 1..27
                       mol_type = other DNA
                       organism = synthetic construct
SEQUENCE: 72
aggaccaaaa ttctcataag tctctct                                      27

SEQ ID NO: 73          moltype = DNA  length = 21
FEATURE                Location/Qualifiers
misc_feature           1..21
                       note = Primer X295_F
source                 1..21
                       mol_type = other DNA
                       organism = synthetic construct
SEQUENCE: 73
caatttaccc aacaactccg c                                            21

SEQ ID NO: 74          moltype = DNA  length = 23
FEATURE                Location/Qualifiers
misc_feature           1..23
                       note = Primer X296_R
source                 1..23
                       mol_type = other DNA
                       organism = synthetic construct
SEQUENCE: 74
tgagttcggc gatgtagcca cct                                          23

SEQ ID NO: 75          moltype = DNA  length = 22
FEATURE                Location/Qualifiers
misc_feature           1..22
                       note = Primer X297_F
source                 1..22
                       mol_type = other DNA
                       organism = synthetic construct
SEQUENCE: 75
ggtggctaca tcgccgaact ca                                           22

SEQ ID NO: 76          moltype = DNA  length = 24
FEATURE                Location/Qualifiers
misc_feature           1..24
                       note = Primer X298_R
source                 1..24
                       mol_type = other DNA
                       organism = synthetic construct
SEQUENCE: 76
```

-continued

```
cgttcgcgtc ggctagaaca ggag                                        24

SEQ ID NO: 77          moltype = DNA  length = 22
FEATURE                Location/Qualifiers
misc_feature           1..22
                       note = Primer X299_F
source                 1..22
                       mol_type = other DNA
                       organism = synthetic construct
SEQUENCE: 77
tgttctagcc gacgcgaacg ct                                          22

SEQ ID NO: 78          moltype = DNA  length = 26
FEATURE                Location/Qualifiers
misc_feature           1..26
                       note = Primer X300_R
source                 1..26
                       mol_type = other DNA
                       organism = synthetic construct
SEQUENCE: 78
gtagaaaaga tcaaaggatc ttcttg                                      26

SEQ ID NO: 79          moltype = DNA  length = 45
FEATURE                Location/Qualifiers
misc_feature           1..45
                       note = Primer X301_F
source                 1..45
                       mol_type = other DNA
                       organism = synthetic construct
SEQUENCE: 79
gtagcctggt cgaaaccgtc tcatttttca aatcagtgcg caaga                 45

SEQ ID NO: 80          moltype = DNA  length = 44
FEATURE                Location/Qualifiers
misc_feature           1..44
                       note = Primer X302_R
source                 1..44
                       mol_type = other DNA
                       organism = synthetic construct
SEQUENCE: 80
cagctcttct ccctttgaaa ccattgttgt tacccgattt ggtg                  44

SEQ ID NO: 81          moltype = DNA  length = 20
FEATURE                Location/Qualifiers
misc_feature           1..20
                       note = Primer X303_R
source                 1..20
                       mol_type = other DNA
                       organism = synthetic construct
SEQUENCE: 81
tggccctgga ttttcctcaa                                             20

SEQ ID NO: 82          moltype = DNA  length = 39
FEATURE                Location/Qualifiers
misc_feature           1..39
                       note = Primer X304_F
source                 1..39
                       mol_type = other DNA
                       organism = synthetic construct
SEQUENCE: 82
ttgaggaaaa tccagggcca atggcagata cacgccgac                        39

SEQ ID NO: 83          moltype = DNA  length = 24
FEATURE                Location/Qualifiers
misc_feature           1..24
                       note = Primer X305_R
source                 1..24
                       mol_type = other DNA
                       organism = synthetic construct
SEQUENCE: 83
tccagcacag attgcgtgag agaa                                        24

SEQ ID NO: 84          moltype = DNA  length = 24
FEATURE                Location/Qualifiers
misc_feature           1..24
                       note = Primer X306_F
source                 1..24
                       mol_type = other DNA
                       organism = synthetic construct
```

-continued

```
SEQUENCE: 84
ctctcacgca atctgtgctg gatg                                      24

SEQ ID NO: 85           moltype = DNA  length = 27
FEATURE                 Location/Qualifiers
misc_feature            1..27
                        note = Primer X307_R
source                  1..27
                        mol_type = other DNA
                        organism = synthetic construct
SEQUENCE: 85
agctacaaga agctgtcaac tttccca                                   27

SEQ ID NO: 86           moltype = DNA  length = 43
FEATURE                 Location/Qualifiers
misc_feature            1..43
                        note = Primer X308_F
source                  1..43
                        mol_type = other DNA
                        organism = synthetic construct
SEQUENCE: 86
ggaaagttga cagcttcttg tagctcttgg actcccatgt tgg                 43

SEQ ID NO: 87           moltype = DNA  length = 48
FEATURE                 Location/Qualifiers
misc_feature            1..48
                        note = Primer X309_R
source                  1..48
                        mol_type = other DNA
                        organism = synthetic construct
SEQUENCE: 87
gcatccttgt cccgtctcct gacgataatt tatttgaaaa ttcataag            48

SEQ ID NO: 88           moltype = DNA  length = 50
FEATURE                 Location/Qualifiers
misc_feature            1..50
                        note = Primer X310_F
source                  1..50
                        mol_type = other DNA
                        organism = synthetic construct
SEQUENCE: 88
caacattaca attactattt acaattacaa tggtgagcaa gggagaggag          50

SEQ ID NO: 89           moltype = DNA  length = 19
FEATURE                 Location/Qualifiers
misc_feature            1..19
                        note = Primer X321_F
source                  1..19
                        mol_type = other DNA
                        organism = synthetic construct
SEQUENCE: 89
gagacgggac aaggatgcg                                            19

SEQ ID NO: 90           moltype = DNA  length = 46
FEATURE                 Location/Qualifiers
misc_feature            1..46
                        note = Primer X322_F
source                  1..46
                        mol_type = other DNA
                        organism = synthetic construct
SEQUENCE: 90
cctggtcgaa accgtctcag tcaggagaga gaccaaaagc aaaaac              46

SEQ ID NO: 91           moltype = DNA  length = 42
FEATURE                 Location/Qualifiers
misc_feature            1..42
                        note = Primer X323_R
source                  1..42
                        mol_type = other DNA
                        organism = synthetic construct
SEQUENCE: 91
cgcatccttg tcccgtctcc agcgagagac ctcactcatt ag                  42

SEQ ID NO: 92           moltype = DNA  length = 19
FEATURE                 Location/Qualifiers
misc_feature            1..19
                        note = Primer X324_R
source                  1..19
                        mol_type = other DNA
```

-continued

```
                        organism = synthetic construct
SEQUENCE: 92
tgagaccgtt tcgaccagg                                              19

SEQ ID NO: 93           moltype = DNA  length = 19
FEATURE                 Location/Qualifiers
misc_feature            1..19
                        note = Primer X325_F
source                  1..19
                        mol_type = other DNA
                        organism = synthetic construct
SEQUENCE: 93
gagaccggac aaggatgcg                                              19

SEQ ID NO: 94           moltype = DNA  length = 42
FEATURE                 Location/Qualifiers
misc_feature            1..42
                        note = Primer X326_F
source                  1..42
                        mol_type = other DNA
                        organism = synthetic construct
SEQUENCE: 94
cctggtcgaa acggtctcag gagagagacg aaaagcaaaa ac                    42

SEQ ID NO: 95           moltype = DNA  length = 46
FEATURE                 Location/Qualifiers
misc_feature            1..46
                        note = Primer X327_R
source                  1..46
                        mol_type = other DNA
                        organism = synthetic construct
SEQUENCE: 95
cgcatccttg tccggtctcc tgacagcgag agacgtcact cattag                46

SEQ ID NO: 96           moltype = DNA  length = 46
FEATURE                 Location/Qualifiers
misc_feature            1..46
                        note = Primer X328_F
source                  1..46
                        mol_type = other DNA
                        organism = synthetic construct
SEQUENCE: 96
cctggtcgaa acggtctcag tcaggagaga gacgaaaagc aaaaac                46

SEQ ID NO: 97           moltype = DNA  length = 37
FEATURE                 Location/Qualifiers
misc_feature            1..37
                        note = primer X80_R
source                  1..37
                        mol_type = other DNA
                        organism = synthetic construct
SEQUENCE: 97
ctcaatgctg ctgccttcat ctggatatga gcttcac                          37

SEQ ID NO: 98           moltype = DNA  length = 49
FEATURE                 Location/Qualifiers
misc_feature            1..49
                        note = Primer X228_F
source                  1..49
                        mol_type = other DNA
                        organism = synthetic construct
SEQUENCE: 98
cctcgagtac gtaggatcca tttaaattcc ttcaagagag caaaccatt             49

SEQ ID NO: 99           moltype = DNA  length = 46
FEATURE                 Location/Qualifiers
misc_feature            1..46
                        note = Primer X229_R
source                  1..46
                        mol_type = other DNA
                        organism = synthetic construct
SEQUENCE: 99
atcagctctt ctccctttga aaccattttt tcttgttgtt ttgttg                46

SEQ ID NO: 100          moltype = DNA  length = 31
FEATURE                 Location/Qualifiers
misc_feature            1..31
                        note = Primer X333_R
source                  1..31
```

```
                         mol_type = other DNA
                         organism = synthetic construct
SEQUENCE: 100
cgtgtcgtgc tccaccatgt tcacgaagat t                                31

SEQ ID NO: 101           moltype = DNA  length = 49
FEATURE                  Location/Qualifiers
misc_feature             1..49
                         note = Primer X334_F
source                   1..49
                         mol_type = other DNA
                         organism = synthetic construct
SEQUENCE: 101
aaaaaaaaaa atcggttccc cctagagcag atcgttcaaa catttggca             49

SEQ ID NO: 102           moltype = DNA  length = 25
FEATURE                  Location/Qualifiers
misc_feature             1..25
                         note = Right border
source                   1..25
                         mol_type = other DNA
                         organism = synthetic construct
SEQUENCE: 102
tggcaggata tatgcggttg taatt                                       25

SEQ ID NO: 103           moltype = DNA  length = 25
FEATURE                  Location/Qualifiers
misc_feature             1..25
                         note = Left border
source                   1..25
                         mol_type = other DNA
                         organism = synthetic construct
SEQUENCE: 103
cggcaggata tattcaattg taaat                                       25

SEQ ID NO: 104           moltype = DNA  length = 25
FEATURE                  Location/Qualifiers
misc_feature             1..25
                         note = Left border
source                   1..25
                         mol_type = other DNA
                         organism = synthetic construct
SEQUENCE: 104
tggcaggata tattgtggtg taaac                                       25

SEQ ID NO: 105           moltype = DNA  length = 1522
FEATURE                  Location/Qualifiers
misc_feature             1..1522
                         note = pBBR1 origin (oriV+rep)
rep_origin               1..663
source                   1..1522
                         mol_type = other DNA
                         organism = synthetic construct
SEQUENCE: 105
ctaccggcgc ggcagcgtta cccgtgtcgg cggctccaac ggctcgccat cgtccagaaa  60
acacggctca tcgggcatcg gcaggcgctg ctgcccgcgc cgttcccatt cctccgtttc  120
ggtcaaggct ggcaggtctg gttccatgcc cggaatgccg ggctggctgg gcggctcctc  180
gccggggccg gtcggtagtt gctgctcgcc cggatacagg gtcgggatgc ggcgcaggtc  240
gccatgcccc aacagcgatt cgtcctggtc gtcgtgatca accaccacgg cggcactgaa  300
caccgacagg cgcaactggt cgcggggctg gccccacgcc acgcggtcat tgaccacgta  360
ggccgacacg gtgccggggc cgttgagctt cacgacggag atccagcgct cggccaccaa  420
gtccttgact gcgtattgga ccgtccgcaa agaacgtccg atgagcttgg aaagtgtctt  480
ctggctgacc accacggcgt tctggtggcc catctgcgcc acgaggtgat gcagcagcat  540
tgccgccgtg ggtttcctcg caataagccc ggcccacgcc tcatgcgctt tgcgttccgt  600
ttgcacccag tgaccgggct tgttcttggc ttgaatgccg atttctctgg actgcgtggc  660
catgcttatc tccatgcggt aggggtgccg cacggttgcg gcaccatgcg caatcagctg  720
caacttttcg gcagcgcgac aacaattatg cgttgcgtaa aagtggcagt caattacaga  780
ttttctttaa cctacgcaat gagctattgc ggggggtgcc gcaatgagct gttgcgtacc  840
ccccttttt aagttgttga tttttaagtc tttcgcattt cgccctatat ctagttcttt  900
ggtgcccaaa gaagggcacc cctgcggggt tcccccacgc cttcggcgcg gctccccctc  960
cggcaaaaag tggcccctcc ggggcttgtt gatcgactgc gcggccttcg gccttgccca  1020
aggtggcgct gccccccttgg aacccccgca ctcgccgccg tgaggctcgg ggggcaggcg  1080
ggcgggcttc gcccttcgac tgcccccact cgcataggct tgggtcgttc caggcgcgtc  1140
aaggccaagc cgctgcgcgg tcgctgcgcg agccttgacc cgccttccac ttggtgtcca  1200
accggcaagc gaagcgcgca ggccgcaggc cggaggcttt tccccagaga aaattaaaaa  1260
aattgatggg gcaaggccgc aggccgcgca gttggagccg gtgggtatgt ggtcgaaggc  1320
tgggtagccg gtgggcaatc cctgtggtca agctcgtggg caggcgcagc ctgtccatca  1380
gcttgtccag cagggttgtc cacgggccga gcgaagcgag ccagccggtg gccgctcgcg  1440
gccatcgtcc acatatccac gggctggcaa gggagcgcag cgaccgcgca gggcgaagcc  1500
```

```
cggagagcaa gcccgtaggg gg                                          1522

SEQ ID NO: 106          moltype = DNA  length = 2222
FEATURE                 Location/Qualifiers
misc_feature            1..2222
                        note = RK2 origin
rep_origin              1..2222
source                  1..2222
                        mol_type = other DNA
                        organism = synthetic construct
SEQUENCE: 106
gcgatgcagg tggctgctga acccccagcc ggaactgacc ccacaaggcc ctagcgtttg  60
caatgcacca ggtcatcatt gacccaggcg tgttccacca ggccgctgcc tcgcaactct  120
tcgcaggctt cgccgacctg ctcgcgccac ttcttcacgc gggtggaatc cgatccgcac  180
atgaggcgga aggtttccag cttgagcggg tacggctccc ggtgcgagct gaaatagtcg  240
aacatccgtc gggccgtcgg cgacagcttg cggtacttct cccatatgaa tttcgtgtag  300
tggtcgccag caaacagcac gacgatttcc tcgtcgatca ggacctggca acgggacgtt  360
ttcttgccac ggtccaggac gcggaagcgg tgcagcagcg acaccgattc caggtgccca  420
acgcggtcgg acgtgaagcc catcgccgtc gcctgtaggc gcgacaggca ttcctcggcc  480
ttcgtgtaat accggccatt gatcgaccag cccaggtcct ggcaaagctc gtagaacgtg  540
aaggtgatcg gctcgccgat aggggtgcgc ttcgcgtact ccaacacctg ctgccacacc  600
agttcgtcat cgtcggcccg cagctcgacg ccggtgtagg tgatcttcac gtccttgttg  660
acgtggaaaa tgaccttgtt ttgcagcgcc tcgcgcggga ttttcttgtt gcgcgtggtg  720
aacagggcag agcgggccgt gtcgtttggc atcgctcgca tcgtgtccgg ccacggcgca  780
atatcgaaca aggaaagctg catttccttg atctgctgct tcgtgtgttt cagcaacgcg  840
gcctgcttgg cttcgctgac ctgttttgcc aggtcctcgc cggcggtttt tcgcttcttg  900
gtcgtcatag ttcctcgcgt gtcgatggtc atcgacttcg ccaaacctgc cgcctcctgt  960
tcgagacgac gcgaacgctc cacggcggcc gatggcgcgg gcagggcagg gggagccagt  1020
tgcacgctgt cgcgctcgat cttggccgta gcttgctgga ctatcgagcc gacggactgg  1080
aaggtttcgc ggggcgcacg catgacggtg cggcttgcga tggtttcggc atcctcggcg  1140
gaaaaccccg cgtcgatcag ttcttgcctg tatgccttcc ggtcaaacgt ccgattcatt  1200
caccctcctt gcgggattgc cccggaatta attccccgga tcgatccgtc gatcttgatc  1260
ccctgcgcca tcagatcctt ggcggcaaga aagccatcca gtttactttg cagggcttcc  1320
caaccttacc agagggcgcc ccagctggca attccggttc gcttgctgtc cataaaaccg  1380
cccagtctag ctatcgccat gtaagcccac tgcaagctac ctgctttctc tttgcgcttg  1440
cgttttccct tgtccagata gcccagtagc tgacattcat ccggggtcag caccgtttct  1500
gcggactggc tttctacgtg gctgccattt ttggggtgag gccgttcgcg gccgaggggc  1560
gcagcccctg gggggatggg aggcccgcgt tagcgggccg ggagggttcg agaagggggg  1620
gcaccccct tcggcgtgcg cggtcacgcg cacagggcgc agccctggtt aaaaacaagg  1680
tttataaata ttggtttaaa agcaggttaa aagacaggtt agcggtggcc gaaaaacggg  1740
cggaaaccct tgcaaatgct ggattttctg cctgtggaca gcccctcaaa tgtcaatagg  1800
tgcgcccctc atctgtcagc actctgcccc tcaagtgtca aggatcgcgc ccctcatctg  1860
tcagtagtcg cgcccctcaa gtgtcaatac cgcagggcac ttatccccag gcttgtccac  1920
atcatctgtg ggaaactcgc gtaaaatcag gcgttttcgc cgatttgcga ggctggccag  1980
ctccacgtcg ccggccgaaa tcgagcctgc ccctcatctg tcaacgccgc gccgggtgag  2040
tcggcccctc aagtgtcaac gtccgcccct catctgtcag tgagggccaa gttttccgcg  2100
aggtatccac aacgccggcg gccctacatg gctctgctgt agtgagtggg ttgcgctccg  2160
gcagcggtcc tgatcccccg cagaaaaaaa ggatctcaag aagatccttt gatcttttct  2220
ac                                                                2222

SEQ ID NO: 107          moltype = DNA  length = 2222
FEATURE                 Location/Qualifiers
misc_feature            1..2222
                        note = RK2 origin without BsmBI sites
rep_origin              1..2222
source                  1..2222
                        mol_type = other DNA
                        organism = synthetic construct
SEQUENCE: 107
gcgatgcagg tggctgctga acccccagcc ggaactgacc ccacaaggcc ctagcgtttg  60
caatgcacca ggtcatcatt gacccaggcg tgttccacca ggccgctgcc tcgcaactct  120
tcgcaggctt cgccgacctg ctcgcgccac ttcttcacgc gggtggaatc cgatccgcac  180
atgaggcgga aggtttccag cttgagcggg tacggctccc ggtgcgagct gaaatagtcg  240
aacatccgtc gggccgtcgg cgacagcttg cggtacttct cccatatgaa tttcgtgtag  300
tggtcgccag caaacagcac gacgatttcc tcgtcgatca ggacctggca acgggacgtt  360
ttcttgccac ggtccaggac gcggaagcgg tgcagcagcg acaccgattc caggtgccca  420
acgcggtcgg acgtgaagcc catcgccgtc gcctgtaggc gcgacaggca ttcctcggcc  480
ttcgtgtaat accggccatt gatcgaccag cccaggtcct ggcaaagctc gtagaacgtg  540
aaggtgatcg gctcgccgat aggggtgcgc ttcgcgtact ccaacacctg ctgccacacc  600
agttcgtcat cgtcggcccg cagctcgacg ccggtgtagg tgatcttcac gtccttgttg  660
acgtggaaaa tgaccttgtt ttgcagcgcc tcgcgcggga ttttcttgtt gcgcgtggtg  720
aacagggcag agcgggccgt gtcgtttggc atcgctcgca tcgtgtccgg ccacggcgca  780
atatcgaaca aggaaagctg catttccttg atctgctgct tcgtgtgttt cagcaacgcg  840
gcctgcttgg cttcgctgac ctgttttgcc aggtcctcgc cggcggtttt tcgcttcttg  900
gtcgtcatag ttcctcgcgt gtcgatggtc atcgacttcg ccaaacctgc cgcctcctgt  960
tctagccgac gcgaacgctc cacggcggcc gatggcgcgg gcagggcagg gggagccagt  1020
tgcacgctgt cgcgctcgat cttggccgta gcttgctgga ctatcgagcc gacggactgg  1080
aaggtttcgc ggggcgcacg catgacggtg cggcttgcga tggtttcggc atcctcggcg  1140
gaaaaccccg cgtcgatcag ttcttgcctg tatgccttcc ggtcaaacgt ccgattcatt  1200
```

```
caccctcctt gcgggattgc cccggaatta attccccgga tcgatccgtc gatcttgatc  1260
ccctgcgcca tcagatcctt ggcggcaaga aagccatcca gtttactttg cagggcttcc  1320
caaccttacc agagggcgcc ccagctggca attccggttc gcttgctgtc cataaaaccg  1380
cccagtctag ctatcgccat gtaagcccac tgcaagctac ctgctttctc tttgcgcttg  1440
cgttttccct tgtccagata gcccagtagc tgacattcat ccggggtcag caccgtttct  1500
gcggactggc tttctacgtg gctgccattt ttggggtgag gccgttcgcg gccgaggggc  1560
gcagcccctg gggggatggg aggcccgcgt tagcgggccg ggagggttcg agaagggggg  1620
gcaccccccct tcggcgtgcg cggtcacgcg cacagggcgc agccctggtt aaaaacaagg  1680
tttataaata ttggtttaaa agcaggttaa aagacaggtt agcggtggcc gaaaaacggg  1740
cggaaaccct tgcaaatgct ggattttctg cctgtggaca gcccctcaaa tgtcaatagg  1800
tgcgcccctc atctgtcagc actctgcccc tcaagtgtca aggatcgcgc ccctcatctg  1860
tcagtagtcg cgcccctcaa gtgtcaatac cgcagggcac ttatccccag gcttgtccac  1920
atcatctgtg ggaaactcgc gtaaaatcag gcgttttcgc cgatttgcga ggctggccag  1980
ctccacgtcg ccggccgaaa tcgagcctgc ccctcatctg tcaacgccgc gccgggtgag  2040
tcggcccctc aagtgtcaac gtccgcccct catctgtcag tgagggccaa gttttccgcg  2100
aggtatccac aacgccggcg gccctacatg gctctgctgt agtgagtggg ttgcgctccg  2160
gcagcggtcc tgatccccg cagaaaaaaa ggatctcaag aagatccttt gatcttttct  2220
ac                                                                 2222

SEQ ID NO: 108          moltype = DNA  length = 48
FEATURE                 Location/Qualifiers
misc_feature            1..48
                        note = Transcriptional terminator T1
source                  1..48
                        mol_type = other DNA
                        organism = synthetic construct
SEQUENCE: 108
gacgaacaat aaggccgcaa atcgcggcct tttttattga taacaaaa                48

SEQ ID NO: 109          moltype = DNA  length = 41
FEATURE                 Location/Qualifiers
misc_feature            1..41
                        note = Transcriptional terminator T2
source                  1..41
                        mol_type = other DNA
                        organism = synthetic construct
SEQUENCE: 109
caagaaaaga aaaaacaccc gttagggtgt ttttagttag t                       41

SEQ ID NO: 110          moltype = DNA  length = 32
FEATURE                 Location/Qualifiers
misc_feature            1..32
                        note = Transcriptional terminator lambda T1
source                  1..32
                        mol_type = other DNA
                        organism = synthetic construct
SEQUENCE: 110
aggcctgctg gtaatcgcag gcctttttat tt                                 32

SEQ ID NO: 111          moltype = DNA  length = 53
FEATURE                 Location/Qualifiers
misc_feature            1..53
                        note = Transcriptional terminator lambda T2
source                  1..53
                        mol_type = other DNA
                        organism = synthetic construct
SEQUENCE: 111
aaaaaattag cgcaagaaga caaaaatcac cttgcgctaa tgctctgtta cag          53

SEQ ID NO: 112          moltype = DNA  length = 24
FEATURE                 Location/Qualifiers
misc_feature            1..24
                        note = Linker 1
source                  1..24
                        mol_type = other DNA
                        organism = synthetic construct
SEQUENCE: 112
ccatcatcag ttcggtggtc ttcc                                          24

SEQ ID NO: 113          moltype = DNA  length = 24
FEATURE                 Location/Qualifiers
misc_feature            1..24
                        note = Linker 2
source                  1..24
                        mol_type = other DNA
                        organism = synthetic construct
SEQUENCE: 113
cgacttgcga catgcggtcc tttg                                          24
```

-continued

```
SEQ ID NO: 114         moltype = DNA  length = 24
FEATURE                Location/Qualifiers
misc_feature           1..24
                       note = Linker 3
source                 1..24
                       mol_type = other DNA
                       organism = synthetic construct
SEQUENCE: 114
gatcggattg gcggttatgc ggtt                                            24

SEQ ID NO: 115         moltype = DNA  length = 25
FEATURE                Location/Qualifiers
misc_feature           1..25
                       note = Right border pTiBo542
source                 1..25
                       mol_type = other DNA
                       organism = synthetic construct
SEQUENCE: 115
tggcaggata tatgtggttg taatt                                           25

SEQ ID NO: 116         moltype = DNA  length = 25
FEATURE                Location/Qualifiers
misc_feature           1..25
                       note = Left border pTiBo542
source                 1..25
                       mol_type = other DNA
                       organism = synthetic construct
SEQUENCE: 116
cggcaggata tatggcagtg taaac                                           25
```